(12) United States Patent
Foster et al.

(10) Patent No.: US 10,238,749 B2
(45) Date of Patent: Mar. 26, 2019

(54) ANGIOTENSINOGEN (AGT) IRNA COMPOSITIONS AND METHODS OF USE THEREOF

(71) Applicant: Alnylam Pharmaceuticals, Inc., Cambridge, MA (US)

(72) Inventors: Donald Foster, Attleboro, MA (US); Brian Bettencourt, Groton, MA (US); Klaus Charisse, Acton, MA (US); Gregory Hinkle, Plymouth, MA (US); Satyanarayana Kuchimanchi, Acton, MA (US); Martin Maier, Belmont, MA (US); Stuart Milstein, Arlington, MA (US)

(73) Assignee: Alnylam Pharmaceuticals, Inc., Cambridge, MA (US)

( * ) Notice: Subject to any disclaimer, the term of this patent is extended or adjusted under 35 U.S.C. 154(b) by 179 days.

(21) Appl. No.: 15/313,145

(22) PCT Filed: May 22, 2015

(86) PCT No.: PCT/US2015/032099
§ 371 (c)(1),
(2) Date: Nov. 22, 2016

(87) PCT Pub. No.: WO2015/179724
PCT Pub. Date: Nov. 26, 2015

(65) Prior Publication Data
US 2017/0189541 A1    Jul. 6, 2017

Related U.S. Application Data

(60) Provisional application No. 62/047,978, filed on Sep. 9, 2014, provisional application No. 62/001,731, filed on May 22, 2014.

(51) Int. Cl.
*A61K 48/00* (2006.01)
*C12N 15/11* (2006.01)
(Continued)

(52) U.S. Cl.
CPC .......... *A61K 47/549* (2017.08); *A61K 45/06* (2013.01); *C12N 15/113* (2013.01);
(Continued)

(58) Field of Classification Search
CPC .............. C12N 15/113; C12N 2310/14; C12N 2310/351; C12N 2320/51; A61K 47/549
See application file for complete search history.

(56) References Cited

FOREIGN PATENT DOCUMENTS

| WO | WO-2009/073809 A2 | 6/2009 |
| WO | WO-2010/042749 A2 | 4/2010 |
| WO | WO-2014/018930 A1 | 1/2014 |

OTHER PUBLICATIONS

See Corvol et al. (Endocrine Reviews, 1997 vol. 18(5):662-677).*
(Continued)

*Primary Examiner* — Terra C Gibbs
(74) *Attorney, Agent, or Firm* — McCarter & English, LLP; Maria Laccotripe Zacharakis; Deborah L. Nagle

(57) ABSTRACT

The present invention relates to RNAi agents, e.g., double-stranded RNAi agents, targeting the angiotensinogen (AGT) gene, and methods of using such RNAi agents to inhibit expression of AGT and methods of treating subjects having an AGT-associated disorder, e.g., hypertension.

44 Claims, 10 Drawing Sheets
Specification includes a Sequence Listing.

(51) Int. Cl.
  *C07H 21/02*  (2006.01)
  *C07H 21/04*  (2006.01)
  *A61K 47/54*  (2017.01)
  *C12N 15/113* (2010.01)
  *A61K 45/06*  (2006.01)

(52) U.S. Cl.
  CPC .... *C12N 2310/14* (2013.01); *C12N 2310/343* (2013.01); *C12N 2310/351* (2013.01); *C12N 2320/32* (2013.01); *C12N 2320/51* (2013.01)

(56) References Cited

OTHER PUBLICATIONS

Olearczyk et al. "Targeting of hepatic angiotensinogen using chemically modified siRNAs results in significant and sustained blood pressure lowering in a rat model of hypertension", Hypertension Research vol. 37, pp. 405-412 (2013).

Anonymous: "ALN-AGT, an RNAi Therapeutic in Development for the Treatment of Hypertensive Disorders of Pregnancy", American Heart Association's High Blood Pressure Research 2014, Sep. 11, 2014.

Z-W Ye et al., "Knockdown of angiotensinogen by shRNA-mediated RNA interference inhibits human visceral preadipocytes differentiation", International Journal of Obesity, vol. 34, No. 1 (2009).

International Preliminary Report on Patentability from PCT/US2015/032099 dated Nov. 22, 2016.

\* cited by examiner

ENHANCED NUTRITIONAL EXCHANGE DUE TO LARGER LABYRINTH PROFILE

PE RNAi

PE CONTROL

UTEROPLACENTAL UNIT STAINED FOR CYTOKERATIN

SEQUENCE LISTING

```
<160> NUMBER OF SEQ ID NOS: 1050

<210> SEQ ID NO 1
<211> LENGTH: 2587
<212> TYPE: DNA
<213> ORGANISM: Homo sapiens

<400> SEQUENCE: 1
atcccatgag cgggcagcag ggtcagaagt ggcccccgtg ttgcctaagc aagactctcc      60
cctgccctct gccctctgca cctccggcct gcatgtccct gtggcctctt gggggtacat     120
ctcccggggc tgggtcagaa ggcctgggtg gttggcctca ggctgtcaca cacctaggga     180
gatgctcccg tttctgggaa ccttggcccc gactcctgca aacttcggta aatgtgtaac     240
tcgaccctgc accggctcac tctgttcagc agtgaaactc tgcatcgatc actaagactt     300
cctggaagag gtcccagcgt gagtgtcgct tctggcatct gtccttctgg ccagcctgtg     360
gtctggccaa gtgatgtaac cctcctctcc agcctgtgca caggcagcct gggaacagct     420
ccatccccac ccctcagcta taaatagggc atcgtgaccc ggccggggga agaagctgcc     480
gttgttctgg gtactacagc agaagggtat gcggaagcga gcaccccagt ctgagatggc     540
tcctgccggt gtgagcctga gggccaccat cctctgcctc ctggcctggg ctggcctggc     600
tgcaggtgac cgggtgtaca tacacccctt ccacctcgtc atccacaatg agagtacctg     660
tgagcagctg gcaaaggcca atgccgggaa gcccaaagac cccaccttca tacctgctcc     720
aattcaggcc aagacatccc ctgtggatga aaaggcccta caggaccagc tggtgctagt     780
cgctgcaaaa cttgacaccg aagacaagtt gagggccgca atggtcggga tgctggccaa     840
cttcttgggc ttccgtatat atggcatgca cagtgagcta tggggcgtgg tccatggggc     900
caccgtcctc tccccaacgg ctgtctttgg caccctggcc tctctctatc tgggagcctt     960
ggaccacaca gctgacaggc tacaggcaat cctgggtgtt ccttggaagg acaagaactg    1020
cacctcccgg ctggatgcgc acaaggtcct gtctgccctg caggctgtac agggcctgct    1080
agtggcccag ggcagggctg atagccaggc ccagctgctg ctgtccacgg tggtgggcgt    1140
gttcacagcc ccaggcctgc acctgaagca gccgtttgtg cagggcctgg ctctctatac    1200
ccctgtggtc ctcccacgct ctctggactt cacagaactg gatgttgctg ctgagaagat    1260
tgacaggttc atgcaggctg tgacaggatg gaagactggc tgctccctga tgggagccag    1320
tgtggacagc accctggctt tcaacaccta cgtccacttc caagggaaga tgaagggctt    1380
```

```
ctccctgctg gccgagcccc aggagttctg ggtggacaac agcacctcag tgtctgttcc   1440
catgctctct ggcatgggca ccttccagca ctggagtgac atccaggaca acttctcggt   1500
gactcaagtg cccttcactg agagcgcctg cctgctgctg atccagcctc actatgcctc   1560
tgacctggac aaggtggagg gtctcacttt ccagcaaaac tccctcaact ggatgaagaa   1620
actatctccc cggaccatcc acctgaccat gccccaactg gtgctgcaag atcttatga   1680 cctgcaggac ctgctcgccc aggctgagct gcccgccatt ctgcacaccg agctgaacct   1740
gcaaaaattg agcaatgacc gcatcagggt gggggaggtg ctgaacagca ttttttttga   1800
gcttgaagcg gatgagagag agcccacaga gtctacccaa cagcttaaca agcctgaggt   1860
cttggaggtg accctgaacc gcccattcct gtttgctgtg tatgatcaaa gcgccactgc   1920
cctgcacttc ctgggccgcg tggccaaccc gctgagcaca gcatgaggcc agggccccag   1980
aacacagtgc ctggcaaggc ctctgccccct ggcctttgag gcaaaggcca gcagcagata   2040
acaaccccgg acaaatcagc gatgtgtcac ccccagtctc ccaccttttc ttctaatgag   2100
tcgactttga gctggaaagc agccgttct ccttggtcta agtgtgctgc atggagtgag   2160
cagtagaagc ctgcagcggc acaaatgcac ctcccagttt gctgggttta ttttagagaa   2220
tggggtgggg gaggcaagaa ccagtgttta gcgcgggact actgttccaa aagaattcc   2280 aaccgaccag cttgttttgtg aaacaaaaaa gtgttccctt ttcaagttga gaacaaaaat   2340
tgggttttaa aattaaagta tacattttgt cattgccttc ggtttgtatt tagtgtcttg   2400
aatgtaagaa catgacctcc gtgtagtgtc tgtaatacct tagttttttc cacagatgct   2460
tgtgattttt gaacaatacg tgaaagatgc aagcacctga atttctgttt gaatgcggaa   2520
ccatagctgg ttatttctcc cttgtgttag taataaacgt cttgccacaa taagcctcca   2580
aaaaaaa                                                             2587

<210> SEQ ID NO 2
<211> LENGTH: 2587
<212> TYPE: DNA
<213> ORGANISM: Homo sapiens

<400> SEQUENCE: 2
ttttttttgg aggcttattg tggcaagacg tttattacta acacaaggga gaaataacca    60
gctatggttc cgcattcaaa cagaaattca ggtgcttgca tctttcacgt attgttcaaa   120
aatcacaagc atctgtggaa aaaactaagg tattacagac actacacgga ggtcatgttc   180
ttacattcaa gacactaaat acaaaccgaa ggcaatgcaa aaatgtatac tttaattta    240 aaacccaatt tttgttctca acttgaaaag ggaacacttt tttgtttcac aaacaagctg   300
gtcggtggaa attcttttg gaacagtagt cccgcgctaa acactggttc ttgcctcccc   360 accccattc tctaaaataa acccagcaaa ctgggaggtg catttgtgcc gctgcaggct   420
tctactgctc actccatgca gcacacttag accaaggaga acggctgct ttccagctca   480 aagtcgactc attagaagaa aaggtgggag actggggtg acacatcgct gatttgtccg   540 ggttgttat ctgctgctgg cctttgcctc aaaggccagg ggcagaggcc ttgccaggca   600
ctgtgttctg gggccctggc ctcatgctgt gctcagcggt ttggccacgc ggcccaggaa   660
gtgcagggca gtggcgcttt gatcatacac agcaaacagg aatgggcggt tcagggtcac   720
ctccaagacc tcaggcttgt taagctgttg ggtagactct gtgggctctc tctcatccgc   780
ttcaagctca aaaaaaatgc tgttcagcac ctcccccacc ctgatgcggt cattgctcaa   840 ttttgcagg ttcagctcgg tgtgcagaat ggcgggcagc tcagcctggg cgagcaggtc   900
```

```
ctgcaggtca taagatcctt gcagcaccag ttggggcatg gtcaggtgga tggtccgggg    960
agatagtttc ttcatccagt tgagggagtt ttgctggaaa gtgagaccct ccaccttgtc   1020
caggtcagag gcatagtgag gctggatcag cagcaggcag gcgctctcag tgaagggcac   1080
ttgagtcacc gagaagttgt cctggatgtc actccagtgc tggaaggtgc ccatgccaga   1140
gagcatggga acagacactg aggtgctgtt gtccacccag aactcctggg gctcggccag   1200
cagggagaag cccttcatct tcccttggaa gtggacgtag gtgttgaaag ccagggtgct   1260
gtccacactg gctcccatca gggagcagcc agtcttccat cctgtcacag cctgcatgaa   1320
cctgtcaatc ttctcagcag caacatccag ttctgtgaag tccagagagc gtgggaggac   1380
cacaggggta tagagagcca ggccctgcac aaacggctgc ttcaggtgca ggcctggggc   1440
tgtgaacacg cccaccaccg tggacagcag cagctgggcc tggctatcag ccctgccctg   1500
ggccactagc aggccctgta cagcctgcag ggcagacagg accttgtgcg catccagccg   1560
ggaggtgcag ttcttgtcct tccaaggaac acccaggatt gcctgtagcc tgtcagctgt   1620
gtggtccaag gctcccagat agagagaggc cagggtgcca agacagccg ttggggagag   1680 gacggtggcc ccatggacca cgccccatag ctcactgtgc atgccatata tacggaagcc   1740
caagaagttg gccagcatcc cgaccattgc ggccctcaac ttgtcttcgg tgtcaagttt   1800
tgcagcgact agcaccagct ggtcctgtag ggccttttca tccacagggg atgtcttggc   1860
ctgaattgga gcaggtatga aggtggggtc tttgggcttc ccggcattgg cctttgccag   1920
ctgctcacag gtactctcat tgtggatgac gaggtggaag gggtgtatgt acacccggtc   1980
acctgcagcc aggccagccc aggccaggag gcagaggatg gtggccctca ggctcacacc   2040
ggcaggagcc atctcagact ggggtgctcg cttccgcata cccttctgct gtagtaccca   2100
gaacaacggc agcttcttcc cccggccggg tcacgatgcc ctatttatag ctgaggggtg   2160
gggatggagc tgttcccagg ctgcctgtgc acaggctgga gaggaggggtt acatcacttg   2220 gccagaccac aggctggcca gaaggacaga tgccagaagc gacactcacg ctgggaccct   2280
ttccaggaag tcttagtgat cgatgcagag tttcactgct gaacagagtg agccggtgca   2340
gggtcgagtt acacatttac cgaagtttgc aggagtcggg gccaaggttc ccagaaacgg   2400
gagcatctcc ctaggtgtgt gacagcctga ggccaaccac ccaggccttc tgacccagcc   2460
ccgggagatg taccccccaag aggccacagg gacatgcagg ccggaggtgc agagggcaga   2520
gggcagggga gagtcttgct taggcaacac gggggccact tctgaccctg ctgcccgctc   2580
atgggat                                                             2587
```

<210> SEQ ID NO 3
<211> LENGTH: 1834
<212> TYPE: DNA
<213> ORGANISM: Macaca fascicularis

<400> SEQUENCE: 3

```
aagaagctgc cattgttctg ggtactacag cagaagggta tgcagaagcg agcaccccag     60
tccgagatgg ctcctgccag cgtgagcctg agggccacca tcctctgcct cctggcctgg    120
gctggcctgg ccacaggtga ccgggtgtac atacacccct tccacctcgt catccacaat    180
gagagtacct gtgagcagct ggcaaaggcc gatgctggga agcccaaaga tcccaccttc    240
acacctgttc cgatacaggc caagacgtct cctgtggatg aaaaggccct gcaggaccag    300
ctagtgctgg ttgccgcaaa actcgacacc gaggacaagt tgagagccgc gatggtcggg    360
```

```
atgctggcca acttcttggg cttccgtata tatggcatgc acagtgagct atggggcgtg      420
gtccatgggg ccaccatcct ctccccaacg gctgtctttg gcaccctggc ctctctctac      480
ctgggagcgt tggaccacac agccgacagg ctacaggcaa tcctgggcgt cccttggaag      540
gacaagaact gcacctcccg gctggatgcg cacaaggtcc tctctgccct gcaggctgta      600
cagggcctgc tggtggccca gggcagggct gacggccagt cccagctgct gttgtccaca      660
gtggtgggtc tcttcacagc cccagatctg cacctgaagc agccgtttgt gcagggcctg      720
gctctctatg cccctgtggt cctcccacgc tctctggact tcacagacct ggaagtcgct      780
gctgagaaga ttgacaggtt catgcaggct gtgacaggat ggaagattag cagcccctg       840 acgggagcca gtgcggacag caccctggtt ttcaacacct acgtccattt ccaagggaag      900
atgagggact tcttcctgct ggctgagccc caggagttct gggtggacaa cagcacctca      960
gtgtctgtcc ccatgctgtc tggcgtgggc accttccagc actggagcga cgcccaggac     1020
aacttctcag tgactcaagt gccctttact gagagcgcct gcttgctgct gattcagcct     1080
cactacgcct ctgacctgga caaggtggag gtctcactt ccagcaaaa ctccctcaac       1140 tggatgaaga aactgtctcc ccgggccatc cacctgacca tgccccgact ggtgctgcga     1200
ggatcttatg acctgcagga cctgcttgcc caggctgagc tgcccgccat tctgggcacc     1260
gagctgaacc tgcaaaaatt gagcaatgac aacctcaggg tggggaaggt gctgaacagc     1320 attcttttg aactcgaagc ggatgagaga gagcccacag agtctacccg acagctgaac      1380
aggcctgagt tcttggaggt gaccctggac cgcccattcc tgtttgctgt gtatgatcaa     1440
agtgccactg ccctgcactt cctgggccgt gtggccaacc cgctgagccc agcatgaggc     1500
cagggcccca gaacacagcg cctggcaagg cctctgcccc tggcctttga ggcgaaggcc     1560
agcagcagat atgtaactct ggaaaaacca gcgatttgtc accccagtc tcccaccttt      1620 tcttctaatg agtcaacttc gagctggaaa gcagtcgttt ctccttggtc taagtggtgc     1680
tgcgtgagca gtaagaaacc tgtggcagca caaatgcgcc tcccaggttg ctgggtttat     1740
tttagagaat gggggtgggg aggcaagaac cagtgtttag cgcgggacca ccgttccaaa     1800
aagaattcca accgaccagc ttgtttgtga aaca                                 1834
```

<210> SEQ ID NO 4
<211> LENGTH: 1834
<212> TYPE: DNA
<213> ORGANISM: Macaca fascicularis

<400> SEQUENCE: 4

```
tgtttcacaa acaagctggt cggttggaat tctttttgga acggtggtcc cgcgctaaac       60
actggttctt gcctcccccac ccccattctc taaaataaac ccagcaacct gggaggcgca     120
tttgtgctgc cacaggtttc ttactgctca cgcagcacca cttagaccaa ggagaaacga     180
ctgctttcca gctcgaagtt gactcattag aagaaaggt gggagactgg gggtgacaaa      240
tcgctggttt ttccagagtt acatatctgc tgctggcctt cgcctcaaag gccaggggca     300
gaggccttgc caggcgctgt gttctggggc cctggcctca tgctgggctc agcgggttgg     360
ccacacggcc caggaagtgc agggcagtgg cactttgatc atacacagca aacaggaatg     420
ggcggtccag ggtcacctcc aagaactcag gcctgttcag ctgtcgggta gactctgtgg     480
gctctctctc atccgcttcg agttcaaaaa gaatgctgtt cagcaccttc cccaccctga     540
ggttgtcatt gctcaatttt tgcaggttca gtccggtgcc cagaatgcg ggcagctcag      600 cctgggcaag caggtcctgc aggtcataag atcctcgcag caccagtcgg ggcatggtca     660
```

```
ggtggatggc cgggggagac agtttcttca tccagttgag ggagttttgc tggaaagtga      720
gaccctccac cttgtccagg tcagaggcgt agtgaggctg aatcagcagc aagcaggcgc      780
tctcagtaaa gggcacttga gtcactgaga agttgtcctg ggcgtcgctc cagtgctgga      840
aggtgcccac gccagacagc atggggacag acactgaggt gctgttgtcc acccagaact      900
cctggggctc agccagcagg aagaagtccc tcatcttccc ttggaaatgg acgtaggtgt      960
tgaaaaccag ggtgctgtcc gcactggctc ccgtcagggg gctgctaatc ttccatcctg     1020
tcacagcctg catgaacctg tcaatcttct cagcagcgac ttccaggtct gtgaagtcca     1080
gagagcgtgg gaggaccaca ggggcataga gagccaggcc ctgcacaaac ggctgcttca     1140
ggtgcagatc tggggctgtg aagagaccca ccactgtgga caacagcagc tgggactggc     1200
cgtcagccct gccctgggcc accagcaggc cctgtacagc ctgcagggca gagaggacct     1260
tgtgcgcatc cagccgggag gtgcagttct tgtccttcca agggacgccc aggattgcct     1320
gtagcctgtc ggctgtgtgg tccaacgctc caggtagag agaggccagg gtgccaaaga      1380
cagccgttgg ggagaggatg gtggccccat ggaccacgcc ccatagctca ctgtgcatgc     1440
catatatacg gaagcccaag aagttggcca gcatcccgac catcgcggct ctcaacttgt     1500
cctcggtgtc gagttttgcg gcaaccagca ctagctggtc ctgcagggcc ttttcatcca     1560
caggagacgt cttggcctgt atcggaacag gtgtgaaggt gggatctttg ggcttcccag     1620
catcggcctt tgccagctgc tcacaggtac tctcattgtg gatgacgagg tggaaggggt     1680
gtatgtacac ccggtcacct gtggccaggc cagcccaggc caggaggcag aggatggtgg     1740
ccctcaggct cacgctggca ggagccatct cggactgggg tgctcgcttc tgcatacccT     1800
tctgctgtag tacccagaac aatggcagct tctt                                1834

<210> SEQ ID NO 5
<211> LENGTH: 1856
<212> TYPE: DNA
<213> ORGANISM: Mus musculus

<400> SEQUENCE: 5
gatagctgtg cttgtctagg ttggcgctga aggatacaca gaagcaaatg cacagatcgg       60
agatgactcc cacggggggca ggcctgaagg ccaccatctt ctgcatcttg acctgggtca     120
gcctgacggc tggggaccgc gtatacatcc accccttcca tctcctttac cacaacaaga     180
gcacctgcgc ccagctggag aaccccagtg tggagacact cccagagtca cgttcgagc      240 ctgtgcccat tcaggccaag acctcccctg tgaatgagaa gaccctgcat gatcagctcg     300
tgctggccgc cgagaagcta gaggatgagg accggaagcg ggctgcccag gtcgcaatga     360
tcgccaactt cgtgggcttc cgcatgtaca agatgctgaa tgaggcagga agtggggcca     420
gtggggccat cctctcacca ccagctctct ttggcaccct ggtctctttc taccttggat     480
ccttagatcc cacggccagc cagctgcaga cgctgctgga tgtccctgtg aaggagggag     540
actgcacctc ccgactagat ggacacaagg tcctcgctgc cctgcgggcc attcagggct     600
tgctggtcac ccagggtggg agcagcagcc agacacccct gctacagtcc attgtggtgg     660
ggctcttcac tgctccaggc tttcgtctaa agcactcatt tgttcagagc ctggctctct     720 ttaccccctgc cctcttccca cgctctctgg atttatccac tgacccagtt cttgccactg     780
agaaaatcaa caggttcata aaggctgtga caggtggaa gatgaacttg ccactggagg     840
gggtcagtac agacagcacc ctactttcca acacctacgt tcacttccaa ggaacgatga     900
```

```
gaggtttctc tcagctgcct ggagtccatg aattctgggt ggacaacagc atctcggtgt    960
ctgtgcccat gatctccggc actggcaact tccagcactg gagtgacacc cagaacaact   1020
tctccgtgac gtgcgtgccc ctaggtgaga gagccaccct gctgctcatc cagccccact   1080
gcacctcaga tctcgacagg gtggaggccc tcatcttccg gaacgacctc ctgacttgga   1140
tagagaaccc gcctcctcgg gccatccgcc tgactctgcc ccagctggaa atccgaggat   1200
cctacaatct gcaggacctg ctggctgagg acaagctgcc caccctttg ggtgcggagg    1260
caaatctgaa caacattggt gacaccaacc cccgagtggg agaggttctc aatagcatcc   1320
tcctcgaact caaagcagga gaggaggaac agccgaccac gtctgtccag cagcctggct   1380
caccggaggc actggatgtg accctgagca gccccttcct gttcgccatc tacgagcagg   1440
actcaggcac gctgcacttt ctgggcagag tgaataaccc ccagagtgtg gtgtgaggcc   1500
ttgtgcctag ccatggagac aaggccggtg tcggagaacc gttctgggca aaactcagtg   1560
ctgtcacccc tggctcccca tcacgccttg tagcgcggca gaggccgtct ccttggagac   1620
tgcgctgacc gagaataaat gatgagcagc agagcctcct gggatgtggg tttgtttgga   1680
tactggggtg acagccagaa gctggcactc tgcacaggac tgccactctg gaagaaattt   1740
ggaccaaaaa actgtttgtg acaccaaaaa gcacccccc ttttttttat ttgaggacag     1800
aaattgggtt ttaacattaa aatgcacatt atccccttaa aaaaaaaaa aaaaaa        1856

<210> SEQ ID NO 6
<211> LENGTH: 1856
<212> TYPE: DNA
<213> ORGANISM: Mus musculus

<400> SEQUENCE: 6
tttttttttt tttttttaa ggggataatg tgcattttaa tgttaaaacc caatttctgt    60
cctcaaataa aaaaagggg gggtgctttt tggtgtcaca acagtttttt tggtccaaat    120
ttcttccaga gtggcagtcc tgtgcagagt gccagcttct ggctgtcacc ccagtatcca   180
aacaaaccca catcccagga ggctctgctg ctcatcattt attctcggtc agcgcagtct   240
ccaaggagac ggcctctgcc gcgctacaag gcgtgatggg gagccagggg tgacagcact   300
gagttttgcc cagaacggtt ctccgacacc ggccttgtct ccatggctag gcacaaggcc   360
tcacaccaca ctctgggggt tattcactct gcccagaaag tgcagcgtgc ctgagtcctg   420
ctcgtagatg gcgaacagga aggggctgct cagggtcaca tccagtgcct ccggtgagcc   480
aggctgctgg acagacgtgg tcggctgttc ctcctctcct gctttgagtt cgaggaggat   540
gctattgaga acctctccca ctcggggggtt ggtgtcacca atgttgttca gatttgcctc   600
cgcacccaaa agggtgggca gcttgtcctc agccagcagg tcctgcagat tgtaggatcc   660
tcggatttcc agctggggca gagtcaggcg gatggcccga ggaggcgggt tctctatcca   720
agtcaggagg tcgttccgga agatgagggc ctccaccctg tcgagatctg aggtgcagtg   780
gggctggatg agcagcaggg tggctctctc acctaggggac acgcacgtca cggagaagtt   840
gttctgggtg tcactccagt gctggaagtt gccagtgccg agatcatggg gcacagacac   900
cgagatgctg ttgtccaccc agaattcatg gactccaggc agctgagaga aacctctcat   960
cgttccttgg aagtgaacgt aggtgttgaa agtagggtg ctgtctgtac tgaccccctc    1020
cagtggcaag ttcatcttcc accctgtcac agccttatg aacctgttga ttttctcagt   1080
ggcaagaact gggtcagtgg ataaatccag agagcgtggg aagagggcag gggtaaagag   1140
agccaggctc tgaacaaatg agtgctttag acgaaagcct ggagcagtga agagcccac    1200
```

```
cacaatggac tgtagcaggg gtgtctggct gctgctccca ccctgggtga ccagcaagcc    1260
ctgaatggcc cgcagggcag cgaggacctt gtgtccatct agtcgggagg tgcagtctcc    1320
ctccttcaca gggacatcca gcagcgtctg cagctggctg ccgtgggat  ctaaggatcc    1380 aaggtagaaa gagaccaggg tgccaaagag agctggtggt gagaggatgg ccccactggc    1440
cccacttcct gcctcattca gcatcttgta catgcggaag cccacgaagt tggcgatcat    1500
tgcgacctgg gcagcccgct tccggtcctc atcctctagc ttctcggcgg ccagcacgag    1560
ctgatcatgc agggtcttct cattcacagg ggaggtcttg gcctgaatgg cacaggctc     1620 gaacgttgac tctgggagtg tctccacact ggggttctcc agctgggcgc aggtgctctt    1680
gttgtggtaa aggagatgga aggggtggat gtatacgcgg tccccagccg tcaggctgac    1740
ccaggtcaag atgcagaaga tggtggcctt caggcctgcc ccgtgggag  tcatctccga    1800 tctgtgcatt tgcttctgtg tatccttcag cgccaaccta gacaagcaca gctatc       1856
```

<210> SEQ ID NO 7
<211> LENGTH: 1958
<212> TYPE: DNA
<213> ORGANISM: Rattus norvegicus

<400> SEQUENCE: 7

```
ccttgctcca tcttggctaa gcctggattc ccatggtccc ccgacctggg tcctccccca      60
gcctctgtac agagtagcct gggaatagat ccatcttcac cccctcgagt ataaataagg     120
ctgcttggtt caccagggga tagctgtgct tgtctgggct ggagctaaag gacacacaga     180
agcaagtcca cagatccgtg atgactccca cgggggcagg cctgaaggcc accatcttct     240
gcatcctgac ctgggtcagc ctgacagctg ggaccgcgt  atacatccac ccctttcatc     300
tcctctacta cagcaagagc acctgcgccc agctggagaa ccccagtgtg agacgctcc      360 cagagccaac cttgagcct  tgcccattc  aggccaagac ctcccccgtg atgagaaga      420 ccctgcgaga taagctcgtg ctggccactg agaagctaga ggctgaggat cggcagcgag     480
ctgcccaggt cgcgatgatt gccaacttca tgggtttccg catgtacaag atgctgagtg     540
aggcaagagg tgtagccagt ggggccgtcc tctctccacc ggccctcttt ggcaccctgg     600 tctcttctcta ccttggatcg ttggatccca cggccagcca gttgcaggtg ctgctgggcg    660
tccctgtgaa ggagggagac tgcacctccc ggctggacgg ataaggtc   ctcactgccc     720 tgcaggctgt tcagggcttg ctggtcaccc agggtggaag cagcagccag acaccctgc      780 tacagtccac cgtggtgggc ctcttcactg ccccaggctt gcgcctaaaa cagccatttg     840
ttgagagctt gggtcccttc accccgcca  tcttccctcg ctctctggac ttatccactg     900
acccagttct gctgcccag  aaaatcaaca ggtttgtgca ggctgtgaca gggtggaaga     960
tgaacttgcc actagagggg gtcagcacgg acagcaccct  atttttcaac acctacgttc   1020
acttccaagg gaagatgaga ggcttctccc agctgactgg gctccatgag ttctgggtgg    1080
acaacagcac ctcagtgtct gtgcccatgc tctcgggcac tggcaacttc agcactgga    1140 gtgacgccca gaacaacttc tccgtgacac gcgtgcccct gggtgagagt gtcaccctgc    1200
tgctgatcca gccccagtgc gcctcagatc tcgacagggt ggaggtcctc gtcttccagc    1260
acgacttcct gacttggata aagaacccgc ctcctcgggc catccgtctg accctgccgc    1320
agctggaaat tcggggatcc tacaacctgc aggacctgct ggctcaggcc aagctgtcta    1380
cccttttggg tgctgaggca aatctgggca agatgggtga caccaacccc cgagtgggag    1440
```

```
aggttctcaa cagcatcctc cttgaactcc aagcaggcga ggaggagcag cccacagagt    1500
ctgcccagca gcctggctca cccgaggtgc tggacgtgac cctgagcagt ccgttcctgt    1560
tcgccatcta cgagcgggac tcaggtgcgc tgcactttct gggcagagtg ataaccccc    1620 aaaatgtggt gtgatgcctc ctgtgtagcc atggagacaa ggccagcgtc agagagctat    1680
cctgggcaaa atcagtgcc ttcacccctg gcttcccgtc actccttcca gcaaggcaga    1740
ggccgtctcc ttggagatgg cgctaactga gaataaatga tgagcagcag cctcctgggg    1800
tgtgggtttg tttggacact ggggtgagag ccaggagctg gcactctgta taggaggact    1860
gccatcctgg aaaaaaaaaa tggaccaaac aactgtttgt gaataaaaaa aaaaaaatt    1920 cccttttat ttgaaaaaaa aaaaaaaaa aaaaaaaa                            1958

<210> SEQ ID NO 8
<211> LENGTH: 1958
<212> TYPE: DNA
<213> ORGANISM: Rattus norvegicus

<400> SEQUENCE: 8
tttttttttt tttttttttt tttttcaaat aaaaagggaa tttttttttt tttatttcac      60
aaacagttgt ttggtccatt ttttttttcc aggatggcag tcctcctata cagagtgcca     120
gctcctggct ctcaccccag tgtccaaaca aacccacacc ccaggaggct gctgctcatc     180
atttattctc agttagcgcc atctccaagg agacggcctc tgccttgctg aaggagtga      240 cgggaagcca ggggtgaagg cactgatttt tgcccaggat agctctctga cgctggcctt     300
gtctccatgg ctacacagga ggcatcacac cacattttgg gggttatcca ctctgcccag     360
aaagtgcagc gcacctgagt cccgctcgta gatggcgaac aggaacggac tgctcagggt     420
cacgtccagc acctcgggtg agccaggctg ctgggcagca tctgtgggct gctcctcctc     480
gcctgcttgg agttcaagga ggatgctgtt gagaacctct cccactcggg ggttggtgtc     540
acccatcttg cccagatttg cctcagcacc caaaagggta gacagcttgg cctgagccag     600
caggtcctgc aggttgtagg atccccgaat tccagctgc ggcagggtca gacggatggc      660
ccgaggaggc gggttcttta tccaagtcag gaagtcgtgc tggaagacga ggacctccac     720
cctgtcgaga tctgaggcgc actggggctg gatcagcagc agggtgacac tctcacccag     780
gggcacgcgt gtcacggaga agttgttctg gcgtcactc cagtgctgga agttgccagt      840
gcccgagagc atgggcacag acactgaggt gctgttgtcc acccagaact catggagccc     900
agtcagctgg gagaagcctc tcatcttccc ttggaagtga acgtaggtgt tgaaaaatag     960
ggtgctgtcc gtgctgaccc cctctagtgg caagttcatc ttccaccctg tcacagcctg    1020
cacaaacctg ttgatttct gggcagcaag aactgggtca gtggataagt ccagagagcg     1080
agggaagatg gcgggggtga agggacccaa gctctcaaca aatggctgtt ttaggcgcaa    1140
gcctggggca gtgaagaggc ccaccacggt ggactgtagc aggggtgtct ggctgctgct    1200
tccaccctgg gtgaccagca agcctgaac agcctgcagg gcagtgagga ccttatgtcc     1260
gtccagccgg gaggtgcagt ctccctcctt cacagggacg cccagcagca cctgcaactg    1320 gctgccgtg ggatccaacg atccaaggta gaaagagacc agggtgccaa agagggccgg     1380
tggagagagg acggccccac tggctacacc tcttgcctca ctcagcatct tgtacatgcg    1440
gaaacccatg aagttggcaa tcatcgcgac ctgggcagct cgctgccgat cctcagcctc    1500
tagcttctca gtgccagca cgagcttatc tcgcagggtc ttctcatcca cggggaggt     1560 cttggcctga atgggcacag gctcaaaggt tggctctggg agcgtctcca cactgggggtt   1620
```

```
ctccagctgg gcgcaggtgc tcttgctgta gtagaggaga tgaaaggggt ggatgtatac    1680
gcggtcccca gctgtcaggc tgacccaggt caggatgcag aagatggtgg ccttcaggcc    1740
tgcccccgtg ggagtcatca cggatctgtg gacttgcttc tgtgtgtcct ttagctccag    1800
cccagacaag cacagctatc ccctggtgaa ccaagcagcc ttatttatac tcgagggggt    1860
gaagatggat ctattcccag gctactctgt acagaggctg ggggaggacc caggtcgggg    1920
gaccatggga atccaggctt agccaagatg gagcaagg                            1958

<210> SEQ ID NO 9
<211> LENGTH: 16
<212> TYPE: PRT
<213> ORGANISM: Unknown
<220> FEATURE:
<221> NAME/KEY: source
<223> OTHER INFORMATION: /note="Description of Unknown: RFGF
      sequence"

<400> SEQUENCE: 9

Ala Ala Val Ala Leu Leu Pro Ala Val Leu Leu Ala Leu Leu Ala Pro
1               5                   10                  15

<210> SEQ ID NO 10
<211> LENGTH: 11
<212> TYPE: PRT
<213> ORGANISM: Unknown
<220> FEATURE:
<221> NAME/KEY: source
<223> OTHER INFORMATION: /note="Description of Unknown: RFGF analogue
      sequence"

<400> SEQUENCE: 10

Ala Ala Leu Leu Pro Val Leu Leu Ala Ala Pro
1               5                   10

<210> SEQ ID NO 11
<211> LENGTH: 13
<212> TYPE: PRT
<213> ORGANISM: Human immunodeficiency virus

<400> SEQUENCE: 11

Gly Arg Lys Lys Arg Arg Gln Arg Arg Pro Pro Gln
1               5                   10

<210> SEQ ID NO 12
<211> LENGTH: 16
<212> TYPE: PRT
<213> ORGANISM: Drosophila sp.

<400> SEQUENCE: 12

Arg Gln Ile Lys Ile Trp Phe Gln Asn Arg Arg Met Lys Trp Lys Lys
1               5                   10                  15

<210> SEQ ID NO 13
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 13
cuuacgcuga guacuucgat t                                              21

<210> SEQ ID NO 14
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
ucgaaguacu cagcguaagt t                                              21

<210> SEQ ID NO 15
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
uucuggguac uacagcaga                                                 19

<210> SEQ ID NO 16
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 16
guacuacagc agaagggua                                                 19

<210> SEQ ID NO 17
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 17
gugaccgggu guacauaca                                                 19

<210> SEQ ID NO 18
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 18
cucgucaucc acaaugaga                                                 19

```
<210> SEQ ID NO 19
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 19
ccacaaugag aguaccugu                                                      19

<210> SEQ ID NO 20
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 20
cacaaugaga guaccugug                                                      19

<210> SEQ ID NO 21
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 21
cugugagcag cuggcaaag                                                      19

<210> SEQ ID NO 22
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 22
cuguggauga aaaggcccu                                                      19

<210> SEQ ID NO 23
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 23
uggucgggau gcuggccaa                                                      19

<210> SEQ ID NO 24
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 24
ucgggaugcu ggccaacuu                                                    19

<210> SEQ ID NO 25
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 25
ggaugcuggc caacuucuu                                                    19

<210> SEQ ID NO 26
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 26
uggccaacuu cuugggcuu                                                    19

<210> SEQ ID NO 27
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 27
cuucuugggc uuccguaua                                                    19

<210> SEQ ID NO 28
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 28
cuugggcuuc cguauauau                                                    19

<210> SEQ ID NO 29
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 29
gcuuccguau auauggcau                                                    19

<210> SEQ ID NO 30
<211> LENGTH: 19
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 30
guauauaugg caugcacag                                                   19

<210> SEQ ID NO 31
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 31
ggcaugcaca gugagcuau                                                   19

<210> SEQ ID NO 32
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 32 cuaugggcg ugguccaug                                                    19

<210> SEQ ID NO 33
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 33
cuccccaacg gcugucuuu                                                   19

<210> SEQ ID NO 34
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 34
uccccaacgg cugucuuug                                                   19

<210> SEQ ID NO 35
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 35
cuuggaagga caagaacug                                                   19
```

```
<210> SEQ ID NO 36
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 36
ccacgcucuc uggacuuca                                             19

<210> SEQ ID NO 37
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 37
gcugcugaga agauugaca                                             19

<210> SEQ ID NO 38
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 38
cugcugagaa gauugacag                                             19

<210> SEQ ID NO 39
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 39
ugcugagaag auugacagg                                             19

<210> SEQ ID NO 40
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 40
gcugagaaga uugacaggu                                             19

<210> SEQ ID NO 41
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 41
cugagaagau ugacagguu                                              19

<210> SEQ ID NO 42
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 42
uugacagguu caugcaggc                                              19

<210> SEQ ID NO 43
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 43
gcugugacag gauggaaga                                              19

<210> SEQ ID NO 44
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 44
gaguucuggg uggacaaca                                              19

<210> SEQ ID NO 45
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 45
cuggguggac aacagcacc                                              19

<210> SEQ ID NO 46
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 46
uggacaacag caccucagu                                              19

<210> SEQ ID NO 47
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 47
caacagcacc ucagugucu                                                   19

<210> SEQ ID NO 48
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 48
uggacaaggu ggagggucu                                                   19

<210> SEQ ID NO 49
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 49
caagguggag ggucucacu                                                   19

<210> SEQ ID NO 50
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 50
agguggaggg ucucacuuu                                                   19

<210> SEQ ID NO 51
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 51
cuuuccagca aaacuccccu                                                  19

<210> SEQ ID NO 52
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 52
ccagcaaaac ucccucaac                                                   19
```

<210> SEQ ID NO 53
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 53
cagcaaaacu cccucaacu                                                   19

<210> SEQ ID NO 54
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 54
caaaacuccc ucaacugga                                                   19

<210> SEQ ID NO 55
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 55
ucccucaacu ggaugaaga                                                   19

<210> SEQ ID NO 56
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 56
cccucaacug gaugaagaa                                                   19

<210> SEQ ID NO 57
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 57
ucaacuggau gaagaaacu                                                   19

<210> SEQ ID NO 58
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 58
ccgagcugaa ccugcaaaa                                                19

<210> SEQ ID NO 59
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 59
cgagcugaac cugcaaaaa                                                19

<210> SEQ ID NO 60
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 60
gaaccugcaa aaauugagc                                                19

<210> SEQ ID NO 61
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 61
accugcaaaa auugagcaa                                                19

<210> SEQ ID NO 62
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 62
ccugcaaaaa uugagcaau                                                19

<210> SEQ ID NO 63
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 63
cugcaaaaau ugagcaaug                                                19

<210> SEQ ID NO 64
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 64
ugcaaaaauu gagcaauga                                                19

<210> SEQ ID NO 65
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 65
gcaaaaauug agcaaugac                                                19

<210> SEQ ID NO 66
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 66
ggguggggga ggugcugaa                                                19

<210> SEQ ID NO 67
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 67
ggaugagaga gagcccaca                                                19

<210> SEQ ID NO 68
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 68
ccgcccauuc cuguuugcu                                                19

<210> SEQ ID NO 69
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 69
```

```
auuccuguuu gcuguguau                                                  19
```

```
<210> SEQ ID NO 70
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 70
uccuguuugc uguguauga                                                  19
```

```
<210> SEQ ID NO 71
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 71
guuugcugug uaugaucaa                                                  19
```

```
<210> SEQ ID NO 72
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 72
uuugcugugu augaucaaa                                                  19
```

```
<210> SEQ ID NO 73
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 73
cccccagucu cccaccuuu                                                  19
```

```
<210> SEQ ID NO 74
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 74
cccaccuuuu cuucuaaug                                                  19
```

```
<210> SEQ ID NO 75
<211> LENGTH: 19
<212> TYPE: RNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"

<400> SEQUENCE: 75
ccaccuuuuc uucuaauga                                                      19

<210> SEQ ID NO 76
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 76
caccuuuucu ucuaaugag                                                      19

<210> SEQ ID NO 77
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 77
guuucuccuu ggucuaagu                                                      19

<210> SEQ ID NO 78
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 78
uugcuggguu uauuuaga                                                       19

<210> SEQ ID NO 79
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 79
ugcuggguuu auuuagag                                                       19

<210> SEQ ID NO 80
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 80
gcuggguuua uuuagaga                                                       19

<210> SEQ ID NO 81
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 81
cuggguuuau uuuagagaa                                                  19

<210> SEQ ID NO 82
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 82
uggguuuauu uuagagaau                                                  19

<210> SEQ ID NO 83
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 83
guuuauuuua gagaauggg                                                  19

<210> SEQ ID NO 84
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 84
uauuuuagag aauggggu                                                   19

<210> SEQ ID NO 85
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 85
uggggaggca agaaccagu                                                  19

<210> SEQ ID NO 86
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 86
```
ggaggcaaga accaguguu                                               19

<210> SEQ ID NO 87
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 87 uccaaaaga auuccaacc                                                19

<210> SEQ ID NO 88
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 88
caaaaagaau uccaaccga                                               19

<210> SEQ ID NO 89
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 89
ccaaccgacc agcuuguuu                                               19

<210> SEQ ID NO 90
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 90
ccgaccagcu uguuuguga                                               19

<210> SEQ ID NO 91
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 91
cgaccagcuu guuugugaa                                               19

<210> SEQ ID NO 92
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 92
gaccagcuug uuugugaaa                                                  19

<210> SEQ ID NO 93
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 93
gcuuguuugu gaaacaaaa                                                  19

<210> SEQ ID NO 94
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 94
cuuguuugug aaacaaaaa                                                  19

<210> SEQ ID NO 95
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 95
uuguuuguga aacaaaaaa                                                  19

<210> SEQ ID NO 96
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 96
guuugugaaa caaaaaagu                                                  19

<210> SEQ ID NO 97
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 97
uugugaaaca aaaagugu                                                   19
```

```
<210> SEQ ID NO 98
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 98
ugaaacaaaa aaguguucc                                                  19

<210> SEQ ID NO 99
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 99
caaaaaagug uucccuuuu                                                  19

<210> SEQ ID NO 100
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 100
aaaaaguguu cccuuuuca                                                  19

<210> SEQ ID NO 101
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 101
aaaaguguuc ccuuuucaa                                                  19

<210> SEQ ID NO 102
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 102
uucccuuuuc aaguugaga                                                  19

<210> SEQ ID NO 103
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 103
ccuuuucaag uugagaaca                                              19

<210> SEQ ID NO 104
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 104
uuucaaguug agaacaaaa                                              19

<210> SEQ ID NO 105
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 105
uucaaguuga gaacaaaaa                                              19

<210> SEQ ID NO 106
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 106
caaguugaga acaaaaauu                                              19

<210> SEQ ID NO 107
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 107
aguugagaac aaaaauugg                                              19

<210> SEQ ID NO 108
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 108
guugagaaca aaaauuggg                                              19

<210> SEQ ID NO 109
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 109
ugagaacaaa aauuggguu                                                   19

<210> SEQ ID NO 110
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 110
gagaacaaaa auuggguuu                                                   19

<210> SEQ ID NO 111
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 111
gaacaaaaau uggguuuua                                                   19

<210> SEQ ID NO 112
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 112
aacaaaaauu ggguuuuaa                                                   19

<210> SEQ ID NO 113
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 113
acaaaaauug gguuuuaaa                                                   19

<210> SEQ ID NO 114
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 114
caaaaauugg guuuuaaaa                                                   19
```

```
<210> SEQ ID NO 115
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 115
auuggguuuu aaaauuaaa                                              19

<210> SEQ ID NO 116
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 116
uuggguuuua aaauuaaag                                              19

<210> SEQ ID NO 117
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 117
uggguuuuaa aauuaaagu                                              19

<210> SEQ ID NO 118
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 118
uuuaaaauua aaguauaca                                              19

<210> SEQ ID NO 119
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 119
uuaaaauuaa aguauacau                                              19

<210> SEQ ID NO 120
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 120
uuguauuuag ugucuugaa                                                19

<210> SEQ ID NO 121
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 121
uguauuuagu gucuugaau                                                19

<210> SEQ ID NO 122
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 122
uagugucuug aauguaaga                                                19

<210> SEQ ID NO 123
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 123
cuugaaugua agaacauga                                                19

<210> SEQ ID NO 124
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 124
uugaauguaa gaacaugac                                                19

<210> SEQ ID NO 125
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 125
cuuaguuuuu uccacagau                                                19

<210> SEQ ID NO 126
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 126
ccacagaugc uugugauuu                                              19

<210> SEQ ID NO 127
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 127
acagaugcuu gugauuuuu                                              19

<210> SEQ ID NO 128
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 128
cugaauuucu guuugaaug                                              19

<210> SEQ ID NO 129
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 129
aaccauagcu gguuauuuc                                              19

<210> SEQ ID NO 130
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 130
ccauagcugg uuauuucuc                                              19

<210> SEQ ID NO 131
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 131
ucugcuguag uacccagaa                                              19
```

```
<210> SEQ ID NO 132
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 132
uacccuucug cuguaguac                                                19

<210> SEQ ID NO 133
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 133
uguauguaca cccggucac                                                19

<210> SEQ ID NO 134
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 134
ucucauugug gaugacgag                                                19

<210> SEQ ID NO 135
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 135
acagguacuc ucauugugg                                                19

<210> SEQ ID NO 136
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 136
cacagguacu cucauugug                                                19

<210> SEQ ID NO 137
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

```
<210> SEQ ID NO 137 (continued)
Synthetic oligonucleotide"

<400> SEQUENCE: 137
cuuugccagc ugcucacag                                                19

<210> SEQ ID NO 138
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 138
agggccuuuu cauccacag                                                19

<210> SEQ ID NO 139
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 139
uuggccagca ucccgacca                                                19

<210> SEQ ID NO 140
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 140
aaguuggcca gcaucccga                                                19

<210> SEQ ID NO 141
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 141
aagaaguugg ccagcaucc                                                19

<210> SEQ ID NO 142
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 142
aagcccaaga aguuggcca                                                19

<210> SEQ ID NO 143
<211> LENGTH: 19
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 143
uauacggaag cccaagaag                                                19

<210> SEQ ID NO 144
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 144
auauauacgg aagcccaag                                                19

<210> SEQ ID NO 145
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 145
augccauaua uacggaagc                                                19

<210> SEQ ID NO 146
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 146
cugugcaugc cauauauac                                                19

<210> SEQ ID NO 147
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 147
auagcucacu gugcaugcc                                                19

<210> SEQ ID NO 148
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 148
```
cauggaccac gccccauag                              19

<210> SEQ ID NO 149
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 149
aaagacagcc guuggggag                              19

<210> SEQ ID NO 150
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 150
caaagacagc cguugggga                              19

<210> SEQ ID NO 151
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 151
caguucuugu ccuuccaag                              19

<210> SEQ ID NO 152
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 152
ugaaguccag agagcgugg                              19

<210> SEQ ID NO 153
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 153
ugucaaucuu cucagcagc                              19

<210> SEQ ID NO 154
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 154
cugucaaucu ucucagcag                                                      19

<210> SEQ ID NO 155
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 155
ccugucaauc uucucagca                                                      19

<210> SEQ ID NO 156
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 156
accugucaau cuucucagc                                                      19

<210> SEQ ID NO 157
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 157
aaccugucaa ucuucucag                                                      19

<210> SEQ ID NO 158
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 158
gccugcauga accugucaa                                                      19

<210> SEQ ID NO 159
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 159
ucuuccaucc ugucacagc                                                      19

<210> SEQ ID NO 160

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 160
uguuguccac ccagaacuc                                          19

<210> SEQ ID NO 161
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 161
ggugcuguug uccacccag                                          19

<210> SEQ ID NO 162
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 162
acugaggugc uguugucca                                          19

<210> SEQ ID NO 163
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 163
agacacugag gugcuguug                                          19

<210> SEQ ID NO 164
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 164
agacccucca ccuugucca                                          19

<210> SEQ ID NO 165
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 165
```
agugagaccc uccaccuug                                             19

<210> SEQ ID NO 166
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 166
aaagugagac ccuccaccu                                             19

<210> SEQ ID NO 167
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 167
agggaguuuu gcuggaaag                                             19

<210> SEQ ID NO 168
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 168
guugagggag uuuugcugg                                             19

<210> SEQ ID NO 169
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 169
aguugaggga guuuugcug                                             19

<210> SEQ ID NO 170
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 170
uccaguugag ggaguuuug                                             19

<210> SEQ ID NO 171
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 171
ucuucaucca guugaggga                                              19

<210> SEQ ID NO 172
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 172
uucuucaucc aguugaggg                                              19

<210> SEQ ID NO 173
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 173
aguuucuuca uccaguuga                                              19

<210> SEQ ID NO 174
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 174
uuuugcaggu ucagcucgg                                              19

<210> SEQ ID NO 175
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 175
uuuuugcagg uucagcucg                                              19

<210> SEQ ID NO 176
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 176
gcucaauuuu ugcagguuc                                              19
```

```
<210> SEQ ID NO 177
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 177
uugcucaauu uuugcaggu                                                     19

<210> SEQ ID NO 178
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 178
auugcucaau uuuugcagg                                                     19

<210> SEQ ID NO 179
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 179
cauugcucaa uuuuugcag                                                     19

<210> SEQ ID NO 180
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 180
ucauugcuca auuuuugca                                                     19

<210> SEQ ID NO 181
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 181
gucauugcuc aauuuuugc                                                     19

<210> SEQ ID NO 182
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 182
uucagcaccu cccccaccc                                              19

<210> SEQ ID NO 183
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 183
ugugggcucu cucucaucc                                              19

<210> SEQ ID NO 184
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 184
agcaaacagg aaugggcgg                                              19

<210> SEQ ID NO 185
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 185
auacacagca aacaggaau                                              19

<210> SEQ ID NO 186
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 186
ucauacacag caaacagga                                              19

<210> SEQ ID NO 187
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 187
uugaucauac acagcaaac                                              19

<210> SEQ ID NO 188
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 188
uuugaucaua cacagcaaa                                                    19

<210> SEQ ID NO 189
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 189
aaagguggga gacuggggg                                                    19

<210> SEQ ID NO 190
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 190
cauuagaaga aaagguggg                                                    19

<210> SEQ ID NO 191
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 191
ucauuagaag aaaaggugg                                                    19

<210> SEQ ID NO 192
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 192
cucauuagaa gaaaaggug                                                    19

<210> SEQ ID NO 193
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 193
acuuagacca aggagaaac                                                    19
```

```
<210> SEQ ID NO 194
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 194
ucuaaaauaa acccagcaa                                                      19

<210> SEQ ID NO 195
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 195
cucuaaaaua aacccagca                                                      19

<210> SEQ ID NO 196
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 196
ucucuaaaau aaacccagc                                                      19

<210> SEQ ID NO 197
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 197
uucucuaaaa uaaacccag                                                      19

<210> SEQ ID NO 198
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 198
auucucuaaa auaaaccca                                                      19

<210> SEQ ID NO 199
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 199
cccauucucu aaaauaaac                                              19

<210> SEQ ID NO 200
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 200 accccccauuc ucuaaaaua                                             19

<210> SEQ ID NO 201
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 201
acugguucuu gccucccca                                              19

<210> SEQ ID NO 202
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 202
aacacugguu cuugccucc                                              19

<210> SEQ ID NO 203
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 203
gguuggaauu cuuuuugga                                              19

<210> SEQ ID NO 204
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 204
ucgguuggaa uucuuuuug                                              19

<210> SEQ ID NO 205
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 205
aaacaagcug gucgguugg                                              19

<210> SEQ ID NO 206
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 206
ucacaaacaa gcuggucgg                                              19

<210> SEQ ID NO 207
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 207
uucacaaaca agcuggucg                                              19

<210> SEQ ID NO 208
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 208
uuucacaaac aagcugguc                                              19

<210> SEQ ID NO 209
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 209
uuuuguuuca caaacaagc                                              19

<210> SEQ ID NO 210
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 210
uuuuuguuuc acaaacaag                                              19
```

<210> SEQ ID NO 211
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 211
uuuuuuguuu cacaaacaa                                              19

<210> SEQ ID NO 212
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 212 acuuuuugu uucacaaac                                               19

<210> SEQ ID NO 213
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 213
acacuuuuuu guuucacaa                                              19

<210> SEQ ID NO 214
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 214
ggaacacuuu uuuguuuca                                              19

<210> SEQ ID NO 215
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 215
aaaagggaac acuuuuuug                                              19

<210> SEQ ID NO 216
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

Synthetic oligonucleotide"

<400> SEQUENCE: 216
ugaaaaggga acacuuuuu                    19

<210> SEQ ID NO 217
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 217
uugaaaaggg aacacuuuu                    19

<210> SEQ ID NO 218
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 218
ucucaacuug aaaagggaa                    19

<210> SEQ ID NO 219
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 219
uguucucaac uugaaaagg                    19

<210> SEQ ID NO 220
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 220
uuuuguucuc aacuugaaa                    19

<210> SEQ ID NO 221
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 221
uuuuuguucu caacuugaa                    19

<210> SEQ ID NO 222
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 222
aauuuuuguu cucaacuug                                              19

<210> SEQ ID NO 223
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 223
ccaauuuuug uucucaacu                                              19

<210> SEQ ID NO 224
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 224
cccaauuuuu guucucaac                                              19

<210> SEQ ID NO 225
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 225
aacccaauuu uuguucuca                                              19

<210> SEQ ID NO 226
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 226
aaacccaauu uuuguucuc                                              19

<210> SEQ ID NO 227
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 227
```
uaaaacccaa uuuuuguuc                                            19

<210> SEQ ID NO 228
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 228
uuaaaaccca auuuuuguu                                            19

<210> SEQ ID NO 229
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 229
uuuaaaaccc aauuuuugu                                            19

<210> SEQ ID NO 230
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 230
uuuuaaaacc caauuuuug                                            19

<210> SEQ ID NO 231
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 231
uuuaauuuua aaacccaau                                            19

<210> SEQ ID NO 232
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 232
cuuuaauuuu aaaacccaa                                            19

<210> SEQ ID NO 233
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 233
acuuuaauuu uaaaaccca                                                   19

<210> SEQ ID NO 234
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 234
uguauacuuu aauuuaaa                                                    19

<210> SEQ ID NO 235
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 235
auguauacuu uaauuuaa                                                    19

<210> SEQ ID NO 236
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 236
uucaagacac uaaauacaa                                                   19

<210> SEQ ID NO 237
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 237
auucaagaca cuaaauaca                                                   19

<210> SEQ ID NO 238
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 238
ucuuacauuc aagacacua                                                   19

<210> SEQ ID NO 239

<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 239
ucauguucuu acauucaag         19

<210> SEQ ID NO 240
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 240
gucauguucu uacauucaa         19

<210> SEQ ID NO 241
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 241
aucuguggaa aaacuaag          19

<210> SEQ ID NO 242
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 242
aaaucacaag caucugugg         19

<210> SEQ ID NO 243
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 243
aaaaaucaca agcaucugu         19

<210> SEQ ID NO 244
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 244

-continued cauucaaaca gaaauucag                                          19

<210> SEQ ID NO 245
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 245
gaaauaacca gcuaugguu                                          19

<210> SEQ ID NO 246
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 246
gagaaauaac cagcuaugg                                          19

<210> SEQ ID NO 247
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 247
uucuggguac uacagcagat t                                       21

<210> SEQ ID NO 248
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 248
guacuacagc agaaggguat t                                       21

<210> SEQ ID NO 249
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA -continued Molecule: Synthetic oligonucleotide"

<400> SEQUENCE: 249
gugaccgggu guacauacat t                                         21

<210> SEQ ID NO 250
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 250
cucgucaucc acaaugagat t                                         21

<210> SEQ ID NO 251
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 251
ccacaaugag aguaccugut t                                         21

<210> SEQ ID NO 252
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 252
cacaaugaga guaccugugt t                                         21

<210> SEQ ID NO 253
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 253
cugugagcag cuggcaaagt t                                         21

```
<210> SEQ ID NO 254
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 254
cuguggauga aaaggcccut t                                              21

<210> SEQ ID NO 255
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 255
uggucgggau gcuggccaat t                                              21

<210> SEQ ID NO 256
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 256
ucgggaugcu ggccaacuut t                                              21

<210> SEQ ID NO 257
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 257
ggaugcuggc caacuucuut t                                              21

<210> SEQ ID NO 258
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 258
uggccaacuu cuugggcuut t                                              21

<210> SEQ ID NO 259
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 259
cuucuugggc uuccguauat t                                              21

<210> SEQ ID NO 260
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 260
cuugggcuuc cguauauaut t                                              21

<210> SEQ ID NO 261
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 261
gcuuccguau auauggcaut t                                              21

<210> SEQ ID NO 262
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 262
guauauaugg caugcacagt t                                              21

<210> SEQ ID NO 263
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 263
ggcaugcaca gugagcuaut t                                              21

<210> SEQ ID NO 264
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 264 cuaugggcg ugguccaugt t                                               21

<210> SEQ ID NO 265
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 265
cuccccaacg gcugucuuut t                                              21

<210> SEQ ID NO 266
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 266
uccccaacgg cugucuuugt t                                              21

<210> SEQ ID NO 267
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 267
cuuggaagga caagaacugt t                                              21

<210> SEQ ID NO 268
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 268
ccacgcucuc uggacuucat t                                              21

<210> SEQ ID NO 269
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 269
gcugcugaga agauugacat t                                              21

<210> SEQ ID NO 270
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 270
cugcugagaa gauugacagt t                                              21

<210> SEQ ID NO 271
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

```
<223> OTHER INFORMATION: /note="Description of Combined DNA/RNA
      Molecule: Synthetic oligonucleotide"

<400> SEQUENCE: 271
ugcugagaag auugacaggt t                                              21

<210> SEQ ID NO 272
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 272
gcugagaaga uugacagguu t                                              21

<210> SEQ ID NO 273
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 273
cugagaagau ugacagguut t                                              21

<210> SEQ ID NO 274
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 274
uugacagguu caugcaggct t                                              21

<210> SEQ ID NO 275
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 275
gcugugacag gauggaagat t                                              21
```

<210> SEQ ID NO 276
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 276
gaguucuggg uggacaacat t                                              21

<210> SEQ ID NO 277
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 277
cuggguggac aacagcacct t                                              21

<210> SEQ ID NO 278
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 278
uggacaacag caccucagut t                                              21

<210> SEQ ID NO 279
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 279
caacagcacc ucagugucut t                                              21

<210> SEQ ID NO 280
<211> LENGTH: 21
<212> TYPE: DNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 280
uggacaaggu ggagggucut t                                              21

<210> SEQ ID NO 281
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 281
caagguggag ggucucacut t                                              21

<210> SEQ ID NO 282
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 282
agguggaggg ucucacuuut t                                              21

<210> SEQ ID NO 283
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 283
cuuuccagca aaacucccut t                                              21

<210> SEQ ID NO 284
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 284
ccagcaaaac ucccucaact t                                              21

<210> SEQ ID NO 285
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 285
cagcaaaacu cccucaacut t                                              21

<210> SEQ ID NO 286
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 286
caaaacuccc ucaacuggat t                                              21

<210> SEQ ID NO 287
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 287
ucccucaacu ggaugaagat t                                              21

<210> SEQ ID NO 288
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 288
cccucaacug gaugaagaat t                                              21

<210> SEQ ID NO 289
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 289
ucaacuggau gaagaaacut t                                          21

<210> SEQ ID NO 290
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 290
ccgagcugaa ccugcaaaat t                                          21

<210> SEQ ID NO 291
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 291
cgagcugaac cugcaaaaat t                                          21

<210> SEQ ID NO 292
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 292
gaaccugcaa aaauugagct t                                          21

<210> SEQ ID NO 293
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 293
accugcaaaa auugagcaat t                                              21

<210> SEQ ID NO 294
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 294
ccugcaaaaa uugagcaaut t                                              21

<210> SEQ ID NO 295
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 295
cugcaaaaau ugagcaaugt t                                              21

<210> SEQ ID NO 296
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 296
ugcaaaaauu gagcaaugat t                                              21

<210> SEQ ID NO 297
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 297
gcaaaaauug agcaaugact t                                              21
```

<210> SEQ ID NO 298
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 298
ggguggggga ggugcugaat t                                              21

<210> SEQ ID NO 299
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 299
ggaugagaga gagcccacat t                                              21

<210> SEQ ID NO 300
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 300
ccgcccauuc cuguuugcut t                                              21

<210> SEQ ID NO 301
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 301
auuccuguuu gcuguguaut t                                              21

<210> SEQ ID NO 302
<211> LENGTH: 21
<212> TYPE: DNA
<213> ORGANISM: Artificial Sequence
<220> FEATURE:

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 302
uccuguuugc uguguaugat t                                              21

<210> SEQ ID NO 303
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 303
guuugcugug uaugaucaat t                                              21

<210> SEQ ID NO 304
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 304
uuugcugugu augaucaaat t                                              21

<210> SEQ ID NO 305
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 305
cccccagucu cccaccuuut t                                              21

<210> SEQ ID NO 306
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

```
<400> SEQUENCE: 306
cccaccuuuu cuucuaaugt t                                        21

<210> SEQ ID NO 307
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 307
ccaccuuuuc uucuaaugat t                                        21

<210> SEQ ID NO 308
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 308
caccuuuucu ucuaaugagt t                                        21

<210> SEQ ID NO 309
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 309
guuucuccuu ggucuaagut t                                        21

<210> SEQ ID NO 310
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 310 uugcugggmuu uauuuagat t                                        21

<210> SEQ ID NO 311
```

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 311
ugcuggguuu auuuuagagt t                                              21

<210> SEQ ID NO 312
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 312
gcuggguuua uuuuagagat t                                              21

<210> SEQ ID NO 313
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 313
cuggguuuau uuuagagaat t                                              21

<210> SEQ ID NO 314
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 314
uggguuuauu uuagagaaut t                                              21

<210> SEQ ID NO 315
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 315
guuuauuuua gagaaugggt t                                              21

<210> SEQ ID NO 316
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 316
uauuuuagag aauggggut t                                               21

<210> SEQ ID NO 317
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 317
uggggaggca agaaccagut t                                              21

<210> SEQ ID NO 318
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 318
ggaggcaaga accaguguut t                                              21

<210> SEQ ID NO 319
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 319
```

```
uccaaaaaga auuccaacct t                                              21
```

<210> SEQ ID NO 320
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 320

```
caaaagaau uccaaccgat t                                               21
```

<210> SEQ ID NO 321
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 321

```
ccaaccgacc agcuuguuut t                                              21
```

<210> SEQ ID NO 322
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 322

```
ccgaccagcu uguuugugat t                                              21
```

<210> SEQ ID NO 323
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 323

```
cgaccagcuu guuugugaat t                                              21
```

<210> SEQ ID NO 324
<211> LENGTH: 21
<212> TYPE: DNA
<213> ORGANISM: Artificial Sequence -continued
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 324
gaccagcuug uuugugaaat t                                            21

<210> SEQ ID NO 325
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 325
gcuuguuugu gaaacaaaat t                                            21

<210> SEQ ID NO 326
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 326
cuuguuugug aaacaaaaat t                                            21

<210> SEQ ID NO 327
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 327
uuguuuguga aacaaaaaat t                                            21

<210> SEQ ID NO 328
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA

```
      Molecule: Synthetic oligonucleotide"

<400> SEQUENCE: 328
guuugugaaa caaaaaagut t                                    21

<210> SEQ ID NO 329
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 329
uugugaaaca aaaagugut t                                     21

<210> SEQ ID NO 330
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 330
ugaaacaaaa aguguucct t                                     21

<210> SEQ ID NO 331
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 331
caaaaaagug uucccuuuut t                                    21

<210> SEQ ID NO 332
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 332
aaaaaguguu cccuuuucat t                                    21
```

```
<210> SEQ ID NO 333
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 333
aaaaguguuc ccuuuucaat t                                          21

<210> SEQ ID NO 334
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 334
uucccuuuuc aaguugagat t                                          21

<210> SEQ ID NO 335
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 335
ccuuuucaag uugagaacat t                                          21

<210> SEQ ID NO 336
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 336
uuucaaguug agaacaaaat t                                          21

<210> SEQ ID NO 337
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 337
uucaaguuga gaacaaaaat t                                              21

<210> SEQ ID NO 338
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 338
caaguugaga acaaaaauut t                                              21

<210> SEQ ID NO 339
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 339
aguugagaac aaaaauuggt t                                              21

<210> SEQ ID NO 340
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 340
guugagaaca aaaauugggt t                                              21

<210> SEQ ID NO 341
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
    Synthetic oligonucleotide"
<220> FEATURE:
<221> NAME/KEY: source
<223> OTHER INFORMATION: /note="Description of Combined DNA/RNA
    Molecule: Synthetic oligonucleotide"

<400> SEQUENCE: 341
ugagaacaaa aauugggguut t                                    21

<210> SEQ ID NO 342
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 342
gagaacaaaa auuggguuut t                                     21

<210> SEQ ID NO 343
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 343
gaacaaaaau uggguuuuat t                                     21

<210> SEQ ID NO 344
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 344
aacaaaaauu ggguuuuaat t                                     21

<210> SEQ ID NO 345
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 345
acaaaaauug gguuuuaaat t                                     21

<210> SEQ ID NO 346
<211> LENGTH: 21
<212> TYPE: DNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 346
caaaaauugg guuuuaaaat t                                              21

<210> SEQ ID NO 347
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 347
auuggguuuu aaaauuaaat t                                              21

<210> SEQ ID NO 348
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 348
uuggguuuua aaauuaaagt t                                              21

<210> SEQ ID NO 349
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 349
uggguuuuaa aauuaaagut t                                              21

<210> SEQ ID NO 350
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
```

<223> OTHER INFORMATION: /note="Description of Combined DNA/RNA
      Molecule: Synthetic oligonucleotide"

<400> SEQUENCE: 350
uuuaaaauua aaguauacat t                                              21

<210> SEQ ID NO 351
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 351
uuaaaauuaa aguauacaut t                                              21

<210> SEQ ID NO 352
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 352
uuguauuuag ugucuugaat t                                              21

<210> SEQ ID NO 353
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 353
uguauuuagu gucuugaaut t                                              21

<210> SEQ ID NO 354
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 354
uagugucuug aauguaagat t                                              21

-continued

```
<210> SEQ ID NO 355
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 355
cuugaaugua agaacaugat t                                              21

<210> SEQ ID NO 356
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 356
uugaauguaa gaacaugact t                                              21

<210> SEQ ID NO 357
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 357
cuuaguuuuu uccacagaut t                                              21

<210> SEQ ID NO 358
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 358
ccacagaugc uugugauuut t                                              21

<210> SEQ ID NO 359
<211> LENGTH: 21
<212> TYPE: DNA
<213> ORGANISM: Artificial Sequence
<220> FEATURE:
<221> NAME/KEY: source
```

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 359
acagaugcuu gugauuuuut t                                              21

<210> SEQ ID NO 360
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 360
cugaauuucu guuugaaugt t                                              21

<210> SEQ ID NO 361
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 361
aaccauagcu gguuauuuct t                                              21

<210> SEQ ID NO 362
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 362
ccauagcugg uuauuucuct t                                              21

<210> SEQ ID NO 363
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

-continued

<400> SEQUENCE: 363
ucugcuguag uacccagaat t                                              21

<210> SEQ ID NO 364
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 364
uacccuucug cuguaguact t                                              21

<210> SEQ ID NO 365
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 365
uguauguaca cccggucact t                                              21

<210> SEQ ID NO 366
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 366
ucucauugug gaugacgagt t                                              21

<210> SEQ ID NO 367
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 367
acagguacuc ucauuguggt t                                              21

<210> SEQ ID NO 368
<211> LENGTH: 21

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 368
cacagguacu cucauugugt t                                              21

<210> SEQ ID NO 369
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 369
cuuugccagc ugcucacagt t                                              21

<210> SEQ ID NO 370
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 370
agggccuuuu cauccacagt t                                              21

<210> SEQ ID NO 371
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 371
uuggccagca ucccgaccat t                                              21

<210> SEQ ID NO 372
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

<221> NAME/KEY: source
<223> OTHER INFORMATION: /note="Description of Combined DNA/RNA
      Molecule: Synthetic oligonucleotide"

<400> SEQUENCE: 372
aaguuggcca gcaucccgat t                                            21

<210> SEQ ID NO 373
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 373
aagaaguugg ccagcaucct t                                            21

<210> SEQ ID NO 374
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 374
aagcccaaga aguuggccat t                                            21

<210> SEQ ID NO 375
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 375
uauacggaag cccaagaagt t                                            21

<210> SEQ ID NO 376
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 376
auauauacgg aagcccaagt t                                            21

```
<210> SEQ ID NO 377
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 377
augccauaua uacggaagct t                                               21

<210> SEQ ID NO 378
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 378
cugugcaugc cauauauact t                                               21

<210> SEQ ID NO 379
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 379
auagcucacu gugcaugcct t                                               21

<210> SEQ ID NO 380
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 380
cauggaccac gccccauagt t                                               21

<210> SEQ ID NO 381
<211> LENGTH: 21
<212> TYPE: DNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 381
aaagacagcc guugggagt t                                              21

<210> SEQ ID NO 382
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 382
caaagacagc cguuggggat t                                             21

<210> SEQ ID NO 383
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 383
caguucuugu ccuuccaagt t                                             21

<210> SEQ ID NO 384
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 384
ugaaguccag agagcguggt t                                             21

<210> SEQ ID NO 385
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

<400> SEQUENCE: 385
ugucaaucuu cucagcagct t                                              21

<210> SEQ ID NO 386
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 386
cugucaaucu ucucagcagt t                                              21

<210> SEQ ID NO 387
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 387
ccugucaauc uucucagcat t                                              21

<210> SEQ ID NO 388
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 388
accugucaau cuucucagct t                                              21

<210> SEQ ID NO 389
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 389
aaccugucaa ucuucucagt t                                              21

<210> SEQ ID NO 390

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 390
gccugcauga accugucaat t                                             21

<210> SEQ ID NO 391
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 391
ucuuccaucc ugucacagct t                                             21

<210> SEQ ID NO 392
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 392
uguuguccac ccagaacuct t                                             21

<210> SEQ ID NO 393
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 393
ggugcuguug uccacccagt t                                             21

<210> SEQ ID NO 394
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<220> FEATURE:
<221> NAME/KEY: source
<223> OTHER INFORMATION: /note="Description of Combined DNA/RNA
      Molecule: Synthetic oligonucleotide"

<400> SEQUENCE: 394
acugaggugc uguuguccat t                                              21

<210> SEQ ID NO 395
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 395
agacacugag gugcuguugt t                                              21

<210> SEQ ID NO 396
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 396
agacccucca ccuuguccat t                                              21

<210> SEQ ID NO 397
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 397
agugagaccc uccaccuugt t                                              21

<210> SEQ ID NO 398
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 398
aaagugagac ccuccaccut t                                              21

<210> SEQ ID NO 399
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 399
agggaguuuu gcuggaaagt t                                              21

<210> SEQ ID NO 400
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 400
guugagggag uuuugcuggt t                                              21

<210> SEQ ID NO 401
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 401
aguugaggga guuuugcugt t                                              21

<210> SEQ ID NO 402
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 402
uccaguugag ggaguuuugt t                                              21

<210> SEQ ID NO 403
<211> LENGTH: 21
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 403
ucuucaucca guugagggat t                                              21

<210> SEQ ID NO 404
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 404
uucuucaucc aguugagggt t                                              21

<210> SEQ ID NO 405
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 405
aguuucuuca uccaguugat t                                              21

<210> SEQ ID NO 406
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 406
uuuugcaggu ucagcucggt t                                              21

<210> SEQ ID NO 407
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
```

-continued

Molecule: Synthetic oligonucleotide"

<400> SEQUENCE: 407
uuuuugcagg uucagcucgt t                                              21

<210> SEQ ID NO 408
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 408
gcucaauuuu ugcagguuct t                                              21

<210> SEQ ID NO 409
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 409
uugcucaauu uuugcaggut t                                              21

<210> SEQ ID NO 410
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 410
auugcucaau uuuugcaggt t                                              21

<210> SEQ ID NO 411
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 411
cauugcucaa uuuuugcagt t                                              21

```
<210> SEQ ID NO 412
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 412
ucauugcuca auuuuugcat t                                              21

<210> SEQ ID NO 413
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 413
gucauugcuc aauuuuugct t                                              21

<210> SEQ ID NO 414
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 414
uucagcaccu cccccaccct t                                              21

<210> SEQ ID NO 415
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 415
ugugggcucu cucucaucct t                                              21

<210> SEQ ID NO 416
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
```

-continued

```
         Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 416
agcaaacagg aaugggcggt t                                            21

<210> SEQ ID NO 417
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 417
auacacagca aacaggaaut t                                            21

<210> SEQ ID NO 418
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 418
ucauacacag caaacaggat t                                            21

<210> SEQ ID NO 419
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 419
uugaucauac acagcaaact t                                            21

<210> SEQ ID NO 420
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 420
```
uuugaucaua cacagcaaat t                                              21

<210> SEQ ID NO 421
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 421
aaagguggga gacuggggt t                                               21

<210> SEQ ID NO 422
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 422
cauuagaaga aaaggugggt t                                              21

<210> SEQ ID NO 423
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 423
ucauuagaag aaaagguggt t                                              21

<210> SEQ ID NO 424
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 424
cucauuagaa gaaaaggugt t                                              21

<210> SEQ ID NO 425
<211> LENGTH: 21
<212> TYPE: DNA

<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 425
acuuagacca aggagaaact t                                              21

<210> SEQ ID NO 426
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 426
ucuaaaauaa acccagcaat t                                              21

<210> SEQ ID NO 427
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 427
cucuaaaaua aacccagcat t                                              21

<210> SEQ ID NO 428
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 428
ucucuaaaau aaacccagct t                                              21

<210> SEQ ID NO 429
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source

```
<223> OTHER INFORMATION: /note="Description of Combined DNA/RNA
      Molecule: Synthetic oligonucleotide"

<400> SEQUENCE: 429
uucucuaaaa uaaacccagt t                                              21

<210> SEQ ID NO 430
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 430
auucucuaaa auaaacccat t                                              21

<210> SEQ ID NO 431
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 431
cccauucucu aaauaaact t                                               21

<210> SEQ ID NO 432
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 432 accccccauuc ucuaaaauat t                                             21

<210> SEQ ID NO 433
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 433
acugguucuu gccuccccat t                                              21
```

```
<210> SEQ ID NO 434
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 434
aacacugguu cuugccucct t                                         21

<210> SEQ ID NO 435
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 435
gguuggaauu cuuuuuggat t                                         21

<210> SEQ ID NO 436
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 436
ucgguuggaa uucuuuuugt t                                         21

<210> SEQ ID NO 437
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 437
aaacaagcug gucgguuggt t                                         21

<210> SEQ ID NO 438
<211> LENGTH: 21
<212> TYPE: DNA
<213> ORGANISM: Artificial Sequence
<220> FEATURE:
<221> NAME/KEY: source
```

-continued

```
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 438
ucacaaacaa gcuggucggt t                                                 21

<210> SEQ ID NO 439
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 439
uucacaaaca agcuggucgt t                                                 21

<210> SEQ ID NO 440
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 440
uuucacaaac aagcugguct t                                                 21

<210> SEQ ID NO 441
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 441
uuuuguuuca caaacaagct t                                                 21

<210> SEQ ID NO 442
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"
```

```
<400> SEQUENCE: 442
uuuuuguuuc acaaacaagt t                                              21

<210> SEQ ID NO 443
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 443
uuuuuuguuu cacaaacaat t                                              21

<210> SEQ ID NO 444
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 444 acuuuuugu uucacaaact t                                               21

<210> SEQ ID NO 445
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 445
acacuuuuuu guuucacaat t                                              21

<210> SEQ ID NO 446
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 446
ggaacacuuu uuuguuucat t                                              21

<210> SEQ ID NO 447
<211> LENGTH: 21
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 447
aaaagggaac acuuuuugt t                                              21

<210> SEQ ID NO 448
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 448
ugaaagggga acacuuuuut t                                             21

<210> SEQ ID NO 449
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 449 uugaaaggg aacacuuuut t                                              21

<210> SEQ ID NO 450
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 450
ucucaacuug aaagggaat t                                              21

<210> SEQ ID NO 451
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
```

```
<221> NAME/KEY: source
<223> OTHER INFORMATION: /note="Description of Combined DNA/RNA
      Molecule: Synthetic oligonucleotide"

<400> SEQUENCE: 451
uguucucaac uugaaaaggt t                                            21

<210> SEQ ID NO 452
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 452
uuuuguucuc aacuugaaat t                                            21

<210> SEQ ID NO 453
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 453
uuuuuguucu caacuugaat t                                            21

<210> SEQ ID NO 454
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 454
aauuuuuguu cucaacuugt t                                            21

<210> SEQ ID NO 455
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 455
ccaauuuuug uucucaacut t                                            21
```

```
<210> SEQ ID NO 456
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 456
cccaauuuuu guucucaact t                                           21

<210> SEQ ID NO 457
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 457
aacccaauuu uuguucucat t                                           21

<210> SEQ ID NO 458
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 458
aaacccaauu uuuguucuct t                                           21

<210> SEQ ID NO 459
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 459
uaaaacccaa uuuuuguuct t                                           21

<210> SEQ ID NO 460
<211> LENGTH: 21
<212> TYPE: DNA
<213> ORGANISM: Artificial Sequence
<220> FEATURE:
```

<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 460
uuaaaaccca auuuuuguut t                                              21

<210> SEQ ID NO 461
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 461
uuuaaaaccc aauuuuugut t                                              21

<210> SEQ ID NO 462
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 462
uuuuaaaacc caauuuuugt t                                              21

<210> SEQ ID NO 463
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 463
uuuaauuuua aaacccaaut t                                              21

<210> SEQ ID NO 464
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

-continued

<400> SEQUENCE: 464
cuuuaauuuu aaaacccaat t                                              21

<210> SEQ ID NO 465
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 465
acuuuaauuu uaaaacccat t                                              21

<210> SEQ ID NO 466
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 466
uguauacuuu aauuuuaaat t                                              21

<210> SEQ ID NO 467
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 467
auguauacuu uaauuuuaat t                                              21

<210> SEQ ID NO 468
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 468
uucaagacac uaaauacaat t                                              21

<210> SEQ ID NO 469

```
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 469
auucaagaca cuaaauacat t                                              21

<210> SEQ ID NO 470
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 470
ucuuacauuc aagacacuat t                                              21

<210> SEQ ID NO 471
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 471
ucauguucuu acauucaagt t                                              21

<210> SEQ ID NO 472
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 472
gucauguucu uacauucaat t                                              21

<210> SEQ ID NO 473
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<220> FEATURE:
<221> NAME/KEY: source
<223> OTHER INFORMATION: /note="Description of Combined DNA/RNA
      Molecule: Synthetic oligonucleotide"

<400> SEQUENCE: 473
aucuguggaa aaacuaagt t                                               21

<210> SEQ ID NO 474
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 474
aaaucacaag caucuguggt t                                              21

<210> SEQ ID NO 475
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 475
aaaaaucaca agcaucugut t                                              21

<210> SEQ ID NO 476
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 476
cauucaaaca gaaauucagt t                                              21

<210> SEQ ID NO 477
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 477
```
gaaauaacca gcuaugguut t                                              21

<210> SEQ ID NO 478
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 478
gagaaauaac cagcuauggt t                                              21

<210> SEQ ID NO 479
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 479
cgggaugcug gccaacuucu u                                              21

<210> SEQ ID NO 480
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 480
aacuucuugg gcuuccguau a                                              21

<210> SEQ ID NO 481
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 481
uuccguauau auggcaugca a                                              21

<210> SEQ ID NO 482
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 482
ccguauauau ggcaugcaca a                                              21

<210> SEQ ID NO 483
<211> LENGTH: 21

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 483
agcuaugggg cgugguccau a                                          21

<210> SEQ ID NO 484
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 484 cucucccaa cggcugucuu u                                           21

<210> SEQ ID NO 485
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 485
ucuccccaac ggcugucuuu a                                          21

<210> SEQ ID NO 486
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 486
ugcaggcugu gacaggaugg a                                          21

<210> SEQ ID NO 487
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 487
ccuggacaag guggaggguc u                                          21

<210> SEQ ID NO 488
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 488
```
gacaaggugg agggucucac u            21

<210> SEQ ID NO 489
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 489
caagguggag ggucucacuu u            21

<210> SEQ ID NO 490
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 490
uccagcaaaa cucccucaac u            21

<210> SEQ ID NO 491
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 491
acucccucaa cuggaugaag a            21

<210> SEQ ID NO 492
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 492
cugaaccugc aaaaauugag a            21

<210> SEQ ID NO 493
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 493
gaaccugcaa aaauugagca a            21

<210> SEQ ID NO 494
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 494
accugcaaaa auugagcaau a                                              21

<210> SEQ ID NO 495
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 495
ccugcaaaaa uugagcaaug a                                              21

<210> SEQ ID NO 496
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 496
gcggaugaga gagagcccac a                                              21

<210> SEQ ID NO 497
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 497
uguuugcugu guaugaucaa a                                              21

<210> SEQ ID NO 498
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 498 caccccccagu cucccaccuu u                                             21

<210> SEQ ID NO 499
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 499
ucucccaccu uuucuucuaa u                                              21

<210> SEQ ID NO 500
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 500
cccaccuuuu cuucuaauga a                                              21

<210> SEQ ID NO 501
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 501
uccaaaaaga auuccaaccg a                                              21

<210> SEQ ID NO 502
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 502
uuccaaccga ccagcuuguu u                                              21

<210> SEQ ID NO 503
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 503
accgaccagc uuguuuguga a                                              21

<210> SEQ ID NO 504
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 504
ccagcuuguu ugugaaacaa a                                              21

<210> SEQ ID NO 505
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 505
```
cagcuuguuu gugaaacaaa a                                              21

<210> SEQ ID NO 506
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 506
aaaaaagugu ucccuuuuca a                                              21

<210> SEQ ID NO 507
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 507
uguucccuuu ucaaguugag a                                              21

<210> SEQ ID NO 508
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 508
aaguugagaa caaaaauugg a                                              21

<210> SEQ ID NO 509
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 509
aguugagaac aaaaauuggg u                                              21

<210> SEQ ID NO 510
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 510
agaacaaaaa uuggguuuua a                                              21

<210> SEQ ID NO 511
<211> LENGTH: 21
<212> TYPE: RNA
<213> ORGANISM: Artificial Sequence
<220> FEATURE:

<211> NAME/KEY: source
<223> OTHER INFORMATION: /note="Description of Artificial Sequence:
      Synthetic oligonucleotide"

<400> SEQUENCE: 511
gaacaaaaau uggguuuuaa a                                              21

<210> SEQ ID NO 512
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 512
guuuguauuu agugcuuga a                                               21

<210> SEQ ID NO 513
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 513
uuuguauuua gugcuugaa u                                               21

<210> SEQ ID NO 514
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 514
gucuugaaug uaagaacaug a                                              21

<210> SEQ ID NO 515
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 515
ucuugaaugu aagaacauga a                                              21

<210> SEQ ID NO 516
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 516
uuccacagau gcuugugauu u                                              21

```
<210> SEQ ID NO 517
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 517
aagaaguugg ccagcauccc gac                                              23

<210> SEQ ID NO 518
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 518
uauacggaag cccaagaagu ugg                                              23

<210> SEQ ID NO 519
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 519
uugcaugcca uauauacgga agc                                              23

<210> SEQ ID NO 520
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 520
uugugcaugc cauauauacg gaa                                              23

<210> SEQ ID NO 521
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 521
uauggaccac gccccauagc uca                                              23

<210> SEQ ID NO 522
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 522
aaagacagcc guuggggaga gga                                              23

<210> SEQ ID NO 523
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 523
uaaagacagc cguuggggag agg                                              23

<210> SEQ ID NO 524
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 524
uccauccugu cacagccugc aug                                              23

<210> SEQ ID NO 525
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 525
agacccucca ccuuguccag guc                                              23

<210> SEQ ID NO 526
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 526
agugagaccc uccaccuugu cca                                              23

<210> SEQ ID NO 527
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 527
aaagugagac ccuccaccuu guc                                              23

<210> SEQ ID NO 528
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 528
aguugaggga guuuugcugg aaa                                              23

<210> SEQ ID NO 529
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 529
ucuucaucca guugagggag uuu                                              23

<210> SEQ ID NO 530
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 530
ucucaauuuu ugcagguuca gcu                                              23

<210> SEQ ID NO 531
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 531
uugcucaauu uuugcagguu cag                                              23

<210> SEQ ID NO 532
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 532
uauugcucaa uuuugcagg uuc                                               23

<210> SEQ ID NO 533
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 533
ucauugcuca auuuugcag guu                                               23
```

<210> SEQ ID NO 534
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 534
ugugggcucu cucucauccg cuu                                          23

<210> SEQ ID NO 535
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 535
uuugaucaua cacagcaaac agg                                          23

<210> SEQ ID NO 536
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 536
aaagguggga gacuggggu gac                                           23

<210> SEQ ID NO 537
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 537
auuagaagaa aagguggag acu                                           23

<210> SEQ ID NO 538
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 538
uucauuagaa gaaaaggugg gag                                          23

<210> SEQ ID NO 539
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 539
ucgguuggaa uucuuuuugg aac                                              23

<210> SEQ ID NO 540
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 540
aaacaagcug gucgguugga auu                                              23

<210> SEQ ID NO 541
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 541
uucacaaaca agcuggucgg uug                                              23

<210> SEQ ID NO 542
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 542
uuuguuucac aaacaagcug guc                                              23

<210> SEQ ID NO 543
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 543
uuuuguuuca caaacaagcu ggu                                              23

<210> SEQ ID NO 544
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 544
uugaaaaggg aacacuuuuu ugu                                              23

<210> SEQ ID NO 545
<211> LENGTH: 23
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 545
ucucaacuug aaagggaac acu                                            23

<210> SEQ ID NO 546
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 546
uccaauuuuu guucucaacu uga                                           23

<210> SEQ ID NO 547
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 547
acccaauuuu uguucucaac uug                                           23

<210> SEQ ID NO 548
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 548
uuaaaaccca auuuuuguuc uca                                           23

<210> SEQ ID NO 549
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 549
uuuaaaaccc aauuuuuguu cuc                                           23

<210> SEQ ID NO 550
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 550
uucaagacac uaaauacaaa ccg                                           23
```

```
<210> SEQ ID NO 551
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 551
auucaagaca cuaaauacaa acc                                              23

<210> SEQ ID NO 552
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 552
ucauguucuu acauucaaga cac                                              23

<210> SEQ ID NO 553
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 553
uucauguucu uacauucaag aca                                              23

<210> SEQ ID NO 554
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 554
aaaucacaag caucugugga aaa                                              23

<210> SEQ ID NO 555
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 555
cagcuuguuu gugaaacaaa a                                                21

<210> SEQ ID NO 556
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
```

```
                          Synthetic oligonucleotide"

<400> SEQUENCE: 556
agaacaaaaa uuggguuuua a                                              21

<210> SEQ ID NO 557
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 557
uccagcaaaa cucccucaac u                                              21

<210> SEQ ID NO 558
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 558
acucccucaa cuggaugaag a                                              21

<210> SEQ ID NO 559
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 559
gucuugaaug uaagaacaug a                                              21

<210> SEQ ID NO 560
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 560
aacuucuugg gcuuccguau a                                              21

<210> SEQ ID NO 561
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 561
aaaaaagugu ucccuuuuca a                                              21

<210> SEQ ID NO 562
<211> LENGTH: 21
```

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 562
cccaccuuuu cuucuaauga a                                              21

<210> SEQ ID NO 563
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 563
gacaaggugg agggucucac u                                              21

<210> SEQ ID NO 564
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 564
uuccguauau auggcaugca a                                              21

<210> SEQ ID NO 565
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 565
gaacaaaaau uggguuuuaa a                                              21

<210> SEQ ID NO 566
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 566
uguuugcugu guaugaucaa a                                              21

<210> SEQ ID NO 567
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 567
```
cugaaccugc aaaaauugag a                                        21

<210> SEQ ID NO 568
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 568
uuccaaccga ccagcuuguu u                                        21

<210> SEQ ID NO 569
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 569
ucucccaccu uuucuucuaa u                                        21

<210> SEQ ID NO 570
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 570
accugcaaaa auugagcaau a                                        21

<210> SEQ ID NO 571
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 571
guuuguauuu agugucuuga a                                        21

<210> SEQ ID NO 572
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 572
cucuccccaa cggcugucuu u                                        21

<210> SEQ ID NO 573
<211> LENGTH: 21
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 573
accgaccagc uuguuuguga a                                              21

<210> SEQ ID NO 574
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 574
ccagcuuguu ugugaaacaa a                                              21

<210> SEQ ID NO 575
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 575
uuuguauuua gugucuugaa u                                              21

<210> SEQ ID NO 576
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 576
aguugagaac aaaaauuggg u                                              21

<210> SEQ ID NO 577
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 577
caagguggag ggucucacuu u                                              21

<210> SEQ ID NO 578
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 578 caccccagu cucccaccuu u                                               21

<210> SEQ ID NO 579
```

```
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 579
ugcaggcugu gacaggaugg a                                             21

<210> SEQ ID NO 580
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 580
uccaaaaaga auuccaaccg a                                             21

<210> SEQ ID NO 581
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 581
ccuggacaag guggaggguc u                                             21

<210> SEQ ID NO 582
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 582
ccguauauau ggcaugcaca a                                             21

<210> SEQ ID NO 583
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 583
uguucccuuu ucaaguugag a                                             21

<210> SEQ ID NO 584
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 584
```
gcggaugaga gagagcccac a                              21

<210> SEQ ID NO 585
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 585
gaaccugcaa aaauugagca a                              21

<210> SEQ ID NO 586
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 586
aaguugagaa caaaaauugg a                              21

<210> SEQ ID NO 587
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 587
ccugcaaaaa uugagcaaug a                              21

<210> SEQ ID NO 588
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 588
cgggaugcug gccaacuucu u                              21

<210> SEQ ID NO 589
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 589
ucuugaaugu aagaacauga a                              21

<210> SEQ ID NO 590
<211> LENGTH: 21
<212> TYPE: RNA
<213> ORGANISM: Artificial Sequence
<220> FEATURE:

<221> NAME/KEY: source
<223> OTHER INFORMATION: /note="Description of Artificial Sequence:
      Synthetic oligonucleotide"

<400> SEQUENCE: 590
uuccacagau gcuugugauu u                                              21

<210> SEQ ID NO 591
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 591
agcuaugggg cgugguccau a                                              21

<210> SEQ ID NO 592
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 592
ucuccccaac ggcugucuuu a                                              21

<210> SEQ ID NO 593
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 593
uuuuguuuca caaacaagcu ggu                                            23

<210> SEQ ID NO 594
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 594
uuaaaaccca auuuuuguuc uca                                            23

<210> SEQ ID NO 595
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 595
aguugaggga guuuugcugg aaa                                            23

```
<210> SEQ ID NO 596
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 596
ucuucaucca guugagggag uuu                                              23

<210> SEQ ID NO 597
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 597
ucauguucuu acauucaaga cac                                              23

<210> SEQ ID NO 598
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 598
uauacggaag cccaagaagu ugg                                              23

<210> SEQ ID NO 599
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 599
uugaaaaggg aacacuuuuu ugu                                              23

<210> SEQ ID NO 600
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 600
uucauuagaa gaaaaggugg gag                                              23

<210> SEQ ID NO 601
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 601
agugagaccc uccaccuugu cca                                          23

<210> SEQ ID NO 602
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 602
uugcaugcca uauauacgga agc                                          23

<210> SEQ ID NO 603
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 603
uuuaaaaccc aauuuuuguu cuc                                          23

<210> SEQ ID NO 604
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 604
uuugaucaua cacagcaaac agg                                          23

<210> SEQ ID NO 605
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 605
ucucaauuuu ugcagguuca gcu                                          23

<210> SEQ ID NO 606
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 606
aaacaagcug gucgguugga auu                                          23

<210> SEQ ID NO 607
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 607
auuagaagaa aagugggag acu                                           23

<210> SEQ ID NO 608
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 608
uauugcucaa uuuuugcagg uuc                                          23

<210> SEQ ID NO 609
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 609
uucaagacac uaaauacaaa ccg                                          23

<210> SEQ ID NO 610
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 610
aaagacagcc guuggggaga gga                                          23

<210> SEQ ID NO 611
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 611
uucacaaaca agcuggucgg uug                                          23

<210> SEQ ID NO 612
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 612
uuuguuucac aaacaagcug guc                                          23
```

```
<210> SEQ ID NO 613
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 613
auucaagaca cuaaauacaa acc                                             23

<210> SEQ ID NO 614
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 614
acccaauuuu uguucucaac uug                                             23

<210> SEQ ID NO 615
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 615
aaagugagac ccuccaccuu guc                                             23

<210> SEQ ID NO 616
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 616
aaagguggga gacuggggu gac                                              23

<210> SEQ ID NO 617
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 617
uccauccugu cacagccugc aug                                             23

<210> SEQ ID NO 618
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

<400> SEQUENCE: 618
ucgguuggaa uucuuuuugg aac                                    23

<210> SEQ ID NO 619
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 619
agacccucca ccuuguccag guc                                    23

<210> SEQ ID NO 620
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 620
uugugcaugc cauauauacg gaa                                    23

<210> SEQ ID NO 621
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 621
ucucaacuug aaaagggaac acu                                    23

<210> SEQ ID NO 622
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 622
ugugggcucu cucucauccg cuu                                    23

<210> SEQ ID NO 623
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 623
uugcucaauu uuugcagguu cag                                    23

<210> SEQ ID NO 624
<211> LENGTH: 23
<212> TYPE: RNA

<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 624
uccaauuuuu guucucaacu uga                                              23

<210> SEQ ID NO 625
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 625
ucauugcuca auuuuugcag guu                                              23

<210> SEQ ID NO 626
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 626
aagaaguugg ccagcauccc gac                                              23

<210> SEQ ID NO 627
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 627
uucauguucu uacauucaag aca                                              23

<210> SEQ ID NO 628
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 628
aaaucacaag caucugugga aaa                                              23

<210> SEQ ID NO 629
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 629
uauggaccac gccccauagc uca                                              23

```
<210> SEQ ID NO 630
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 630
uaaagacagc cguuggggag agg                                           23

<210> SEQ ID NO 631
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 631
cgggcagcag ggucagaaa                                                19

<210> SEQ ID NO 632
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 632
ucagaagugg cccccgugu                                                19

<210> SEQ ID NO 633
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 633
cccguguugc cuaagcaaa                                                19

<210> SEQ ID NO 634
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 634
ugcaccuccg gccugcaua                                                19

<210> SEQ ID NO 635
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 635
ugcauguccc uguggccua                           19

<210> SEQ ID NO 636
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 636
uguggccucu uggggguaa                           19

<210> SEQ ID NO 637
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 637
ggucagaagg ccuggguga                           19

<210> SEQ ID NO 638
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 638
ugggugguug gccucagga                           19

<210> SEQ ID NO 639
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 639
ccucaggcug ucacacaca                           19

<210> SEQ ID NO 640
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 640
cacacaccua gggagauga                           19

<210> SEQ ID NO 641
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 641
agggagaugc ucccguuua                                               19

<210> SEQ ID NO 642
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 642
ccguuucugg gaaccuuga                                               19

<210> SEQ ID NO 643
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 643
aaccuuggcc ccgacuccu                                               19

<210> SEQ ID NO 644
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 644
cgacuccugc aaacuucga                                               19

<210> SEQ ID NO 645
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 645
aacuucggua aauguguaa                                               19

<210> SEQ ID NO 646
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 646
```
uguguaacuc gacccugca                                                19

<210> SEQ ID NO 647
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 647
acccugcacc ggcucacua                                                19

<210> SEQ ID NO 648
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 648
gcucacucug uucagcagu                                                19

<210> SEQ ID NO 649
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 649
uucagcagug aaacucuga                                                19

<210> SEQ ID NO 650
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 650
aaacucugca ucgaucacu                                                19

<210> SEQ ID NO 651
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 651
cgaucacuaa gacuuccua                                                19

<210> SEQ ID NO 652
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 652
gaggucccag cgugagugu                                                  19

<210> SEQ ID NO 653
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 653
uucuggcauc uguccuucu                                                  19

<210> SEQ ID NO 654
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 654
ccuucuggcc agccuguga                                                  19

<210> SEQ ID NO 655
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 655
agccuguggu cuggccaaa                                                  19

<210> SEQ ID NO 656
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 656
ggccaaguga uguaacccu                                                  19

<210> SEQ ID NO 657
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 657
uguaacccuc cucuccaga                                                  19

<210> SEQ ID NO 658

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 658
ucuccagccu gugcacaga                                                    19

<210> SEQ ID NO 659
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 659
ugcacaggca gccugggaa                                                    19

<210> SEQ ID NO 660
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 660
ccugggaaca gcuccauca                                                    19

<210> SEQ ID NO 661
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 661
uccaucccca ccccucaga                                                    19

<210> SEQ ID NO 662
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 662
cccucagcua uaaauagga                                                    19

<210> SEQ ID NO 663
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 663
```
uaaauagggc aucgugaca                                              19

<210> SEQ ID NO 664
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 664
aucgugaccc ggccgggga                                              19

<210> SEQ ID NO 665
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 665 ccggggaag aagcugcca                                               19

<210> SEQ ID NO 666
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 666
agcugccguu guucugggu                                              19

<210> SEQ ID NO 667
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 667
uucuggguac uacagcaga                                              19

<210> SEQ ID NO 668
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 668
uacagcagaa ggguaugca                                              19

<210> SEQ ID NO 669
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 669
uaugcggaag cgagcacca                                                  19

<210> SEQ ID NO 670
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 670
cgagcacccc agucugaga                                                  19

<210> SEQ ID NO 671
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 671
cuccugccgg ugugagccu                                                  19

<210> SEQ ID NO 672
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 672
ugugagccug agggccaca                                                  19

<210> SEQ ID NO 673
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 673
gggccaccau ccucugccu                                                  19

<210> SEQ ID NO 674
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 674
cugccuccug gccugggcu                                                  19
```

```
<210> SEQ ID NO 675
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 675
ccuggcugca ggugaccga                                                  19

<210> SEQ ID NO 676
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 676
ugaccgggug uacauacaa                                                  19

<210> SEQ ID NO 677
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 677
uacauacacc ccuuccaca                                                  19

<210> SEQ ID NO 678
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 678
uuccaccucg ucauccaca                                                  19

<210> SEQ ID NO 679
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 679
ucauccacaa ugagaguaa                                                  19

<210> SEQ ID NO 680
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 680
aaaggccaau gccgggaaa                                              19

<210> SEQ ID NO 681
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 681
ccgggaagcc caaagacca                                              19

<210> SEQ ID NO 682
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 682
aaagacccca ccuucauaa                                              19

<210> SEQ ID NO 683
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 683
ccuucauacc ugcuccaau                                              19

<210> SEQ ID NO 684
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 684
cuccaauuca ggccaagaa                                              19

<210> SEQ ID NO 685
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 685
aggccaagac aucccugu                                               19

<210> SEQ ID NO 686
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 686
uccccugugg augaaaaga                                                      19

<210> SEQ ID NO 687
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 687
aaaaggcccu acaggacca                                                      19

<210> SEQ ID NO 688
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 688
uacaggacca gcuggugcu                                                      19

<210> SEQ ID NO 689
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 689
uugacaccga agacaaguu                                                      19

<210> SEQ ID NO 690
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 690
acaaguugag ggccgcaau                                                      19

<210> SEQ ID NO 691
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 691
gccgcaaugg ucgggauga                                                      19
```

```
<210> SEQ ID NO 692
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 692
cgggaugcug gccaacuua                                              19

<210> SEQ ID NO 693
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 693
caacuucuug ggcuuccgu                                              19

<210> SEQ ID NO 694
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 694
ggcuuccgua uauauggca                                              19

<210> SEQ ID NO 695
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 695
uauggcaugc acagugaga                                              19

<210> SEQ ID NO 696
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 696
acagugagcu augggcgu                                               19

<210> SEQ ID NO 697
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 697
cguccucucc ccaacggcu                                              19

<210> SEQ ID NO 698
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 698
uuuggcaccc uggccucua                                              19

<210> SEQ ID NO 699
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 699
cuggccucuc ucuaucuga                                              19

<210> SEQ ID NO 700
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 700
uaucugggag ccuuggaca                                              19

<210> SEQ ID NO 701
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 701
uuggaccaca cagcugaca                                              19

<210> SEQ ID NO 702
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 702
acagcugaca ggcuacaga                                              19

<210> SEQ ID NO 703
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 703
uacaggcaau ccugggugu                                                  19

<210> SEQ ID NO 704
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 704
uccugggugu uccuuggaa                                                  19

<210> SEQ ID NO 705
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 705
uuggaaggac aagaacuga                                                  19

<210> SEQ ID NO 706
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 706
agaacugcac cucccggcu                                                  19

<210> SEQ ID NO 707
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 707
ugcgcacaag guccugucu                                                  19

<210> SEQ ID NO 708
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 708
cugcaggcug uacagggca                                                  19
```

```
<210> SEQ ID NO 709
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 709
uacagggccu gcuagugga                                                     19

<210> SEQ ID NO 710
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 710
uaguggccca gggcaggga                                                     19

<210> SEQ ID NO 711
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 711
agggcagggc ugauagcca                                                     19

<210> SEQ ID NO 712
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 712
uagccaggcc cagcugcua                                                     19

<210> SEQ ID NO 713
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 713
agcugcugcu guccacggu                                                     19

<210> SEQ ID NO 714
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

```
                        Synthetic oligonucleotide"

<400> SEQUENCE: 714
ugggcguguu cacagccca                                                  19

<210> SEQ ID NO 715
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 715
cacagcccca ggccugcaa                                                  19

<210> SEQ ID NO 716
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 716
cugcaccuga agcagccgu                                                  19

<210> SEQ ID NO 717
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 717
agcagccguu ugugcagga                                                  19

<210> SEQ ID NO 718
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 718
ugcagggccu ggcucucua                                                  19

<210> SEQ ID NO 719
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 719
uggcucucua uaccccugu                                                  19

<210> SEQ ID NO 720
<211> LENGTH: 19
```

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 720
accccugugg uccucccaa                                                19

<210> SEQ ID NO 721
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 721
cuggacuuca cagaacuga                                                19

<210> SEQ ID NO 722
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 722
agaacuggau guugcugcu                                                19

<210> SEQ ID NO 723
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 723
uugcugcuga gaagauuga                                                19

<210> SEQ ID NO 724
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 724
agaagauuga cagguucau                                                19

<210> SEQ ID NO 725
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 725
```

-continued agguucaugc aggcuguga                                      19

<210> SEQ ID NO 726
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 726
gcugugacag gauggaaga                                      19

<210> SEQ ID NO 727
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 727
uggaagacug gcugcucca                                      19

<210> SEQ ID NO 728
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 728
augggagcca guguggaca                                      19

<210> SEQ ID NO 729
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 729
uguggacagc acccuggcu                                      19

<210> SEQ ID NO 730
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 730
ccuggcuuuc aacaccuaa                                      19

<210> SEQ ID NO 731
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 731
caacaccuac guccacuua                                                     19

<210> SEQ ID NO 732
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 732 cacuccaag ggaagauga                                                      19

<210> SEQ ID NO 733
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 733
gggaagauga agggcuucu                                                     19

<210> SEQ ID NO 734
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 734
gcuucucccu gcuggccga                                                     19

<210> SEQ ID NO 735
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 735
ccaggaguuc uggguggaa                                                     19

<210> SEQ ID NO 736
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
        Synthetic oligonucleotide"

<400> SEQUENCE: 736
uggguggaca acagcaccu                                                     19

<210> SEQ ID NO 737

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 737
acagcaccuc agugucugu                                                  19

<210> SEQ ID NO 738
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 738
ugucuguucc caugcucua                                                  19

<210> SEQ ID NO 739
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 739
caugcucucu ggcauggga                                                  19

<210> SEQ ID NO 740
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 740
augggcaccu uccagcacu                                                  19

<210> SEQ ID NO 741
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 741
uuccagcacu ggagugaca                                                  19

<210> SEQ ID NO 742
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 742
```

-continued aggacaacuu cucggugaa                                                  19

<210> SEQ ID NO 743
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 743
ucggugacuc aagugcccu                                                  19

<210> SEQ ID NO 744
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 744
ugcccuucac ugagagcga                                                  19

<210> SEQ ID NO 745
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 745
ugagagcgcc ugccugcua                                                  19

<210> SEQ ID NO 746
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 746
ccugcugcug auccagccu                                                  19

<210> SEQ ID NO 747
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 747
auccagccuc acuaugccu                                                  19

<210> SEQ ID NO 748
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 748
uaugccucug accuggaca                                                       19

<210> SEQ ID NO 749
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 749
accuggacaa gguggagga                                                       19

<210> SEQ ID NO 750
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 750
uggagggucu cacuuucca                                                       19

<210> SEQ ID NO 751
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 751
cacuuuccag caaaacuca                                                       19

<210> SEQ ID NO 752
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 752
aaaacuCccu caacuggau                                                       19

<210> SEQ ID NO 753
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 753
aacuggauga agaaacuau                                                       19
```

```
<210> SEQ ID NO 754
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 754
aaacuaucuc cccggacca                                                 19

<210> SEQ ID NO 755
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 755
ccggaccauc caccugaca                                                 19

<210> SEQ ID NO 756
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 756
ugccccaacu ggugcugca                                                 19

<210> SEQ ID NO 757
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 757
ugcugcaagg aucuuauga                                                 19

<210> SEQ ID NO 758
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 758
ucuuaugacc ugcaggaca                                                 19

<210> SEQ ID NO 759
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 759
ugcaggaccu gcucgccca                                                19

<210> SEQ ID NO 760
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 760
ucgcccaggc ugagcugca                                                19

<210> SEQ ID NO 761
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 761
ugagcugccc gccauucua                                                19

<210> SEQ ID NO 762
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 762
ugcaaaaauu gagcaauga                                                19

<210> SEQ ID NO 763
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 763
agcaaugacc gcaucagga                                                19

<210> SEQ ID NO 764
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 764
caucagggug ggggaggua                                                19

<210> SEQ ID NO 765
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 765
ggggaggugc ugaacagca                                                      19

<210> SEQ ID NO 766
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 766
aacagcauuu uuuugaga                                                       19

<210> SEQ ID NO 767
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 767
uuuuugagcu ugaagcgga                                                      19

<210> SEQ ID NO 768
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 768
agagucuacc caacagcuu                                                      19

<210> SEQ ID NO 769
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 769
caacagcuua acaagccua                                                      19

<210> SEQ ID NO 770
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 770
caagccugag gucuuggaa                                                      19
```

<210> SEQ ID NO 771
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 771
cuuggaggug acccugaaa                                              19

<210> SEQ ID NO 772
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 772
acccugaacc gcccauuca                                              19

<210> SEQ ID NO 773
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 773
gcccauuccu guuugcugu                                              19

<210> SEQ ID NO 774
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 774
cacuuccugg gccgcguga                                              19

<210> SEQ ID NO 775
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 775
cgcguggcca acccgcuga                                              19

<210> SEQ ID NO 776
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 776
acccgcugag cacagcaua                                                19

<210> SEQ ID NO 777
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 777
acagcaugag gccagggca                                                19

<210> SEQ ID NO 778
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 778
cagggcccca gaacacagu                                                19

<210> SEQ ID NO 779
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 779
ucugccccug gccuuugaa                                                19

<210> SEQ ID NO 780
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 780
uuugaggcaa aggccagca                                                19

<210> SEQ ID NO 781
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 781
aggccagcag cagauaaca                                                19

<210> SEQ ID NO 782
<211> LENGTH: 19
<212> TYPE: RNA
```

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 782
agauaacaac cccggacaa                                                 19

<210> SEQ ID NO 783
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 783
ccggacaaau cagcgaugu                                                 19

<210> SEQ ID NO 784
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 784
agcgaugugu caccccaa                                                  19

<210> SEQ ID NO 785
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 785
uucuaaugag ucgacuuua                                                 19

<210> SEQ ID NO 786
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 786
guuucuccuu ggucuaagu                                                 19

<210> SEQ ID NO 787
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 787
agccugcagc ggcacaaau                                                 19
```

```
<210> SEQ ID NO 788
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 788
cacaaaugca ccucccagu                                                  19

<210> SEQ ID NO 789
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 789
accucccagu uugcugggu                                                  19

<210> SEQ ID NO 790
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 790
ugcuggguuu auuuuagaa                                                  19

<210> SEQ ID NO 791
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 791
caagaaccag uguuuagca                                                  19

<210> SEQ ID NO 792
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 792
aguguucccu uuucaaguu                                                  19

<210> SEQ ID NO 793
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 793
uucaaguuga gaacaaaaa                                                    19

<210> SEQ ID NO 794
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 794
caaaaauugg guuuuaaaa                                                    19

<210> SEQ ID NO 795
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 795
aaaguauaca uuuugcau                                                     19

<210> SEQ ID NO 796
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 796
uuuagugucu ugaauguaa                                                    19

<210> SEQ ID NO 797
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 797
gaauguaaga acaugaccu                                                    19

<210> SEQ ID NO 798
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 798
uguagugucu guaauaccu                                                    19

<210> SEQ ID NO 799
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 799
uguaauaccu uaguuuuu                                                  19

<210> SEQ ID NO 800
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 800 uuuuuccac agaugcuua                                                  19

<210> SEQ ID NO 801
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 801 uuuugaaca auacgugaa                                                  19

<210> SEQ ID NO 802
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 802
accauagcug guuauuucu                                                 19

<210> SEQ ID NO 803
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 803
uuauuucucc cuuguguua                                                 19

<210> SEQ ID NO 804
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 804
```
ucccaccuuu ucuucuaau                                          19

<210> SEQ ID NO 805
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 805
ucgacuuuga gcuggaaag                                          19

<210> SEQ ID NO 806
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 806
cuggaaagca gccguuucu                                          19

<210> SEQ ID NO 807
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 807
uggucuaagu gugcugcau                                          19

<210> SEQ ID NO 808
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 808
gcugcaugga gugagcagu                                          19

<210> SEQ ID NO 809
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 809
ugagcaguag aagccugca                                          19

<210> SEQ ID NO 810
<211> LENGTH: 19
<212> TYPE: RNA
<213> ORGANISM: Artificial Sequence
<220> FEATURE:
<221> NAME/KEY: source -continued

```
<223> OTHER INFORMATION: /note="Description of Artificial Sequence:
      Synthetic oligonucleotide"

<400> SEQUENCE: 810
uuagagaaug ggguggga                                                   19

<210> SEQ ID NO 811
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 811 gggugggag gcaagaaca                                                   19

<210> SEQ ID NO 812
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 812
uguuuagcgc gggacuacu                                                  19

<210> SEQ ID NO 813
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 813
ggacuacugu uccaaaaag                                                  19

<210> SEQ ID NO 814
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 814
agcuuguuug ugaaacaaa                                                  19

<210> SEQ ID NO 815
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 815
aaacaaaaaa guguucccu                                                  19

<210> SEQ ID NO 816
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 816
uuuuaaaauu aaaguauaa                                                   19

<210> SEQ ID NO 817
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 817
uuuugcauug ccuucgguu                                                   19

<210> SEQ ID NO 818
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 818
uucgguuugu auuuagugu                                                   19

<210> SEQ ID NO 819
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 819
aacaugaccu ccguguagu                                                   19

<210> SEQ ID NO 820
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 820
cagaugcuug ugauuuuua                                                   19

<210> SEQ ID NO 821
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 821
```

-continued uacgugaaag augcaagca                                              19

<210> SEQ ID NO 822
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 822
ugcaagcacc ugaauuucu                                              19

<210> SEQ ID NO 823
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 823
gaauuucugu uugaaugca                                              19

<210> SEQ ID NO 824
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 824
uuugaaugcg gaaccauaa                                              19

<210> SEQ ID NO 825
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 825
uuguguuagu aauaaacgu                                              19

<210> SEQ ID NO 826
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 826
auaaacgucu ugccacaau                                              19

<210> SEQ ID NO 827
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 827
ugccacaaua agccuccaa                                                      19

<210> SEQ ID NO 828
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 828
uuucugaccc ugcugcccg                                                      19

<210> SEQ ID NO 829
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 829 acacggggc cacuucuga                                                       19

<210> SEQ ID NO 830
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 830
uuugcuuagg caacacggg                                                      19

<210> SEQ ID NO 831
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 831
uaugcaggcc ggaggugca                                                      19

<210> SEQ ID NO 832
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 832
uaggccacag ggacaugca                                                      19
```

```
<210> SEQ ID NO 833
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 833
uuacccccaa gaggccaca                                              19

<210> SEQ ID NO 834
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 834
ucacccaggc cuucugacc                                              19

<210> SEQ ID NO 835
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 835
uccugaggcc aaccaccca                                              19

<210> SEQ ID NO 836
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 836
ugugugugac agccugagg                                              19

<210> SEQ ID NO 837
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 837 ucaucuccccu aggugugug                                             19

<210> SEQ ID NO 838
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 838
uaaacgggag caucuccu                                                    19

<210> SEQ ID NO 839
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 839
ucaagguucc cagaaacgg                                                   19

<210> SEQ ID NO 840
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 840
aggagucggg gccaagguu                                                   19

<210> SEQ ID NO 841
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 841
ucgaaguuug caggagucg                                                   19

<210> SEQ ID NO 842
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 842
uuacacauuu accgaaguu                                                   19

<210> SEQ ID NO 843
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 843
ugcagggucg aguuacaca                                                   19

<210> SEQ ID NO 844
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 844
uagugagccg gugcagggu                                                      19

<210> SEQ ID NO 845
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 845
acugcugaac agagugagc                                                      19

<210> SEQ ID NO 846
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 846
ucagaguuuc acugcugaa                                                      19

<210> SEQ ID NO 847
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 847
agugaucgau gcagaguuu                                                      19

<210> SEQ ID NO 848
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 848
uaggaagucu uagugaucg                                                      19

<210> SEQ ID NO 849
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 849
acacucacgc ugggaccuc                                                      19
```

```
<210> SEQ ID NO 850
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 850
agaaggacag augccagaa                                                      19

<210> SEQ ID NO 851
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 851
ucacaggcug gccagaagg                                                      19

<210> SEQ ID NO 852
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 852
uuuggccaga ccacaggcu                                                      19

<210> SEQ ID NO 853
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 853
aggguuacau cacuuggcc                                                      19

<210> SEQ ID NO 854
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 854
ucuggagagg aggguuaca                                                      19

<210> SEQ ID NO 855
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

```
<400> SEQUENCE: 855
ucugugcaca ggcuggaga                                                    19

<210> SEQ ID NO 856
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 856
uucccaggcu gccugugca                                                    19

<210> SEQ ID NO 857
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 857
ugauggagcu guucccagg                                                    19

<210> SEQ ID NO 858
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 858 ucgaggggu ggggaugga                                                     19

<210> SEQ ID NO 859
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 859
uccuauuuau agcugaggg                                                    19

<210> SEQ ID NO 860
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 860
ugucacgaug cccuauuua                                                    19

<210> SEQ ID NO 861
<211> LENGTH: 19
<212> TYPE: RNA
```

-continued

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 861
uccccggccg ggucacgau                                                19

<210> SEQ ID NO 862
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 862
uggcagcuuc uuccccgg                                                 19

<210> SEQ ID NO 863
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 863
acccagaaca acggcagcu                                                19

<210> SEQ ID NO 864
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 864
ucugcuguag uacccagaa                                                19

<210> SEQ ID NO 865
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 865
ugcauacccu ucugcugua                                                19

<210> SEQ ID NO 866
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 866
uggugcucgc uuccgcaua                                                19
```

-continued

```
<210> SEQ ID NO 867
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 867
ucucagacug gggugcucg                                                  19

<210> SEQ ID NO 868
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 868
aggcucacac cggcaggag                                                  19

<210> SEQ ID NO 869
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 869
uguggcccuc aggcucaca                                                  19

<210> SEQ ID NO 870
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 870
aggcagagga ugguggccc                                                  19

<210> SEQ ID NO 871
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 871
agcccaggcc aggaggcag                                                  19

<210> SEQ ID NO 872
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
```

-continued

Synthetic oligonucleotide"

<400> SEQUENCE: 872
ucggucaccu gcagccagg                                        19

<210> SEQ ID NO 873
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 873
uuguauguac acccgguca                                        19

<210> SEQ ID NO 874
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 874
uguggaaggg guguaugua                                        19

<210> SEQ ID NO 875
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 875
uguggaugac gagguggaa                                        19

<210> SEQ ID NO 876
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 876
uuacucucau uguggauga                                        19

<210> SEQ ID NO 877
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 877
uuucccggca uuggccuuu                                        19

<210> SEQ ID NO 878
<211> LENGTH: 19

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 878
uggucuuugg gcuucccgg                                              19

<210> SEQ ID NO 879
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 879
uuaugaaggu ggggucuuu                                              19

<210> SEQ ID NO 880
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 880
auuggagcag guaugaagg                                              19

<210> SEQ ID NO 881
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 881
uucuuggccu gaauuggag                                              19

<210> SEQ ID NO 882
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 882 acagggaug ucuuggccu                                               19

<210> SEQ ID NO 883
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 883
```
ucuuuucauc cacagggga                                                19

<210> SEQ ID NO 884
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 884
ugguccugua gggccuuuu                                                19

<210> SEQ ID NO 885
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 885
agcaccagcu gguccugua                                                19

<210> SEQ ID NO 886
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 886
aacuugucuu cggugucaa                                                19

<210> SEQ ID NO 887
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 887
auugcggccc ucaacuugu                                                19

<210> SEQ ID NO 888
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 888
ucaucccgac cauugcggc                                                19

<210> SEQ ID NO 889
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 889
uaaguuggcc agcaucccg                                                19

<210> SEQ ID NO 890
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 890
acggaagccc aagaaguug                                                19

<210> SEQ ID NO 891
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 891
ugccauauau acggaagcc                                                19

<210> SEQ ID NO 892
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 892
ucucacugug caugccaua                                                19

<210> SEQ ID NO 893
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 893
acgccccaua gcucacugu                                                19

<210> SEQ ID NO 894
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
       Synthetic oligonucleotide"

<400> SEQUENCE: 894
agccguuggg gagaggacg                                                19

<210> SEQ ID NO 895

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 895
uagaggccag ggugccaaa                                                   19

<210> SEQ ID NO 896
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 896
ucagauagag agaggccag                                                   19

<210> SEQ ID NO 897
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 897
uguccaaggc ucccagaua                                                   19

<210> SEQ ID NO 898
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 898
ugucagcugu gugguccaa                                                   19

<210> SEQ ID NO 899
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 899
ucuguagccu gucagcugu                                                   19

<210> SEQ ID NO 900
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 900
```

```
acacccagga uugccugua                                         19

<210> SEQ ID NO 901
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 901
uuccaaggaa cacccagga                                         19

<210> SEQ ID NO 902
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 902
ucaguucuug uccuuccaa                                         19

<210> SEQ ID NO 903
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 903
agccgggagg ugcaguucu                                         19

<210> SEQ ID NO 904
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 904
agacaggacc uugugcgca                                         19

<210> SEQ ID NO 905
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 905
ugcccuguac agccugcag                                         19

<210> SEQ ID NO 906
<211> LENGTH: 19
<212> TYPE: RNA
<213> ORGANISM: Artificial Sequence
<220> FEATURE:
```

```
<221> NAME/KEY: source
<223> OTHER INFORMATION: /note="Description of Artificial Sequence:
      Synthetic oligonucleotide"

<400> SEQUENCE: 906
uccacuagca ggcccugua                                                   19

<210> SEQ ID NO 907
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 907
ucccugcccu gggccacua                                                   19

<210> SEQ ID NO 908
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 908
uggcuaucag cccugcccu                                                   19

<210> SEQ ID NO 909
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 909
uagcagcugg gccuggcua                                                   19

<210> SEQ ID NO 910
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 910
accguggaca gcagcagcu                                                   19

<210> SEQ ID NO 911
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 911
ugggcuguga acacgccca                                                   19
```

```
<210> SEQ ID NO 912
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 912
uugcaggccu ggggcugug                                                19

<210> SEQ ID NO 913
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 913
acggcugcuu caggugcag                                                19

<210> SEQ ID NO 914
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 914
uccugcacaa acggcugcu                                                19

<210> SEQ ID NO 915
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 915
uagagagcca ggcccugca                                                19

<210> SEQ ID NO 916
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 916 acaggguau agagagcca                                                 19

<210> SEQ ID NO 917
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 917
uugggaggac cacaggggu                                                    19

<210> SEQ ID NO 918
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 918
ucaguucugu gaaguccag                                                    19

<210> SEQ ID NO 919
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 919
agcagcaaca uccaguucu                                                    19

<210> SEQ ID NO 920
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 920
ucaaucuucu cagcagcaa                                                    19

<210> SEQ ID NO 921
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 921
augaaccugu caaucuucu                                                    19

<210> SEQ ID NO 922
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 922
ucacagccug caugaaccu                                                    19

<210> SEQ ID NO 923
<211> LENGTH: 19
<212> TYPE: RNA
<213> ORGANISM: Artificial Sequence

```
<220> FEATURE:
<221> NAME/KEY: source
<223> OTHER INFORMATION: /note="Description of Artificial Sequence:
      Synthetic oligonucleotide"

<400> SEQUENCE: 923
ucuuccaucc ugucacagc                                                19

<210> SEQ ID NO 924
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 924
uggagcagcc agucuucca                                                19

<210> SEQ ID NO 925
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 925
uguccacacu ggcucccau                                                19

<210> SEQ ID NO 926
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 926
agccagggug cuguccaca                                                19

<210> SEQ ID NO 927
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 927
uuagguguug aaagccagg                                                19

<210> SEQ ID NO 928
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 928
uaaguggacg uagguguug                                                19
```

```
<210> SEQ ID NO 929
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 929
ucaucuuccc uuggaagug                                                     19

<210> SEQ ID NO 930
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 930
agaagcccuu caucuuccc                                                     19

<210> SEQ ID NO 931
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 931
ucggccagca gggagaagc                                                     19

<210> SEQ ID NO 932
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 932
uuccacccag aacuccugg                                                     19

<210> SEQ ID NO 933
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 933
aggugcuguu guccaccca                                                     19

<210> SEQ ID NO 934
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 934
acagacacug aggugcugu                                                    19

<210> SEQ ID NO 935
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 935
uagagcaugg gaacagaca                                                    19

<210> SEQ ID NO 936
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 936
ucccaugcca gagagcaug                                                    19

<210> SEQ ID NO 937
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 937
agugcuggaa ggugcccau                                                    19

<210> SEQ ID NO 938
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 938 ugcacucca gugcuggaa                                                     19

<210> SEQ ID NO 939
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 939
uucaccgaga aguuguccu                                                    19

<210> SEQ ID NO 940
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 940
agggcacuug agucaccga                                                  19

<210> SEQ ID NO 941
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 941
ucgcucucag ugaagggca                                                  19

<210> SEQ ID NO 942
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 942
uagcaggcag gcgcucuca                                                  19

<210> SEQ ID NO 943
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 943
aggcuggauc agcagcagg                                                  19

<210> SEQ ID NO 944
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 944
aggcauagug aggcuggau                                                  19

<210> SEQ ID NO 945
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 945
uguccagguc agaggcaua                                                  19
```

<210> SEQ ID NO 946
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 946
uccuccaccu uguccaggu                                              19

<210> SEQ ID NO 947
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 947
uggaaaguga gacccucca                                              19

<210> SEQ ID NO 948
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 948
ugaguuuugc uggaaagug                                              19

<210> SEQ ID NO 949
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 949
auccaguuga gggaguuuu                                              19

<210> SEQ ID NO 950
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 950
auaguuucuu cauccaguu                                              19

<210> SEQ ID NO 951
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:

-continued

Synthetic oligonucleotide"

<400> SEQUENCE: 951
ugguccgggg agauaguuu                                                19

<210> SEQ ID NO 952
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 952
ugucaggugg augguccgg                                                19

<210> SEQ ID NO 953
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 953
ugcagcacca guuggggca                                                19

<210> SEQ ID NO 954
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 954
ucauaagauc cuugcagca                                                19

<210> SEQ ID NO 955
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 955
uguccugcag gucauaaga                                                19

<210> SEQ ID NO 956
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 956
ugggcgagca gguccugca                                                19

<210> SEQ ID NO 957
<211> LENGTH: 19

-continued

```
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 957
ugcagcucag ccugggcga                                                        19

<210> SEQ ID NO 958
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 958
uagaauggcg ggcagcuca                                                        19

<210> SEQ ID NO 959
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 959
ucauugcuca auuuuugca                                                        19

<210> SEQ ID NO 960
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 960
uccugaugcg gucauugcu                                                        19

<210> SEQ ID NO 961
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 961
uaccuccccc acccugaug                                                        19

<210> SEQ ID NO 962
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 962
```
ugcuguucag caccucccc						19

<210> SEQ ID NO 963
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 963
ucucaaaaaa aaugcuguu						19

<210> SEQ ID NO 964
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 964
uccgcuucaa gcucaaaaa						19

<210> SEQ ID NO 965
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 965
aagcuguugg guagacucu						19

<210> SEQ ID NO 966
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 966
uaggcuuguu aagcuguug						19

<210> SEQ ID NO 967
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 967
uuccaagacc ucaggcuug						19

<210> SEQ ID NO 968
<211> LENGTH: 19
<212> TYPE: RNA
<213> ORGANISM: Artificial Sequence
<220> FEATURE:
<221> NAME/KEY: source

```
<223> OTHER INFORMATION: /note="Description of Artificial Sequence:
      Synthetic oligonucleotide"

<400> SEQUENCE: 968
uuucaggguc accuccaag                                                    19

<210> SEQ ID NO 969
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 969
ugaaugggcg guucagggu                                                    19

<210> SEQ ID NO 970
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 970
acagcaaaca ggaaugggc                                                    19

<210> SEQ ID NO 971
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 971
ucacgcggcc caggaagug                                                    19

<210> SEQ ID NO 972
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 972
ucagcggguu ggccacgcg                                                    19

<210> SEQ ID NO 973
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 973
uaugcugugc ucagcgggu                                                    19

<210> SEQ ID NO 974
```

```
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 974
ugcccuggcc ucaugcugu                                                    19

<210> SEQ ID NO 975
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 975
acuguguucu ggggcccug                                                    19

<210> SEQ ID NO 976
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 976
uucaaaggcc agggcaga                                                     19

<210> SEQ ID NO 977
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 977
ugcuggccuu ugccucaaa                                                    19

<210> SEQ ID NO 978
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 978
uguuaucugc ugcuggccu                                                    19

<210> SEQ ID NO 979
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 979
```
uuguccgggg uuguuaucu                                            19

<210> SEQ ID NO 980
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 980
acaucgcuga uuuguccgg                                            19

<210> SEQ ID NO 981
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 981
uuggggguga cacaucgcu                                            19

<210> SEQ ID NO 982
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 982
uaaagucgac ucauuagaa                                            19

<210> SEQ ID NO 983
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 983
acuuagacca aggagaaac                                            19

<210> SEQ ID NO 984
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 984
auuugugccg cugcaggcu                                            19

<210> SEQ ID NO 985
<211> LENGTH: 19
<212> TYPE: RNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"

<400> SEQUENCE: 985
acugggaggu gcauuugug                                                  19

<210> SEQ ID NO 986
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 986
acccagcaaa cugggaggu                                                  19

<210> SEQ ID NO 987
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 987
uucuaaaaua aacccagca                                                  19

<210> SEQ ID NO 988
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 988
ugcuaaacac ugguucuug                                                  19

<210> SEQ ID NO 989
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 989
aacuugaaaa gggaacacu                                                  19

<210> SEQ ID NO 990
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 990
uuuuuguucu caacuugaa                                                  19
```

<210> SEQ ID NO 991
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 991
uuuuaaaacc caauuuuug          19

<210> SEQ ID NO 992
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 992
augcaaaaau guauacuuu          19

<210> SEQ ID NO 993
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 993
uuacauucaa gacacuaaa          19

<210> SEQ ID NO 994
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 994
aggucauguu cuuacauuc          19

<210> SEQ ID NO 995
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

<400> SEQUENCE: 995
agguauuaca gacacuaca          19

<210> SEQ ID NO 996
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence: Synthetic oligonucleotide"

```
<400> SEQUENCE: 996
aaaaaacuaa gguauuaca                                                19

<210> SEQ ID NO 997
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 997
uaagcaucug uggaaaaaa                                                19

<210> SEQ ID NO 998
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 998
uucacguauu guucaaaaa                                                19

<210> SEQ ID NO 999
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 999
agaaauaacc agcuauggu                                                19

<210> SEQ ID NO 1000
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1000
uaacacaagg gagaaauaa                                                19

<210> SEQ ID NO 1001
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1001
auuagaagaa aagguggga                                                19

<210> SEQ ID NO 1002
<211> LENGTH: 19
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1002
cuuuccagcu caaagucga                                               19

<210> SEQ ID NO 1003
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1003
agaaacggcu gcuuccag                                                19

<210> SEQ ID NO 1004
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1004
augcagcaca cuuagacca                                               19

<210> SEQ ID NO 1005
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1005
acugcucacu ccaugcagc                                               19

<210> SEQ ID NO 1006
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1006
ugcaggcuuc uacugcuca                                               19

<210> SEQ ID NO 1007
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1007
ucccaccccc auucucuaa                                               19
```

```
<210> SEQ ID NO 1008
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1008
uguucuugcc uccccaccc                                                      19

<210> SEQ ID NO 1009
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1009
aguagucccg cgcuaaaca                                                      19

<210> SEQ ID NO 1010
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1010
cuuuuuggaa caguagucc                                                      19

<210> SEQ ID NO 1011
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1011
uuuguuucac aaacaagcu                                                      19

<210> SEQ ID NO 1012
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1012
agggaacacu uuuuuguuu                                                      19

<210> SEQ ID NO 1013
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

-continued

<400> SEQUENCE: 1013
uuauacuuua auuuuaaaa                                                19

<210> SEQ ID NO 1014
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1014
aaccgaaggc aaugcaaaa                                                19

<210> SEQ ID NO 1015
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1015
acacuaaaua caaaccgaa                                                19

<210> SEQ ID NO 1016
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1016
acuacacgga ggucauguu                                                19

<210> SEQ ID NO 1017
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1017
uaaaaaucac aagcaucug                                                19

<210> SEQ ID NO 1018
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1018
ugcuugcauc uuucacgua                                                19

<210> SEQ ID NO 1019
<211> LENGTH: 19
<212> TYPE: RNA

```
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1019
agaaauucag gugcuugca                                                      19

<210> SEQ ID NO 1020
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1020
ugcauucaaa cagaaauuc                                                      19

<210> SEQ ID NO 1021
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1021
uuaugguucc gcauucaaa                                                      19

<210> SEQ ID NO 1022
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1022
acguuuauua cuaacacaa                                                      19

<210> SEQ ID NO 1023
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1023
auuguggcaa gacguuuau                                                      19

<210> SEQ ID NO 1024
<211> LENGTH: 19
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1024
uuggaggcuu auuguggca                                                      19
```

```
<210> SEQ ID NO 1025
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1025
ucucccaccu uuucuucuaa u                                              21

<210> SEQ ID NO 1026
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1026
auuagaagaa aagugggag acu                                             23

<210> SEQ ID NO 1027
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1027
uguuugcugu guaugaucaa a                                              21

<210> SEQ ID NO 1028
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1028
uuugaucaua cacagcaaac agg                                            23

<210> SEQ ID NO 1029
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1029
uuccguauau auggcaugca a                                              21

<210> SEQ ID NO 1030
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1030
uugcaugcca uauauacgga agc                                          23

<210> SEQ ID NO 1031
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1031
accugcaaaa auugagcaau a                                            21

<210> SEQ ID NO 1032
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1032
uauugcucaa uuuuugcagg uuc                                          23

<210> SEQ ID NO 1033
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1033
accugcaaaa auugagcaau a                                            21

<210> SEQ ID NO 1034
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1034
uauugcucaa uuuuugcagg uuc                                          23

<210> SEQ ID NO 1035
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1035
uguuugcugu guaugaucaa a                                            21

<210> SEQ ID NO 1036
<211> LENGTH: 23
<212> TYPE: RNA
<213> ORGANISM: Artificial Sequence
```

```
<220> FEATURE:
<221> NAME/KEY: source
<223> OTHER INFORMATION: /note="Description of Artificial Sequence:
      Synthetic oligonucleotide"

<400> SEQUENCE: 1036
uuugaucaua cacagcaaac agg                                              23

<210> SEQ ID NO 1037
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1037
ucucccaccu uuucuucuaa u                                                21

<210> SEQ ID NO 1038
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1038
auuagaagaa aagguggag acu                                               23

<210> SEQ ID NO 1039
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1039
cccaccuuuu cuucuaauga a                                                21

<210> SEQ ID NO 1040
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1040
uucauuagaa gaaaaggugg gag                                              23

<210> SEQ ID NO 1041
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1041
cccaccuuuu cuucuaauga a                                                21
```

```
<210> SEQ ID NO 1042
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1042
uucauuagaa gaaaaggugg gag                                           23

<210> SEQ ID NO 1043
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1043
ccagcuuguu ugugaaacaa a                                             21

<210> SEQ ID NO 1044
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1044
uuuguuucac aaacaagcug guc                                           23

<210> SEQ ID NO 1045
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1045
ccagcuuguu ugugaaacaa a                                             21

<210> SEQ ID NO 1046
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1046
uuuguuucac aaacaagcug guc                                           23

<210> SEQ ID NO 1047
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
```

```
<400> SEQUENCE: 1047
aaaaaagugu ucccuuuuca a                                              21

<210> SEQ ID NO 1048
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1048
uugaaaaggg aacacuuuuu ugu                                            23

<210> SEQ ID NO 1049
<211> LENGTH: 21
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1049
aaaaaagugu ucccuuuuca a                                              21

<210> SEQ ID NO 1050
<211> LENGTH: 23
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1050
uugaaaaggg aacacuuuuu ugu                                            23
```

ANGIOTENSINOGEN (AGT) IRNA COMPOSITIONS AND METHODS OF USE THEREOF

CROSS-REFERENCE TO RELATED APPLICATIONS

This application claims the benefit of priority to U.S. Provisional Application No. 62/001,731, filed on May 22, 2014, and U.S. Provisional Application No. 62/047,978, filed on Sep. 9, 2014. The entire contents of each of the foregoing applications are hereby incorporated herein by reference.

SEQUENCE LISTING

The instant application contains a Sequence Listing which has been submitted electronically in ASCII format and is hereby incorporated by reference in its entirety. The ASCII copy, created on May 18, 2015, is named 121301-01320_SL.txt and is 318,688 bytes in size.

BACKGROUND OF THE INVENTION

The renin-angiotensin-aldosterone system (RAAS) plays a crucial role in the regulation of blood pressure. The RAAS cascade begins with the release of renin by the juxtaglomerular cells of the kidney into the circulation. Renin secretion is stimulated by several factors, including Na+ load in the distal tubule, β-sympathetic stimulation, and/or reduced renal perfusion. Active renin in the plasma cleaves angiotensinogen (produced by the liver) to angiotensin I, which is then converted by circulating and locally expressed angiotensin-converting enzyme (ACE) to angiotensin II. Most of the effects of angiotensin II on the RAAS are exerted by its binding to angiotensin II type 1 receptors ($AT_1R$), leading to arterial vasoconstriction, tubular and glomerular effects, such as enhanced Na+ reabsorption or modulation of glomerular filtration rate. In addition, together with other stimuli such as adrenocorticotropin, anti-diuretic hormone, catecholamines, endothelin, serotonin, and levels of Mg2+ and K+, $AT_1R$ stimulation leads to aldosterone release which, in turn, promotes Na+ and K+ excretion in the renal distal convoluted tubule.

Dysregulation of the RAAS leading to, for example, excessive angiotensin II production and/or $AT_1R$ stimulation results in hypertension which can lead to, e.g., increased oxidative stress, promotion of inflammation, hypertrophy, and fibrosis in the heart, kidneys, and arteries, and result in, e.g., left ventricular fibrosis, arterial remodeling, and glomerulosclerosis.

Hypertension is the most prevalent, controllable disease in developed countries, affecting 20-50% of adult populations. It is a major risk factor for various diseases, disorders and conditions such as, shortened life expectancy, chronic kidney disease, stroke, myocardial infarction, heart failure, aneurysms (e.g. aortic aneurysm), peripheral artery disease, heart damage (e.g., heart enlargement or hypertrophy) and other cardiovascular related diseases, disorders and/or conditions. In addition, hypertension has been shown to be an important risk factor for cardiovascular morbidity and mortality accounting for, or contributing to, 62% of all strokes and 49% of all cases of heart disease.

Despite the number of anti-hypertensive drugs available for treating hypertension, more than two-thirds of subjects are not controlled with one anti-hypertensive agent and require two or more anti-hypertensive agents selected from different drug classes. This further reduces the number of subjects with controlled blood pressure as compliance and side-effects increase with increasing medication.

Accordingly, there is a need in the art for alternative therapies and combination therapies for subjects having an angiotensinogen-associated disease.

SUMMARY OF THE INVENTION

The present invention provides iRNA compositions which effect the RNA-induced silencing complex (RISC)-mediated cleavage of RNA transcripts of an angiotensinogen (AGT) gene. The AGT gene may be within a cell, e.g., a cell within a subject, such as a human.

The present invention also provides methods and therapies for treating a subject having a disorder that would benefit from inhibiting or reducing the expression of an AGT gene, e.g., an angiotensinogen-associated disease, such as hypertension, using iRNA compositions which effect the RNA-induced silencing complex (RISC)-mediated cleavage of RNA transcripts of an AGT gene for inhibiting the expression of an AGT gene.

Accordingly, in one aspect, the present invention provides double-stranded ribonucleic acid (RNAi) agents for inhibiting expression of angiotensinogen (AGT), which comprise a sense strand and an antisense strand forming a double-stranded region, wherein the sense strand comprises at least 15 contiguous nucleotides differing by no more than 3 nucleotides from the nucleotide sequence of SEQ ID NO: 1 and the antisense strand comprises at least 15 contiguous nucleotides differing by no more than 3 nucleotides from the nucleotide sequence of SEQ ID NO:2, wherein substantially all of the nucleotides of the sense strand and substantially all of the nucleotides of the antisense strand are modified nucleotides, and wherein the sense strand is conjugated to a ligand attached at the 3'-terminus. In one embodiment, all of the nucleotides of the sense strand and all of the nucleotides of the antisense strand are modified nucleotides.

In another aspect, the present invention provides double-stranded ribonucleic acid (RNAi) agents for inhibiting expression of angiotensinogen (AGT), which comprise a sense strand and an antisense strand forming a double-stranded region, wherein the sense strand comprises at least 15 contiguous nucleotides differing by no more than 3 nucleotides from nucleotides 2801-2101; 803-843; 834-859; 803-859; 803-875; 834-875; 847-875; 1247-1271; 1566-1624; 1570-1624; 1584-1624; 1584-1624; 1584-1621; 2035-2144; 2070-2144; 2070-2103; 2201-2223; 2227-2360; 2227-2304; 2290-2318; 2304-2350; 2304-2326; 2320-2342; 2333-2360; 2333-2358; 485-503; 517-535; 560-578; 635-653; 803-821; 814-832; 822-840; 825-843; 834-852; 837-855; 841-859; 855-873; 967-985; 1247-1265; 1248-1266; 1249-1267; 1251-1269; 1253-1271; 1566-1584; 1570-1588; 1572-1590; 1574-1592; 1584-1602; 1587-1605; 1591-1609; 1592-1610; 1595-1613; 1601-1619; 1602-1620; 1605-1623; 1729-1747; 1738-1756; 1739-1757; 1741-1769; 1767-1785; 1810-1828; 1827-1845; 1880-1989; 1892-1914; 1894-1914; 1894-2012; 2035-2053; 2046-2064; 2057-2075; 2070-2088; 2072-2090; 2078-2096; 2078-2107; 2078-2011; 2080-2098; 2081-2099; 2081-2104; 2081-2011; 2082-2100; 2084-2102; 2084-2011; 2090-2108; 2100-2118; 2111-2129; 2124-2142; 2125-2143; 2167-2185; 2179-2197; 2201-2219; 2202-2220; 2203-2221; 2204-2222; 2227-2245; 2230-2248; 2234-2252; 2244-2264; 2255-2273; 2266-2284; 2268-2286; 2270-2288; 2279-2297; 2281-2299; 2283-2301; 2284-2302; 2285-2303; 2286-2304; 2288-2306; 2290-2308; 2291-2309; 2291-2311; 2291-2318; 2291-2315; 2292-2310; 2294-2312; 2296-2314; 2299-2317; 2304-2322; 2304-2329; 2306-2324; 2307-2325; 2309-2327; 2309-2329; 2309-2342; 2309-2350; 2309-2358; 2314-2332; 2316-2334; 2317-2335; 2320-2338; 2321-2339; 2323-2341; 2325-2343; 2326-2344; 2328-2346; 2329-2347; 2331-2349; 2333-2351; 2334-2352; 2335-2353; 2339-2357; 2340-2358; or 2341-2359 of the nucleotide sequence of SEQ ID NO: 1 and the antisense strand comprises at least 15 contiguous nucleotides differing by no more than 3 nucleotides from the nucleotides at the corresponding position of the nucleotide sequence of SEQ ID NO:2 such that the antisense strand is substantially complementary to the at least 15 contiguous nucleotides in the sense strand. In certain embodiments, substantially all of the nucleotides of the sense strand are modified nucleotides. In other embodiments, substantially all of the nucleotides of the antisense strand are modified nucleotides. In yet other embodiments, substantially all of the nucleotides of both strands are modified nucleotides. In one embodiment, all of the nucleotides of the sense strand and all of the nucleotides of the antisense strand are modified nucleotides. In one embodiment, the sense strand is conjugated to a ligand attached at the 3'-terminus. In one embodiment, the sense strand comprises at least 15 contiguous nucleotides differing by no more than 3 nucleotides from nucleotides 2801-2101 of the nucleotide sequence of SEQ ID NO: 1 and the antisense strand comprises at least 15 contiguous nucleotides differing by no more than 3 nucleotides from the nucleotides at the corresponding position of the nucleotide sequence of SEQ ID NO:2 such that the antisense strand is substantially complementary to the at least 15 contiguous nucleotides in the sense strand.

In one aspect, the present invention provides double-stranded ribonucleic acid (RNAi) agents for inhibiting expression of angiotensinogen (AGT), which comprise a sense strand and an antisense strand forming a double-stranded region, wherein the sense strand comprises at least 15 contiguous nucleotides from nucleotides 803-843; 834-859; 803-859; 1247-1271; 1566-1624; 1570-1624; 1584-1624; 1584-1624; 1584-1621; 2035-2144; 2070-2144; 2070-2103; 2201-2223; 2227-2360; 2227-2304; 2290-2318; 2304-2350; 2304-2326; 2320-2342; 2333-2360; 2333-2358; 485-503; 517-535; 560-578; 635-653; 803-821; 814-832; 822-840; 825-843; 834-852; 837-855; 841-859; 855-873; 967-985; 1247-1265; 1248-1266; 1249-1267; 1251-1269; 1253-1271; 1566-1584; 1570-1588; 1572-1590; 1574-1592; 1584-1602; 1587-1605; 1591-1609; 1592-1610; 1595-1613; 1601-1619; 1602-1620; 1605-1623; 1729-1747; 1738-1756; 1739-1757; 1741-1769; 1767-1785; 1810-1828; 1827-1845; 1880-1989; 1894-2012; 2035-2053; 2046-2064; 2057-2075; 2070-2088; 2072-2090; 2078-2096; 2080-2098; 2081-2099; 2082-2100; 2084-2102; 2090-2108; 2100-2118; 2111-2129; 2124-2142; 2125-2143; 2167-2185; 2179-2197; 2201-2219; 2202-2220; 2203-2221; 2204-2222; 2227-2245; 2230-2248; 2234-2252; 2244-2264; 2255-2273; 2266-2284; 2268-2286; 2270-2288; 2279-2297; 2281-2299; 2283-2301; 2284-2302; 2285-2303; 2286-2304; 2288-2306; 2290-2308; 2291-2309; 2292-2310; 2294-2312; 2296-2314; 2299-2317; 2304-2322; 2306-2324; 2307-2325; 2309-2327; 2314-2332; 2316-2334; 2317-2335; 2320-2338; 2321-2339; 2323-2341; 2325-2343; 2326-2344; 2328-2346; 2329-2347; 2331-2349; 2333-2351; 2334-2352; 2335-2353; 2339-2357; 2340-2358; or 2341-2359 of the nucleotide sequence of SEQ ID NO: 1 and the antisense strand comprises at least 15 contiguous nucleotides differing by no more than 3 nucleosides from the nucleotides at the corresponding position of the nucleotide sequence of SEQ ID NO:2 such that the antisense strand is substantially complementary to the at least 15 contiguous nucleotides in the sense strand. In certain embodiments, substantially all of the nucleotides of the sense strand are modified nucleotides. In other embodiments, substantially all of the nucleotides of the antisense strand are modified nucleotides. In yet other embodiments, substantially all of the nucleotides of both strands are modified nucleotides. In one embodiment, the sense strand is conjugated to a ligand attached at the 3'-terminus.

In one embodiment, the sense strand and the antisense strand comprise a region of complementarity which comprises at least 15 contiguous nucleotides differing by no more than 3 nucleotides from any one of the antisense sequences listed in any one of Tables 3, 4, 7, 8, 11, 13, and 15. For example, in certain embodiments, the sense strand and the antisense strand comprise a region of complementarity which comprises at least 15 contiguous nucleotides differing by no more than 3 nucleotides from any one of the antisense sequences of the duplexes AD-52433.1, AD-52438.1, AD-52439.1, AD-52445.1, AD-52449.1, AD-52451.1, AD-52456.1, AD-52457.1, AD-52462.1, AD-52463.1, AD-52469.1, AD-52474.1, AD-55976.1, AD-55978.1, AD-55979.1, AD-55980.1, AD-55981.1, AD-55982.1, AD-55983.1, AD-55984.1, AD-55987.1, AD-55988.1, AD-55989.1, AD-55990.1, AD-55991.1, AD-55994.1, AD-55995.1, AD-55996.1, AD-55999.1, AD-56000.1, AD-56001.1, AD-56002.1, AD-56003.1, AD-56006.1, AD-56007.1, AD-56008.1, AD-56009.1, AD-56011.1, AD-56012.1, AD-56013.1, AD-56016.1, AD-56017.1, AD-56019.1, AD-56020.1, AD-56021.1, AD-56022.1, AD-56024.1, AD-56026.1, AD-56027.1, AD-56029.1, AD-56030.1, AD-56031.1, AD-56032.1, AD-56035.1, AD-56039.1, AD-56041.1, AD-56043.1, AD-56044.1, AD-56047.1, AD-56048.1, AD-56051.1, AD-56053.1, AD-56054.1, AD-56059.1, AD-56062.1, AD-56065.1, AD-56066.1, AD-60770.1, AD-60771.1, AD-60776.1, AD-60777.1, AD-60778.1, AD-60779.1, AD-60780.1, AD-60781.1, AD-60783.1, AD-60784.1, AD-60785.1, AD-60788.1, AD-60789.1, AD-60791.1, AD-60793.1, AD-60795.1, AD-60798.1, AD-60801.1, AD-67903.1, AD-67906.1, AD-67923.1, AD-67924.1, AD-67925.1, AD-67926.1, AD-67935.1, AD-67965.1, AD-67994.1, AD-67995.1, AD-67996.1, AD-68017.1, AD-68022.1, AD-68035.1, AD-68036.1, AD-68037.1, AD-68084.2, AD-68085.2, AD-68086.2, AD-68087.2, AD-68090.2, AD-68091.2, AD-68092.2, AD-68093.2, AD-68116.1, AD-68117.1, AD-68118.1, AD-68124.1, AD-68125.1, or AD-68126.1. In certain embodiments, the sense strand and the antisense strand comprise a region of complementarity which comprises at least 15 contiguous nucleotides of the region of complementarity of any one of duplexes AD-52433.1, AD-52438.1, AD-52439.1, AD-52445.1, AD-52449.1, AD-52451.1, AD-52456.1, AD-52457.1, AD-52462.1, AD-52463.1, AD-52469.1, AD-52474.1, AD-55976.1, AD-55978.1, AD-55979.1, AD-55980.1, AD-55981.1, AD-55982.1, AD-55983.1, AD-55984.1, AD-55987.1, AD-55988.1, AD-55989.1, AD-55990.1, AD-55991.1, AD-55994.1, AD-55995.1, AD-55996.1, AD-55999.1, AD-56000.1, AD-56001.1, AD-56002.1, AD-56003.1, AD-56006.1, AD-56007.1, AD-56008.1, AD-56009.1, AD-56011.1, AD-56012.1, AD-56013.1, AD-56016.1, AD-56017.1, AD-56019.1, AD-56020.1, AD-56021.1, AD-56022.1, AD-56024.1, AD-56026.1, AD-56027.1, AD-56029.1, AD-56030.1, AD-56031.1, AD-56032.1, AD-56035.1, AD-56039.1, AD-56041.1, AD-56043.1, AD-56044.1, AD-56047.1, AD-56048.1, AD-56051.1, AD-56053.1, AD-56054.1, AD-56059.1, AD-56062.1, AD-56065.1, AD-56066.1, AD-60770.1, AD-60771.1, AD-60776.1, AD-60777.1, AD-60778.1, AD-60779.1, AD-60780.1, AD-60781.1, AD-60783.1, AD-60784.1, AD-60785.1, AD-60788.1, AD-60789.1, AD-60791.1, AD-60793.1, AD-60795.1, AD-60798.1, AD-60801.1, AD-67903.1, AD-67906.1, AD-67923.1, AD-67924.1, AD-67925.1, AD-67926.1, AD-67935.1, AD-67965.1, AD-67994.1, AD-67995.1, AD-67996.1, AD-68017.1, AD-68022.1, AD-68035.1, AD-68036.1, AD-68037.1, AD-68084.2, AD-68085.2, AD-68086.2, AD-68087.2, AD-68090.2, AD-68091.2, AD-68092.2, AD-68093.2, AD-68116.1, AD-68117.1, AD-68118.1, AD-68124.1, AD-68125.1, or AD-68126.1.

In one embodiment, the antisense strand comprises a region of complementarity which comprises at least 15 contiguous unmodified nucleotides differing by no more than 3 nucleotides from the antisense nucleotide sequence of AD-67327 (5'-AUUAGAAGAAAAGGUGGGAGACU-3'; SEQ ID NO:537). In another embodiment, the region of complementarity consists of the antisense unmodified nucleotide sequence of AD-67327 (5'-AUUA-GAAGAAAAGGUGGGAGACU-3'; SEQ ID NO:537). In one embodiment, the dsRNA comprises a sense strand consisting of the nucleotide sequence of 5'-UCUCCCAC-CUUUUCUUCUAAU-3' (SEQ ID NO:499), and an antisense strand consisting of the nucleotide sequence of 5'-UUAGAAGAAAAGGUGGGAGACU-3' (SEQ ID NO:537). In one embodiment, the double-stranded RNAi agent comprises the modified nucleotide sequence of AD-67327 (5'-uscsucccAfcCfUfUfuucuucuaau-3'; SEQ ID NO: 1037 and 5'-asUfsuagAfagaaaagGfuGfggagascsu-3'; SEQ ID NO: 1038.

In some embodiments, the modified nucleotide(s) is independently selected from the group consisting of a 2'-O-methyl modified nucleotide, a 2'-fluoro modified nucleotide, a nucleotide comprising a 5'-phosphorothioate group, and a terminal nucleotide linked to a cholesteryl derivative or a dodecanoic acid bisdecylamide group. In further embodiments, the modified nucleotide is selected from the group consisting of a 2'-deoxy-2'-fluoro modified nucleotide, a 2'-deoxy-modified nucleotide, a locked nucleotide, an unlocked nucleotide a conformationally restricted nucleotide, a contrained ethyl nucleotide, an abasic nucleotide, a 2'-amino-modified nucleotide, a 2'-alkyl-modified nucleotide, a 2'-O-allyl modified nucleotide, a 2'-C-allyl modified nucleotide, a 2'-hydroxyl modified nucleotide, a morpholino nucleotide, a phosphoramidate, and a non-natural base comprising nucleotide.

In another embodiment of the double-stranded RNAi agent, at least one strand comprises a 3' overhang of at least 1 nucleotide. In another embodiment, at least one strand comprises a 3' overhang of at least 2 nucleotides.

In another aspect, the present invention provides RNAi agents, e.g., double-stranded ribonucleic acid (RNAi) agents capable of inhibiting the expression of angiotensinogen (AGT) in a cell, wherein the double-stranded RNAi agent comprises a sense strand complementary to an antisense strand, wherein the antisense strand comprises a region complementary to part of an mRNA encoding AGT, wherein each strand is about 14 to about 30 nucleotides in length, wherein the double-stranded RNAi agent is represented by formula (III):

(III)
sense:
5' $n_p$-$N_a$-(X X X)$_i$-$N_b$-Y Y Y-$N_b$-(Z Z Z)$_j$-$N_a$-$n_q$ 3' antisense:
3' $n_{p'}$'-$N_{a'}$-(X'X'X')$_k$-$N_{b'}$'-Y'Y'Y'-$N_{b'}$'-(Z'Z'Z')$_l$-$N_{a'}$'-$n_{q'}$' 5' wherein:
i, j, k, and l are each independently 0 or 1;
p, p', q, and q' are each independently 0-6;
each $N_a$ and $N_a$' independently represents an oligonucleotide sequence comprising 0-25 nucleotides which are either modified or unmodified or combinations thereof, each sequence comprising at least two differently modified nucleotides;
each $N_b$ and $N_b$' independently represents an oligonucleotide sequence comprising 0-10 nucleotides which are either modified or unmodified or combinations thereof; each $n_p$, $n_p$', $n_q$, and $n_q$', each of which may or may not be present, independently represents an overhang nucleotide;
XXX, YYY, ZZZ, X'X'X', Y'Y'Y', and Z'Z'Z' each independently represent one motif of three identical modifications on three consecutive nucleotides;
modifications on $N_b$ differ from the modification on Y and modifications on $N_b$' differ from the modification on Y'; and
wherein the sense strand is conjugated to at least one ligand.

In one embodiment, i is 0; j is 0; i is 1; j is 1; both i and j are 0; or both i and j are 1. In another embodiment, k is 0; 1 is 0; k is 1; 1 is 1; both k and 1 are 0; or both k and 1 are 1.

In one embodiment, XXX is complementary to X'X'X', YYY is complementary to Y'Y'Y', and ZZZ is complementary to Z'Z'Z'.

In one embodiment, the YYY motif occurs at or near the cleavage site of the sense strand.

In another embodiment, the Y'Y'Y' motif occurs at the 11, 12 and 13 positions of the antisense strand from the 5'-end.

In one embodiment, Y' is 2'-O-methyl.

In one embodiment, formula (III) is represented by formula (IIIa):

(IIIa)
sense:
5' $n_p$-$N_a$-Y Y Y-$N_a$-$n_q$ 3' antisense:
3' $n_{p'}$'-$N_{a'}$-Y'Y'Y'-$N_{a'}$-$n_{q'}$' 5'.

In another embodiment, formula (III) is represented by formula (IIIb):

(IIIb)
sense:
5' $n_p$-$N_a$-Y Y Y-$N_b$-Z Z Z-$N_a$-$n_q$ 3' antisense:
3' $n_{p'}$'-$N_{a'}$-Y'Y'Y'-$N_{b'}$'-Z'Z'Z'-$N_{a'}$-$n_{q'}$' 5' wherein each $N_b$ and $N_b$' independently represents an oligonucleotide sequence comprising 1-5 modified nucleotides.

In yet another embodiment, formula (III) is represented by formula (IIIc):

(IIIc)
sense:
5' $n_p$-$N_a$-X X X-$N_b$-Y Y Y-$N_a$-$n_q$ 3' antisense:
3' $n_{p'}$'-$N_{a'}$-X'X'X'-$N_{b'}$'-Y'Y'Y'-$N_{a'}$-$n_{q'}$' 5' wherein each $N_b$ and $N_b$' independently represents an oligonucleotide sequence comprising 1-5 modified nucleotides.

In a further embodiment, formula (III) is represented by formula (IIId):

(IIId)
sense:
5' $n_p$-$N_a$-X X X-$N_b$-Y Y Y-$N_b$-Z Z Z-$N_a$-$n_q$ 3' antisense:
3' $n_{p'}$'-$N_{a'}$-X'X'X'-$N_{b'}$'-Y'Y'Y'-$N_{b'}$'-Z'Z'Z'-$N_{a'}$-$n_{q'}$' 5' wherein each $N_b$ and $N_b$' independently represents an oligonucleotide sequence comprising 1-5 modified nucleotides and each $N_a$ and $N_a$' independently represents an oligonucleotide sequence comprising 2-10 modified nucleotides.

In one embodiment, the double-stranded region is 15-30 nucleotide pairs in length. In another embodiment, the double-stranded region is 17-23 nucleotide pairs in length. In yet another embodiment, the double-stranded region is 17-25 nucleotide pairs in length. In a further embodiment, the double-stranded region is 23-27 nucleotide pairs in length. In another embodiment, the double-stranded region is 19-21 nucleotide pairs in length. In another embodiment, the double-stranded region is 19-23 nucleotide pairs in length. In another embodiment, the double-stranded region is 21-23 nucleotide pairs in length. In yet another embodiment, each strand has 15-30 nucleotides. In yet another embodiment, each strand has 19-30 nucleotides.

In one embodiment, the modifications on the nucleotides are selected from the group consisting of LNA, UNA, CRN, cEt, HNA, CeNA, 2'-methoxyethyl, 2'-O-alkyl, 2'-O-allyl, 2'-C-allyl, 2'-fluoro, 2'-deoxy, 2'-hydroxyl, and combinations thereof. In another embodiment, the modifications on the nucleotides are 2'-O-methyl or 2'-fluoro modifications.

In one embodiment, the ligand the ligand is one or more GalNAc derivatives attached through a bivalent or trivalent branched linker. In another embodiment, the ligand is

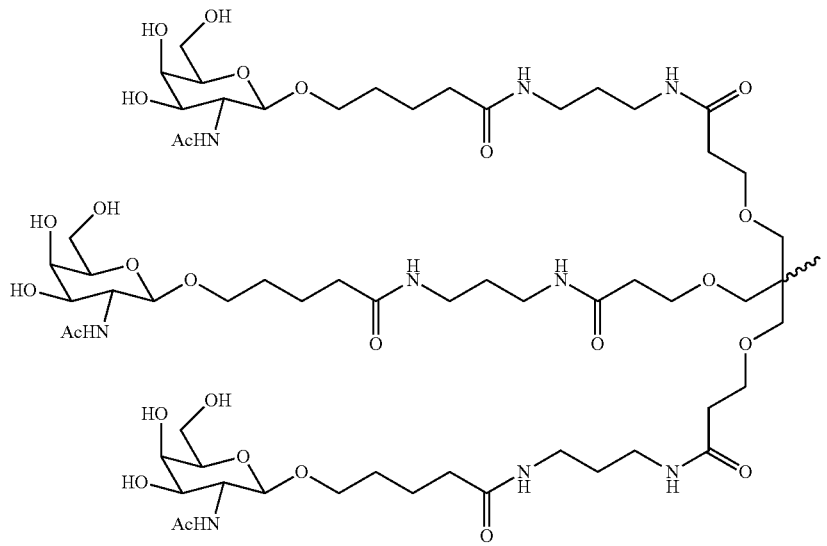

In one embodiment, the ligand is attached to the 3' end of the sense strand.

In another embodiment, the RNAi agent is conjugated to the ligand as shown in the following schematic

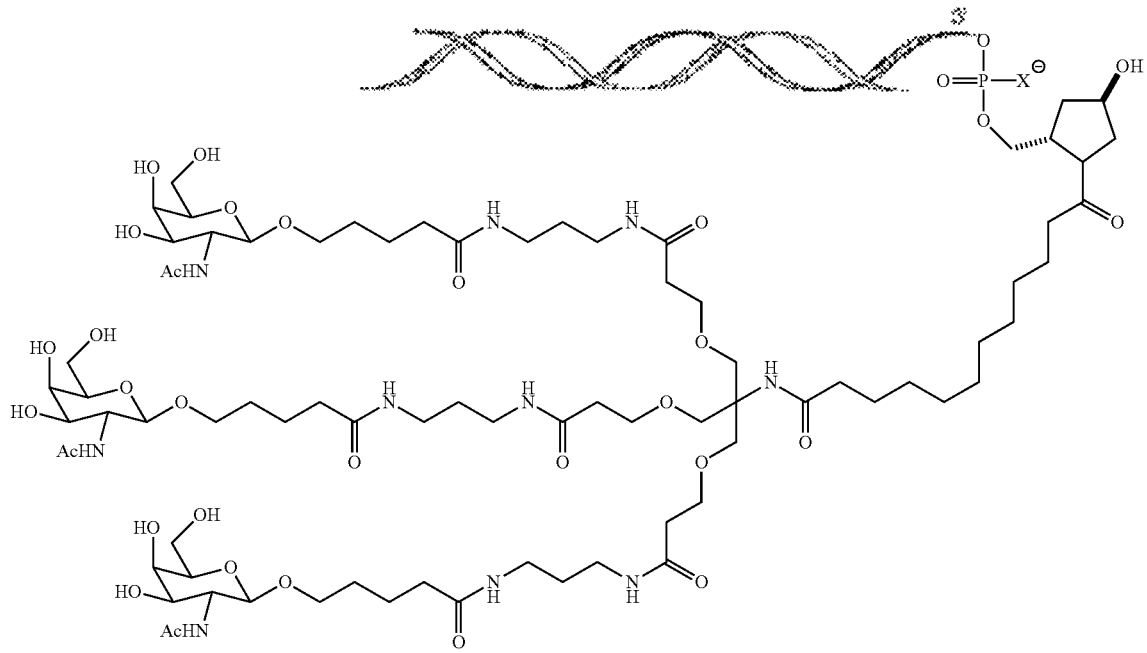

wherein X is O or S. In a specific embodiment, X is O.

In one embodiment, the agent further comprises at least one phosphorothioate or methylphosphonate internucleotide linkage.

In a further embodiment, the phosphorothioate or methylphosphonate internucleotide linkage is at the 3'-terminus of one strand. In another embodiment, the strand is the antisense strand. In another embodiment, the strand is the sense strand.

In one embodiment, the phosphorothioate or methylphosphonate internucleotide linkage is at the 5'-terminus of one strand. In another embodiment, the strand is the antisense strand. In a further embodiment, the strand is the sense strand.

In one embodiment, the phosphorothioate or methylphosphonate internucleotide linkage is at the both the 5'- and 3'-terminus of one strand. In another embodiment, the strand is the antisense strand.

In another embodiment, the double-stranded RNAi agent comprises 6-8 phosphorothioate internucleotide linkages. In a further embodiment, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus of the sense strand.

In one embodiment, the base pair at the 1 position of the 5'-end of the antisense strand of the duplex is an AU base pair. In another embodiment, the Y nucleotides contain a 2'-fluoro modification. In a further embodiment, the Y' nucleotides contain a 2'-O-methyl modification.

In one embodiment, $p'>0$. In another embodiment, $p'=2$. In a further embodiment, $q'=0$, $p=0$, $q=0$, and p' overhang nucleotides are complementary to the target mRNA. In yet a further embodiment, $q'=0$, $p=0$, $q=0$, and p' overhang nucleotides are non-complementary to the target mRNA.

In one embodiment, the sense strand has a total of 21 nucleotides and the antisense strand has a total of 23 nucleotides.

In another embodiment, at least one $n_p'$ is linked to a neighboring nucleotide via a phosphorothioate linkage. In a further embodiment, all $n_p'$ are linked to neighboring nucleotides via phosphorothioate linkages.

In another embodiment, the RNAi agent is selected from the group of RNAi agents listed in any one of Tables 3, 4, 7, 8, 11, 13, and 15.

In one aspect, the present invention provides double-stranded ribonucleic acid (RNAi) agents for inhibiting expression of angiotensinogen (AGT). The double-stranded RNAi agents include a sense strand and an antisense strand forming a double-stranded region, wherein the sense strand comprises at least 15 contiguous nucleotides differing by no more than 3 nucleotides from the nucleotide sequence of SEQ ID NO: 1 and the antisense strand comprises at least 15 contiguous nucleotides differing by no more than 3 nucleotides from the nucleotide sequence of SEQ ID NO:2, wherein substantially all of the nucleotides of the sense strand comprise a modification selected from the group consisting of a 2'-O-methyl modification and a 2'-fluoro modification wherein the sense strand comprises two phosphorothioate internucleotide linkages at the 5'-terminus, wherein substantially all of the nucleotides of the antisense strand comprise a modification selected from the group consisting of a 2'-O-methyl modification and a 2'-fluoro modification, wherein the antisense strand comprises two phosphorothioate internucleotide linkages at the 5'-terminus and two phosphorothioate internucleotide linkages at the 3'-terminus, and wherein the sense strand is conjugated to one or more GalNAc derivatives attached through a branched bivalent or trivalent linker at the 3'-terminus.

In one embodiment, all of the nucleotides of the sense strand and all of the nucleotides of the antisense strand comprise a modification.

In another aspect, the present invention provides RNAi agents, e.g., double-stranded ribonucleic acid (RNAi) agents capable of inhibiting the expression of AGT (angiotensinogen) in a cell, wherein the double-stranded RNAi agent comprises a sense strand complementary to an antisense strand, wherein the antisense strand comprises a region complementary to part of an mRNA encoding AGT, wherein each strand is about 14 to about 30 nucleotides in length, wherein the double-stranded RNAi agent is represented by formula (III):

(III)
sense:
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:
i, j, k, and l are each independently 0 or 1;
p, p', q, and q' are each independently 0-6;
each $N_a$ and $N_a'$ independently represents an oligonucleotide sequence comprising 0-25 nucleotides which are either modified or unmodified or combinations thereof, each sequence comprising at least two differently modified nucleotides;
each $N_b$ and $N_b'$ independently represents an oligonucleotide sequence comprising 0-10 nucleotides which are either modified or unmodified or combinations thereof;
each $n_p$, $n_p'$, $n_q$, and $n_q'$, each of which may or may not be present independently represents an overhang nucleotide;
XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;
modifications on $N_b$ differ from the modification on Y and modifications on $N_b'$ differ from the modification on Y'; and
wherein the sense strand is conjugated to at least one ligand.

In yet another aspect, the present invention provides RNAi agents, e.g., double-stranded ribonucleic acid (RNAi) agents capable of inhibiting the expression of angiotensinogen (AGT) in a cell, wherein the double-stranded RNAi agent comprises a sense strand complementary to an antisense strand, wherein the antisense strand comprises a region complementary to part of an mRNA encoding AGT, wherein each strand is about 14 to about 30 nucleotides in length, wherein the double-stranded RNAi agent is represented by formula (III):

(III)
sense:
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:
i, j, k, and l are each independently 0 or 1;
each $n_p$, $n_q$, and $n_q'$, each of which may or may not be present, independently represents an overhang nucleotide;
p, q, and q' are each independently 0-6;
$n_p'>0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand.

In a further aspect, the present invention provides RNAi agents, e.g., double-stranded ribonucleic acid (RNAi agent) capable of inhibiting the expression of angiotensinogen (AGT) in a cell, wherein the double-stranded RNAi agent comprises a sense strand complementary to an antisense strand, wherein the antisense strand comprises a region complementary to part of an mRNA encoding AGT, wherein each strand is about 14 to about 30 nucleotides in length, wherein the double-stranded RNAi agent is represented by formula (III):

$$\text{sense:} \quad 5' \; n_p\text{-}N_a\text{-}(X\,X\,X)_i\text{-}N_b\text{-}Y\,Y\,Y\text{-}N_b\text{-}(Z\,Z\,Z)_j\text{-}N_a\text{-}n_q \; 3' \quad (III)$$

$$\text{antisense:} \quad 3' \; n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q' \; 5'$$

wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p' > 0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y'; and wherein the sense strand is conjugated to at least one ligand, wherein the ligand is one or more GalNAc derivatives attached through a bivalent or trivalent branched linker.

In another aspect, the present invention provides RNAi agents, e.g., double-stranded ribonucleic acid (RNAi) agents capable of inhibiting the expression of angiotensinogen (AGT) in a cell, wherein the double-stranded RNAi agent comprises a sense strand complementary to an antisense strand, wherein the antisense strand comprises a region complementary to part of an mRNA encoding AGT, wherein each strand is about 14 to about 30 nucleotides in length, wherein the double-stranded RNAi agent is represented by formula (III):

$$\text{sense:} \quad 5' \; n_p\text{-}N_a\text{-}(X\,X\,X)_i\text{-}N_b\text{-}Y\,Y\,Y\text{-}N_b\text{-}(Z\,Z\,Z)_j\text{-}N_a\text{-}n_q \; 3' \quad (III)$$

$$\text{antisense:} \quad 3' \; n_p'\text{-}N_a'\text{-}(X'X'X')_k\text{-}N_b'\text{-}Y'Y'Y'\text{-}N_b'\text{-}(Z'Z'Z')_l\text{-}N_a'\text{-}n_q' \; 5'$$

wherein:

i, j, k, and l are each independently 0 or 1;

each $n_p$, $n_q$, and $n_q'$, each of which may or may not be present, independently represents an overhang nucleotide;

p, q, and q' are each independently 0-6;

$n_p' > 0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

each $N_b$ and $N_b'$ independently represents an oligonucleotide sequence comprising 0-10 nucleotides which are either modified or unmodified or combinations thereof;

XXX, YYY, ZZZ, X'X'X', Y'Y'Y', and Z'Z'Z' each independently represent one motif of three identical modifications on three consecutive nucleotides, and wherein the modifications are 2'-O-methyl or 2'-fluoro modifications;

modifications on $N_b$ differ from the modification on Y and modifications on $N_b'$ differ from the modification on Y';

wherein the sense strand comprises at least one phosphorothioate linkage; and wherein the sense strand is conjugated to at least one ligand, wherein the ligand is one or more GalNAc derivatives attached through a bivalent or trivalent branched linker.

In yet another aspect, the present invention provides RNAi agents, e.g., double-stranded ribonucleic acid (RNAi) agent capable of inhibiting the expression of angiotensinogen (AGT) in a cell, wherein the double-stranded RNAi agent comprises a sense strand complementary to an antisense strand, wherein the antisense strand comprises a region complementary to part of an mRNA encoding AGT, wherein each strand is about 14 to about 30 nucleotides in length, wherein the double-stranded RNAi agent is represented by formula (III):

$$\text{sense:} \quad 5' \; n_p\text{-}N_a\text{-}Y\,Y\,Y\text{-}N_a\text{-}n_q \; 3' \quad (IIIa)$$

$$\text{antisense:} \quad 3' \; n_p'\text{-}N_a'\text{-}Y'Y'Y'\text{-}N_a'\text{-}n_q' \; 5'$$

wherein:

each $n_p$, $n_q$, and $n_q'$, each of which may or may not be present, independently represents an overhang nucleotide;

p, q, and q' are each independently 0-6;

$n_p' > 0$ and at least one $n_p'$ is linked to a neighboring nucleotide via a phosphorothioate linkage;

each $N_a$ and $N_a'$ independently represents an oligonucleotide sequence comprising 0-25 nucleotides which are either modified or unmodified or combinations thereof, each sequence comprising at least two differently modified nucleotides;

YYY and Y'Y'Y' each independently represent one motif of three identical modifications on three consecutive nucleotides, and wherein the modifications are 2'-O-methyl or 2'-fluoro modifications;

wherein the sense strand comprises at least one phosphorothioate linkage; and wherein the sense strand is conjugated to at least one ligand, wherein the ligand is one or more GalNAc derivatives attached through a bivalent or trivalent branched linker.

In another aspect, the present invention provides a double-stranded RNAi agent comprising the RNAi agents listed in any one of Tables 3, 4, 7, 8, 11, 13, and 15.

In another aspect, the present invention provides a composition comprising a modified antisense polynucleotide agent, wherein the agent is capable of inhibiting the expression of angiotensinogen (AGT) in a cell, and comprises a sequence complementary to a sense sequence selected from the group of the sequences listed in Tables 3, 4, 7, 8, 11, 13, and 15, wherein the polynucleotide is about 14 to about 30 nucleotides in length, The present invention also provides cells, vectors, host cells and pharmaceutical compositions comprising the double-stranded RNAi agents of the invention.

In one embodiment, a cell contains the double-stranded RNAi agent.

In some embodiments, the double-stranded RNAi agent or the composition comprising a modified antisense polynucleotide agent is administered using a pharmaceutical composition.

In one embodiment, the pharmaceutical compositions of the invention comprise a lipid formulation, such as XTC or MC3.

In preferred embodiments, the double-stranded RNAi agent is administered in a solution. In some embodiments, the double-stranded RNAi agent is administered in an unbuffered solution. In another embodiment, the unbuffered solution is saline or water. In another embodiment, the double-stranded RNAi agent is administered with a buffer solution. In yet another embodiment, the buffer solution comprises acetate, citrate, prolamine, carbonate, or phosphate or any combination thereof. In some embodiment, the buffer solution is phosphate buffered saline (PBS).

In another aspect, the present invention provides methods of inhibiting angiotensinogen (AGT) expression in a cell. The methods include contacting the cell with the double-stranded RNAi agent, a pharmaceutical composition, a composition comprising a modified antisense polynucleotide agent, or a vector comprising the RNAi agent and maintaining the cell produced for a time sufficient to obtain degradation of the mRNA transcript of a AGT gene, thereby inhibiting expression of the AGT gene in the cell.

In one embodiment, the cell is within a subject. In a further embodiment, the subject is a human. In a further embodiment, the subject suffers from an angiotensinogen-associated disease.

In one embodiment, the AGT expression is inhibited by at least about 30%, about 40%, about 50%, about 60%, about 70%, about 80%, about 90%, about 95%, about 98% or about 100%.

In one embodiment, the sense strand comprises at least 15 contiguous nucleotides differing by no more than 3 nucleotides from nucleotides 2801-2101; 803-843; 834-859; 803-859; 803-875; 834-875; 847-875; 1247-1271; 1566-1624; 1570-1624; 1584-1624; 1584-1624; 1584-1621; 2035-2144; 2070-2144; 2070-2103; 2201-2223; 2227-2360; 2227-2304; 2290-2318; 2304-2350; 2304-2326; 2320-2342; 2333-2360; 2333-2358; 485-503; 517-535; 560-578; 635-653; 803-821; 814-832; 822-840; 825-843; 834-852; 837-855; 841-859; 855-873; 967-985; 1247-1265; 1248-1266; 1249-1267; 1251-1269; 1253-1271; 1566-1584; 1570-1588; 1572-1590; 1574-1592; 1584-1602; 1587-1605; 1591-1609; 1592-1610; 1595-1613; 1601-1619; 1602-1620; 1605-1623; 1729-1747; 1738-1756; 1739-1757; 1741-1769; 1767-1785; 1810-1828; 1827-1845; 1880-1989; 1892-1914; 1894-1914; 1894-2012; 2035-2053; 2046-2064; 2057-2075; 2070-2088; 2072-2090; 2078-2096; 2078-2107; 2078-2011; 2080-2098; 2081-2099; 2081-2104; 2081-2011; 2082-2100; 2084-2102; 2084-2011; 2090-2108; 2100-2118; 2111-2129; 2124-2142; 2125-2143; 2167-2185; 2179-2197; 2201-2219; 2202-2220; 2203-2221; 2204-2222; 2227-2245; 2230-2248; 2234-2252; 2244-2264; 2255-2273; 2266-2284; 2268-2286; 2270-2288; 2279-2297; 2281-2299; 2283-2301; 2284-2302; 2285-2303; 2286-2304; 2288-2306; 2290-2308; 2291-2309; 2291-2311; 2291-2318; 2291-2315; 2292-2310; 2294-2312; 2296-2314; 2299-2317; 2304-2322; 2304-2329; 2306-2324; 2307-2325; 2309-2327; 2309-2329; 2309-2342; 2309-2350; 2309-2358; 2314-2332; 2316-2334; 2317-2335; 2320-2338; 2321-2339; 2323-2341; 2325-2343; 2326-2344; 2328-2346; 2329-2347; 2331-2349; 2333-2351; 2334-2352; 2335-2353; 2339-2357; 2340-2358; or 2341-2359 of the nucleotide sequence of SEQ ID NO: 1.

In another aspect, the present invention provides methods of treating a subject having a angiotensinogen (AGT)-associated disorder, comprising administering to the subject a therapeutically effective amount of the double-stranded RNAi agent, a composition comprising a modified antisense polynucleotide agent, or a pharmaceutical composition comprising the double-stranded RNAi agent, thereby treating the subject.

In another aspect, the present invention provides methods of treating a subject having a angiotensinogen (AGT)-associated disorder which include subcutaneously administering to the subject a therapeutically effective amount of a double-stranded ribonucleic acid (RNAi agent), wherein the double-stranded RNAi agent comprises a sense strand and an antisense strand forming a double-stranded region, wherein the sense strand comprises at least 15 contiguous nucleotides differing by no more than 3 nucleotides from the nucleotide sequence of SEQ ID NO: 1 and the antisense strand comprises at least 15 contiguous nucleotides differing by no more than 3 nucleotides from the nucleotide sequence of SEQ ID NO:2, wherein substantially all of the nucleotides of the antisense strand comprise a modification selected from the group consisting of a 2'-O-methyl modification and a 2'-fluoromodification, wherein the antisense strand comprises two phosphorothioate internucleotide linkages at the 5'-terminus and two phosphorothioate internucleotide linkages at the 3'-terminus, wherein substantially all of the nucleotides of the sense strand comprise a modification selected from the group consisting of a 2'-O-methyl modification and a 2'-fluoro modification, wherein the sense strand comprises two phosphorothioate internucleotide linkages at the 5'-terminus and, wherein the sense strand is conjugated to one or more GalNAc derivatives attached through a branched bivalent or trivalent linker at the 3'-terminus.

In one embodiment, all of the nucleotides of the sense strand and all of the nucleotides of the antisense strand comprise a modification.

In another aspect, the present invention provides methods of treating a subject having a angiotensinogen (AGT)-associated disorder which include administering to the subject a therapeutically effective amount of a double-stranded ribonucleic acid (RNAi agent), wherein the double-stranded RNAi agent comprises a sense strand and an antisense strand forming a double-stranded region, wherein the sense strand comprises at least 15 contiguous nucleotides differing by no more than 3 nucleotides from nucleotides 2801-2101; 803-843; 834-859; 803-859; 803-875; 834-875; 847-875; 1247-1271; 1566-1624; 1570-1624; 1584-1624; 1584-1624; 1584-1621; 2035-2144; 2070-2144; 2070-2103; 2201-2223; 2227-2360; 2227-2304; 2290-2318; 2304-2350; 2304-2326; 2320-2342; 2333-2360; 2333-2358; 485-503; 517-535; 560-578; 635-653; 803-821; 814-832; 822-840; 825-843; 834-852; 837-855; 841-859; 855-873; 967-985; 1247-1265; 1248-1266; 1249-1267; 1251-1269; 1253-1271; 1566-1584; 1570-1588; 1572-1590; 1574-1592; 1584-1602; 1587-1605; 1591-1609; 1592-1610; 1595-1613; 1601-1619; 1602-1620; 1605-1623; 1729-1747; 1738-1756; 1739-1757; 1741-1769; 1767-1785; 1810-1828; 1827-1845; 1880-1989; 1892-1914; 1894-1914; 1894-2012; 2035-2053; 2046-2064; 2057-2075; 2070-2088; 2072-2090; 2078-2096; 2078-2107; 2078-2011; 2080-2098; 2081-2099; 2081-2104; 2081-2011; 2082-2100; 2084-2102; 2084-2011; 2090-2108; 2100-2118; 2111-2129; 2124-2142; 2125-2143; 2167-2185; 2179-2197; 2201-2219; 2202-2220; 2203-2221; 2204-2222; 2227-2245; 2230-2248; 2234-2252; 2244-2264; 2255-2273; 2266-2284; 2268-2286; 2270-2288; 2279-2297; 2281-2299; 2283-2301; 2284-2302; 2285-2303; 2286-2304; 2288-2306; 2290-2308; 2291-2309; 2291-2311; 2291-2318; 2291-2315; 2292-2310; 2294-2312; 2296-2314; 2299-2317; 2304-2322; 2304-2329; 2306-2324; 2307-2325; 2309-2327; 2309-2329; 2309-2342; 2309-2350; 2309-2358; 2314-2332; 2316-2334; 2317-2335; 2320-2338; 2321-2339; 2323-2341; 2325-2343; 2326-2344; 2328-2346; 2329-2347; 2331-2349; 2333-2351; 2334-2352; 2335-2353; 2339-2357; 2340-2358; or 2341-2359 of the nucleotide sequence of SEQ ID NO: 1 and the antisense strand comprises at least 15 contiguous nucleotides differing by no more than 3 nucleotides from the nucleotides at the corresponding position of the nucleotide sequence of SEQ ID NO:2 such that the antisense strand is substantially complementary to the at least 15 contiguous nucleotides in the sense strand. In certain embodiments, substantially all of the nucleotides of the sense strand are modified nucleotides. In other embodiments, substantially all of the nucleotides of the antisense strand are modified nucleotides. In yet other embodiments, substantially all of the nucleotides of both strands are modified nucleotides. In one embodiment, all of the nucleotides of the sense strand and all of the nucleotides of the antisense strand are modified nucleotides. In one embodiment, the sense strand is conjugated to a ligand attached at the 3'-terminus.

In another aspect, the present invention provides methods of treating a subject having a angiotensinogen (AGT)-associated disorder which include administering to the subject a therapeutically effective amount of a double-stranded ribonucleic acid (RNAi agent), wherein the double-stranded RNAi agent comprises a sense strand and an antisense strand forming a double-stranded region, wherein the sense strand comprises at least 15 contiguous nucleotides from nucleotides 803-843; 834-859; 803-859; 1247-1271; 1566-1624; 1570-1624; 1584-1624; 1584-1624; 1584-1621; 2035-2144; 2070-2144; 2070-2103; 2201-2223; 2227-2360; 2227-2304; 2290-2318; 2304-2350; 2304-2326; 2320-2342; 2333-2360; 2333-2358; 485-503; 517-535; 560-578; 635-653; 803-821; 814-832; 822-840; 825-843; 834-852; 837-855; 841-859; 855-873; 967-985; 1247-1265; 1248-1266; 1249-1267; 1251-1269; 1253-1271; 1566-1584; 1570-1588; 1572-1590; 1574-1592; 1584-1602; 1587-1605; 1591-1609; 1592-1610; 1595-1613; 1601-1619; 1602-1620; 1605-1623; 1729-1747; 1738-1756; 1739-1757; 1741-1769; 1767-1785; 1810-1828; 1827-1845; 1880-1989; 1894-2012; 2035-2053; 2046-2064; 2057-2075; 2070-2088; 2072-2090; 2078-2096; 2080-2098; 2081-2099; 2082-2100; 2084-2102; 2090-2108; 2100-2118; 2111-2129; 2124-2142; 2125-2143; 2167-2185; 2179-2197; 2201-2219; 2202-2220; 2203-2221; 2204-2222; 2227-2245; 2230-2248; 2234-2252; 2244-2264; 2255-2273; 2266-2284; 2268-2286; 2270-2288; 2279-2297; 2281-2299; 2283-2301; 2284-2302; 2285-2303; 2286-2304; 2288-2306; 2290-2308; 2291-2309; 2292-2310; 2294-2312; 2296-2314; 2299-2317; 2304-2322; 2306-2324; 2307-2325; 2309-2327; 2314-2332; 2316-2334; 2317-2335; 2320-2338; 2321-2339; 2323-2341; 2325-2343; 2326-2344; 2328-2346; 2329-2347; 2331-2349; 2333-2351; 2334-2352; 2335-2353; 2339-2357; 2340-2358; or 2341-2359 of the nucleotide sequence of SEQ ID NO: 1 and the antisense strand comprises at least 15 contiguous nucleotides from the nucleotides at the corresponding position of the nucleotide sequence of SEQ ID NO:2 such that the antisense strand is substantially complementary to the at least 15 contiguous nucleotides in the sense strand. In certain embodiments, substantially all of the nucleotides of the sense strand are modified nucleotides. In other embodiments, substantially all of the nucleotides of the antisense strand are modified nucleotides. In yet other embodiments, substantially all of the nucleotides of both strands are modified nucleotides. In one embodiment, the sense strand is conjugated to a ligand attached at the 3'-terminus.

In one embodiment, the subject is a human.

In one embodiment, the angiotensinogen-associated disease is selected from the group consisting of hypertension, borderline hypertension, primary hypertension, secondary hypertension, hypertensive emergency, hypertensive urgency, isolated systolic or diastolic hypertension, pregnancy-associated hypertension, diabetic hypertension, resistant hypertension, refractory hypertension, paroxysmal hypertension, renovascular hypertension, Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy, diabetic nephropathy, diabetic retinopathy, chronic heart failure, cardiomyopathy, diabetic cardiac myopathy, glomerulosclerosis, coarctation of the aorta, aortic aneurism, ventricular fibrosis, Cushing's syndrome, and other glucocorticoid excess states including chronic steroid therapy, pheochromocytoma, reninoma, secondary aldosteronism and other mineralocorticoid excess states, sleep apnea, thyroid/parathyroid disease, heart failure, myocardial infarction, angina, stroke, diabetes mellitus, renal disease, renal failure, systemic sclerosis, intrauterine growth restriction (IUGR), and fetal growth restriction.

In another embodiment, the angiotensinogen-associated disease is selected from the group consisting of hypertension, hypertensive heart disease, hypertensive nephropathy, pregnancy-associated hypertension, atherosclerosis, arteriosclerosis, chronic kidney disease, glomerulosclerosis, coarctation of the aorta, aortic aneurism, ventricular fibrosis, Cushing's syndrome, and other glucocorticoid excess states including chronic steroid therapy, pheochromocytoma, primary aldosteronism and other mineralocorticoid excess states, sleep apnea, thyroid/parathyroid disease, heart failure, myocardial infarction, stroke, diabetes mellitus, renal failure, and systemic sclerosis.

In one embodiment, the angiotensinogen-associated disease is pregnancy-associated hypertension (e.g., pregnancy-induced hypertension, preeclampsia, and eclampsia) and administration of an iRNA of the invention to a subject results in a decrease in maternal blood pressure; a decrease in maternal albuminuria; an increase in uteroplacental unit weight; an increase in fetal weight; normalization of the fetal brain:liver ratio; a decrease in AGT mRNA expression in the maternal liver and no significant decrease in hAGT mRNA expression in the placenta; an increase in overall placenta size; an increase in the size of the villous placenta; no significant change in the size of the trophospongium of the placenta; a reduction in the ratio of sFLT1:PLGF mRNA expression in the maternal kidney; a reduction in the ratio of serum sFLT1:PLGF levels; and/or a decrease in the level of agonistic autoantibodies to AT1.

In one embodiment, the double-stranded RNAi agent is administered at a dose of about 0.01 mg/kg to about 10 mg/kg or about 0.5 mg/kg to about 50 mg/kg. In a preferred embodiment, the double-stranded RNAi agent is administered at a dose of about 10 mg/kg, about 30 mg/kg, or about 3.0 mg/kg. In one embodiment, the double-stranded RNAi agent is administered at a dose of about 10 mg/kg. In one embodiment, the double-stranded RNAi agent is administered at a dose of about 0.5 mg/kg twice per week. In another embodiment, the double-stranded RNAi agent is administered at a dose of about 10 mg/kg every other week. In another embodiment, the double-stranded RNAi agent is administered at a dose of about 0.5-1.0 mg/kg once per week. In another embodiment, the RNAi agent is administered about once per week, once per month, once every other two months, or once a quarter (i.e., once every three months) at a dose of about 0.1 mg/kg to about 5.0 mg/kg.

In one embodiment, the double-stranded RNAi agent is administered subcutaneously or intravenously.

In one embodiment, the RNAi agent is administered in two or more doses.

In one embodiment, the RNAi agent is administered at intervals selected from the group consisting of once every about 12 hours, once every about 24 hours, once every about 48 hours, once every about 72 hours, and once every about 96 hours.

In one embodiment, the RNAi agent is administered twice per week.

In one embodiment, the RNAi agent is administered every other week.

In certain embodiments, the RNAi agent is administered once per month.

In certain embodiments, the RNAi agent is administered once every other month.

In certain embodiments, the RNAi agent is administered once per quarter (i.e., every three months).

In yet another embodiment, the methods further comprise administering to the subject, an additional therapeutic agent. In some embodiments, the additional therapeutic agent is selected from the group consisting of a diuretic, an angiotensin converting enzyme (ACE) inhibitor, an angiotensin II receptor antagonist, a beta-blocker, a vasodialator, a calcium channel blocker, an aldosterone antagonist, an alpha$_2$-agonist, a renin inhibitor, an alpha-blocker, a peripheral acting adrenergic agent, a selective D1 receptor partial agonist, a nonselective alpha-adrenergic antagonist, a synthetic, steroidal antimineralocorticoid agent, or a combination of any of the foregoing, and a hypertension therapeutic agent formulated as a combination of agents.

DETAILED DESCRIPTION OF THE INVENTION

Figure 1:
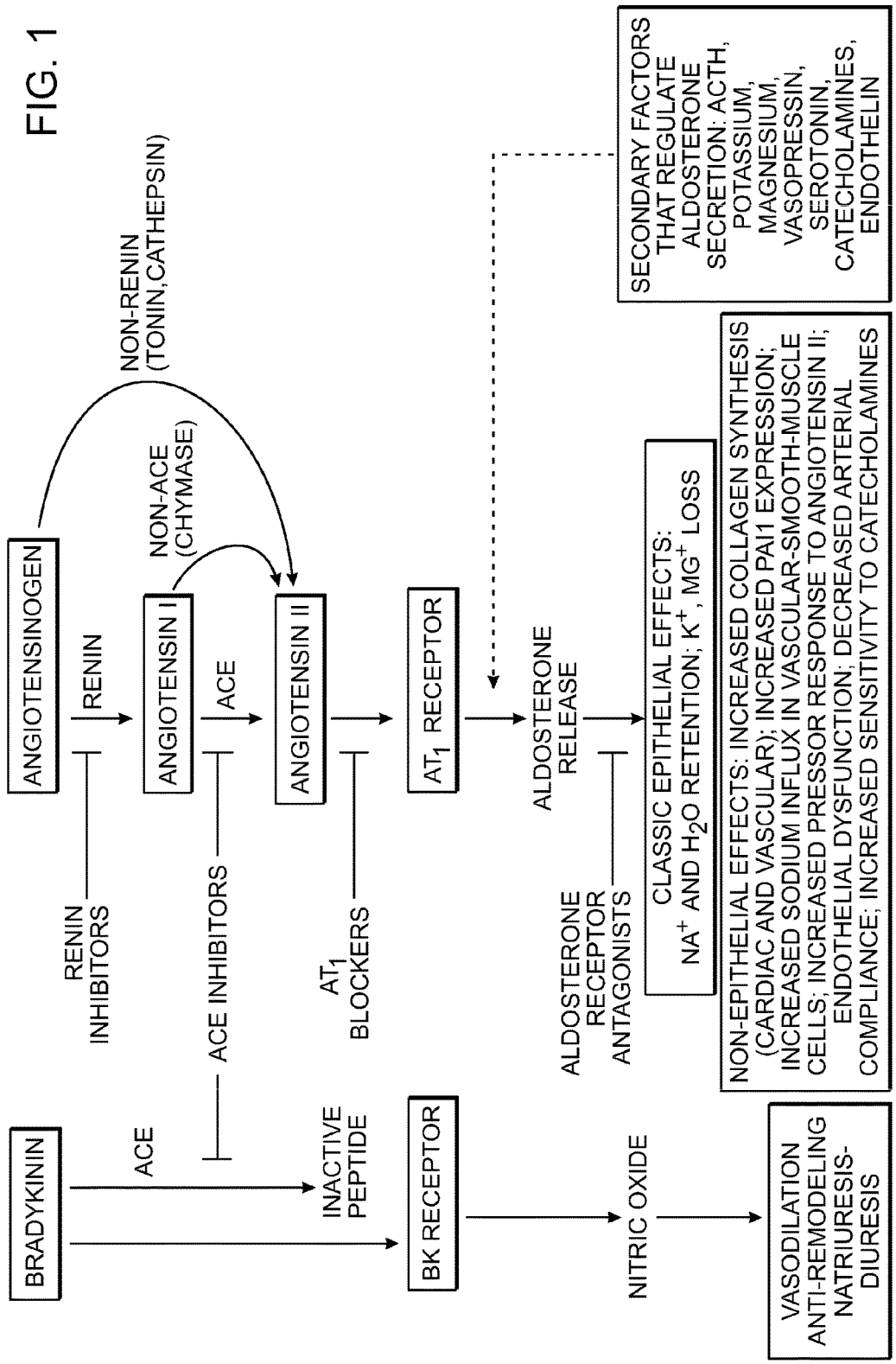
FIG. 1 is a schematic of the renin-angiotensin-aldosterone system (RAAS) including an indication of the various points in the system which have been the targets for therapeutic intervention (from Zaman, et al. (2002) *Nat Rev Drug Disc* 1:621).

The present invention provides iRNA compositions, which effect the RNA-induced silencing complex (RISC)-mediated cleavage of RNA transcripts of an angiotensinogen (AGT) gene. The gene may be within a cell, e.g., a cell within a subject, such as a human.

The present invention also provides methods for treating a subject having a disorder that would benefit from inhibiting or reducing the expression of an AGT gene, e.g., an angiotensinogen-associated disease, such as hypertension or pregnancy-associated hypertension, using iRNA compositions which effect the RNA-induced silencing complex (RISC)-mediated cleavage of RNA transcripts of an AGT gene.

The iRNAs of the invention include an RNA strand (the antisense strand) having a region which is about 30 nucleotides or less in length, e.g., 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length, which region is substantially complementary to at least part of an mRNA transcript of an AGT gene. In certain embodiments, the iRNAs of the invention include an RNA strand (the antisense strand) which can include longer lengths, for example up to 66 nucleotides, e.g., 36-66, 26-36, 25-36, 31-60, 22-43, 27-53 nucleotides in length with a region of at least 19 contiguous nucleotides that is substantially complementary to at least a part of an mRNA transcript of an AGT gene. These iRNAs with the longer length antisense strands include a second RNA strand (the sense strand) of 20-60 nucleotides in length wherein the sense and antisense strands form a duplex of 18-30 contiguous nucleotides. The use of these iRNAs enables the targeted degradation of mRNAs of the corresponding gene (AGT gene) in mammals. Very low dosages of the iRNAs of the invention, in particular, can specifically and efficiently mediate RNA interference (RNAi), resulting in significant inhibition of expression of the corresponding gene (AGT gene). Using in vitro and in vivo assays, the present inventors have demonstrated that iRNAs targeting an angiotensinogen gene can mediate RNAi, resulting in significant inhibition of expression of AGT, as well as reducing the symptoms associated with an angiotensinogen-associated disease, such as pregnancy-associated hypertension (e.g., pregnancy-induced hypertension, preeclampsia, and eclampsia). Thus, methods and compositions including these iRNAs are useful for treating a subject having an angiotensinogen-associated disease, such as hypertension.

The following detailed description discloses how to make and use compositions containing iRNAs to inhibit the expression of an angiotensinogen gene as well as compositions, uses, and methods for treating subjects having diseases and disorders that would benefit from inhibition and/or reduction of the expression of AGT.

I. Definitions

In order that the present invention may be more readily understood, certain terms are first defined. In addition, it should be noted that whenever a value or range of values of a parameter are recited, it is intended that values and ranges intermediate to the recited values are also intended to be part of this invention.

The articles "a" and "an" are used herein to refer to one or to more than one (i.e., to at least one) of the grammatical object of the article. By way of example, "an element" means one element or more than one element, e.g., a plurality of elements.

The term "including" is used herein to mean, and is used interchangeably with, the phrase "including but not limited to".

The term "or" is used herein to mean, and is used interchangeably with, the term "and/or," unless context clearly indicates otherwise.

The term "about" is used herein to mean within the typical ranges of tolerances in the art. As used herein, "angiotensinogen," used interchangeably with the term "AGT" refers to the well-known gene and polypeptide, also known in the art as Serpin Peptidase Inhibitor, Clade A, Member 8; Alpha-1 Antiproteinase; Antitrypsin; SERPINA8; Angiotensin I; Serpin A8; Angiotensin II; Alpha-1 Antiproteinase angiotensinogen; antitrypsin; pre-angiotensinogen2; ANHU; Serine Proteinase Inhibitor; and Cysteine Proteinase Inhibitor.

The term "AGT" includes human AGT, the amino acid and complete coding sequence of which may be found in for example, GenBank Accession No. GI: 188595658 (NM_000029.3; SEQ ID NO: 1); *Macaca fascicularis* AGT, the amino acid and complete coding sequence of which may be found in for example, GenBank Accession No. GI: 90075391 (AB170313.1: SEQ ID NO:3); mouse (*Mus musculus*) AGT, the amino acid and complete coding sequence of which may be found in for example, GenBank Accession No. GI: 113461997 (NM_007428.3; SEQ ID NO:5); and rat AGT (*Rattus norvegicus*) AGT the amino acid and complete coding sequence of which may be found in for example, for example GenBank Accession No. GI:51036672 (NM_134432; SEQ ID NO:7).

Additional examples of AGT mRNA sequences are readily available using publicly available databases, e.g., GenBank, UniProt, OMIM, and the *Macaca* genome project web site.

The term "AGT," as used herein, also refers to naturally occurring DNA sequence variations of the AGT gene, such as a single nucleotide polymorphism (SNP) in the AGT gene. Exemplary SNPs may be found in the dbSNP database available at www.ncbi.nlm.nih.gov/projects/SNP/snp_ref.cgi?geneId=183. Non-limiting examples of sequence variations within the AGT gene include, for example, those described in U.S. Pat. No. 5,589,584, the entire contents of which are incorporated herein by reference. For example, sequence variations within the AGT gene may include as a C→T at position −532 (relative to the transcription start site); a G→A at position −386; a G-A at position −218; a C→T at position −18; a G→A and a A→C at position −6 and −10; a C→T at position +10 (untanslated); a C→T at position +521 (T174M); a T→C at position +597 (P199P); a T→C at position +704 (M235T; also see, e.g., Reference SNP (refSNP) Cluster Report: rs699, available at www.ncbi.nlm.nih.gov/SNP); a A-G at position +743 (Y248C); a C-T at position +813 (N271N); a G-A at position +1017 (L339L); a C-A at position +1075 (L359M); and/or a G-A at position +1162 (V388M).

As used herein, "target sequence" refers to a contiguous portion of the nucleotide sequence of an mRNA molecule formed during the transcription of an AGT gene, including mRNA that is a product of RNA processing of a primary transcription product. In one embodiment, the target portion of the sequence will be at least long enough to serve as a substrate for iRNA-directed cleavage at or near that portion of the nucleotide sequence of an mRNA molecule formed during the transcription of an AGT gene.

The target sequence may be from about 9-36 nucleotides in length, e.g., about 15-30 nucleotides in length. For example, the target sequence can be from about 15-30 nucleotides, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

As used herein, the term "strand comprising a sequence" refers to an oligonucleotide comprising a chain of nucleotides that is described by the sequence referred to using the standard nucleotide nomenclature.

"G," "C," "A," "T" and "U" each generally stand for a nucleotide that contains guanine, cytosine, adenine, thymidine and uracil as a base, respectively. However, it will be understood that the term "ribonucleotide" or "nucleotide" can also refer to a modified nucleotide, as further detailed below, or a surrogate replacement moiety (see, e.g., Table 2). The skilled person is well aware that guanine, cytosine, adenine, and uracil can be replaced by other moieties without substantially altering the base pairing properties of an oligonucleotide comprising a nucleotide bearing such replacement moiety. For example, without limitation, a nucleotide comprising inosine as its base can base pair with nucleotides containing adenine, cytosine, or uracil. Hence, nucleotides containing uracil, guanine, or adenine can be replaced in the nucleotide sequences of dsRNA featured in the invention by a nucleotide containing, for example, inosine. In another example, adenine and cytosine anywhere in the oligonucleotide can be replaced with guanine and uracil, respectively to form G-U Wobble base pairing with the target mRNA. Sequences containing such replacement moieties are suitable for the compositions and methods featured in the invention.

The terms "iRNA", "RNAi agent," "iRNA agent,", "RNA interference agent" as used interchangeably herein, refer to an agent that contains RNA as that term is defined herein, and which mediates the targeted cleavage of an RNA transcript via an RNA-induced silencing complex (RISC) pathway. iRNA directs the sequence-specific degradation of mRNA through a process known as RNA interference (RNAi). The iRNA modulates, e.g., inhibits, the expression of AGT in a cell, e.g., a cell within a subject, such as a mammalian subject.

In one embodiment, an RNAi agent of the invention includes a single stranded RNA that interacts with a target RNA sequence, e.g., an AGT target mRNA sequence, to direct the cleavage of the target RNA. Without wishing to be bound by theory it is believed that long double-stranded RNA introduced into cells is broken down into siRNA by a Type III endonuclease known as Dicer (Sharp et al. (2001) Genes Dev. 15:485). Dicer, a ribonuclease-III-like enzyme, processes the dsRNA into 19-23 base pair short interfering RNAs with characteristic two base 3' overhangs (Bernstein, et al., (2001) Nature 409:363). The siRNAs are then incorporated into an RNA-induced silencing complex (RISC) where one or more helicases unwind the siRNA duplex, enabling the complementary antisense strand to guide target recognition (Nykanen, et al., (2001) Cell 107:309). Upon binding to the appropriate target mRNA, one or more endonucleases within the RISC cleave the target to induce silencing (Elbashir, et al., (2001) Genes Dev. 15:188). Thus, in one aspect the invention relates to a single stranded RNA (siRNA) generated within a cell and which promotes the formation of a RISC complex to effect silencing of the target gene, i.e., an AGT gene. Accordingly, the term "siRNA" is also used herein to refer to an RNAi as described above.

In certain embodiments, the RNAi agent may be a single-stranded siRNA (ssRNAi) that is introduced into a cell or organism to inhibit a target mRNA. Single-stranded RNAi agents bind to the RISC endonuclease, Argonaute 2, which then cleaves the target mRNA. The single-stranded siRNAs are generally 15-30 nucleotides and are chemically modified. The design and testing of single-stranded siRNAs are described in U.S. Pat. No. 8,101,348 and in Lima et al., (2012) Cell 150:883-894, the entire contents of each of which are hereby incorporated herein by reference. Any of the antisense nucleotide sequences described herein may be used as a single-stranded siRNA as described herein or as chemically modified by the methods described in Lima et al., (2012) Cell 150:883-894.

In another embodiment, an "iRNA" for use in the compositions, uses, and methods of the invention is a double-stranded RNA and is referred to herein as a "double-stranded RNAi agent," "double-stranded RNA (dsRNA) molecule," "dsRNA agent," or "dsRNA". The term "dsRNA", refers to a complex of ribonucleic acid molecules, having a duplex structure comprising two anti-parallel and substantially complementary nucleic acid strands, referred to as having "sense" and "antisense" orientations with respect to a target RNA, i.e., an AGT gene. In some embodiments of the invention, a double-stranded RNA (dsRNA) triggers the degradation of a target RNA, e.g., an mRNA, through a post-transcriptional gene-silencing mechanism referred to herein as RNA interference or RNAi.

In general, the majority of nucleotides of each strand of a dsRNA molecule are ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified internucleotide linkage, and/or a modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The majority of nucleotides of each strand of a dsRNA molecule may be ribonucleotides, but as described in detail herein, each or both strands can also include one or more non-ribonucleotides, e.g., a deoxyribonucleotide and/or a modified nucleotide. In addition, as used in this specification, an "RNAi agent" may include ribonucleotides with chemical modifications; an RNAi agent may include substantial modifications at multiple nucleotides. As used herein, the term "modified nucleotide" refers to a nucleotide having, independently, a modified sugar moiety, a modified intemucleotide linkage, and/or modified nucleobase. Thus, the term modified nucleotide encompasses substitutions, additions or removal of, e.g., a functional group or atom, to internucleoside linkages, sugar moieties, or nucleobases. The modifications suitable for use in the agents of the invention include all types of modifications disclosed herein or known in the art. Any such modifications, as used in a siRNA type molecule, are encompassed by "RNAi agent" for the purposes of this specification and claims.

The duplex region may be of any length that permits specific degradation of a desired target RNA through a RISC pathway, and may range from about 9 to 36 base pairs in length, e.g., about 15-30 base pairs in length, for example, about 9, 10, 11, 12, 13, 14, 15, 16, 17, 18, 19, 20, 21, 22, 23, 24, 25, 26, 27, 28, 29, 30, 31, 32, 33, 34, 35, or 36 base pairs in length, such as about 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

The two strands forming the duplex structure may be different portions of one larger RNA molecule, or they may be separate RNA molecules. Where the two strands are part of one larger molecule, and therefore are connected by an uninterrupted chain of nucleotides between the 3'-end of one strand and the 5'-end of the respective other strand forming the duplex structure, the connecting RNA chain is referred to as a "hairpin loop." A hairpin loop can comprise at least one unpaired nucleotide. In some embodiments, the hairpin loop can comprise at least 2, at least 3, at least 4, at least 5, at least 6, at least 7, at least 8, at least 9, at least 10, at least 20, at least 23 or more unpaired nucleotides.

Where the two substantially complementary strands of a dsRNA are comprised by separate RNA molecules, those molecules need not, but can be covalently connected. Where the two strands are connected covalently by means other than an uninterrupted chain of nucleotides between the 3'-end of one strand and the 5'-end of the respective other strand forming the duplex structure, the connecting structure is referred to as a "linker." The RNA strands may have the same or a different number of nucleotides. The maximum number of base pairs is the number of nucleotides in the shortest strand of the dsRNA minus any overhangs that are present in the duplex. In addition to the duplex structure, an RNAi may comprise one or more nucleotide overhangs.

In certain embodiments, an RNAi agent of the invention is a dsRNA, each strand of which comprises 19-23 nucleotides, that interacts with a target RNA sequence, e.g., an AGT gene, without wishing to be bound by theory, long double-stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

In one embodiment, an RNAi agent of the invention is a dsRNA of 24-30 nucleotides that interacts with a target RNA sequence, e.g., an AGT target mRNA sequence, to direct the cleavage of the target RNA. Without wishing to be bound by theory, long double-stranded RNA introduced into cells is broken down into siRNA by a Type III endonuclease known as Dicer (Sharp et al. (2001) *Genes Dev.* 15:485). Dicer, a ribonuclease-III-like enzyme, processes the dsRNA into 19-23 base pair short interfering RNAs with characteristic two base 3' overhangs (Bernstein, et al., (2001) *Nature* 409:363). The siRNAs are then incorporated into an RNA-induced silencing complex (RISC) where one or more helicases unwind the siRNA duplex, enabling the complementary antisense strand to guide target recognition (Nykanen, et al., (2001) *Cell* 107:309). Upon binding to the appropriate target mRNA, one or more endonucleases within the RISC cleave the target to induce silencing (Elbashir, et al., (2001) *Genes Dev.* 15:188).

As used herein, the term "nucleotide overhang" refers to at least one unpaired nucleotide that protrudes from the duplex structure of an iRNA, e.g., a dsRNA. For example, when a 3'-end of one strand of a dsRNA extends beyond the 5'-end of the other strand, or vice versa, there is a nucleotide overhang. A dsRNA can comprise an overhang of at least one nucleotide; alternatively the overhang can comprise at least two nucleotides, at least three nucleotides, at least four nucleotides, at least five nucleotides or more. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA.

In one embodiment, the antisense strand of a dsRNA has a 1-10 nucleotide, e.g., a 1, 2, 3, 4, 5, 6, 7, 8, 9, or 10 nucleotide, overhang at the 3'-end and/or the 5'-end. In one embodiment, the sense strand of a dsRNA has a 1-10 nucleotide, e.g., a 1, 2, 3, 4, 5, 6, 7, 8, 9, or 10 nucleotide, overhang at the 3'-end and/or the 5'-end. In certain embodiments, the overhang on the sense strand or the antisense strand, or both, can include extended lengths longer than 10 nucleotides, e.g., 1-30 nucleotides, 2-30 nucleotides, 10-30 nucleotides, or 10-15 nucleotides in length. In certain embodiments, an extended overhang is on the sense strand of the duplex. In certain embodiments, an extended overhang is present on the 3'end of the sense strand of the duplex. In certain embodiments, an extended overhang is present on the 5'end of the sense strand of the duplex. In certain embodiments, an extended overhang is on the antisense strand of the duplex. In certain embodiments, an extended overhang is present on the 3'end of the antisense strand of the duplex. In certain embodiments, an extended overhang is present on the 5'end of the antisense strand of the duplex. In certain embodiments, one or more of the nucleotides in the overhang is replaced with a nucleoside thiophosphate.

"Blunt" or "blunt end" means that there are no unpaired nucleotides at that end of the double-stranded RNAi agent, i.e., no nucleotide overhang. A "blunt ended" RNAi agent is a dsRNA that is double-stranded over its entire length, i.e., no nucleotide overhang at either end of the molecule. The RNAi agents of the invention include RNAi agents with nucleotide overhangs at one end (i.e., agents with one overhang and one blunt end) or with nucleotide overhangs at both ends.

The term "antisense strand" or "guide strand" refers to the strand of an iRNA, e.g., a dsRNA, which includes a region that is substantially complementary to a target sequence, e.g., a AGT mRNA. As used herein, the term "region of complementarity" refers to the region on the antisense strand that is substantially complementary to a sequence, for example a target sequence, e.g., an AGT nucleotide sequence, as defined herein. Where the region of complementarity is not fully complementary to the target sequence, the mismatches can be in the internal or terminal regions of the molecule. Generally, the most tolerated mismatches are in the terminal regions, e.g., within 5, 4, 3, or 2 nucleotides of the 5'- and/or 3'-terminus of the iRNA.

The term "sense strand," or "passenger strand" as used herein, refers to the strand of an iRNA that includes a region that is substantially complementary to a region of the antisense strand as that term is defined herein.

As used herein, the term "cleavage region" refers to a region that is located immediately adjacent to the cleavage site. The cleavage site is the site on the target at which cleavage occurs. In some embodiments, the cleavage region comprises three bases on either end of, and immediately adjacent to, the cleavage site. In some embodiments, the cleavage region comprises two bases on either end of, and immediately adjacent to, the cleavage site. In some embodiments, the cleavage site specifically occurs at the site bound by nucleotides 10 and 11 of the antisense strand, and the cleavage region comprises nucleotides 11, 12, and 13.

As used herein, and unless otherwise indicated, the term "complementary," when used to describe a first nucleotide sequence in relation to a second nucleotide sequence, refers to the ability of an oligonucleotide or polynucleotide comprising the first nucleotide sequence to hybridize and form a duplex structure under certain conditions with an oligonucleotide or polynucleotide comprising the second nucleotide sequence, as will be understood by the skilled person. Such conditions can, for example, be stringent conditions, where stringent conditions can include: 400 mM NaCl, 40 mM PIPES pH 6.4, 1 mM EDTA, 50° C. or 70° C. for 12-16 hours followed by washing (see, e.g., "Molecular Cloning: A Laboratory Manual, Sambrook, et al. (1989) Cold Spring Harbor Laboratory Press). Other conditions, such as physiologically relevant conditions as can be encountered inside an organism, can apply. The skilled person will be able to determine the set of conditions most appropriate for a test of complementarity of two sequences in accordance with the ultimate application of the hybridized nucleotides.

Complementary sequences within an iRNA, e.g., within a dsRNA as described herein, include base-pairing of the oligonucleotide or polynucleotide comprising a first nucleotide sequence to an oligonucleotide or polynucleotide comprising a second nucleotide sequence over the entire length of one or both nucleotide sequences. Such sequences can be referred to as "fully complementary" with respect to each other herein. However, where a first sequence is referred to as "substantially complementary" with respect to a second sequence herein, the two sequences can be fully complementary, or they can form one or more, but generally not more than 5, 4, 3 or 2 mismatched base pairs upon hybridization for a duplex up to 30 base pairs, while retaining the ability to hybridize under the conditions most relevant to their ultimate application, e.g., inhibition of gene expression via a RISC pathway. However, where two oligonucleotides are designed to form, upon hybridization, one or more single stranded overhangs, such overhangs shall not be regarded as mismatches with regard to the determination of complementarity. For example, a dsRNA comprising one oligonucleotide 21 nucleotides in length and another oligonucleotide 23 nucleotides in length, wherein the longer oligonucleotide comprises a sequence of 21 nucleotides that is fully complementary to the shorter oligonucleotide, can yet be referred to as "fully complementary" for the purposes described herein.

"Complementary" sequences, as used herein, can also include, or be formed entirely from, non-Watson-Crick base pairs and/or base pairs formed from non-natural and modified nucleotides, in so far as the above requirements with respect to their ability to hybridize are fulfilled. Such non-Watson-Crick base pairs include, but are not limited to, G:U Wobble or Hoogstein base pairing.

The terms "complementary," "fully complementary" and "substantially complementary" herein can be used with respect to the base matching between the sense strand and the antisense strand of a dsRNA, or between the antisense strand of an iRNA agent and a target sequence, as will be understood from the context of their use.

As used herein, a polynucleotide that is "substantially complementary to at least part of" a messenger RNA (mRNA) refers to a polynucleotide that is substantially complementary to a contiguous portion of the mRNA of interest (e.g., an mRNA encoding AGT). For example, a polynucleotide is complementary to at least a part of an AGT mRNA if the sequence is substantially complementary to a non-interrupted portion of an mRNA encoding AGT.

Accordingly, in some embodiments, the antisense strand polynucleotides disclosed herein are fully complementary to the target AGT sequence. In other embodiments, the antisense strand polynucleotides disclosed herein are substantially complementary to the target AGT sequence and comprise a contiguous nucleotide sequence which is at least about 80% complementary over its entire length to the equivalent region of the nucleotide sequence of SEQ ID NO:1, or a fragment of SEQ ID NO:1, such as about 85%, about 90%, or about 95% complementary.

In one embodiment, an RNAi agent of the invention includes a sense strand that is substantially complementary to an antisense polynucleotide which, in turn, is complementary to a target AGT sequence, and wherein the sense strand polynucleotide comprises a contiguous nucleotide sequence which is at least about 80% complementary over its entire length to the equivalent region of the nucleotide sequence of SEQ ID NO:2, or a fragment of any one of SEQ ID NO:2, such as about 85%, about 90%, or about 95% complementary.

In general, the majority of nucleotides of each strand are ribonucleotides, but as described in detail herein, each or both strands can also include one or more non-ribonucleotides, e.g., a deoxyribonucleotide and/or a modified nucleotide. In addition, an "iRNA" may include ribonucleotides with chemical modifications. Such modifications may include all types of modifications disclosed herein or known in the art. Any such modifications, as used in an iRNA molecule, are encompassed by "iRNA" for the purposes of this specification and claims.

In one aspect of the invention, an agent for use in the methods and compositions of the invention is a single-stranded antisense RNA molecule that inhibits a target mRNA via an antisense inhibition mechanism. The single-stranded antisense RNA molecule is complementary to a sequence within the target mRNA. The single-stranded antisense oligonucleotides can inhibit translation in a stoichiometric manner by base pairing to the mRNA and physically obstructing the translation machinery, see Dias, N. et al., (2002) *Mol Cancer Ther* 1:347-355. The single-stranded antisense RNA molecule may be about 15 to about 30 nucleotides in length and have a sequence that is complementary to a target sequence. For example, the single-stranded antisense RNA molecule may comprise a sequence that is at least about 15, 16, 17, 18, 19, 20, or more contiguous nucleotides from any one of the antisense sequences described herein.

The term "inhibiting," as used herein, is used interchangeably with "reducing," "silencing," "downregulating," "suppressing" and other similar terms, and includes any level of inhibition.

The phrase "inhibiting expression of an AGT," as used herein, includes inhibition of expression of any AGT gene (such as, e.g., a mouse AGT gene, a rat AGT gene, a monkey AGT gene, or a human AGT gene) as well as variants or mutants of an AGT gene that encode an AGT protein.

"Inhibiting expression of an AGT gene" includes any level of inhibition of an AGT gene, e.g., at least partial suppression of the expression of an AGT gene, such as an inhibition by at least about 20%. In certain embodiments, inhibition is by at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, or at least about 99%.

The expression of an AGT gene may be assessed based on the level of any variable associated with AGT gene expression, e.g., AGT mRNA level or AGT protein level. Inhibition may be assessed by a decrease in an absolute or relative level of one or more of these variables compared with a control level. The control level may be any type of control level that is utilized in the art, e.g., a pre-dose baseline level, or a level determined from a similar subject, cell, or sample that is untreated or treated with a control (such as, e.g., buffer only control or inactive agent control).

In one embodiment, at least partial suppression of the expression of an AGT gene, is assessed by a reduction of the amount of AGT mRNA which can be isolated from or detected in a first cell or group of cells in which an AGT gene is transcribed and which has or have been treated such that the expression of an AGT gene is inhibited, as compared to a second cell or group of cells substantially identical to the first cell or group of cells but which has or have not been so treated (control cells). The degree of inhibition may be expressed in terms of:

$$\frac{(mRNA \text{ in control cells}) - (mRNA \text{ in treated cells})}{(mRNA \text{ in control cells})} \cdot 100\%$$

The phrase "contacting a cell with an RNAi agent," such as a dsRNA, as used herein, includes contacting a cell by any possible means. Contacting a cell with an RNAi agent includes contacting a cell in vitro with the iRNA or contacting a cell in vivo with the iRNA. The contacting may be done directly or indirectly. Thus, for example, the RNAi agent may be put into physical contact with the cell by the individual performing the method, or alternatively, the RNAi agent may be put into a situation that will permit or cause it to subsequently come into contact with the cell.

Contacting a cell in vitro may be done, for example, by incubating the cell with the RNAi agent. Contacting a cell in vivo may be done, for example, by injecting the RNAi agent into or near the tissue where the cell is located, or by injecting the RNAi agent into another area, e.g., the bloodstream or the subcutaneous space, such that the agent will subsequently reach the tissue where the cell to be contacted is located. For example, the RNAi agent may contain and/or be coupled to a ligand, e.g., GalNAc3, that directs the RNAi agent to a site of interest, e.g., the liver. Combinations of in vitro and in vivo methods of contacting are also possible. For example, a cell may also be contacted in vitro with an RNAi agent and subsequently transplanted into a subject.

In one embodiment, contacting a cell with an iRNA includes "introducing" or "delivering the iRNA into the cell" by facilitating or effecting uptake or absorption into the cell. Absorption or uptake of an iRNA can occur through unaided diffusive or active cellular processes, or by auxiliary agents or devices. Introducing an iRNA into a cell may be in vitro and/or in vivo. For example, for in vivo introduction, iRNA can be injected into a tissue site or administered systemically. In vivo delivery can also be done by a beta-glucan delivery system, such as those described in U.S. Pat. Nos. 5,032,401 and 5,607,677, and U.S. Publication No. 2005/0281781, the entire contents of which are hereby incorporated herein by reference. In vitro introduction into a cell includes methods known in the art such as electroporation and lipofection. Further approaches are described herein below and/or are known in the art.

The term "lipid nanoparticle" or "LNP" is a vesicle comprising a lipid layer encapsulating a pharmaceutically active molecule, such as a nucleic acid molecule, e.g., an iRNA or a plasmid from which an iRNA is transcribed. LNPs are described in, for example, U.S. Pat. Nos. 6,858,225, 6,815,432, 8,158,601, and 8,058,069, the entire contents of which are hereby incorporated herein by reference.

As used herein, a "subject" is an animal, such as a mammal, including a primate (such as a human, a non-human primate, e.g., a monkey, and a chimpanzee), a non-primate (such as a cow, a pig, a camel, a llama, a horse, a goat, a rabbit, a sheep, a hamster, a guinea pig, a cat, a dog, a rat, a mouse, a horse, and a whale), or a bird (e.g., a duck or a goose). In an embodiment, the subject is a human, such as a human being treated or assessed for a disease, disorder or condition that would benefit from reduction in AGT expression; a human at risk for a disease, disorder or condition that would benefit from reduction in AGT expression; a human having a disease, disorder or condition that would benefit from reduction in AGT expression; and/or human being treated for a disease, disorder or condition that would benefit from reduction in AGT expression as described herein.

As used herein, the terms "treating" or "treatment" refer to a beneficial or desired result including, but not limited to, alleviation or amelioration of one or more symptoms associated with unwanted AGT expression, e.g., angiotensin II type 1 receptor activation ($AT_1R$) (e.g., hypertension, chronic kidney disease, stroke, myocardial infarction, heart failure, aneurysms, peripheral artery disease, heart disease, increased oxidative stress, e.g., increased superoxide formation, inflammation, vasoconstriction, sodium and water retention, potassium and magnesium loss, renin suppression, myocyte and smooth muscle hypertrophy, increased collagen synthesis, stimulation of vascular, myocardial and renal fibrosis, increased rate and force of cardiac contractions, altered heart rate, e.g., increased arrhythmia, stimulation of plasminogen activator inhibitor 1 (PAI1), activation of the sympathetic nervous system, and increased endothelin secretion), symptoms of pregnancy-associated hypertension (e.g., preeclampsia, and eclampsia), including, but not limited to intrauterine growth restriction (IUGR) or fetal growth restriction, symptoms associated with malignant hypertension, symptoms associated with hyperaldosteronism; diminishing the extent of unwanted $AT_1R$ activation; stabilization (i.e., not worsening) of the state of chronic $AT_1R$ activation; amelioration or palliation of unwanted $AT_1R$ activation (e.g., hypertension, chronic kidney disease, stroke, myocardial infarction, heart failure, aneurysms, peripheral artery disease, heart disease, increased oxidative stress, e.g., increased superoxide formation, inflammation, vasoconstriction, sodium and water retention, potassium and magnesium loss, renin suppression, myocyte and smooth muscle hypertrophy, increased collagen synthesis, stimulation of vascular, myocardial and renal fibrosis, increased rate and force of cardiac contractions, altered heart rate, e.g., increased arrhythmia, stimulation of plasminogen activator inhibitor 1 (PAI1), activation of the sympathetic nervous system, and increased endothelin secretion) whether detectable or undetectable. "Treatment" can also mean prolonging survival as compared to expected survival in the absence of treatment.

The term "lower" in the context of the level of AGT in a subject or a disease marker or symptom refers to a statistically significant decrease in such level. The decrease can be, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or more and is preferably down to a level accepted as within the range of normal for an individual without such disorder.

As used herein, "prevention" or "preventing," when used in reference to a disease, disorder or condition thereof, that would benefit from a reduction in expression of an AGT gene, refers to a reduction in the likelihood that a subject will develop a symptom associated with such a disease, disorder, or condition, e.g., a symptom of unwanted $AT_1R$ activation, such as a hypertension, chronic kidney disease, stroke, myocardial infarction, heart failure, aneurysms, peripheral artery disease, heart disease, increased oxidative stress, e.g., increased superoxide formation, inflammation, vasoconstriction, sodium and water retention, potassium and magnesium loss, renin suppression, myocyte and smooth muscle hypertrophy, increased collagen synthesis, stimulation of vascular, myocardial and renal fibrosis, increased rate and force of cardiac contractions, altered heart rate, e.g., increased arrhythmia, stimulation of plasminogen activator inhibitor 1 (PAI1), activation of the sympathetic nervous system, and increased endothelin secretion. The likelihood of developing, e.g., hypertension, is reduced, for example, when an individual having one or more risk factors for a hypertension either fails to develop hypertension or develops hypertension with less severity relative to a population having the same risk factors and not receiving treatment as described herein. The failure to develop a disease, disorder or condition, or the reduction in the development of a symptom associated with such a disease, disorder or condition (e.g., by at least about 10% on a clinically accepted scale for that disease or disorder), or the exhibition of delayed symptoms delayed (e.g., by days, weeks, months or years) is considered effective prevention.

As used herein, the term "angiotensinogen-associated disease" or "AGT-associated disease," is a disease or disorder that is caused by, or associated with renin-angiotensin-aldosterone system (RAAS) activation, or a disease or disorder the symptoms of which or progression of which responds to RAAS inactivation. The term "angiotensinogen-associated disease" includes a disease, disorder or condition that would benefit from reduction in AGT expression. Such diseases are typically associated with high blood pressure. Non-limiting examples of angiotensinogen-associated diseases include hypertension, e.g., borderline hypertension (also known as prehypertension), primary hypertension (also known as essential hypertension or idiopathic hypertension), secondary hypertension (also known as inessential hypertension), hypertensive emergency (also known as malignant hypertension), hypertensive urgency, isolated systolic or diastolic hypertension, pregnancy-associated hypertension (e.g., preeclampsia, eclampsia, and post-partum preeclampsia), diabetic hypertension, resistant hypertension, refractory hypertension, paroxysmal hypertension, renovascular hypertension (also known as renal hypertension), Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy (including peripheral vascular disease), diabetic nephropathy, diabetic retinopathy, chronic heart failure, cardiomyopathy, diabetic cardiac myopathy, glomerulosclerosis, coarctation of the aorta, aortic aneurism, ventricular fibrosis, Cushing's syndrome, and other glucocorticoid excess states including chronic steroid therapy, pheochromocytoma, reninoma, secondary aldosteronism and other mineralocorticoid excess states, sleep apnea, thyroid/parathyroid disease, heart failure (e.g., left ventricular systolic dysfunction), myocardial infarction, angina, stroke, diabetes mellitus (e.g., diabetic nephropathy), renal disease e.g., chronic kidney disease or diabetic nephropathy optionally in the context of pregnancy, renal failure, e.g., chronic renal failure, cognitive dysfunction (such as Alzheimer's), and systemic sclerosis (e.g., scleroderma renal crisis). In certain embodiments, AGT-associated disease includes intrauterine growth restriction (IUGR) or fetal growth restriction.

Based on the average of seated blood pressure readings that are properly measured during two or more office visits, a subject having a normal blood pressure is one having a systolic pressure of about 90-119 mmHg (about 12-15.9 kPa ($kN/m^2$)) and a diastolic pressure of about 60-79 mmHg (about 8.0-10.5 kPa ($kN/m^2$)); a subject having prehypertension is one having a systolic pressure of about 120-139 mmHg (about 16.1-18.5 kPa ($kN/m^2$)) and a diastolic pressure of about 60-79 mmHg (about 8.0-10.5 kPa ($kN/m^2$)); a subject having hypertension (e.g., Stage I hypertension) is one having a systolic pressure of about 140-159 mmHg (about 18.7-21.2 kPa ($kN/m^2$)) and a diastolic pressure of about 90-99 mmHg (about 12.0-13.2 kPa ($kN/m^2$)); and a subject having hypertension (e.g., Stage II hypertension) is one having a systolic pressure of about >160 mmHg (about >21.3 kPa ($kN/m^2$)) and a diastolic pressure of about >100 mmHg (about >13.3 kPa ($kN/m^2$)). Subjects with blood pressures over 130/80 mmHg along with Type 1 or Type 2 diabetes, or kidney disease are considered as having hypertension.

In one embodiment, an angiotensinogen-associated disease is primary hypertension. "Primary hypertension" is a result of environmental or genetic causes (e.g., a result of no obvious underlying medical cause).

In one embodiment, an angiotensinogen-associated disease is secondary hypertension. "Secondary hypertension"

has an identifiable underlying disorder which can be of multiple etiologies, including renal, vascular, and endocrine causes, e.g., renal parenchymal disease (e.g., polycystic kidneys, glomerular or interstitial disease), renal vascular disease (e.g., renal artery stenosis, fibromuscular dysplasia), endocrine disorders (e.g., adrenocorticosteroid or mineralocorticoid excess, pheochromocytoma, hyperthyroidism or hypothyroidism, growth hormone excess, hyperparathyroidism), coarctation of the aorta, or oral contraceptive use.

In one embodiment, an angiotensinogen-associated disease is a hypertensive emergency, e.g., malignant hypertension and accelerated hypertension. "Accelerated hypertension" is severely elevated blood pressure (i.e., equal to or greater than a systolic 180 mmHg or diastolic of 110 mmHg) with direct damage to one or more end organs. Blood pressure must be reduced immediately to prevent further organ damage. "Malignant hypertension" is severely elevated blood pressure (i.e., equal to or greater than a systolic 180 mmHg or diastolic of 110 mmHg) with direct damage to one or more end organs and papilledema. Blood pressure must be reduced immediately to prevent further organ damage. Neurologic end-organ damage due to uncontrolled blood pressure may include hypertensive encephalopathy, cerebral vascular accident/cerebral infarction; subarachnoid hemorrhage, and/or intracranial hemorrhage. Cardiovascular end-organ damage may include myocardial ischemia/infarction, acute left ventricular dysfunction, acute pulmonary edema, and/or aortic dissection. Other organ systems may also be affected by uncontrolled hypertension, which may lead to acute renal failure/insufficiency, retinopathy, eclampsia, or microangiopathic hemolytic anemia.

In one embodiment, an angiotensinogen-associated disease is a hypertensive urgency. "Hypertensive urgency" is severely elevated blood pressure (i.e., equal to or greater than a systolic 180 mmHg or diastolic of 110 mmHg) with no direct damage to one or more organs. Blood pressure can be brought down safely within a few hours.

In one embodiment, an angiotensinogen-associated disease is pregnancy-associated hypertension, e.g., chronic hypertension of pregnancy, gestational hypertension, preeclampsia, eclampsia, preeclampsia superimposed on chronic hypertension, HELLP syndrome, and gestational hypertension (also known as transient hypertension of pregnancy, chronic hypertension identified in the latter half of pregnancy, and pregnancy-induced hypertension (PIH)). A subject having "chronic hypertension of pregnancy" is one having a blood pressure exceeding 140/90 mm Hg before pregnancy or before 20 weeks' gestation. "Gestational hypertension" or "pregnancy-induced hypertension" refers to hypertension with onset in the latter part of pregnancy (>20 weeks' gestation) without any other features of preeclampsia, and followed by normalization of the blood pressure postpartum. "Mild preeclampsia" is defined as the presence of hypertension (blood pressure ≥140/90 mm Hg) on two occasions, at least six hours apart, but without evidence of end-organ damage, in a woman who was normotensive before 20 weeks' gestation. In a subject with preexisting essential hypertension, preeclampsia is diagnosed if systolic blood pressure has increased by 30 mm Hg or if diastolic blood pressure has increased by 15 mm Hg. "Severe preeclampsia" is defined as the presence of 1 of the following symptoms or signs in the presence of preeclampsia; asystolic blood pressure of 160 mm Hg or higher or diastolic blood pressure of 110 mm Hg or higher on two occasions at least six hours apart; proteinuria of more than 5 g in a 24-hour collection or more than 3+ on two random urine samples collected at least four hours apart, pulmonary edema or cyanosis, oliguria (<400 mL in 24 hours), persistent headaches, epigastric pain and/or impaired liver function, thrombocytopenia, oligohydramnios, decreased fetal growth, or placental abruption. "Eclampsia" is defined as seizures that cannot be attributable to other causes in a woman with preeclampsia. "HELLP syndrome" (also known as edema-proteinuria-hypertension gestosis type B) is Hemolysis, Elevated Liver enzyme levels, and Low Platelet levels in a pregnant subject.

In one embodiment, an angiotensinogen-associated disease is resistant hypertension. "Resistant hypertension" is blood pressure that remains above goal (e.g., 140/90 mmHg) in spite of concurrent use of three antihypertensive agents of different classes, one of which is a thiazide diuretic. Subjects whose blood pressure is controlled with four or more medications are also considered to have resistant hypertension.

"Therapeutically effective amount," as used herein, is intended to include the amount of an RNAi agent that, when administered to a subject having an angiotensinogen-associated disease, is sufficient to effect treatment of the disease (e.g., by diminishing, ameliorating or maintaining the existing disease or one or more symptoms of disease). The "therapeutically effective amount" may vary depending on the RNAi agent, how the agent is administered, the disease and its severity and the history, age, weight, family history, genetic makeup, the types of preceding or concomitant treatments, if any, and other individual characteristics of the subject to be treated.

"Prophylactically effective amount," as used herein, is intended to include the amount of an iRNA that, when administered to a subject having an angiotensinogen-associated disease, is sufficient to prevent or ameliorate the disease or one or more symptoms of the disease in a subject susceptible to the disease, i.e., more likely to suffer from the disease than those in the general population due to one or more factors, e.g., age, weight, pregnancy. Ameliorating the disease includes slowing the course of the disease or reducing the severity of later-developing disease. The "prophylactically effective amount" may vary depending on the iRNA, how the agent is administered, the degree of risk of disease, and the history, age, weight, family history, genetic makeup, the types of preceding or concomitant treatments, if any, and other individual characteristics of the patient to be treated.

A "therapeutically-effective amount" or "prophylactically effective amount" also includes an amount of an RNAi agent that produces some desired local or systemic effect at a reasonable benefit/risk ratio applicable to any treatment. iRNA employed in the methods of the present invention may be administered in a sufficient amount to produce a reasonable benefit/risk ratio applicable to such treatment.

The phrase "pharmaceutically acceptable" is employed herein to refer to those compounds, materials, compositions, and/or dosage forms which are, within the scope of sound medical judgment, suitable for use in contact with the tissues of human subjects and animal subjects without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the subject being treated. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) lubricating agents, such as magnesium state, sodium lauryl sulfate and talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; (22) bulking agents, such as polypeptides and amino acids (23) serum component, such as serum albumin, HDL and LDL; and (22) other non-toxic compatible substances employed in pharmaceutical formulations.

The term "sample," as used herein, includes a collection of similar fluids, cells, or tissues isolated from a subject, as well as fluids, cells, or tissues present within a subject. Examples of biological fluids include blood, serum and serosal fluids, plasma, cerebrospinal fluid, ocular fluids, lymph, urine, saliva, and the like. Tissue samples may include samples from tissues, organs or localized regions. For example, samples may be derived from particular organs, parts of organs, or fluids or cells within those organs. In certain embodiments, samples may be derived from the liver (e.g., whole liver or certain segments of liver or certain types of cells in the liver, such as, e.g., hepatocytes). In some embodiments, a "sample derived from a subject" refers to blood or plasma drawn from the subject.

II. iRNAs of the Invention

The present invention provides iRNAs which inhibit the expression of an AGT gene. In one embodiment, the iRNA agent includes double-stranded ribonucleic acid (dsRNA) molecules for inhibiting the expression of an AGT gene in a cell, such as a cell within a subject, e.g., a mammal, such as a human having an angiotensinogen-associated disease, e.g., hypertension. The dsRNA includes an antisense strand having a region of complementarity which is complementary to at least a part of an mRNA formed in the expression of an AGT gene. The region of complementarity is about 30 nucleotides or less in length (e.g., about 30, 29, 28, 27, 26, 25, 24, 23, 22, 21, 20, 19, or 18 nucleotides or less in length). Upon contact with a cell expressing the AGT gene, the iRNA inhibits the expression of the AGT gene (e.g., a human, a primate, a non-primate, or a bird AGT gene) by at least about 10% as assayed by, for example, a PCR or branched DNA (bDNA)-based method, or by a protein-based method, such as by immunofluorescence analysis, using, for example, western blotting or flowcytometric techniques.

A dsRNA includes two RNA strands that are complementary and hybridize to form a duplex structure under conditions in which the dsRNA will be used. One strand of a dsRNA (the antisense strand) includes a region of complementarity that is substantially complementary, and generally fully complementary, to a target sequence. The target sequence can be derived from the sequence of an mRNA formed during the expression of an AGT gene. The other strand (the sense strand) includes a region that is complementary to the antisense strand, such that the two strands hybridize and form a duplex structure when combined under suitable conditions. As described elsewhere herein and as known in the art, the complementary sequences of a dsRNA can also be contained as self-complementary regions of a single nucleic acid molecule, as opposed to being on separate oligonucleotides.

Generally, the duplex structure is between 15 and 30 base pairs in length, e.g., between, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs in length. Ranges and lengths intermediate to the above recited ranges and lengths are also contemplated to be part of the invention.

Similarly, the region of complementarity to the target sequence is between 15 and 30 nucleotides in length, e.g., between 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 nucleotides in length. Ranges and lengths intermediate to the above recited ranges and lengths are also contemplated to be part of the invention.

In some embodiments, the dsRNA is about 15 to about 20 nucleotides in length, about 25 to about 30 nucleotides in length, or about 15 to about 23 nucleotides in length. In general, the dsRNA is long enough to serve as a substrate for the Dicer enzyme. For example, it is well-known in the art that dsRNAs longer than about 21-23 nucleotides in length may serve as substrates for Dicer. As the ordinarily skilled person will also recognize, the region of an RNA targeted for cleavage will most often be part of a larger RNA molecule, often an mRNA molecule. Where relevant, a "part" of an mRNA target is a contiguous sequence of an mRNA target of sufficient length to allow it to be a substrate for RNAi-directed cleavage (i.e., cleavage through a RISC pathway).

One of skill in the art will also recognize that the duplex region is a primary functional portion of a dsRNA, e.g., a duplex region of about 9 to 36 base pairs, e.g., about 10-36, 11-36, 12-36, 13-36, 14-36, 15-36, 9-35, 10-35, 11-35, 12-35, 13-35, 14-35, 15-35, 9-34, 10-34, 11-34, 12-34, 13-34, 14-34, 15-34, 9-33, 10-33, 11-33, 12-33, 13-33, 14-33, 15-33, 9-32, 10-32, 11-32, 12-32, 13-32, 14-32, 15-32, 9-31, 10-31, 11-31, 12-31, 13-32, 14-31, 15-31, 15-30, 15-29, 15-28, 15-27, 15-26, 15-25, 15-24, 15-23, 15-22, 15-21, 15-20, 15-19, 15-18, 15-17, 18-30, 18-29, 18-28, 18-27, 18-26, 18-25, 18-24, 18-23, 18-22, 18-21, 18-20, 19-30, 19-29, 19-28, 19-27, 19-26, 19-25, 19-24, 19-23, 19-22, 19-21, 19-20, 20-30, 20-29, 20-28, 20-27, 20-26, 20-25, 20-24, 20-23, 20-22, 20-21, 21-30, 21-29, 21-28, 21-27, 21-26, 21-25, 21-24, 21-23, or 21-22 base pairs. Thus, in one embodiment, to the extent that it becomes processed to a functional duplex, of e.g., 15-30 base pairs, that targets a desired RNA for cleavage, an RNA molecule or complex of RNA molecules having a duplex region greater than 30 base pairs is a dsRNA. Thus, an ordinarily skilled artisan will recognize that in one embodiment, a miRNA is a dsRNA. In another embodiment, a dsRNA is not a naturally occurring miRNA. In another embodiment, an iRNA agent useful to target AGT expression is not generated in the target cell by cleavage of a larger dsRNA.

A dsRNA as described herein can further include one or more single-stranded nucleotide overhangs e.g., 1, 2, 3, or 4 nucleotides. dsRNAs having at least one nucleotide overhang can have unexpectedly superior inhibitory properties relative to their blunt-ended counterparts. A nucleotide overhang can comprise or consist of a nucleotide/nucleoside analog, including a deoxynucleotide/nucleoside. The overhang(s) can be on the sense strand, the antisense strand or any combination thereof. Furthermore, the nucleotide(s) of an overhang can be present on the 5'-end, 3'-end or both ends of either an antisense or sense strand of a dsRNA. As discussed herein, extended overhang of up to 30 nucleotides in length are also contemplated in various embodiments of the invention.

A dsRNA can be synthesized by standard methods known in the art as further discussed below, e.g., by use of an automated DNA synthesizer, such as are commercially available from, for example, Biosearch, Applied Biosystems®, Inc.

iRNA compounds of the invention may be prepared using a two-step procedure. First, the individual strands of the double-stranded RNA molecule are prepared separately. Then, the component strands are annealed. The individual strands of the siRNA compound can be prepared using solution-phase or solid-phase organic synthesis or both. Organic synthesis offers the advantage that the oligonucleotide strands comprising unnatural or modified nucleotides can be easily prepared. Single-stranded oligonucleotides of the invention can be prepared using solution-phase or solid-phase organic synthesis or both.

In one aspect, a dsRNA of the invention includes at least two nucleotide sequences, a sense sequence and an antisense sequence. The sense strand is selected from the group of sequences provided in any one of Tables 3, 4, 7, 8, 11, 13, and 15, and the corresponding antisense strand of the sense strand is selected from the group of sequences of any one of Tables 3, 4, 7, 8, 11, 13, and 15. In this aspect, one of the two sequences is complementary to the other of the two sequences, with one of the sequences being substantially complementary to a sequence of an mRNA generated in the expression of an AGT gene. As such, in this aspect, a dsRNA will include two oligonucleotides, where one oligonucleotide is described as the sense strand in any one of Tables 3, 4, 7, 8, 11, 13, and 15, and the second oligonucleotide is described as the corresponding antisense strand of the sense strand in any one of Tables 3, 4, 7, 8, 11, 13, and 15. In one embodiment, the substantially complementary sequences of the dsRNA are contained on separate oligonucleotides. In another embodiment, the substantially complementary sequences of the dsRNA are contained on a single oligonucleotide.

It will be understood that, although some of the sequences in Tables 3, 4, 7, 8, 11, 13, and 15 are described as modified and/or conjugated sequences, the RNA of the iRNA of the invention e.g., a dsRNA of the invention, may comprise any one of the sequences set forth in Tables 3, 4, 7, 8, 11, 13, and 15 that is un-modified, un-conjugated, and/or modified and/or conjugated differently than described therein.

In another aspect, a double-stranded ribonucleic acid (dsRNA) of the invention for inhibiting expression of angiotensinogen comprises, consists essentially of, or consists of a sense strand and an antisense strand, wherein the sense strand comprises the nucleotide sequence of a sense strand in Table 3, 4, 7, 8, 11, 13, and 15 and the antisense strand comprises the nucleotide sequence of the corresponding antisense strand in Tables 3, 4, 7, 8, 11, 13, and 15.

The skilled person is well aware that dsRNAs having a duplex structure of about 20 to 23 base pairs, e.g., 21, base pairs have been hailed as particularly effective in inducing RNA interference (Elbashir et al., *EMBO* 2001, 20:6877-6888). However, others have found that shorter or longer RNA duplex structures can also be effective (Chu and Rana (2007) *RNA* 14:1714-1719; Kim et al. (2005) *Nat Biotech* 23:222-226). In the embodiments described above, by virtue of the nature of the oligonucleotide sequences provided in any one of Tables 3, 4, 7, 8, 11, 13, and 15, dsRNAs described herein can include at least one strand of a length of minimally 21 nucleotides. It can be reasonably expected that shorter duplexes having one of the sequences of any one of Tables 3, 4, 7, 8, 11, 13, and 15 minus only a few nucleotides on one or both ends can be similarly effective as compared to the dsRNAs described above. Hence, dsRNAs having a sequence of at least 15, 16, 17, 18, 19, 20, or more contiguous nucleotides derived from one of the sequences of any one of Tables 3, 4, 7, 8, 11, 13, and 15, and differing in their ability to inhibit the expression of a AGT gene by not more than about 5, 10, 15, 20, 25, or 30% inhibition from a dsRNA comprising the full sequence, are contemplated to be within the scope of the present invention.

In addition, the RNAs provided in any one of Tables 3, 4, 7, 8, 11, 13, and 15 identify a site(s) in a AGT transcript that is susceptible to RISC-mediated cleavage. As such, the present invention further features iRNAs that target within one of these sites. As used herein, an iRNA is said to target within a particular site of an RNA transcript if the iRNA promotes cleavage of the transcript anywhere within that particular site. Such an iRNA will generally include at least about 15 contiguous nucleotides from one of the sequences provided in any one of Tables 3, 4, 7, 8, 11, 13, and 15 coupled to additional nucleotide sequences taken from the region contiguous to the selected sequence in a AGT gene.

While a target sequence is generally about 15-30 nucleotides in length, there is wide variation in the suitability of particular sequences in this range for directing cleavage of any given target RNA. Various software packages and the guidelines set out herein provide guidance for the identification of optimal target sequences for any given gene target, but an empirical approach can also be taken in which a "window" or "mask" of a given size (as a non-limiting example, 21 nucleotides) is literally or figuratively (including, e.g., in silico) placed on the target RNA sequence to identify sequences in the size range that can serve as target sequences. By moving the sequence "window" progressively one nucleotide upstream or downstream of an initial target sequence location, the next potential target sequence can be identified, until the complete set of possible sequences is identified for any given target size selected. This process, coupled with systematic synthesis and testing of the identified sequences (using assays as described herein or as known in the art) to identify those sequences that perform optimally can identify those RNA sequences that, when targeted with an iRNA agent, mediate the best inhibition of target gene expression. Thus, while the sequences identified, for example, in any one of Tables 3, 4, 7, 8, 11, 13, and 15 represent effective target sequences, it is contemplated that further optimization of inhibition efficiency can be achieved by progressively "walking the window" one nucleotide upstream or downstream of the given sequences to identify sequences with equal or better inhibition characteristics.

Further, it is contemplated that for any sequence identified, e.g., in any one of Tables 3, 4, 7, 8, 11, 13, and 15, further optimization could be achieved by systematically either adding or removing nucleotides to generate longer or shorter sequences and testing those sequences generated by walking a window of the longer or shorter size up or down the target RNA from that point. Again, coupling this approach to generating new candidate targets with testing for effectiveness of iRNAs based on those target sequences in an inhibition assay as known in the art and/or as described herein can lead to further improvements in the efficiency of inhibition. Further still, such optimized sequences can be adjusted by, e.g., the introduction of modified nucleotides as described herein or as known in the art, addition or changes in overhang, or other modifications as known in the art and/or discussed herein to further optimize the molecule (e.g., increasing serum stability or circulating half-life, increasing thermal stability, enhancing transmembrane delivery, targeting to a particular location or cell type, increasing interaction with silencing pathway enzymes, increasing release from endosomes) as an expression inhibitor.

An iRNA as described herein can contain one or more mismatches to the target sequence. In one embodiment, an iRNA as described herein contains no more than 3 mismatches. If the antisense strand of the iRNA contains mismatches to a target sequence, it is preferable that the area of mismatch is not located in the center of the region of complementarity. If the antisense strand of the iRNA contains mismatches to the target sequence, it is preferable that the mismatch be restricted to be within the last 5 nucleotides from either the 5'- or 3'-end of the region of complementarity. For example, for a 23 nucleotide iRNA agent the strand which is complementary to a region of an AGT gene, generally does not contain any mismatch within the central 13 nucleotides. The methods described herein or methods known in the art can be used to determine whether an iRNA containing a mismatch to a target sequence is effective in inhibiting the expression of an AGT gene. Consideration of the efficacy of iRNAs with mismatches in inhibiting expression of an AGT gene is important, especially if the particular region of complementarity in an AGT gene is known to have polymorphic sequence variation within the population.

III. Modified iRNAs of the Invention

In one embodiment, the RNA of the iRNA of the invention e.g., a dsRNA, is un-modified, and does not comprise, e.g., chemical modifications and/or conjugations known in the art and described herein. In another embodiment, the RNA of an iRNA of the invention, e.g., a dsRNA, is chemically modified to enhance stability or other beneficial characteristics. In certain embodiments of the invention, substantially all of the nucleotides of an iRNA of the invention are modified. In other embodiments of the invention, all of the nucleotides of an iRNA of the invention are modified iRNAs of the invention in which "substantially all of the nucleotides are modified" are largely but not wholly modified and can include not more than 5, 4, 3, 2, or 1 unmodified nucleotides.

The nucleic acids featured in the invention can be synthesized and/or modified by methods well established in the art, such as those described in "Current protocols in nucleic acid chemistry," Beaucage, S. L. et al. (Edrs.), John Wiley & Sons, Inc., New York, N.Y., USA, which is hereby incorporated herein by reference. Modifications include, for example, end modifications, e.g., 5'-end modifications (phosphorylation, conjugation, inverted linkages) or 3'-end modifications (conjugation, DNA nucleotides, inverted linkages, etc.); base modifications, e.g., replacement with stabilizing bases, destabilizing bases, or bases that base pair with an expanded repertoire of partners, removal of bases (abasic nucleotides), or conjugated bases; sugar modifications (e.g., at the 2'-position or 4'-position) or replacement of the sugar; and/or backbone modifications, including modification or replacement of the phosphodiester linkages. Specific examples of iRNA compounds useful in the embodiments described herein include, but are not limited to RNAs containing modified backbones or no natural internucleoside linkages. RNAs having modified backbones include, among others, those that do not have a phosphorus atom in the backbone. For the purposes of this specification, and as sometimes referenced in the art, modified RNAs that do not have a phosphorus atom in their internucleoside backbone can also be considered to be oligonucleosides. In some embodiments, a modified iRNA will have a phosphorus atom in its internucleoside backbone.

Modified RNA backbones include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5'-linked analogs of these, and those having inverted polarity wherein the adjacent pairs of nucleoside units are linked 3'-5' to 5'-3' or 2'-5' to 5'-2'. Various salts, mixed salts and free acid forms are also included.

Representative U.S. patents that teach the preparation of the above phosphorus-containing linkages include, but are not limited to, U.S. Pat. Nos. 3,687,808; 4,469,863; 4,476,301; 5,023,243; 5,177,195; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,316; 5,550,111; 5,563,253; 5,571,799; 5,587,361; 5,625,050; 6,028,188; 6,124,445; 6,160,109; 6,169,170; 6,172,209; 6,239,265; 6,277,603; 6,326,199; 6,346,614; 6,444,423; 6,531,590; 6,534,639; 6,608,035; 6,683,167; 6,858,715; 6,867,294; 6,878,805; 7,015,315; 7,041,816; 7,273,933; 7,321,029; and U.S. Pat. RE39464, the entire contents of each of which are hereby incorporated herein by reference.

Modified RNA backbones that do not include a phosphorus atom therein have backbones that are formed by short chain alkyl or cycloalkyl internucleoside linkages, mixed heteroatoms and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative U.S. patents that teach the preparation of the above oligonucleosides include, but are not limited to, U.S. Pat. Nos. 5,034,506; 5,166,315; 5,185,444; 5,214,134; 5,216,141; 5,235,033; 5,64,562; 5,264,564; 5,405,938; 5,434,257; 5,466,677; 5,470,967; 5,489,677; 5,541,307; 5,561,225; 5,596,086; 5,602,240; 5,608,046; 5,610,289;

5,618,704; 5,623,070; 5,663,312; 5,633,360; 5,677,437; and, 5,677,439, the entire contents of each of which are hereby incorporated herein by reference.

In other embodiments, suitable RNA mimetics are contemplated for use in iRNAs, in which both the sugar and the internucleoside linkage, i.e., the backbone, of the nucleotide units are replaced with novel groups. The base units are maintained for hybridization with an appropriate nucleic acid target compound. One such oligomeric compound, an RNA mimetic that has been shown to have excellent hybridization properties, is referred to as a peptide nucleic acid (PNA). In PNA compounds, the sugar backbone of an RNA is replaced with an amide containing backbone, in particular an aminoethylglycine backbone. The nucleobases are retained and are bound directly or indirectly to aza nitrogen atoms of the amide portion of the backbone. Representative U.S. patents that teach the preparation of PNA compounds include, but are not limited to, U.S. Pat. Nos. 5,539,082; 5,714,331; and 5,719,262, the entire contents of each of which are hereby incorporated herein by reference. Additional PNA compounds suitable for use in the iRNAs of the invention are described in, for example, in Nielsen et al., Science, 1991, 254, 1497-1500.

Some embodiments featured in the invention include RNAs with phosphorothioate backbones and oligonucleosides with heteroatom backbones, and in particular —$CH_2$—NH—$CH_2$—, —$CH_2$—N($CH_3$)—O—$CH_2$—[known as a methylene (methylimino) or MMI backbone], —$CH_2$—O—N($CH_3$)—$CH_2$—, —$CH_2$—N($CH_3$)—N($CH_3$)—$CH_2$— and —N($CH_3$)—$CH_2$—$CH_2$—[wherein the native phosphodiester backbone is represented as —O—P—O—$CH_2$—] of the above-referenced U.S. Pat. No. 5,489,677, and the amide backbones of the above-referenced U.S. Pat. No. 5,602,240. In some embodiments, the RNAs featured herein have morpholino backbone structures of the above-referenced U.S. Pat. No. 5,034,506.

Modified RNAs can also contain one or more substituted sugar moieties. The iRNAs, e.g., dsRNAs, featured herein can include one of the following at the 2'-position: OH; F; O—, S—, or N-alkyl; O—, S—, or N-alkenyl; O—, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Exemplary suitable modifications include O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$$ONH_2$, and O($CH_2$)$_n$ON[($CH_2$)$_n$$CH_3$)]$_2$, where n and m are from 1 to about 10. In other embodiments, dsRNAs include one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an iRNA, or a group for improving the pharmacodynamic properties of an iRNA, and other substituents having similar properties. In some embodiments, the modification includes a 2'-methoxyethoxy (2'-O—$CH_2CH_2OCH_3$, also known as 2'-O-(2-methoxyethyl) or 2'-MOE) (Martin et al., Helv. Chim. Acta, 1995, 78:486-504) i.e., an alkoxy-alkoxy group. Another exemplary modification is 2'-dimethylaminooxyethoxy, i.e., a O($CH_2$)$_2$ON($CH_3$)$_2$ group, also known as 2'-DMAOE, as described in examples herein below, and 2'-dimethylaminoethoxyethoxy (also known in the art as 2'-O-dimethylaminoethoxyethyl or 2'-DMAEOE), i.e., 2'-O—$CH_2$—O—$CH_2$—N($CH_2$)$_2$. Further exemplary modifications include: 5'-Me-2'-F nucleotides, 5'-Me-2'-OMe nucleotides, 5'-Me-2'-deoxynucleotides, (both R and S isomers in these three families); 2'-alkoxyalkyl; and 2'-NMA (N-methylacetamide).

Other modifications include 2'-methoxy (2'-$OCH_3$), 2'-aminopropoxy (2'-$OCH_2CH_2CH_2NH_2$) and 2'-fluoro (2'-F). Similar modifications can also be made at other positions on the RNA of an iRNA, particularly the 3' position of the sugar on the 3' terminal nucleotide or in 2'-5' linked dsRNAs and the 5' position of 5' terminal nucleotide. iRNAs can also have sugar mimetics such as cyclobutyl moieties in place of the pentofuranosyl sugar. Representative U.S. patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, certain of which are commonly owned with the instant application. The entire contents of each of the foregoing are hereby incorporated herein by reference.

An iRNA can also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as deoxy-thymine (dT), 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl anal other 8-substituted adenines and guanines, 5-halo, particularly 5-bromo, 5-trifluoromethyl and other 5-substituted uracils and cytosines, 7-methylguanine and 7-methyladenine, 8-azaguanine and 8-azaadenine, 7-deazaguanine and 7-daazaadenine and 3-deazaguanine and 3-deazaadenine. Further nucleobases include those disclosed in U.S. Pat. No. 3,687,808, those disclosed in Modified Nucleosides in Biochemistry, Biotechnology and Medicine, Herdewijn, P. ed. Wiley-VCH, 2008; those disclosed in The Concise Encyclopedia Of Polymer Science And Engineering, pages 858-859, Kroschwitz, J. L, ed. John Wiley & Sons, 1990, these disclosed by Englisch et al., Angewandte Chemie, International Edition, 1991, 30, 613, and those disclosed by Sanghvi, Y S., Chapter 15, dsRNA Research and Applications, pages 289-302, Crooke, S. T. and Lebleu, B., Ed., CRC Press, 1993. Certain of these nucleobases are particularly useful for increasing the binding affinity of the oligomeric compounds featured in the invention. These include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., Eds., dsRNA Research and Applications, CRC Press, Boca Raton, 1993, pp. 276-278) and are exemplary base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. Nos. 3,687,808, 4,845,205; 5,130, 30; 5,134,066; 5,175,273; 5,367,066; 5,432,272; 5,457,187;

5,459,255; 5,484,908; 5,502,177; 5,525,711; 5,552,540; 5,587,469; 5,594,121; 5,596,091; 5,614,617; 5,681,941; 5,750,692; 6,015,886; 6,147,200; 6,166,197; 6,222,025; 6,235,887; 6,380,368; 6,528,640; 6,639,062; 6,617,438; 7,045,610; 7,427,672; and 7,495,088, the entire contents of each of which are hereby incorporated herein by reference.

The RNA of an iRNA can also be modified to include one or more locked nucleic acids (LNA). A locked nucleic acid is a nucleotide having a modified ribose moiety in which the ribose moiety comprises an extra bridge connecting the 2' and 4' carbons. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12): 3185-3193).

In some embodiments, the oligonucleotide of the invention comprises one or more monomers that are UNA (unlocked nucleic acid) nucleotides. UNA is unlocked acyclic nucleic acid, wherein any of the bonds of the sugar has been removed, forming an unlocked "sugar" residue. In one example, UNA also encompasses monomer with bonds between C1'-C4' have been removed (i.e. the covalent carbon-oxygen-carbon bond between the C1' and C4' carbons). In another example, the C2'-C3' bond (i.e. the covalent carbon-carbon bond between the C2' and C3' carbons) of the sugar has been removed (see *Nuc. Acids Symp. Series*, 52, 133-134 (2008) and Fluiter et al., *Mol. Biosyst.*, 2009, 10, 1039 hereby incorporated by reference).

The RNA of an iRNA can also be modified to include one or more bicyclic sugar moieties. A "bicyclic sugar" is a furanosyl ring modified by the bridging of two atoms. A "bicyclic nucleoside" ("BNA") is a nucleoside having a sugar moiety comprising a bridge connecting two carbon atoms of the sugar ring, thereby forming a bicyclic ring system. In certain embodiments, the bridge connects the 4'-carbon and the 2'-carbon of the sugar ring. Thus, in some embodiments an agent of the invention may include one or more locked nucleic acids (LNA). A locked nucleic acid is a nucleotide having a modified ribose moiety in which the ribose moiety comprises an extra bridge connecting the 2' and 4' carbons. In other words, an LNA is a nucleotide comprising a bicyclic sugar moiety comprising a 4'-CH2-O-2' bridge. This structure effectively "locks" the ribose in the 3'-endo structural conformation. The addition of locked nucleic acids to siRNAs has been shown to increase siRNA stability in serum, and to reduce off-target effects (Elmen, J. et al., (2005) *Nucleic Acids Research* 33(1):439-447; Mook, O R. et al., (2007) *Mol Canc Ther* 6(3):833-843; Grunweller, A. et al., (2003) *Nucleic Acids Research* 31(12):3185-3193). Examples of bicyclic nucleosides for use in the polynucleotides of the invention include without limitation nucleosides comprising a bridge between the 4' and the 2' ribosyl ring atoms. In certain embodiments, the antisense polynucleotide agents of the invention include one or more bicyclic nucleosides comprising a 4' to 2' bridge. Examples of such 4' to 2' bridged bicyclic nucleosides, include but are not limited to 4'-($CH_2$)—O-2' (LNA); 4'-(CH2)-S-2'; 4'-($CH_2$)$_2$—O-2' (ENA); 4'-CH($CH_3$)—O-2' (also referred to as "constrained ethyl" or "cEt") and 4'-CH(CH2O$CH_3$)—O-2' (and analogs thereof; see, e.g., U.S. Pat. No. 7,399,845); 4'-C(CH3)(CH3)-O-2' (and analogs thereof; see e.g., U.S. Pat. No. 8,278,283); 4'-CH2-N(O$CH_3$)-2' (and analogs thereof; see e.g., U.S. Pat. No. 8,278,425); 4'-CH2-O—N($CH_3$)-2' (see, e.g., U.S. Patent Publication No. 2004/0171570); 4'-$CH_2$—N(R)—O-2', wherein R is H, C1-C12 alkyl, or a protecting group (see, e.g., U.S. Pat. No. 7,427,672); 4'-$CH_2$—C(H)($CH_3$)-2' (see, e.g., Chattopadhyaya et al., *J. Org. Chem.*, 2009, 74, 118-134); and 4'-$CH_2$—C(=$CH_2$)-2' (and analogs thereof; see, e.g., U.S. Pat. No. 8,278,426). The entire contents of each of the foregoing are hereby incorporated herein by reference.

Additional representative U.S. Patents and US Patent Publications that teach the preparation of locked nucleic acid nucleotides include, but are not limited to, the following: U.S. Pat. Nos. 6,268,490; 6,525,191; 6,670,461; 6,770,748; 6,794,499; 6,998,484; 7,053,207; 7,034,133; 7,084,125; 7,399,845; 7,427,672; 7,569,686; 7,741,457; 8,022,193; 8,030,467; 8,278,425; 8,278,426; 8,278,283; US 2008/0039618; and US 2009/0012281, the entire contents of each of which are hereby incorporated herein by reference.

Any of the foregoing bicyclic nucleosides can be prepared having one or more stereochemical sugar configurations including for example α-L-ribofuranose and β-D-ribofuranose (see WO 99/14226).

The RNA of an iRNA can also be modified to include one or more constrained ethyl nucleotides. As used herein, a "constrained ethyl nucleotide" or "cEt" is a locked nucleic acid comprising a bicyclic sugar moiety comprising a 4'-CH ($CH_3$)—O-2' bridge. In one embodiment, a constrained ethyl nucleotide is in the S conformation referred to herein as "S-cEt."

An iRNA of the invention may also include one or more "conformationally restricted nucleotides" ("CRN"). CRN are nucleotide analogs with a linker connecting the C2' and C4' carbons of ribose or the C3 and —C5' carbons of ribose. CRN lock the ribose ring into a stable conformation and increase the hybridization affinity to mRNA. The linker is of sufficient length to place the oxygen in an optimal position for stability and affinity resulting in less ribose ring puckering.

Representative publications that teach the preparation of certain of the above noted CRN include, but are not limited to, US Patent Publication No. 2013/0190383; and PCT publication WO 2013/036868, the entire contents of each of which are hereby incorporated herein by reference.

One or more of the nucleotides of an iRNA of the invention may also include a hydroxymethyl substituted nucleotide. A "hydroxymethyl substituted nucleotide" is an acyclic 2'-3'-seco-nucleotide, also referred to as an "unlocked nucleic acid" ("UNA") modification Representative U.S. publications that teach the preparation of UNA include, but are not limited to, U.S. Pat. No. 8,314,227; and US Patent Publication Nos. 2013/0096289; 2013/0011922; and 2011/0313020, the entire contents of each of which are hereby incorporated herein by reference.

Potentially stabilizing modifications to the ends of RNA molecules can include N-(acetylaminocaproyl)-4-hydroxyprolinol (Hyp-C6-NHAc), N-(caproyl-4-hydroxyprolinol (Hyp-C6), N-(acetyl-4-hydroxyprolinol (Hyp-NHAc), thymidine-2'-O-deoxythymidine (ether), N-(aminocaproyl)-4-hydroxyprolinol (Hyp-C6-amino), 2-docosanoyl-uridine-3"-phosphate, inverted base dT(idT) and others. Disclosure of this modification can be found in PCT Publication No. WO 2011/005861.

Other modifications of the nucleotides of an iRNA of the invention include a 5' phosphate or 5' phosphate mimic, e.g., a 5'-terminal phosphate or phosphate mimic on the antisense strand of an RNAi agent. Suitable phosphate mimics are disclosed in, for example US Patent Publication No. 2012/0157511, the entire contents of which are incorporated herein by reference.

A. Modified iRNAs Comprising Motifs of the Invention

In certain aspects of the invention, the double-stranded RNAi agents of the invention include agents with chemical modifications as disclosed, for example, in U.S. Provisional Application No. 61/561,710, filed on Nov. 18, 2011, or in PCT/US2012/065691, filed on Nov. 16, 2012, the entire contents of each of which are incorporated herein by reference.

As shown herein and in Provisional Application No. 61/561,710 or PCT Application No. PCT/US2012/065691, a superior result may be obtained by introducing one or more motifs of three identical modifications on three consecutive nucleotides into a sense strand and/or antisense strand of an RNAi agent, particularly at or near the cleavage site. In some embodiments, the sense strand and antisense strand of the RNAi agent may otherwise be completely modified. The introduction of these motifs interrupts the modification pattern, if present, of the sense and/or antisense strand. The RNAi agent may be optionally conjugated with a GalNAc derivative ligand, for instance on the sense strand. The resulting RNAi agents present superior gene silencing activity.

More specifically, it has been surprisingly discovered that when the sense strand and antisense strand of the double-stranded RNAi agent are completely modified to have one or more motifs of three identical modifications on three consecutive nucleotides at or near the cleavage site of at least one strand of an RNAi agent, the gene silencing activity of the RNAi agent was superiorly enhanced.

Accordingly, the invention provides double-stranded RNAi agents capable of inhibiting the expression of a target gene (i.e., angiotensinogen (AGT) gene) in vivo. The RNAi agent comprises a sense strand and an antisense strand. Each strand of the RNAi agent may range from 12-30 nucleotides in length. For example, each strand may be between 14-30 nucleotides in length, 17-30 nucleotides in length, 25-30 nucleotides in length, 27-30 nucleotides in length, 17-23 nucleotides in length, 17-21 nucleotides in length, 17-19 nucleotides in length, 19-25 nucleotides in length, 19-23 nucleotides in length, 19-21 nucleotides in length, 21-25 nucleotides in length, or 21-23 nucleotides in length.

The sense strand and antisense strand typically form a duplex double-stranded RNA ("dsRNA"), also referred to herein as an "RNAi agent." The duplex region of an RNAi agent may be 12-30 nucleotide pairs in length. For example, the duplex region can be between 14-30 nucleotide pairs in length, 17-30 nucleotide pairs in length, 27-30 nucleotide pairs in length, 17-23 nucleotide pairs in length, 17-21 nucleotide pairs in length, 17-19 nucleotide pairs in length, 19-25 nucleotide pairs in length, 19-23 nucleotide pairs in length, 19-21 nucleotide pairs in length, 21-25 nucleotide pairs in length, or 21-23 nucleotide pairs in length. In another example, the duplex region is selected from 15, 16, 17, 18, 19, 20, 21, 22, 23, 24, 25, 26, and 27 nucleotides in length.

In one embodiment, the RNAi agent may contain one or more overhang regions and/or capping groups at the 3'-end, 5'-end, or both ends of one or both strands. The overhang can be 1-6 nucleotides in length, for instance 2-6 nucleotides in length, 1-5 nucleotides in length, 2-5 nucleotides in length, 1-4 nucleotides in length, 2-4 nucleotides in length, 1-3 nucleotides in length, 2-3 nucleotides in length, or 1-2 nucleotides in length. The overhangs can be the result of one strand being longer than the other, or the result of two strands of the same length being staggered. The overhang can form a mismatch with the target mRNA or it can be complementary to the gene sequences being targeted or can be another sequence. As discussed herein, extended overhang of up to 30 nucleotides in length are also contemplated in various embodiments of the invention. The first and second strands can also be joined, e.g., by additional bases to form a hairpin, or by other non-base linkers.

In one embodiment, the nucleotides in the overhang region of the RNAi agent can each independently be a modified or unmodified nucleotide including, but no limited to 2'-sugar modified, such as, 2-F, 2'-Omethyl, thymidine (T), 2'-O-methoxyethyl-5-methyluridine (Teo), 2'-O-methoxyethyladenosine (Aeo), 2'-O-methoxyethyl-5-methylcytidine (m5Ceo), and any combinations thereof. For example, TT can be an overhang sequence for either end on either strand. The overhang can form a mismatch with the target mRNA or it can be complementary to the gene sequences being targeted or can be another sequence.

The 5'- or 3'-overhangs at the sense strand, antisense strand, or both strands of the RNAi agent may be phosphorylated. In some embodiments, the overhang region(s) contains two nucleotides having a phosphorothioate between the two nucleotides, where the two nucleotides can be the same or different. In one embodiment, the overhang is present at the 3'-end of the sense strand, antisense strand, or both strands. In one embodiment, this 3'-overhang is present in the antisense strand. In one embodiment, this 3'-overhang is present in the sense strand.

The RNAi agent may contain only a single overhang, which can strengthen the interference activity of the RNAi, without affecting its overall stability. For example, the single-stranded overhang may be located at the 3'-terminal end of the sense strand or, alternatively, at the 3'-terminal end of the antisense strand. The RNAi may also have a blunt end, located at the 5'-end of the antisense strand (or the 3'-end of the sense strand) or vice versa. Generally, the antisense strand of the RNAi has a nucleotide overhang at the 3'-end, and the 5'-end is blunt. While not wishing to be bound by theory, the asymmetric blunt end at the 5'-end of the antisense strand and 3'-end overhang of the antisense strand favor the guide strand loading into RISC process.

In one embodiment, the RNAi agent is a double ended bluntmer of 19 nucleotides in length, wherein the sense strand contains at least one motif of three 2'-F modifications on three consecutive nucleotides at positions 7, 8, 9 from the 5'end. The antisense strand contains at least one motif of three 2'-O-methyl modifications on three consecutive nucleotides at positions 11, 12, 13 from the 5'end.

In another embodiment, the RNAi agent is a double ended bluntmer of 20 nucleotides in length, wherein the sense strand contains at least one motif of three 2'-F modifications on three consecutive nucleotides at positions 8, 9, 10 from the 5'end. The antisense strand contains at least one motif of three 2'-O-methyl modifications on three consecutive nucleotides at positions 11, 12, 13 from the 5'end.

In yet another embodiment, the RNAi agent is a double ended bluntmer of 21 nucleotides in length, wherein the sense strand contains at least one motif of three 2'-F modifications on three consecutive nucleotides at positions 9, 10, 11 from the 5'end. The antisense strand contains at least one motif of three 2'-O-methyl modifications on three consecutive nucleotides at positions 11, 12, 13 from the 5'end.

In one embodiment, the RNAi agent comprises a 21 nucleotide sense strand and a 23 nucleotide antisense strand, wherein the sense strand contains at least one motif of three 2'-F modifications on three consecutive nucleotides at positions 9, 10, 11 from the 5'end; the antisense strand contains at least one motif of three 2'-O-methyl modifications on three consecutive nucleotides at positions 11, 12, 13 from the 5'end, wherein one end of the RNAi agent is blunt, while the other end comprises a 2 nucleotide overhang. Preferably, the 2 nucleotide overhang is at the 3'-end of the antisense strand.

When the 2 nucleotide overhang is at the 3'-end of the antisense strand, there may be two phosphorothioate internucleotide linkages between the terminal three nucleotides, wherein two of the three nucleotides are the overhang nucleotides, and the third nucleotide is a paired nucleotide next to the overhang nucleotide. In one embodiment, the RNAi agent additionally has two phosphorothioate internucleotide linkages between the terminal three nucleotides at both the 5'-end of the sense strand and at the 5'-end of the antisense strand. In one embodiment, every nucleotide in the sense strand and the antisense strand of the RNAi agent, including the nucleotides that are part of the motifs are modified nucleotides. In one embodiment each residue is independently modified with a 2'-O-methyl or 3'-fluoro, e.g., in an alternating motif. Optionally, the RNAi agent further comprises a ligand (preferably GalNAc$_3$).

In one embodiment, the RNAi agent comprises a sense and an antisense strand, wherein the sense strand is 25-30 nucleotide residues in length, wherein starting from the 5' terminal nucleotide (position 1) positions 1 to 23 of the first strand comprise at least 8 ribonucleotides; the antisense strand is 36-66 nucleotide residues in length and, starting from the 3' terminal nucleotide, comprises at least 8 ribonucleotides in the positions paired with positions 1-23 of sense strand to form a duplex; wherein at least the 3' terminal nucleotide of antisense strand is unpaired with sense strand, and up to 6 consecutive 3' terminal nucleotides are unpaired with sense strand, thereby forming a 3' single stranded overhang of 1-6 nucleotides; wherein the 5' terminus of antisense strand comprises from 10-30 consecutive nucleotides which are unpaired with sense strand, thereby forming a 10-30 nucleotide single stranded 5' overhang; wherein at least the sense strand 5' terminal and 3' terminal nucleotides are base paired with nucleotides of antisense strand when sense and antisense strands are aligned for maximum complementarity, thereby forming a substantially duplexed region between sense and antisense strands; and antisense strand is sufficiently complementary to a target RNA along at least 19 ribonucleotides of antisense strand length to reduce target gene expression when the double-stranded nucleic acid is introduced into a mammalian cell; and wherein the sense strand contains at least one motif of three 2'-F modifications on three consecutive nucleotides, where at least one of the motifs occurs at or near the cleavage site. The antisense strand contains at least one motif of three 2'-O-methyl modifications on three consecutive nucleotides at or near the cleavage site.

In one embodiment, the RNAi agent comprises sense and antisense strands, wherein the RNAi agent comprises a first strand having a length which is at least 25 and at most 29 nucleotides and a second strand having a length which is at most 30 nucleotides with at least one motif of three 2'-O-methyl modifications on three consecutive nucleotides at position 11, 12, 13 from the 5' end; wherein the 3' end of the first strand and the 5' end of the second strand form a blunt end and the second strand is 1-4 nucleotides longer at its 3' end than the first strand, wherein the duplex region which is at least 25 nucleotides in length, and the second strand is sufficiently complementary to a target mRNA along at least 19 nucleotide of the second strand length to reduce target gene expression when the RNAi agent is introduced into a mammalian cell, and wherein dicer cleavage of the RNAi agent preferentially results in an siRNA comprising the 3' end of the second strand, thereby reducing expression of the target gene in the mammal. Optionally, the RNAi agent further comprises a ligand.

In one embodiment, the sense strand of the RNAi agent contains at least one motif of three identical modifications on three consecutive nucleotides, where one of the motifs occurs at the cleavage site in the sense strand.

In one embodiment, the antisense strand of the RNAi agent can also contain at least one motif of three identical modifications on three consecutive nucleotides, where one of the motifs occurs at or near the cleavage site in the antisense strand For an RNAi agent having a duplex region of 17-23 nucleotide in length, the cleavage site of the antisense strand is typically around the 10, 11 and 12 positions from the 5'-end. Thus the motifs of three identical modifications may occur at the 9, 10, 11 positions; 10, 11, 12 positions; 11, 12, 13 positions; 12, 13, 14 positions; or 13, 14, 15 positions of the antisense strand, the count starting from the 1$^{st}$ nucleotide from the 5'-end of the antisense strand, or, the count starting from the 1$^{st}$ paired nucleotide within the duplex region from the 5'-end of the antisense strand. The cleavage site in the antisense strand may also change according to the length of the duplex region of the RNAi from the 5'-end.

The sense strand of the RNAi agent may contain at least one motif of three identical modifications on three consecutive nucleotides at the cleavage site of the strand; and the antisense strand may have at least one motif of three identical modifications on three consecutive nucleotides at or near the cleavage site of the strand. When the sense strand and the antisense strand form a dsRNA duplex, the sense strand and the antisense strand can be so aligned that one motif of the three nucleotides on the sense strand and one motif of the three nucleotides on the antisense strand have at least one nucleotide overlap, i.e., at least one of the three nucleotides of the motif in the sense strand forms a base pair with at least one of the three nucleotides of the motif in the antisense strand. Alternatively, at least two nucleotides may overlap, or all three nucleotides may overlap.

In one embodiment, the sense strand of the RNAi agent may contain more than one motif of three identical modifications on three consecutive nucleotides. The first motif may occur at or near the cleavage site of the strand and the other motifs may be a wing modification. The term "wing modification" herein refers to a motif occurring at another portion of the strand that is separated from the motif at or near the cleavage site of the same strand. The wing modification is either adjacent to the first motif or is separated by at least one or more nucleotides. When the motifs are immediately adjacent to each other then the chemistry of the motifs are distinct from each other and when the motifs are separated by one or more nucleotide than the chemistries can be the same or different. Two or more wing modifications may be present. For instance, when two wing modifications are present, each wing modification may occur at one end relative to the first motif which is at or near cleavage site or on either side of the lead motif.

Like the sense strand, the antisense strand of the RNAi agent may contain more than one motifs of three identical modifications on three consecutive nucleotides, with at least one of the motifs occurring at or near the cleavage site of the strand. This antisense strand may also contain one or more wing modifications in an alignment similar to the wing modifications that may be present on the sense strand.

In one embodiment, the wing modification on the sense strand or antisense strand of the RNAi agent typically does not include the first one or two terminal nucleotides at the 3'-end, 5'-end or both ends of the strand.

In another embodiment, the wing modification on the sense strand or antisense strand of the RNAi agent typically does not include the first one or two paired nucleotides within the duplex region at the 3'-end, 5'-end or both ends of the strand.

When the sense strand and the antisense strand of the RNAi agent each contain at least one wing modification, the wing modifications may fall on the same end of the duplex region, and have an overlap of one, two or three nucleotides.

When the sense strand and the antisense strand of the RNAi agent each contain at least two wing modifications, the sense strand and the antisense strand can be so aligned that two modifications each from one strand fall on one end of the duplex region, having an overlap of one, two or three nucleotides; two modifications each from one strand fall on the other end of the duplex region, having an overlap of one, two, or three nucleotides; two modifications one strand fall on each side of the lead motif, having an overlap of one, two or three nucleotides in the duplex region.

In one embodiment, every nucleotide in the sense strand and antisense strand of the RNAi agent, including the nucleotides that are part of the motifs, may be modified. Each nucleotide may be modified with the same or different modification which can include one or more alteration of one or both of the non-linking phosphate oxygens and/or of one or more of the linking phosphate oxygens; alteration of a constituent of the ribose sugar, e.g., of the 2' hydroxyl on the ribose sugar; wholesale replacement of the phosphate moiety with "dephospho" linkers; modification or replacement of a naturally occurring base; and replacement or modification of the ribose-phosphate backbone.

As nucleic acids are polymers of subunits, many of the modifications occur at a position which is repeated within a nucleic acid, e.g., a modification of a base, or a phosphate moiety, or a non-linking O of a phosphate moiety. In some cases the modification will occur at all of the subject positions in the nucleic acid but in many cases it will not. By way of example, a modification may only occur at a 3' or 5' terminal position, may only occur in a terminal region, e.g., at a position on a terminal nucleotide or in the last 2, 3, 4, 5, or 10 nucleotides of a strand. A modification may occur in a double strand region, a single strand region, or in both. A modification may occur only in the double strand region of a RNA or may only occur in a single strand region of a RNA. For example, a phosphorothioate modification at a non-linking O position may only occur at one or both termini, may only occur in a terminal region, e.g., at a position on a terminal nucleotide or in the last 2, 3, 4, 5, or 10 nucleotides of a strand, or may occur in double strand and single strand regions, particularly at termini. The 5' end or ends can be phosphorylated.

It may be possible, e.g., to enhance stability, to include particular bases in overhangs, or to include modified nucleotides or nucleotide surrogates, in single strand overhangs, e.g., in a 5' or 3' overhang, or in both. For example, it can be desirable to include purine nucleotides in overhangs. In some embodiments all or some of the bases in a 3' or 5' overhang may be modified, e.g., with a modification described herein. Modifications can include, e.g., the use of modifications at the 2' position of the ribose sugar with modifications that are known in the art, e.g., the use of deoxyribonucleotides, 2'-deoxy-2'-fluoro (2'-F) or 2'-O-methyl modified instead of the ribosugar of the nucleobase, and modifications in the phosphate group, e.g., phosphorothioate modifications. Overhangs need not be homologous with the target sequence.

In one embodiment, each residue of the sense strand and antisense strand is independently modified with LNA, CRN, cET, UNA, HNA, CeNA, 2'-methoxyethyl, 2'-O-methyl, 2'-O-allyl, 2'-C-allyl, 2'-deoxy, 2'-hydroxyl, or 2'-fluoro. The strands can contain more than one modification. In one embodiment, each residue of the sense strand and antisense strand is independently modified with 2'-O-methyl or 2'-fluoro.

At least two different modifications are typically present on the sense strand and antisense strand. Those two modifications may be the 2'-O-methyl or 2'-fluoro modifications, or others.

In one embodiment, the $N_a$ and/or $N_b$ comprise modifications of an alternating pattern. The term "alternating motif" as used herein refers to a motif having one or more modifications, each modification occurring on alternating nucleotides of one strand. The alternating nucleotide may refer to one per every other nucleotide or one per every three nucleotides, or a similar pattern. For example, if A, B and C each represent one type of modification to the nucleotide, the alternating motif can be "ABABABABABAB . . . ," "AAB-BAABBAABB . . . ," "AABAABAABAAB . . . ," "AAABAAABAAAB . . . ," "AAABBBAAABBB . . . ," or "ABCABCABCABC . . . ," etc.

The type of modifications contained in the alternating motif may be the same or different. For example, if A, B, C, D each represent one type of modification on the nucleotide, the alternating pattern, i.e., modifications on every other nucleotide, may be the same, but each of the sense strand or antisense strand can be selected from several possibilities of modifications within the alternating motif such as "ABABAB . . . ", "ACACAC . . . " "BDBDBD . . . " or "CDCDCD . . . ," etc.

In one embodiment, the RNAi agent of the invention comprises the modification pattern for the alternating motif on the sense strand relative to the modification pattern for the alternating motif on the antisense strand is shifted. The shift may be such that the modified group of nucleotides of the sense strand corresponds to a differently modified group of nucleotides of the antisense strand and vice versa. For example, the sense strand when paired with the antisense strand in the dsRNA duplex, the alternating motif in the sense strand may start with "ABABAB" from 5'-3' of the strand and the alternating motif in the antisense strand may start with "BABABA" from 5'-3' of the strand within the duplex region. As another example, the alternating motif in the sense strand may start with "AABBAABB" from 5'-3' of the strand and the alternating motif in the antisenese strand may start with "BBAABBAA" from 5'-3' of the strand within the duplex region, so that there is a complete or partial shift of the modification patterns between the sense strand and the antisense strand.

In one embodiment, the RNAi agent comprises the pattern of the alternating motif of 2'-O-methyl modification and 2'-F modification on the sense strand initially has a shift relative to the pattern of the alternating motif of 2'-O-methyl modification and 2'-F modification on the antisense strand initially, i.e., the 2'-O-methyl modified nucleotide on the sense strand base pairs with a 2'-F modified nucleotide on the antisense strand and vice versa. The 1 position of the sense strand may start with the 2'-F modification, and the 1 position of the antisense strand may start with the 2'-O-methyl modification.

The introduction of one or more motifs of three identical modifications on three consecutive nucleotides to the sense strand and/or antisense strand interrupts the initial modification pattern present in the sense strand and/or antisense strand. This interruption of the modification pattern of the sense and/or antisense strand by introducing one or more motifs of three identical modifications on three consecutive nucleotides to the sense and/or antisense strand surprisingly enhances the gene silencing activity to the target gene.

In one embodiment, when the motif of three identical modifications on three consecutive nucleotides is introduced to any of the strands, the modification of the nucleotide next to the motif is a different modification than the modification of the motif. For example, the portion of the sequence containing the motif is " . . . $N_a$YYY$N_b$ . . . ," where "Y" represents the modification of the motif of three identical modifications on three consecutive nucleotide, and "$N_a$" and "$N_b$" represent a modification to the nucleotide next to the motif "YYY" that is different than the modification of Y, and where $N_a$ and $N_b$ can be the same or different modifications. Alternatively, $N_a$ and/or $N_b$ may be present or absent when there is a wing modification present.

The RNAi agent may further comprise at least one phosphorothioate or methylphosphonate internucleotide linkage. The phosphorothioate or methylphosphonate internucleotide linkage modification may occur on any nucleotide of the sense strand or antisense strand or both strands in any position of the strand. For instance, the internucleotide linkage modification may occur on every nucleotide on the sense strand and/or antisense strand; each internucleotide linkage modification may occur in an alternating pattern on the sense strand and/or antisense strand; or the sense strand or antisense strand may contain both internucleotide linkage modifications in an alternating pattern. The alternating pattern of the internucleotide linkage modification on the sense strand may be the same or different from the antisense strand, and the alternating pattern of the internucleotide linkage modification on the sense strand may have a shift relative to the alternating pattern of the internucleotide linkage modification on the antisense strand. In one embodiment, a double-standed RNAi agent comprises 6-8phosphorothioate internucleotide linkages. In one embodiment, the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

In one embodiment, the RNAi comprises a phosphorothioate or methylphosphonate internucleotide linkage modification in the overhang region. For example, the overhang region may contain two nucleotides having a phosphorothioate or methylphosphonate internucleotide linkage between the two nucleotides. Internucleotide linkage modifications also may be made to link the overhang nucleotides with the terminal paired nucleotides within the duplex region. For example, at least 2, 3, 4, or all the overhang nucleotides may be linked through phosphorothioate or methylphosphonate internucleotide linkage, and optionally, there may be additional phosphorothioate or methylphosphonate internucleotide linkages linking the overhang nucleotide with a paired nucleotide that is next to the overhang nucleotide. For instance, there may be at least two phosphorothioate internucleotide linkages between the terminal three nucleotides, in which two of the three nucleotides are overhang nucleotides, and the third is a paired nucleotide next to the overhang nucleotide. These terminal three nucleotides may be at the 3'-end of the antisense strand, the 3'-end of the sense strand, the 5'-end of the antisense strand, and/or the 5'end of the antisense strand.

In one embodiment, the 2 nucleotide overhang is at the 3'-end of the antisense strand, and there are two phosphorothioate internucleotide linkages between the terminal three nucleotides, wherein two of the three nucleotides are the overhang nucleotides, and the third nucleotide is a paired nucleotide next to the overhang nucleotide. Optionally, the RNAi agent may additionally have two phosphorothioate internucleotide linkages between the terminal three nucleotides at both the 5'-end of the sense strand and at the 5'-end of the antisense strand.

In one embodiment, the RNAi agent comprises mismatch(es) with the target, within the duplex, or combinations thereof. The mismatch may occur in the overhang region or the duplex region. The base pair may be ranked on the basis of their propensity to promote dissociation or melting (e.g., on the free energy of association or dissociation of a particular pairing, the simplest approach is to examine the pairs on an individual pair basis, though next neighbor or similar analysis can also be used). In terms of promoting dissociation: A:U is preferred over G:C; G:U is preferred over G:C; and I:C is preferred over G:C (I=inosine). Mismatches, e.g., non-canonical or other than canonical pairings (as described elsewhere herein) are preferred over canonical (A:T, A:U, G:C) pairings; and pairings which include a universal base are preferred over canonical pairings.

In one embodiment, the RNAi agent comprises at least one of the first 1, 2, 3, 4, or 5 base pairs within the duplex regions from the 5'-end of the antisense strand independently selected from the group of: A:U, G:U, I:C, and mismatched pairs, e.g., non-canonical or other than canonical pairings or pairings which include a universal base, to promote the dissociation of the antisense strand at the 5'-end of the duplex.

In one embodiment, the nucleotide at the 1 position within the duplex region from the 5'-end in the antisense strand is selected from the group consisting of A, dA, dU, U, and dT. Alternatively, at least one of the first 1, 2 or 3 base pair within the duplex region from the 5'-end of the antisense strand is an AU base pair. For example, the first base pair within the duplex region from the 5'-end of the antisense strand is an AU base pair.

In another embodiment, the nucleotide at the 3'-end of the sense strand is deoxy-thymine (dT). In another embodiment, the nucleotide at the 3'-end of the antisense strand is deoxy-thymine (dT). In one embodiment, there is a short sequence of deoxy-thymine nucleotides, for example, two dT nucleotides on the 3'-end of the sense and/or antisense strand.

In one embodiment, the sense strand sequence may be represented by formula (I):

wherein:
i and j are each independently 0 or 1;
p and q are each independently 0-6;
each $N_a$ independently represents an oligonucleotide sequence comprising 0-25 modified nucleotides, each sequence comprising at least two differently modified nucleotides;

each $N_b$ independently represents an oligonucleotide sequence comprising 0-10 modified nucleotides;

each $n_p$ and $n_q$ independently represent an overhang nucleotide;

wherein Nb and Y do not have the same modification; and

XXX, YYY and ZZZ each independently represent one motif of three identical modifications on three consecutive nucleotides. Preferably YYY is all 2'-F modified nucleotides.

In one embodiment, the $N_a$ and/or $N_b$ comprise modifications of alternating pattern.

In one embodiment, the YYY motif occurs at or near the cleavage site of the sense strand. For example, when the RNAi agent has a duplex region of 17-23 nucleotides in length, the YYY motif can occur at or the vicinity of the cleavage site (e.g.: can occur at positions 6, 7, 8, 7, 8, 9, 8, 9, 10, 9, 10, 11, 10, 11, 12 or 11, 12, 13) of—the sense strand, the count starting from the $1^{st}$ nucleotide, from the 5'-end; or optionally, the count starting at the $1^{st}$ paired nucleotide within the duplex region, from the 5'-end.

In one embodiment, i is 1 and j is 0, or i is 0 and j is 1, or both i and j are 1. The sense strand can therefore be represented by the following formulas:

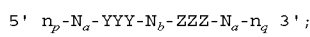 (Ib)

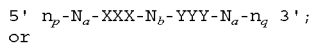 (Ic)

or

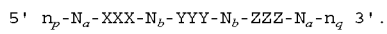 (Id)

When the sense strand is represented by formula (Ib), $N_b$ represents an oligonucleotide sequence comprising 0-10, 0-7, 0-5, 0-4, 0-2 or 0 modified nucleotides. Each $N_a$ independently can represent an oligonucleotide sequence comprising 2-20, 2-15, or 2-10 modified nucleotides.

When the sense strand is represented as formula (Ic), $N_b$ represents an oligonucleotide sequence comprising 0-10, 0-7, 0-10, 0-7, 0-5, 0-4, 0-2 or 0 modified nucleotides. Each $N_a$ can independently represent an oligonucleotide sequence comprising 2-20, 2-15, or 2-10 modified nucleotides.

When the sense strand is represented as formula (Id), each $N_b$ independently represents an oligonucleotide sequence comprising 0-10, 0-7, 0-5, 0-4, 0-2 or 0 modified nucleotides. Preferably, $N_b$ is 0, 1, 2, 3, 4, 5 or 6 Each $N_a$ can independently represent an oligonucleotide sequence comprising 2-20, 2-15, or 2-10 modified nucleotides. Each of X, Y and Z may be the same or different from each other.

In other embodiments, i is 0 and j is 0, and the sense strand may be represented by the formula:

 (Ia)

When the sense strand is represented by formula (Ia), each $N_a$ independently can represent an oligonucleotide sequence comprising 2-20, 2-15, or 2-10 modified nucleotides.

In one embodiment, the antisense strand sequence of the RNAi may be represented by formula (II):

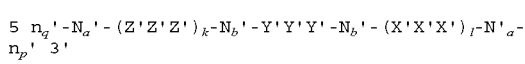 (II)

wherein:
k and l are each independently 0 or 1;
p' and q' are each independently 0-6;

each $N_a'$ independently represents an oligonucleotide sequence comprising 0-25 modified nucleotides, each sequence comprising at least two differently modified nucleotides;

each $N_b'$ independently represents an oligonucleotide sequence comprising 0-10 modified nucleotides;

each $n_p'$ and $n_q'$ independently represent an overhang nucleotide;

wherein $N_b'$ and Y' do not have the same modification; and

X'X'X', Y'Y'Y' and Z'Z'Z' each independently represent one motif of three identical modifications on three consecutive nucleotides.

In one embodiment, the $N_a'$ and/or $N_b'$ comprise modifications of alternating pattern.

The Y'Y'Y' motif occurs at or near the cleavage site of the antisense strand. For example, when the RNAi agent has a duplex region of 17-23nucleotidein length, the Y'Y'Y' motif can occur at positions 9, 10, 11; 10, 11, 12; 11, 12, 13; 12, 13, 14; or 13, 14, 15 of the antisense strand, with the count starting from the $1^{st}$ nucleotide, from the 5'-end; or optionally, the count starting at the $1^{st}$ paired nucleotide within the duplex region, from the 5'-end. Preferably, the Y'Y'Y' motif occurs at positions 11, 12, 13.

In one embodiment, Y'Y'Y' motif is all 2'-OMe modified nucleotides.

In one embodiment, k is 1 and l is 0, or k is 0 and l is 1, or both k and l are 1.

The antisense strand can therefore be represented by the following formulas:

 (IIb)

 (IIc)

or

 (IId)

When the antisense strand is represented by formula (IIb), $N_b$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IIc), $N_b'$ represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides.

When the antisense strand is represented as formula (IId), each $N_b'$ independently represents an oligonucleotide sequence comprising 0-10, 0-7, 0-10, 0-7, 0-5, 0-4, 0-2 or 0 modified nucleotides. Each $N_a'$ independently represents an oligonucleotide sequence comprising 2-20, 2-15, or 2-10 modified nucleotides. Preferably, $N_b$ is 0, 1, 2, 3, 4, 5 or 6.

In other embodiments, k is 0 and l is 0 and the antisense strand may be represented by the formula:

 (Ia)

When the antisense strand is represented as formula (IIa), each $N_a'$ independently represents an oligonucleotide sequence comprising 2-20, 2-15, or 2-10 modified nucleotides. Each of X', Y' and Z' may be the same or different from each other.

Each nucleotide of the sense strand and antisense strand may be independently modified with LNA, CRN, UNA, cEt, HNA, CeNA, 2'-methoxyethyl, 2'-O-methyl, 2'-O-allyl, 2'-C-allyl, 2'-hydroxyl, or 2'-fluoro. For example, each nucleotide of the sense strand and antisense strand is independently modified with 2'-O-methyl or 2'-fluoro. Each X, Y, Z, X', Y¹ and Z', in particular, may represent a 2'-O-methyl modification or a 2'-fluoro modification.

In one embodiment, the sense strand of the RNAi agent may contain YYY motif occurring at 9, 10 and 11 positions of the strand when the duplex region is 21 nt, the count starting from the 1$^{st}$ nucleotide from the 5'-end, or optionally, the count starting at the 1$^{st}$ paired nucleotide within the duplex region, from the 5'-end; and Y represents 2'-F modification. The sense strand may additionally contain XXX motif or ZZZ motifs as wing modifications at the opposite end of the duplex region; and XXX and ZZZ each independently represents a 2'-OMe modification or 2'-F modification.

In one embodiment the antisense strand may contain Y'Y'Y' motif occurring at positions 11, 12, 13 of the strand, the count starting from the 1$^{st}$ nucleotide from the 5'-end, or optionally, the count starting at the 1$^{st}$ paired nucleotide within the duplex region, from the 5'-end; and Y' represents 2'-O-methyl modification. The antisense strand may additionally contain X'X'X' motif or Z'Z'Z' motifs as wing modifications at the opposite end of the duplex region; and X'X'X' and Z'Z'Z' each independently represents a 2'-OMe modification or 2'-F modification.

The sense strand represented by any one of the above formulas (Ia), (Ib), (Ic), and (Id) forms a duplex with a antisense strand being represented by any one of formulas (IIa), (IIb), (IIc), and (IId), respectively.

Accordingly, the RNAi agents for use in the methods of the invention may comprise a sense strand and an antisense strand, each strand having 14 to 30 nucleotides, the RNAi duplex represented by formula (III):

sense: (III)
5' $n_p$-$N_a$-(X X X)$_i$-$N_b$-Y Y Y-$N_b$-(Z Z Z)$_j$-$N_a$-$n_q$ 3' antisense:
3' $n_p'$-$N_a'$-(X'X'X')$_k$-$N_b'$-Y'Y'Y'-$N_b'$-(Z'Z'Z')$_l$-$N_a'$-$n_q'$ 5' wherein:
i, j, k, and 1 are each independently 0 or 1;
p, p', q, and q' are each independently 0-6;
each $N_a$ and $N_a$ independently represents an oligonucleotide sequence comprising 0-25 modified nucleotides, each sequence comprising at least two differently modified nucleotides;
each $N_b$ and $N_b'$ independently represents an oligonucleotide sequence comprising 0-10 modified nucleotides;
wherein each $n_p'$, $n_p$, $n_q'$, and $n_q$, each of which may or may not be present, independently represents an overhang nucleotide; and XXX, YYY, ZZZ, X'X'X', Y'Y'Y', and Z'Z'Z' each independently represent one motif of three identical modifications on three consecutive nucleotides.

In one embodiment, i is 0 and j is 0; or i is 1 and j is 0; or i is 0 and j is 1; or both i and j are 0; or both i and j are 1. In another embodiment, k is 0 and 1 is 0; or k is 1 and 1 is 0; k is 0 and 1 is 1; or both k and 1 are 0; or both k and 1 are 1.

Exemplary combinations of the sense strand and antisense strand forming a RNAi duplex include the formulas below:

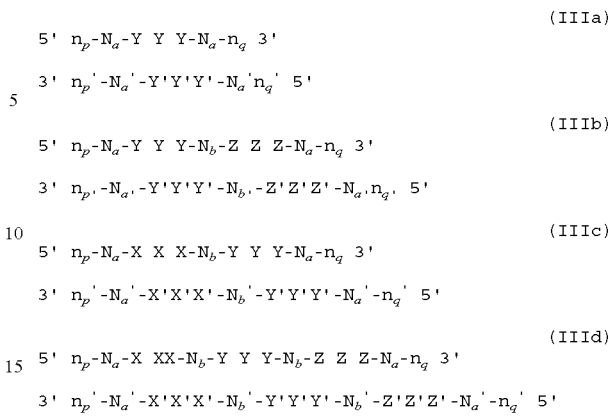

When the RNAi agent is represented by formula (IIIa), each $N_a$ independently represents an oligonucleotide sequence comprising 2-20, 2-15, or 2-10 modified nucleotides.

When the RNAi agent is represented by formula (IIIb), each $N_b$ independently represents an oligonucleotide sequence comprising 1-10, 1-7, 1-5 or 1-4 modified nucleotides. Each $N_a$ independently represents an oligonucleotide sequence comprising 2-20, 2-15, or 2-10 modified nucleotides.

When the RNAi agent is represented as formula (IIIc), each $N_b$, $N_b'$ independently represents an oligonucleotide sequence comprising 0-10, 0-7, 0-10, 0-7, 0-5, 0-4, 0-2 or 0 modified nucleotides. Each $N_a$ independently represents an oligonucleotide sequence comprising 2-20, 2-15, or 2-10 modified nucleotides.

When the RNAi agent is represented as formula (IIId), each $N_b$, $N_b'$ independently represents an oligonucleotide sequence comprising 0-10, 0-7, 0-10, 0-7, 0-5, 0-4, 0-2 or 0 modified nucleotides. Each $N_a$, $N_a$ independently represents an oligonucleotide sequence comprising 2-20, 2-15, or 2-10 modified nucleotides. Each of $N_a$, $N_a'$, $N_b$ and $N_b$ independently comprises modifications of alternating pattern.

Each of X, Y and Z in formulas (III), (IIIa), (IIIb), (IIIc), and (IIId) may be the same or different from each other.

When the RNAi agent is represented by formula (III), (IIIa), (IIIb), (IIIc), and (IIId), at least one of the Y nucleotides may form a base pair with one of the Y' nucleotides. Alternatively, at least two of the Y nucleotides form base pairs with the corresponding Y' nucleotides; or all three of the Y nucleotides all form base pairs with the corresponding Y' nucleotides.

When the RNAi agent is represented by formula (IIIb) or (IIId), at least one of the Z nucleotides may form a base pair with one of the Z' nucleotides. Alternatively, at least two of the Z nucleotides form base pairs with the corresponding Z' nucleotides; or all three of the Z nucleotides all form base pairs with the corresponding Z' nucleotides.

When the RNAi agent is represented as formula (IIIc) or (IIId), at least one of the X nucleotides may form a base pair with one of the X' nucleotides. Alternatively, at least two of the X nucleotides form base pairs with the corresponding X' nucleotides; or all three of the X nucleotides all form base pairs with the corresponding X' nucleotides.

In one embodiment, the modification on the Y nucleotide is different than the modification on the Y' nucleotide, the modification on the Z nucleotide is different than the modification on the Z' nucleotide, and/or the modification on the X nucleotide is different than the modification on the X' nucleotide.

In one embodiment, when the RNAi agent is represented by formula (IIId), the $N_a$ modifications are 2'-O-methyl or 2'-fluoro modifications. In another embodiment, when the RNAi agent is represented by formula (IIId), the $N_a$ modifications are 2'-O-methyl or 2'-fluoro modifications and $n_p'>0$ and at least one $n_p'$ is linked to a neighboring nucleotide a via phosphorothioate linkage. In yet another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, and the sense strand is conjugated to one or more GalNAc derivatives attached through a bivalent or trivalent branched linker (described below). In another embodiment, when the RNAi agent is represented by formula (IIId), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, when the RNAi agent is represented by formula (IIIa), the $N_a$ modifications are 2'-O-methyl or 2'-fluoro modifications, $n_p'>0$ and at least one $n_p'$ is linked to a neighboring nucleotide via phosphorothioate linkage, the sense strand comprises at least one phosphorothioate linkage, and the sense strand is conjugated to one or more GalNAc derivatives attached through a bivalent or trivalent branched linker.

In one embodiment, the RNAi agent is a multimer containing at least two duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, the RNAi agent is a multimer containing three, four, five, six or more duplexes represented by formula (III), (IIIa), (IIIb), (IIIc), and (IIId), wherein the duplexes are connected by a linker. The linker can be cleavable or non-cleavable. Optionally, the multimer further comprises a ligand. Each of the duplexes can target the same gene or two different genes; or each of the duplexes can target same gene at two different target sites.

In one embodiment, two RNAi agents represented by formula (III), (IIIa), (IIIb), (IIIc), and (IIId) are linked to each other at the 5' end, and one or both of the 3' ends and are optionally conjugated to a ligand. Each of the agents can target the same gene or two different genes; or each of the agents can target same gene at two different target sites.

Various publications describe multimeric RNAi agents that can be used in the methods of the invention. Such publications include WO2007/091269, U.S. Pat. No. 7,858,769, WO2010/141511, WO2007/117686, WO2009/014887 and WO2011/031520 the entire contents of each of which are hereby incorporated herein by reference.

As described in more detail below, the RNAi agent that contains conjugations of one or more carbohydrate moieties to a RNAi agent can optimize one or more properties of the RNAi agent. In many cases, the carbohydrate moiety will be attached to a modified subunit of the RNAi agent. For example, the ribose sugar of one or more ribonucleotide subunits of a dsRNA agent can be replaced with another moiety, e.g., a non-carbohydrate (preferably cyclic) carrier to which is attached a carbohydrate ligand. A ribonucleotide subunit in which the ribose sugar of the subunit has been so replaced is referred to herein as a ribose replacement modification subunit (RRMS). A cyclic carrier may be a carbocyclic ring system, i.e., all ring atoms are carbon atoms, or a heterocyclic ring system, i.e., one or more ring atoms may be a heteroatom, e.g., nitrogen, oxygen, sulfur. The cyclic carrier may be a monocyclic ring system, or may contain two or more rings, e.g. fused rings. The cyclic carrier may be a fully saturated ring system, or it may contain one or more double bonds.

The ligand may be attached to the polynucleotide via a carrier. The carriers include (i) at least one "backbone attachment point," preferably two "backbone attachment points" and (ii) at least one "tethering attachment point." A "backbone attachment point" as used herein refers to a functional group, e.g. a hydroxyl group, or generally, a bond available for, and that is suitable for incorporation of the carrier into the backbone, e.g., the phosphate, or modified phosphate, e.g., sulfur containing, backbone, of a ribonucleic acid. A "tethering attachment point" (TAP) in some embodiments refers to a constituent ring atom of the cyclic carrier, e.g., a carbon atom or a heteroatom (distinct from an atom which provides a backbone attachment point), that connects a selected moiety. The moiety can be, e.g., a carbohydrate, e.g. monosaccharide, disaccharide, trisaccharide, tetrasaccharide, oligosaccharide and polysaccharide. Optionally, the selected moiety is connected by an intervening tether to the cyclic carrier. Thus, the cyclic carrier will often include a functional group, e.g., an amino group, or generally, provide a bond, that is suitable for incorporation or tethering of another chemical entity, e.g., a ligand to the constituent ring.

The RNAi agents may be conjugated to a ligand via a carrier, wherein the carrier can be cyclic group or acyclic group; preferably, the cyclic group is selected from pyrrolidinyl, pyrazolinyl, pyrazolidinyl, imidazolinyl, imidazolidinyl, piperidinyl, piperazinyl, [1,3]dioxolane, oxazolidinyl, isoxazolidinyl, morpholinyl, thiazolidinyl, isothiazolidinyl, quinoxalinyl, pyridazinonyl, tetrahydrofuryl and decalin; preferably, the acyclic group is selected from serinol backbone or diethanolamine backbone.

In certain specific embodiments, the RNAi agent for use in the methods of the invention is an agent selected from the group of agents listed in any one of Tables 3, 4, 7, 8, 11, 13, and 15. These agents may further comprise a ligand.

IV. iRNAs Conjugated to Ligands

Another modification of the RNA of an iRNA of the invention involves chemically linking to the RNA one or more ligands, moieties or conjugates that enhance the activity, cellular distribution or cellular uptake of the iRNA. Such moieties include but are not limited to lipid moieties such as a cholesterol moiety (Letsinger et al., *Proc. Natl. Acid. Sci. USA*, 1989, 86: 6553-6556), cholic acid (Manoharan et al., *Biorg. Med. Chem. Let.*, 1994, 4:1053-1060), a thioether, e.g., beryl-S-tritylthiol (Manoharan et al., *Ann. N.Y. Acad. Sci.*, 1992, 660:306-309; Manoharan et al., *Biorg. Med. Chem. Let.*, 1993, 3:2765-2770), a thiocholesterol (Oberhauser et al., *Nucl. Acids Res.*, 1992, 20:533-538), an aliphatic chain, e.g., dodecandiol or undecyl residues (Saison-Behmoaras et al., *EMBO J*, 1991, 10:1111-1118; Kabanov et al., *FEBS Lett.*, 1990, 259:327-330; Svinarchuk et al., *Biochimie*, 1993, 75:49-54), a phospholipid, e.g., di-hexadecyl-rac-glycerol or triethyl-ammonium 1,2-di-O-hexadecyl-rac-glycero-3-phosphonate (Manoharan et al., *Tetrahedron Lett.*, 1995, 36:3651-3654; Shea et al., *Nucl. Acids Res.*, 1990, 18:3777-3783), a polyamine or a polyethylene glycol chain (Manoharan et al., *Nucleosides & Nucleotides,* 1995, 14:969-973), or adamantane acetic acid (Manoharan et al., *Tetrahedron Lett.,* 1995, 36:3651-3654), a palmityl moiety (Mishra et al., *Biochim. Biophys. Acta,* 1995, 1264:229-237), or an octadecylamine or hexylaminocarbonyloxycholesterol moiety (Crooke et al., *J. Pharmacol. Exp. Ther.,* 1996, 277:923-937).

In one embodiment, a ligand alters the distribution, targeting or lifetime of an iRNA agent into which it is incorporated. In preferred embodiments a ligand provides an enhanced affinity for a selected target, e.g., molecule, cell or cell type, compartment, e.g., a cellular or organ compartment, tissue, organ or region of the body, as, e.g., compared to a species absent such a ligand. Preferred ligands will not take part in duplex pairing in a duplexed nucleic acid.

Ligands can include a naturally occurring substance, such as a protein (e.g., human serum albumin (HSA), low-density lipoprotein (LDL), or globulin); carbohydrate (e.g., a dextran, pullulan, chitin, chitosan, inulin, cyclodextrin, N-acetylgalactosamine, or hyaluronic acid); or a lipid. The ligand can also be a recombinant or synthetic molecule, such as a synthetic polymer, e.g., a synthetic polyamino acid. Examples of polyamino acids include polyamino acid is a polylysine (PLL), poly L-aspartic acid, poly L-glutamic acid, styrene-maleic acid anhydride copolymer, poly(L-lactide-co-glycolied) copolymer, divinyl ether-maleic anhydride copolymer, N-(2-hydroxypropyl)methacrylamide copolymer (HMPA), polyethylene glycol (PEG), polyvinyl alcohol (PVA), polyurethane, poly(2-ethylacryllic acid), N-isopropylacrylamide polymers, or polyphosphazine. Example of polyamines include: polyethylenimine, polylysine (PLL), spermine, spermidine, polyamine, pseudopeptide-polyamine, peptidomimetic polyamine, dendrimer polyamine, arginine, amidine, protamine, cationic lipid, cationic porphyrin, quaternary salt of a polyamine, or an alpha helical peptide.

Ligands can also include targeting groups, e.g., a cell or tissue targeting agent, e.g., a lectin, glycoprotein, lipid or protein, e.g., an antibody, that binds to a specified cell type such as a kidney cell. A targeting group can be a thyrotropin, melanotropin, lectin, glycoprotein, surfactant protein A, Mucin carbohydrate, multivalent lactose, multivalent galactose, N-acetyl-galactosamine, N-acetyl-gulucoseamine multivalent mannose, multivalent fucose, glycosylated polyaminoacids, multivalent galactose, transferrin, bisphosphonate, polyglutamate, polyaspartate, a lipid, cholesterol, a steroid, bile acid, folate, vitamin B12, vitamin A, biotin, or an RGD peptide or RGD peptide mimetic.

Other examples of ligands include dyes, intercalating agents (e.g. acridines), cross-linkers (e.g. psoralene, mitomycin C), porphyrins (TPPC4, texaphyrin, Sapphyrin), polycyclic aromatic hydrocarbons (e.g., phenazine, dihydrophenazine), artificial endonucleases (e.g. EDTA), lipophilic molecules, e.g., cholesterol, cholic acid, adamantane acetic acid, 1-pyrene butyric acid, dihydrotestosterone, 1,3-Bis-O (hexadecyl)glycerol, geranyloxyhexyl group, hexadecylglycerol, borneol, menthol, 1,3-propanediol, heptadecyl group, palmitic acid, myristic acid,O3-(oleoyl)lithocholic acid, O3-(oleoyl)cholenic acid, dimethoxytrityl, or phenoxazine) and peptide conjugates (e.g., antennapedia peptide, Tat peptide), alkylating agents, phosphate, amino, mercapto, PEG (e.g., PEG-40K), MPEG, [MPEG]$_2$, polyamino, alkyl, substituted alkyl, radiolabeled markers, enzymes, haptens (e.g. biotin), transport/absorption facilitators (e.g., aspirin, vitamin E, folic acid), synthetic ribonucleases (e.g., imidazole, bisimidazole, histamine, imidazole clusters, acridine-imidazole conjugates, Eu3+ complexes of tetraazamacrocycles), dinitrophenyl, HRP, or AP.

Ligands can be proteins, e.g., glycoproteins, or peptides, e.g., molecules having a specific affinity for a co-ligand, or antibodies e.g., an antibody, that binds to a specified cell type such as a hepatic cell. Ligands can also include hormones and hormone receptors. They can also include non-peptidic species, such as lipids, lectins, carbohydrates, vitamins, cofactors, multivalent lactose, multivalent galactose, N-acetyl-galactosamine, N-acetyl-gulucosamine multivalent mannose, or multivalent fucose. The ligand can be, for example, a lipopolysaccharide, an activator of p38 MAP kinase, or an activator of NF-κB.

The ligand can be a substance, e.g., a drug, which can increase the uptake of the iRNA agent into the cell, for example, by disrupting the cell's cytoskeleton, e.g., by disrupting the cell's microtubules, microfilaments, and/or intermediate filaments. The drug can be, for example, taxon, vincristine, vinblastine, cytochalasin, nocodazole, japlakinolide, latrunculin A, phalloidin, swinholide A, indanocine, or myoservin.

In some embodiments, a ligand attached to an iRNA as described herein acts as a pharmacokinetic modulator (PK modulator). PK modulators include lipophiles, bile acids, steroids, phospholipid analogues, peptides, protein binding agents, PEG, vitamins etc. Exemplary PK modulators include, but are not limited to, cholesterol, fatty acids, cholic acid, lithocholic acid, dialkylglycerides, diacylglyceride, phospholipids, sphingolipids, naproxen, ibuprofen, vitamin E, biotin etc. Oligonucleotides that comprise a number of phosphorothioate linkages are also known to bind to serum protein, thus short oligonucleotides, e.g., oligonucleotides of about 5 bases, 10 bases, 15 bases or 20 bases, comprising multiple of phosphorothioate linkages in the backbone are also amenable to the present invention as ligands (e.g. as PK modulating ligands). In addition, aptamers that bind serum components (e.g. serum proteins) are also suitable for use as PK modulating ligands in the embodiments described herein.

Ligand-conjugated oligonucleotides of the invention may be synthesized by the use of an oligonucleotide that bears a pendant reactive functionality, such as that derived from the attachment of a linking molecule onto the oligonucleotide (described below). This reactive oligonucleotide may be reacted directly with commercially-available ligands, ligands that are synthesized bearing any of a variety of protecting groups, or ligands that have a linking moiety attached thereto.

The oligonucleotides used in the conjugates of the present invention may be conveniently and routinely made through the well-known technique of solid-phase synthesis. Equipment for such synthesis is sold by several vendors including, for example, Applied Biosystems (Foster City, Calif.). Any other means for such synthesis known in the art may additionally or alternatively be employed. It is also known to use similar techniques to prepare other oligonucleotides, such as the phosphorothioates and alkylated derivatives.

In the ligand-conjugated oligonucleotides and ligand-molecule bearing sequence-specific linked nucleosides of the present invention, the oligonucleotides and oligonucleosides may be assembled on a suitable DNA synthesizer utilizing standard nucleotide or nucleoside precursors, or nucleotide or nucleoside conjugate precursors that already bear the linking moiety, ligand-nucleotide or nucleoside-conjugate precursors that already bear the ligand molecule, or non-nucleoside ligand-bearing building blocks.

When using nucleotide-conjugate precursors that already bear a linking moiety, the synthesis of the sequence-specific linked nucleosides is typically completed, and the ligand molecule is then reacted with the linking moiety to form the ligand-conjugated oligonucleotide. In some embodiments, the oligonucleotides or linked nucleosides of the present invention are synthesized by an automated synthesizer using phosphoramidites derived from ligand-nucleoside conjugates in addition to the standard phosphoramidites and non-standard phosphoramidites that are commercially available and routinely used in oligonucleotide synthesis.

A. Lipid Conjugates

In one embodiment, the ligand or conjugate is a lipid or lipid-based molecule. Such a lipid or lipid-based molecule preferably binds a serum protein, e.g., human serum albumin (HSA). An HSA binding ligand allows for distribution of the conjugate to a target tissue, e.g., a non-kidney target tissue of the body. For example, the target tissue can be the liver, including parenchymal cells of the liver. Other molecules that can bind HSA can also be used as ligands. For example, naproxen or aspirin can be used. A lipid or lipid-based ligand can (a) increase resistance to degradation of the conjugate, (b) increase targeting or transport into a target cell or cell membrane, and/or (c) can be used to adjust binding to a serum protein, e.g., HSA.

A lipid based ligand can be used to inhibit, e.g., control the binding of the conjugate to a target tissue. For example, a lipid or lipid-based ligand that binds to HSA more strongly will be less likely to be targeted to the kidney and therefore less likely to be cleared from the body. A lipid or lipid-based ligand that binds to HSA less strongly can be used to target the conjugate to the kidney.

In a preferred embodiment, the lipid based ligand binds HSA. Preferably, it binds HSA with a sufficient affinity such that the conjugate will be preferably distributed to a non-kidney tissue. However, it is preferred that the affinity not be so strong that the HSA-ligand binding cannot be reversed.

In another preferred embodiment, the lipid based ligand binds HSA weakly or not at all, such that the conjugate will be preferably distributed to the kidney. Other moieties that target to kidney cells can also be used in place of or in addition to the lipid based ligand.

In another aspect, the ligand is a moiety, e.g., a vitamin, which is taken up by a target cell, e.g., a proliferating cell. These are particularly useful for treating disorders characterized by unwanted cell proliferation, e.g., of the malignant or non-malignant type, e.g., cancer cells. Exemplary vitamins include vitamin A, E, and K. Other exemplary vitamins include are B vitamin, e.g., folic acid, B12, riboflavin, biotin, pyridoxal or other vitamins or nutrients taken up by target cells such as liver cells. Also included are HSA and low density lipoprotein (LDL).

B. Cell Permeation Agents

In another aspect, the ligand is a cell-permeation agent, preferably a helical cell-permeation agent. Preferably, the agent is amphipathic. An exemplary agent is a peptide such as tat or antennopedia. If the agent is a peptide, it can be modified, including a peptidylmimetic, invertomers, non-peptide or pseudo-peptide linkages, and use of D-amino acids. The helical agent is preferably an alpha-helical agent, which preferably has a lipophilic and a lipophobic phase.

The ligand can be a peptide or peptidomimetic. A peptidomimetic (also referred to herein as an oligopeptidomimetic) is a molecule capable of folding into a defined three-dimensional structure similar to a natural peptide. The attachment of peptide and peptidomimetics to iRNA agents can affect pharmacokinetic distribution of the iRNA, such as by enhancing cellular recognition and absorption. The peptide or peptidomimetic moiety can be about 5-50 amino acids long, e.g., about 5, 10, 15, 20, 25, 30, 35, 40, 45, or 50 amino acids long.

A peptide or peptidomimetic can be, for example, a cell permeation peptide, cationic peptide, amphipathic peptide, or hydrophobic peptide (e.g., consisting primarily of Tyr, Trp or Phe). The peptide moiety can be a dendrimer peptide, constrained peptide or crosslinked peptide. In another alternative, the peptide moiety can include a hydrophobic membrane translocation sequence (MTS). An exemplary hydrophobic MTS-containing peptide is RFGF having the amino acid sequence AAVALLPAVLLALLAP (SEQ ID NO: 9). An RFGF analogue (e.g., amino acid sequence AALLPVLLAAP (SEQ ID NO: 10) containing a hydrophobic MTS can also be a targeting moiety. The peptide moiety can be a "delivery" peptide, which can carry large polar molecules including peptides, oligonucleotides, and protein across cell membranes. For example, sequences from the HIV Tat protein (GRKKRRQRRRPPQ (SEQ ID NO: 11) and the *Drosophila* Antennapedia protein (RQIKIWFQNRRMKWKK (SEQ ID NO: 12) have been found to be capable of functioning as delivery peptides. A peptide or peptidomimetic can be encoded by a random sequence of DNA, such as a peptide identified from a phage-display library, or one-bead-one-compound (OBOC) combinatorial library (Lam et al., Nature, 354:82-84, 1991). Examples of a peptide or peptidomimetic tethered to a dsRNA agent via an incorporated monomer unit for cell targeting purposes is an arginine-glycine-aspartic acid (RGD)-peptide, or RGD mimic. A peptide moiety can range in length from about 5 amino acids to about 40 amino acids. The peptide moieties can have a structural modification, such as to increase stability or direct conformational properties. Any of the structural modifications described below can be utilized.

An RGD peptide for use in the compositions and methods of the invention may be linear or cyclic, and may be modified, e.g., glycosylated or methylated, to facilitate targeting to a specific tissue(s). RGD-containing peptides and peptidiomimemtics may include D-amino acids, as well as synthetic RGD mimics. In addition to RGD, one can use other moieties that target the integrin ligand. Preferred conjugates of this ligand target PECAM-1 or VEGF.

A "cell permeation peptide" is capable of permeating a cell, e.g., a microbial cell, such as a bacterial or fungal cell, or a mammalian cell, such as a human cell. A microbial cell-permeating peptide can be, for example, an α-helical linear peptide (e.g., LL-37 or Ceropin P1), a disulfide bond-containing peptide (e.g., α-defensin, β-defensin or bactenecin), or a peptide containing only one or two dominating amino acids (e.g., PR-39 or indolicidin). A cell permeation peptide can also include a nuclear localization signal (NLS). For example, a cell permeation peptide can be a bipartite amphipathic peptide, such as MPG, which is derived from the fusion peptide domain of HIV-1 gp41 and the NLS of SV40 large T antigen (Simeoni et al., Nucl. Acids Res. 31:2717-2724, 2003).

C. Carbohydrate Conjugates

In some embodiments of the compositions and methods of the invention, an iRNA oligonucleotide further comprises a carbohydrate. The carbohydrate conjugated iRNA are advantageous for the in vivo delivery of nucleic acids, as well as compositions suitable for in vivo therapeutic use, as described herein. As used herein, "carbohydrate" refers to a compound which is either a carbohydrate per se made up of one or more monosaccharide units having at least 6 carbon atoms (which can be linear, branched or cyclic) with an oxygen, nitrogen or sulfur atom bonded to each carbon atom; or a compound having as a part thereof a carbohydrate moiety made up of one or more monosaccharide units each having at least six carbon atoms (which can be linear, branched or cyclic), with an oxygen, nitrogen or sulfur atom bonded to each carbon atom. Representative carbohydrates include the sugars (mono-, di-, tri- and oligosaccharides containing from about 4, 5, 6, 7, 8, or 9 monosaccharide units), and polysaccharides such as starches, glycogen, cellulose and polysaccharide gums. Specific monosaccharides include AGT and above (e.g., AGT, C6, C7, or C8) sugars; di- and trisaccharides include sugars having two or three monosaccharide units (e.g., AGT, C6, C7, or C8).

In one embodiment, a carbohydrate conjugate for use in the compositions and methods of the invention is a monosaccharide. In one embodiment, the monosaccharide is an N-acetylgalactosamine, such as

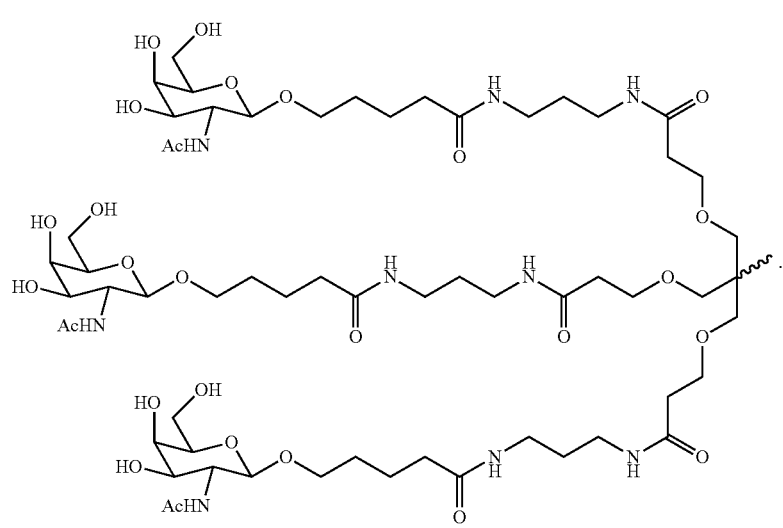 [SMILES: CC(=O)NC1C(OCCCCC(=O)NCCCNC(=O)CCOCC(C)(COCCC(=O)NCCCNC(=O)CCCCOC2OC(CO)C(O)C(O)C2NC(C)=O)COCCC(=O)NCCCNC(=O)CCCCOC2OC(CO)C(O)C(O)C2NC(C)=O)OC(CO)C(O)C1O]

Formula II

In another embodiment, a carbohydrate conjugate for use in the compositions and methods of the invention is selected from the group consisting of:

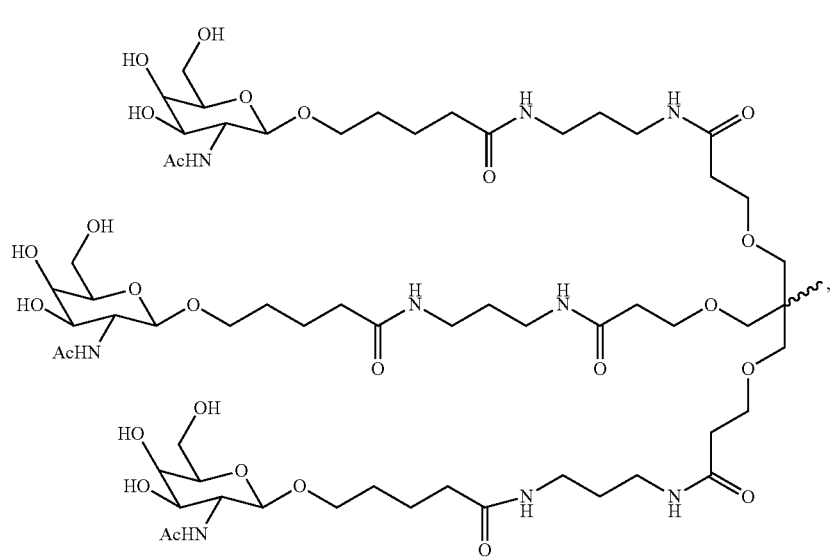

Formula II

Formula III
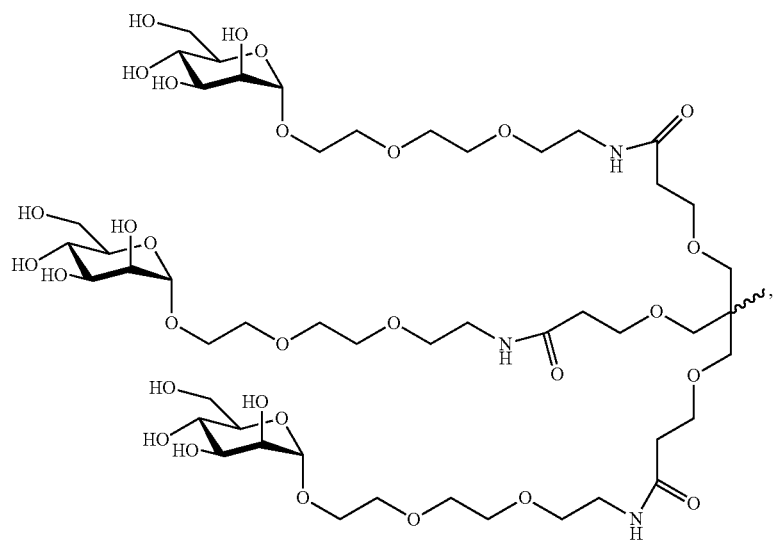
Formula IV
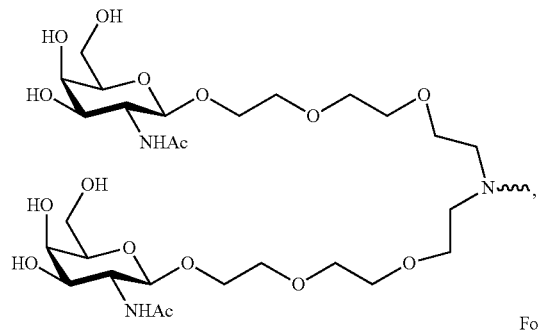
Formula V
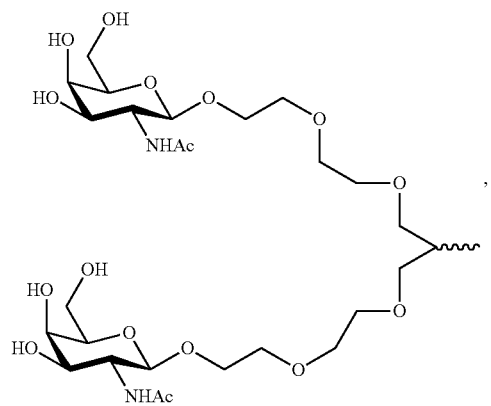
Formula VI
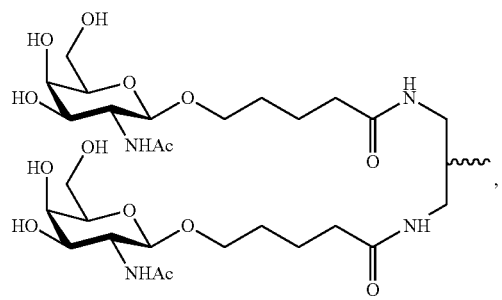
Formula VII
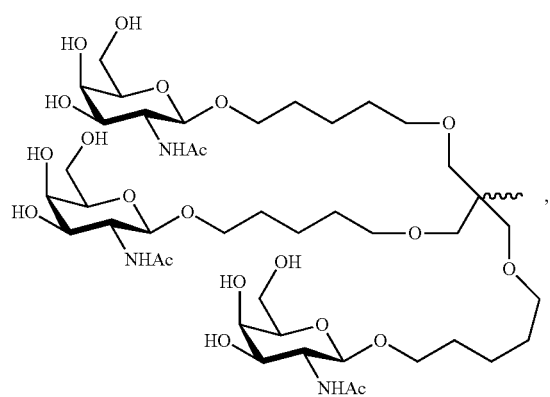
Formula VIII
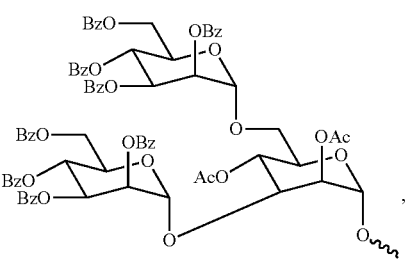

Formula IX
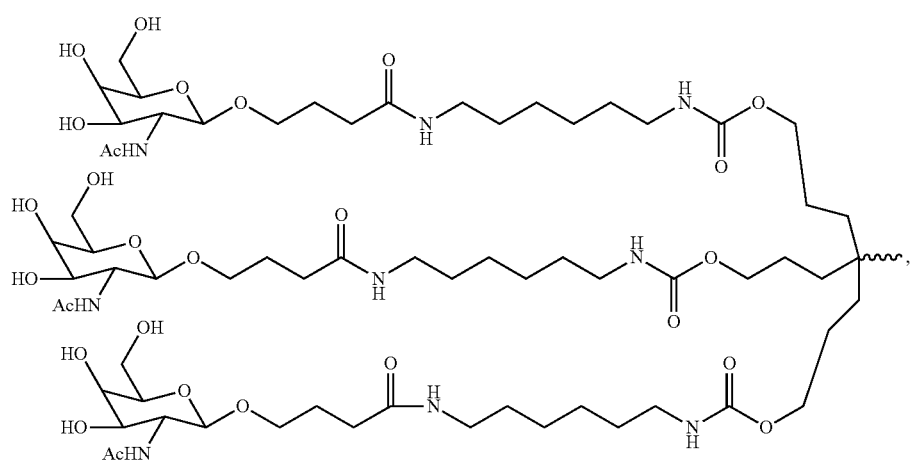
Formula X
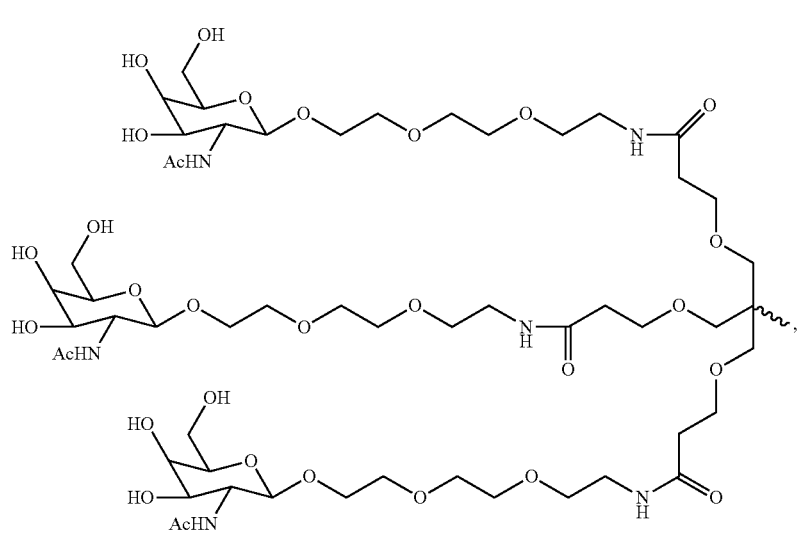
Formula XI
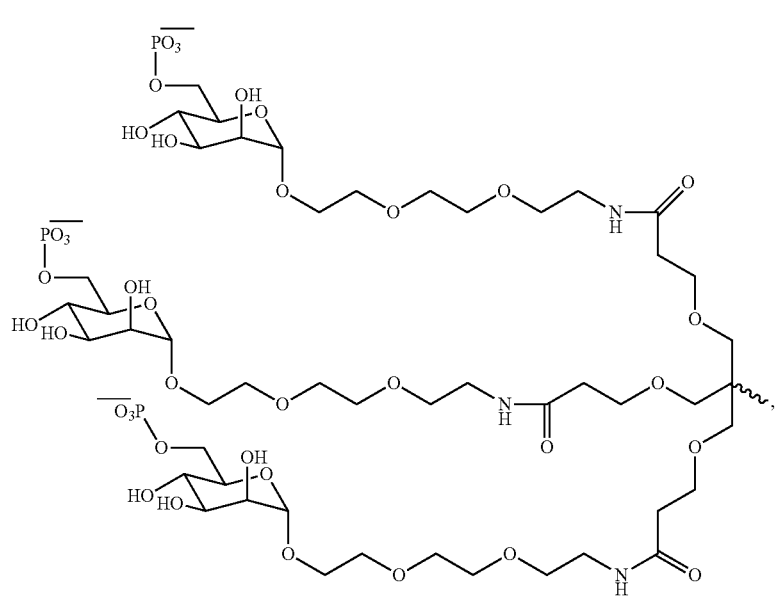

-continued
Formula XII
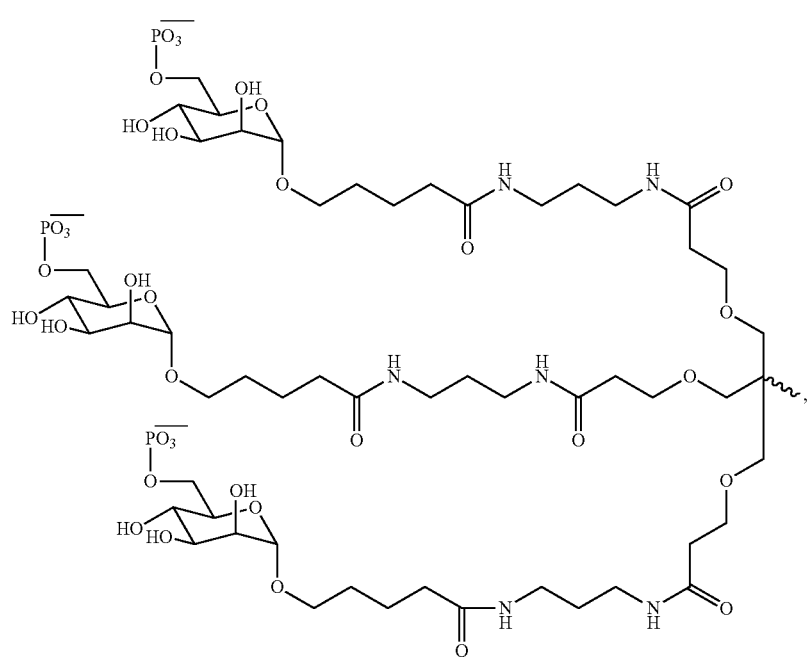
Formula XIII
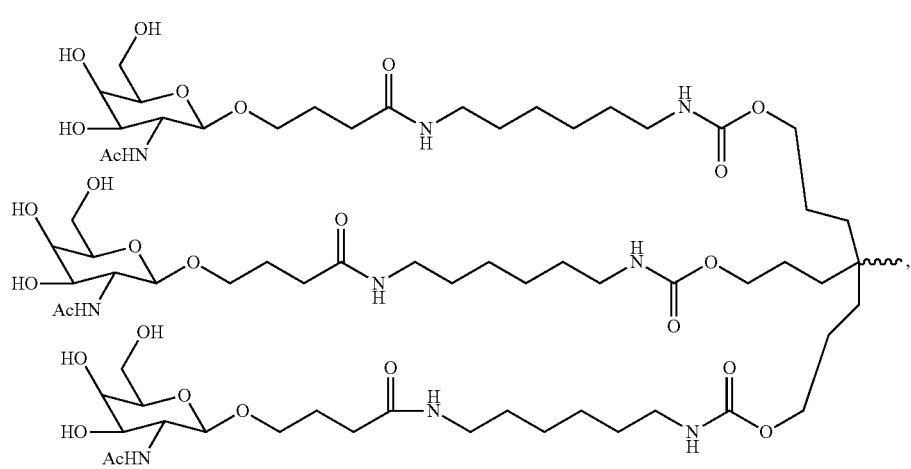
Formula XIV
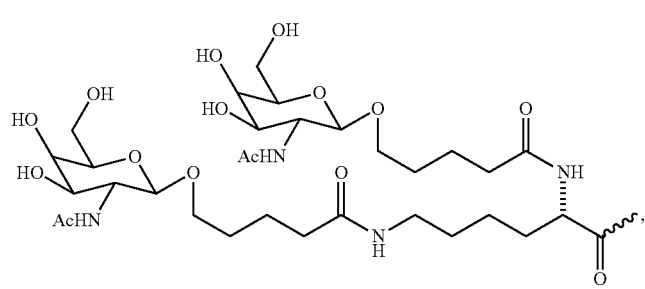
Formula XV
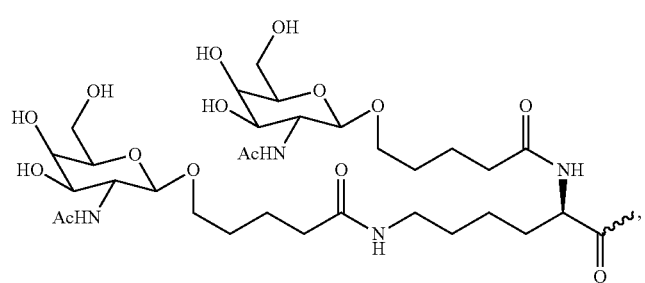

-continued
Formula XVI
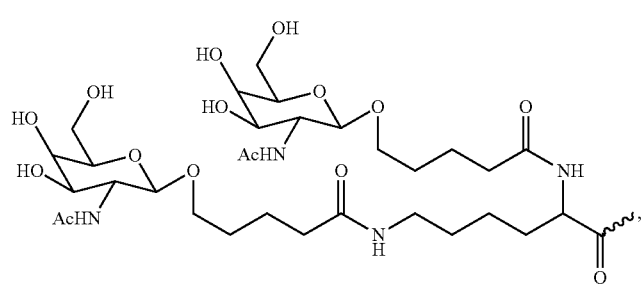
Formula XVII
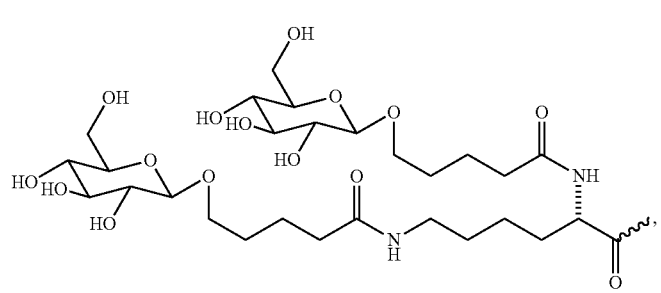
Formula XVIII
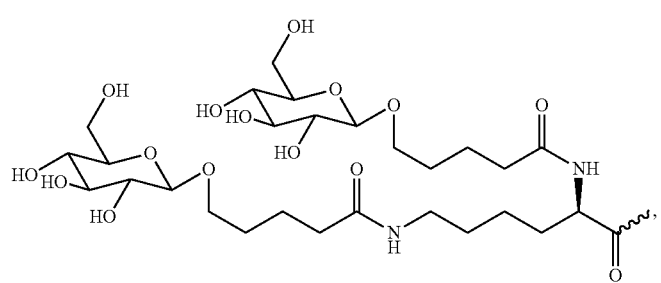
Formula XIX
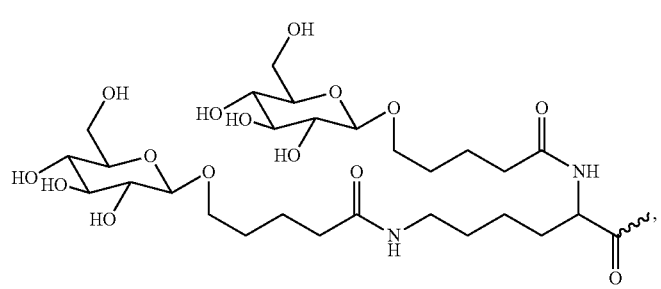
Formula XX
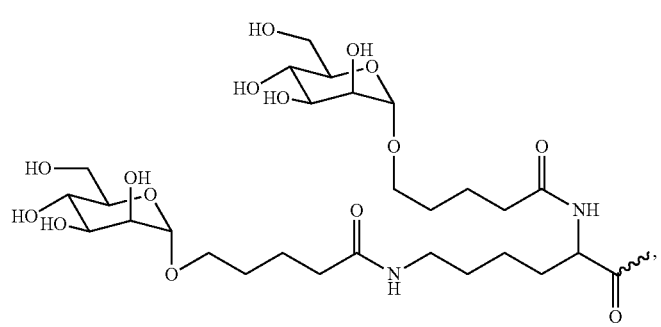

-continued
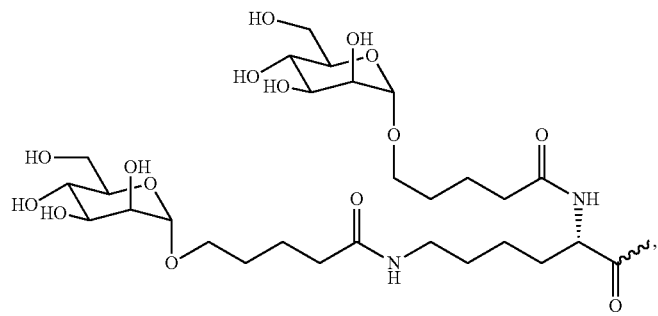
Formula XXI
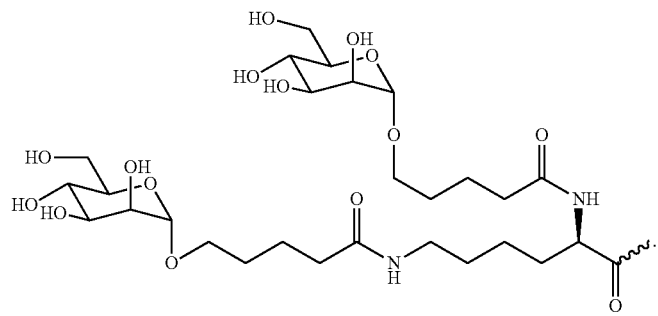
Formula XXII
Another representative carbohydrate conjugate for use in the embodiments described herein includes, but is not limited to,

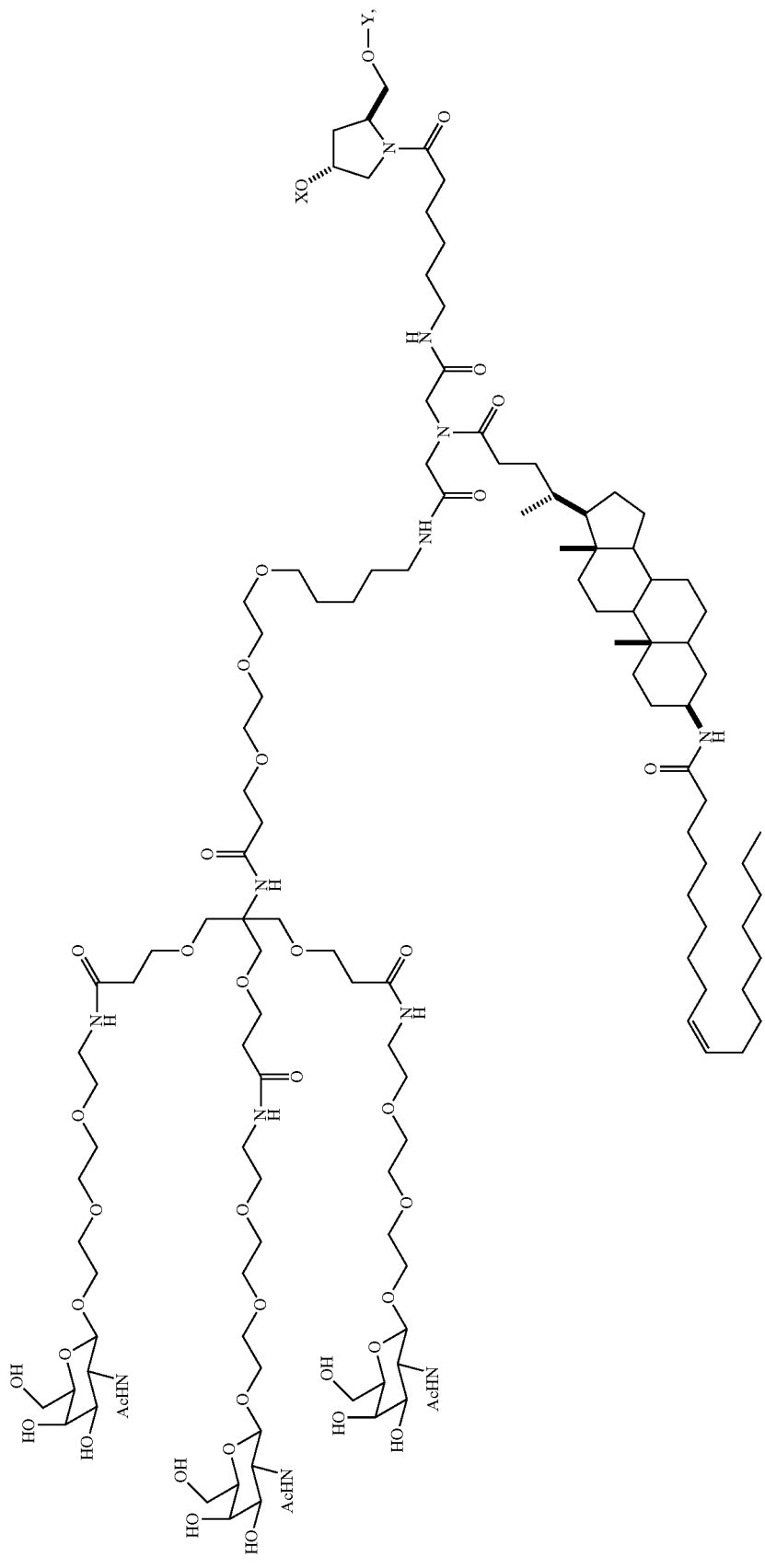
(Formula XXIII)

when one of X or Y is an oligonucleotide, the other is a hydrogen.

In some embodiments, the carbohydrate conjugate further comprises one or more additional ligands as described above, such as, but not limited to, a PK modulator and/or a cell permeation peptide.

Additional carbohydrate conjugates (and linkers) suitable for use in the present invention include those described in PCT Publication Nos. WO 2014/179620 and WO 2014/179627, the entire contents of each of which are incorporated herein by reference.

D. Linkers

In some embodiments, the conjugate or ligand described herein can be attached to an iRNA oligonucleotide with various linkers that can be cleavable or non-cleavable.

The term "linker" or "linking group" means an organic moiety that connects two parts of a compound, e.g., covalently attaches two parts of a compound. Linkers typically comprise a direct bond or an atom such as oxygen or sulfur, a unit such as NR8, C(O), C(O)NH, SO, $SO_2$, $SO_2$NH or a chain of atoms, such as, but not limited to, substituted or unsubstituted alkyl, substituted or unsubstituted alkenyl, substituted or unsubstituted alkynyl, arylalkyl, arylalkenyl, arylalkynyl, heteroarylalkyl, heteroarylalkenyl, heteroarylalkynyl, heterocyclylalkyl, heterocyclylalkenyl, heterocyclylalkynyl, aryl, heteroaryl, heterocyclyl, cycloalkyl, cycloalkenyl, alkylarylalkyl, alkylarylalkenyl, alkylarylalkynyl, alkenylarylalkyl, alkenylarylalkenyl, alkenylarylalkynyl, alkynylarylalkyl, alkynylarylalkenyl, alkynylarylalkynyl, alkylheteroarylalkyl, alkylheteroarylalkenyl, alkylheteroarylalkynyl, alkenylheteroarylalkyl, alkenylheteroarylalkenyl, alkenylheteroarylalkynyl, alkynylheteroarylalkyl, alkynylheteroarylalkenyl, alkynylheteroarylalkynyl, alkylheterocyclylalkyl, alkylheterocyclylalkenyl, alkylhererocyclylalkynyl, alkenylheterocyclylalkyl, alkenylheterocyclylalkenyl, alkenylheterocyclylalkynyl, alkynylheterocyclylalkyl, alkynylheterocyclylalkenyl, alkynylheterocyclylalkynyl, alkylaryl, alkenylaryl, alkynylaryl, alkylheteroaryl, alkenylheteroaryl, alkynylhereroaryl, which one or more methylenes can be interrupted or terminated by O, S, S(O), $SO_2$, N(R8), C(O), substituted or unsubstituted aryl, substituted or unsubstituted heteroaryl, substituted or unsubstituted heterocyclic; where R8 is hydrogen, acyl, aliphatic or substituted aliphatic. In one embodiment, the linker is between about 1-24 atoms, 2-24, 3-24, 4-24, 5-24, 6-24, 6-18, 7-18, 8-18 atoms, 7-17, 8-17, 6-16, 7-16, or 8-16 atoms.

A cleavable linking group is one which is sufficiently stable outside the cell, but which upon entry into a target cell is cleaved to release the two parts the linker is holding together. In a preferred embodiment, the cleavable linking group is cleaved at least about 10 times, 20, times, 30 times, 40 times, 50 times, 60 times, 70 times, 80 times, 90 times or more, or at least about 100 times faster in a target cell or under a first reference condition (which can, e.g., be selected to mimic or represent intracellular conditions) than in the blood of a subject, or under a second reference condition (which can, e.g., be selected to mimic or represent conditions found in the blood or serum).

Cleavable linking groups are susceptible to cleavage agents, e.g., pH, redox potential or the presence of degradative molecules. Generally, cleavage agents are more prevalent or found at higher levels or activities inside cells than in serum or blood. Examples of such degradative agents include: redox agents which are selected for particular substrates or which have no substrate specificity, including, e.g., oxidative or reductive enzymes or reductive agents such as mercaptans, present in cells, that can degrade a redox cleavable linking group by reduction; esterases; endosomes or agents that can create an acidic environment, e.g., those that result in a pH of five or lower; enzymes that can hydrolyze or degrade an acid cleavable linking group by acting as a general acid, peptidases (which can be substrate specific), and phosphatases.

A cleavable linkage group, such as a disulfide bond can be susceptible to pH. The pH of human serum is 7.4, while the average intracellular pH is slightly lower, ranging from about 7.1-7.3. Endosomes have a more acidic pH, in the range of 5.5-6.0, and lysosomes have an even more acidic pH at around 5.0. Some linkers will have a cleavable linking group that is cleaved at a preferred pH, thereby releasing a cationic lipid from the ligand inside the cell, or into the desired compartment of the cell.

A linker can include a cleavable linking group that is cleavable by a particular enzyme. The type of cleavable linking group incorporated into a linker can depend on the cell to be targeted. For example, a liver-targeting ligand can be linked to a cationic lipid through a linker that includes an ester group. Liver cells are rich in esterases, and therefore the linker will be cleaved more efficiently in liver cells than in cell types that are not esterase-rich. Other cell-types rich in esterases include cells of the lung, renal cortex, and testis.

Linkers that contain peptide bonds can be used when targeting cell types rich in peptidases, such as liver cells and synoviocytes.

In general, the suitability of a candidate cleavable linking group can be evaluated by testing the ability of a degradative agent (or condition) to cleave the candidate linking group. It will also be desirable to also test the candidate cleavable linking group for the ability to resist cleavage in the blood or when in contact with other non-target tissue. Thus, one can determine the relative susceptibility to cleavage between a first and a second condition, where the first is selected to be indicative of cleavage in a target cell and the second is selected to be indicative of cleavage in other tissues or biological fluids, e.g., blood or serum. The evaluations can be carried out in cell free systems, in cells, in cell culture, in organ or tissue culture, or in whole animals. It can be useful to make initial evaluations in cell-free or culture conditions and to confirm by further evaluations in whole animals. In preferred embodiments, useful candidate compounds are cleaved at least about 2, 4, 10, 20, 30, 40, 50, 60, 70, 80, 90, or about 100 times faster in the cell (or under in vitro conditions selected to mimic intracellular conditions) as compared to blood or serum (or under in vitro conditions selected to mimic extracellular conditions).

i. Redox Cleavable Linking Groups

In one embodiment, a cleavable linking group is a redox cleavable linking group that is cleaved upon reduction or oxidation. An example of reductively cleavable linking group is a disulphide linking group (—S—S—). To determine if a candidate cleavable linking group is a suitable "reductively cleavable linking group," or for example is suitable for use with a particular iRNA moiety and particular targeting agent one can look to methods described herein. For example, a candidate can be evaluated by incubation with dithiothreitol (DTT), or other reducing agent using reagents know in the art, which mimic the rate of cleavage which would be observed in a cell, e.g., a target cell. The candidates can also be evaluated under conditions which are selected to mimic blood or serum conditions. In one, candidate compounds are cleaved by at most about 10% in the blood. In other embodiments, useful candidate compounds are degraded at least about 2, 4, 10, 20, 30, 40, 50, 60, 70, 80, 90, or about 100 times faster in the cell (or under in vitro conditions selected to mimic intracellular conditions) as compared to blood (or under in vitro conditions selected to mimic extracellular conditions). The rate of cleavage of candidate compounds can be determined using standard enzyme kinetics assays under conditions chosen to mimic intracellular media and compared to conditions chosen to mimic extracellular media.

ii. Phosphate-Based Cleavable Linking Groups

In another embodiment, a cleavable linker comprises a phosphate-based cleavable linking group. A phosphate-based cleavable linking group is cleaved by agents that degrade or hydrolyze the phosphate group. An example of an agent that cleaves phosphate groups in cells are enzymes such as phosphatases in cells. Examples of phosphate-based linking groups are —O—P(O)(ORk)-O—, —O—P(S)(ORk)-O—, —O—P(S)(SRk)-O—, —S—P(O)(ORk)-O—, —O—P(O)(ORk)-S—, —S—P(O)(ORk)-S—, —O—P(S)(ORk)-S—, —S—P(S)(ORk)-O—, —O—P(O)(Rk)-O—, —O—P(S)(Rk)-O—, —S—P(O)(Rk)-O—, —S—P(S)(Rk)-O—, —S—P(O)(Rk)-S—, —O—P(S)(Rk)-S—. Preferred embodiments are —O—P(O)(OH)—O—, —O—P(S)(OH)—O—, —O—P(S)(SH)—O—, —S—P(O)(OH)—O—, —O—P(O)(OH)—S—, —S—P(O)(OH)—S—, —O—P(S)(OH)—S—, —S—P(S)(OH)—O—, —O—P(O)(H)—O—, —O—P(S)(H)—O—, —S—P(O)(H)—O, —S—P(S)(H)—O—, —S—P(O)(H)—S—, —O—P(S)(H)—S—. A preferred embodiment is —O—P(O)(OH)—O—. These candidates can be evaluated using methods analogous to those described above.

iii. Acid Cleavable Linking Groups

In another embodiment, a cleavable linker comprises an acid cleavable linking group. An acid cleavable linking group is a linking group that is cleaved under acidic conditions. In preferred embodiments acid cleavable linking groups are cleaved in an acidic environment with a pH of about 6.5 or lower (e.g., about 6.0, 5.75, 5.5, 5.25, 5.0, or lower), or by agents such as enzymes that can act as a general acid. In a cell, specific low pH organelles, such as endosomes and lysosomes can provide a cleaving environment for acid cleavable linking groups. Examples of acid cleavable linking groups include but are not limited to hydrazones, esters, and esters of amino acids. Acid cleavable groups can have the general formula —C=NN—, C(O)O, or —OC(O). A preferred embodiment is when the carbon attached to the oxygen of the ester (the alkoxy group) is an aryl group, substituted alkyl group, or tertiary alkyl group such as dimethyl pentyl or t-butyl. These candidates can be evaluated using methods analogous to those described above.

iv. Ester-Based Linking Groups

In another embodiment, a cleavable linker comprises an ester-based cleavable linking group. An ester-based cleavable linking group is cleaved by enzymes such as esterases and amidases in cells. Examples of ester-based cleavable linking groups include but are not limited to esters of alkylene, alkenylene and alkynylene groups. Ester cleavable linking groups have the general formula —C(O)O—, or —OC(O)—. These candidates can be evaluated using methods analogous to those described above.

v. Peptide-Based Cleaving Groups

In yet another embodiment, a cleavable linker comprises a peptide-based cleavable linking group. A peptide-based cleavable linking group is cleaved by enzymes such as peptidases and proteases in cells. Peptide-based cleavable linking groups are peptide bonds formed between amino acids to yield oligopeptides (e.g., dipeptides, tripeptides etc.) and polypeptides. Peptide-based cleavable groups do not include the amide group (—C(O)NH—). The amide group can be formed between any alkylene, alkenylene or alkynelene. A peptide bond is a special type of amide bond formed between amino acids to yield peptides and proteins. The peptide based cleavage group is generally limited to the peptide bond (i.e., the amide bond) formed between amino acids yielding peptides and proteins and does not include the entire amide functional group. Peptide-based cleaving linking groups have the general formula—NHCHRAC(O)NHCHRBC(O)—, where RA and RB are the R groups of the two adjacent amino acids. These candidates can be evaluated using methods analogous to those described above.

In one embodiment, an iRNA of the invention is conjugated to a carbohydrate through a linker. Non-limiting examples of iRNA carbohydrate conjugates with linkers of the compositions and methods of the invention include, but are not limited to, (Formula XXIV)

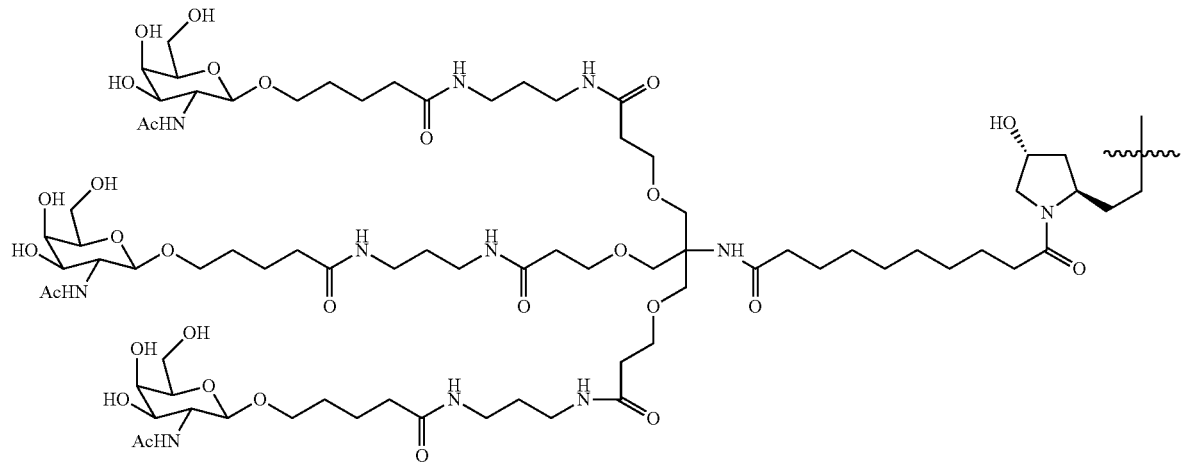

-continued
(Formula XXV)
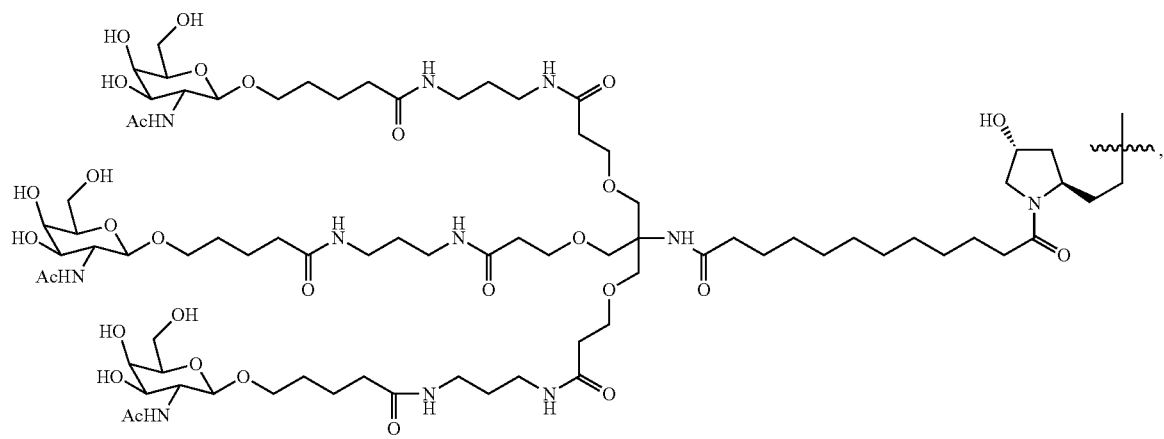
(Formula XXVI)
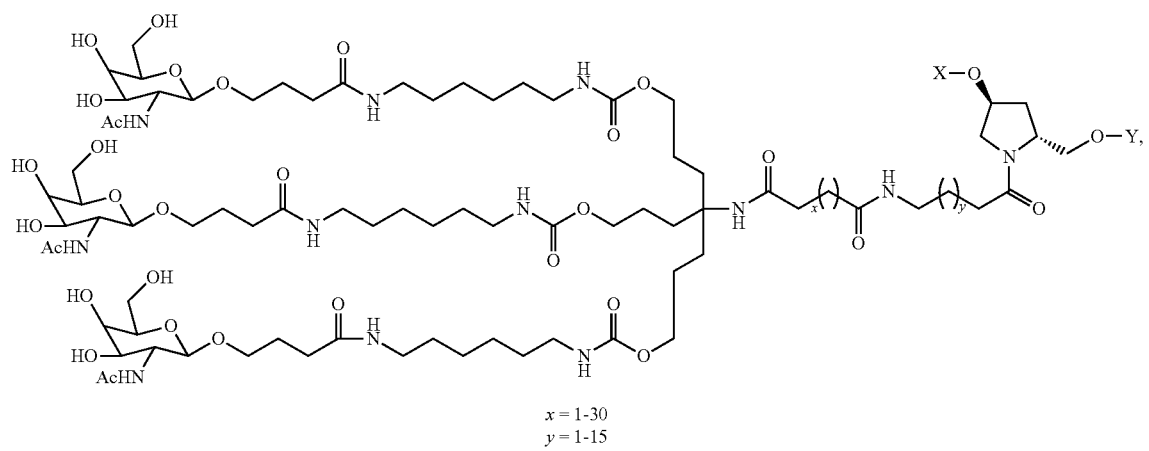
x = 1-30
y = 1-15
(Formula XXVII)
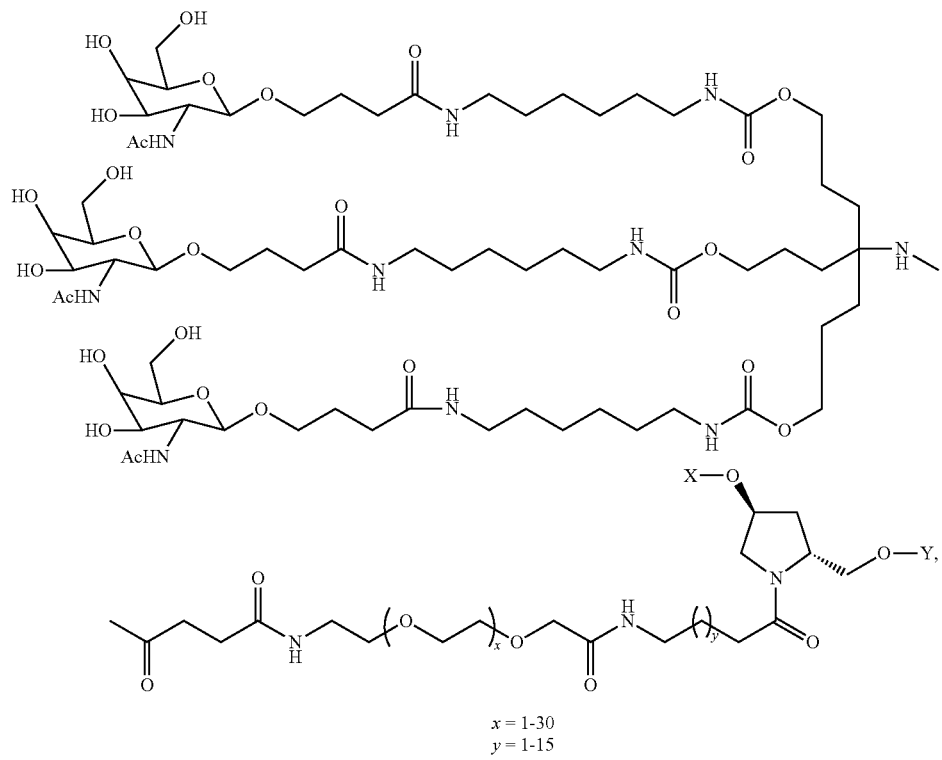
x = 1-30
y = 1-15

(Formula XXVIII)
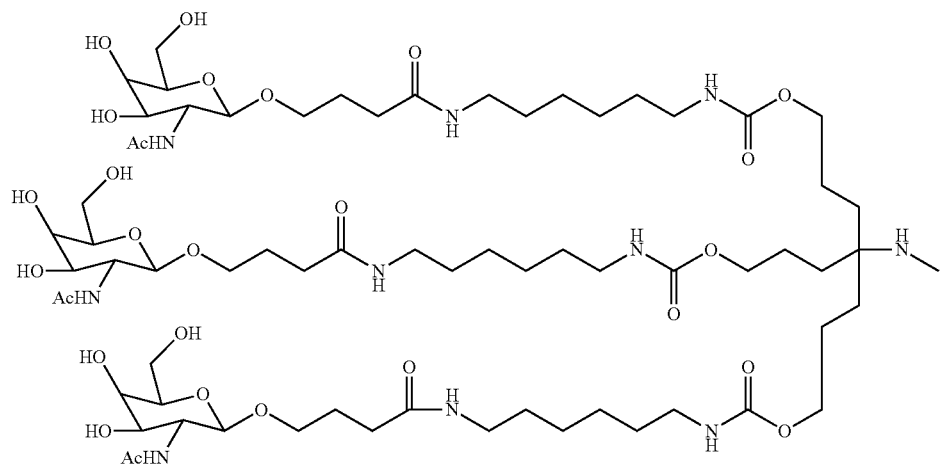
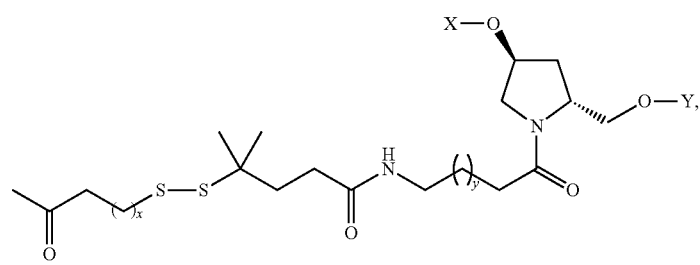
x = 0-30
y = 1-15
(Formula XXIX)
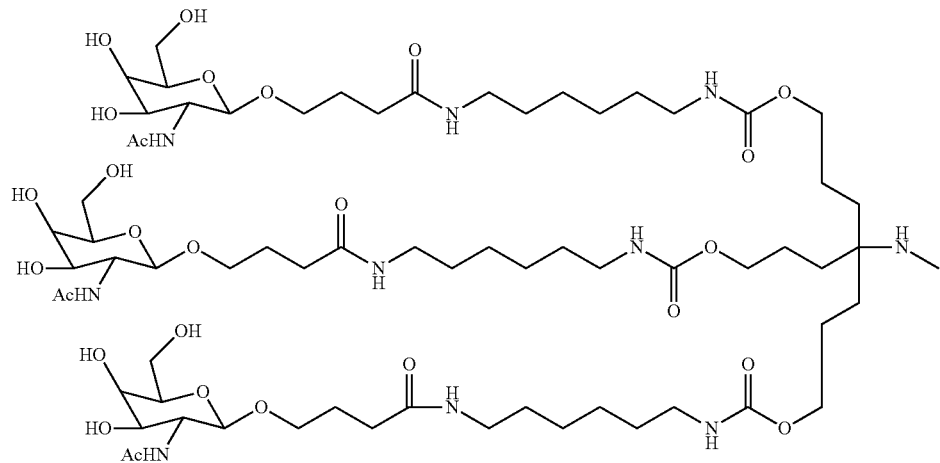
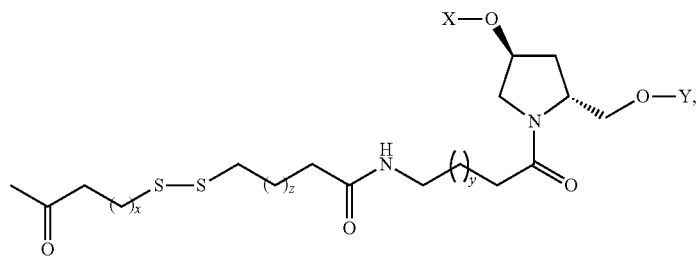
x = 0-30
y = 1-15
z = 1-20

(Formula XXX)
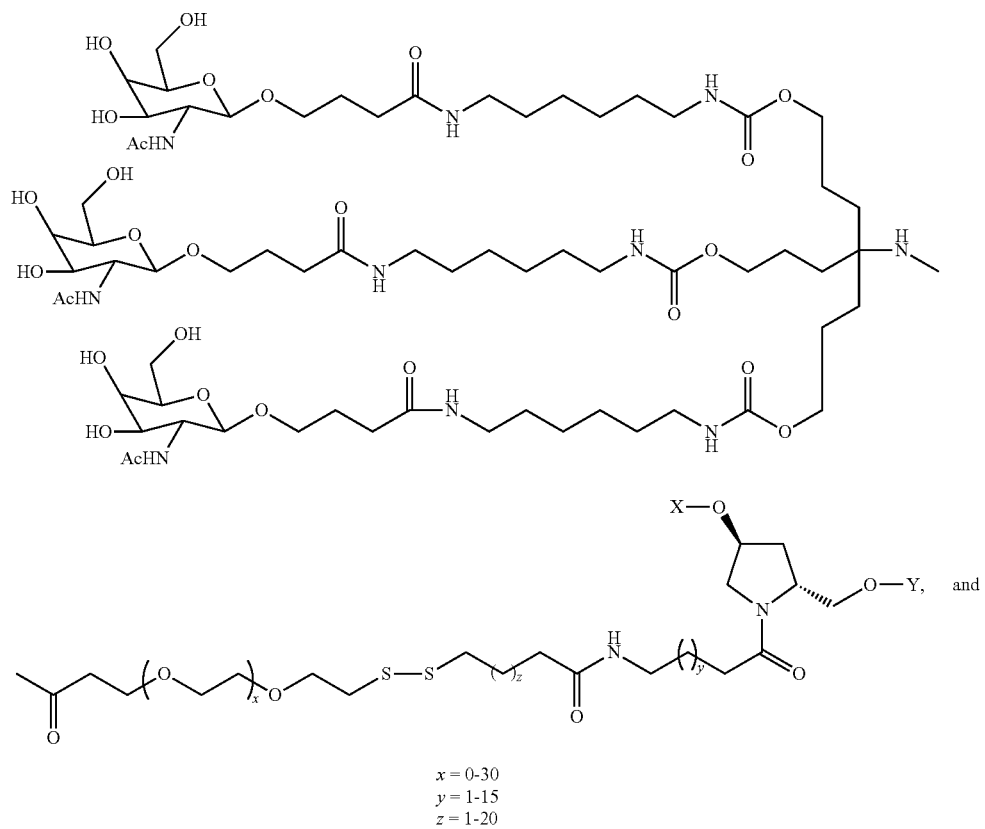
x = 0-30
y = 1-15
z = 1-20
(Formula XXXI)
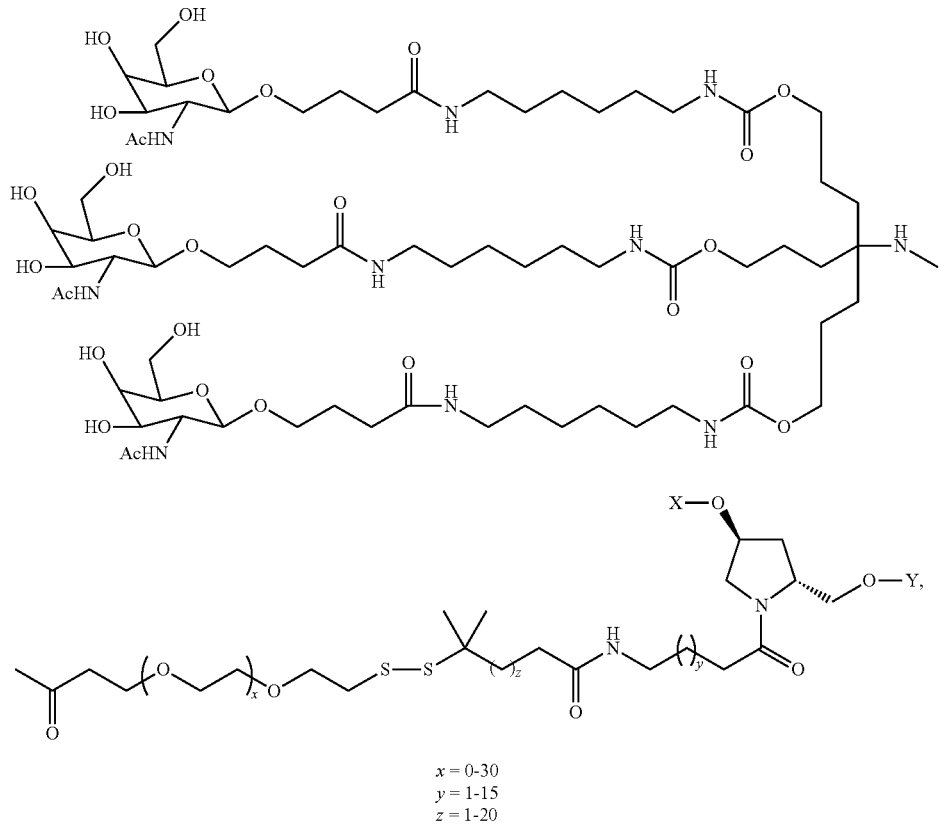
x = 0-30
y = 1-15
z = 1-20 when one of X or Y is an oligonucleotide, the other is a hydrogen.

In certain embodiments of the compositions and methods of the invention, a ligand is one or more "GalNAc" (N-acetylgalactosamine) derivatives attached through a bivalent or trivalent branched linker.

In one embodiment, a dsRNA of the invention is conjugated to a bivalent or trivalent branched linker selected from the group of structures shown in any of formula (XXXII)-(XXXV):

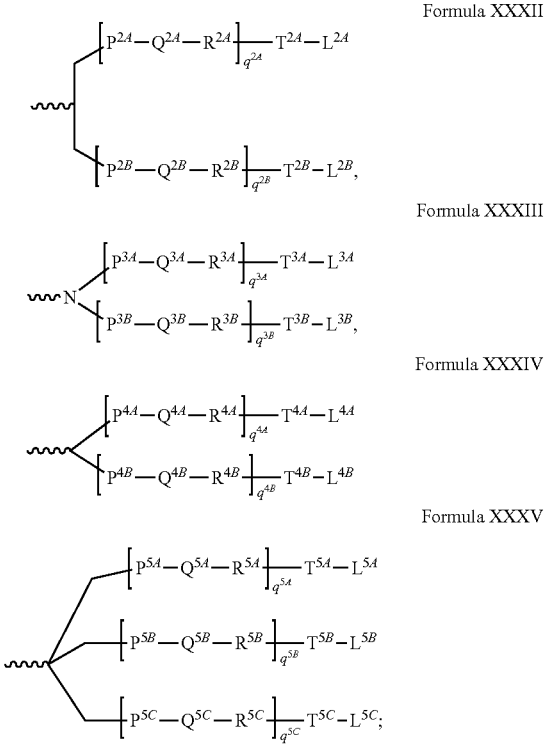

Formula XXXII

Formula XXXIII

Formula XXXIV

Formula XXXV wherein:
q2A, q2B, q3A, q3B, q4A, q4B, q5A, q5B and q5C represent independently for each occurrence 0-20 and wherein the repeating unit can be the same or different;
$P^{2A}$, $P^{2B}$, $P^{3A}$, $P^{3B}$, $P^{4A}$, $P^{4B}$, $P^{5A}$, $P^{5B}$, $P^{5C}$, $T^{2A}$, $T^{2B}$, $T^{3A}$, $T^{3B}$, $T^{4A}$, $T^{4B}$, $T^{4A}$, $T^{5B}$, $T^{5C}$ are each independently for each occurrence absent, CO, NH, O, S, OC(O), NHC(O), CH$_2$, CH$_2$NH or CH$_2$O;
$Q^{2A}$, $Q^{2B}$, $Q^{3A}$, $Q^{3B}$, $Q^{4A}$, $Q^{4B}$, $Q^{5A}$, $Q^{5B}$, $Q^{5C}$ are independently for each occurrence absent, alkylene, substituted alkylene wherein one or more methylenes can be interrupted or terminated by one or more of O, S, S(O), SO$_2$, N(R$^N$), C(R')=C(R"), C≡C or C(O);
$R^{2A}$, $R^{2B}$, $R^{3A}$, $R^{3B}$, $R^{4A}$, $R^{4B}$, $R^{5A}$, $R^{5B}$, $R^{5C}$ are each independently for each occurrence absent, NH, O, S, CH$_2$, C(O)O, C(O)NH, NHCH(R$^a$)C(O), —C(O)—CH(R$^a$)—NH—, CO, CH=N—

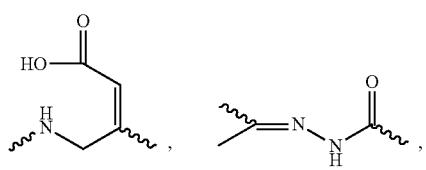

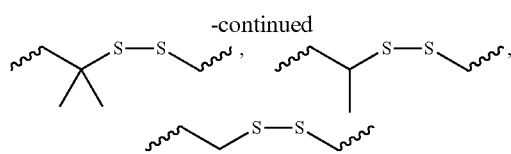

$L^{2A}$, $L^{2B}$, $L^{3A}$, $L^{3B}$, $L^{4A}$, $L^{4B}$, $L^{5A}$, $L^{5B}$ and $L^{5C}$ represent the ligand; i.e. each independently for each occurrence a monosaccharide (such as GalNAc), disaccharide, trisaccharide, tetrasaccharide, oligosaccharide, or polysaccharide; and R$^a$ is H or amino acid side chain. Trivalent conjugating GalNAc derivatives are particularly useful for use with RNAi agents for inhibiting the expression of a target gene, such as those of formula (XXXV):

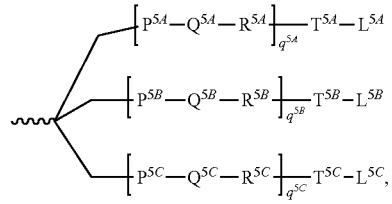

Formula XXXV wherein $L^{5A}$, $L^{5B}$ and $L^{5C}$ represent a monosaccharide, such as GalNAc derivative.

Examples of suitable bivalent and trivalent branched linker groups conjugating GalNAc derivatives include, but are not limited to, the structures recited above as formulas II, VII, XI, X, and XIII.

Representative U.S. patents that teach the preparation of RNA conjugates include, but are not limited to, U.S. Pat. Nos. 4,828,979; 4,948,882; 5,218,105; 5,525,465; 5,541,313; 5,545,730; 5,552,538; 5,578,717; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241, 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941; 6,294,664; 6,320,017; 6,576,752; 6,783,931; 6,900,297; 7,037,646; 8,106,022, the entire contents of each of which are hereby incorporated herein by reference.

It is not necessary for all positions in a given compound to be uniformly modified, and in fact more than one of the aforementioned modifications can be incorporated in a single compound or even at a single nucleoside within an iRNA. The present invention also includes iRNA compounds that are chimeric compounds.

"Chimeric" iRNA compounds or "chimeras," in the context of this invention, are iRNA compounds, preferably dsRNAs, which contain two or more chemically distinct regions, each made up of at least one monomer unit, i.e., a nucleotide in the case of a dsRNA compound. These iRNAs typically contain at least one region wherein the RNA is modified so as to confer upon the iRNA increased resistance to nuclease degradation, increased cellular uptake, and/or increased binding affinity for the target nucleic acid. An additional region of the iRNA can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of iRNA inhibition of gene expression. Consequently, comparable results can often be obtained with shorter iRNAs when chimeric dsRNAs are used, compared to phosphorothioate deoxy dsRNAs hybridizing to the same target region. Cleavage of the RNA target can be routinely detected by gel electrophoresis and, if necessary, associated nucleic acid hybridization techniques known in the art.

In certain instances, the RNA of an iRNA can be modified by a non-ligand group. A number of non-ligand molecules have been conjugated to iRNAs in order to enhance the activity, cellular distribution or cellular uptake of the iRNA, and procedures for performing such conjugations are available in the scientific literature. Such non-ligand moieties have included lipid moieties, such as cholesterol (Kubo, T. et al., *Biochem. Biophys. Res. Comm.*, 2007, 365(1):54-61; Letsinger et al., *Proc. Natl. Acad. Sci. USA*, 1989, 86:6553), cholic acid (Manoharan et al., *Bioorg. Med. Chem. Lett.*, 1994, 4:1053), a thioether, e.g., hexyl-S-tritylthiol (Manoharan et al., *Ann. N.Y. Acad. Sci.*, 1992, 660:306; Manoharan et al., *Bioorg. Med. Chem. Let.*, 1993, 3:2765), a thiocholesterol (Oberhauser et al., *Nucl. Acids Res.*, 1992, 20:533), an aliphatic chain, e.g., dodecandiol or undecyl residues (Saison-Behmoaras et al., *EMBO J.*, 1991, 10:111; Kabanov et al., *FEBS Lett.*, 1990, 259:327; Svinarchuk et al., *Biochimie*, 1993, 75:49), a phospholipid, e.g., di-hexadecyl-rac-glycerol or triethylammonium 1,2-di-O-hexadecyl-rac-glycero-3-H-phosphonate (Manoharan et al., *Tetrahedron Lett.*, 1995, 36:3651; Shea et al., *Nucl. Acids Res.*, 1990, 18:3777), a polyamine or a polyethylene glycol chain (Manoharan et al., *Nucleosides & Nucleotides*, 1995, 14:969), or adamantane acetic acid (Manoharan et al., *Tetrahedron Lett.*, 1995, 36:3651), a palmityl moiety (Mishra et al., *Biochim. Biophys. Acta*, 1995, 1264:229), or an octadecylamine or hexylamino-carbonyl-oxycholesterol moiety (Crooke et al., *J. Pharmacol. Exp. Ther.*, 1996, 277:923). Representative United States patents that teach the preparation of such RNA conjugates have been listed above. Typical conjugation protocols involve the synthesis of an RNAs bearing an aminolinker at one or more positions of the sequence. The amino group is then reacted with the molecule being conjugated using appropriate coupling or activating reagents. The conjugation reaction can be performed either with the RNA still bound to the solid support or following cleavage of the RNA, in solution phase. Purification of the RNA conjugate by HPLC typically affords the pure conjugate.

V. Delivery of an iRNA of the Invention

The delivery of an iRNA of the invention to a cell e.g., a cell within a subject, such as a human subject (e.g., a subject in need thereof, such as a subject having an antgiotensin associated disease or condition) can be achieved in a number of different ways. For example, delivery may be performed by contacting a cell with an iRNA of the invention either in vitro or in vivo. In vivo delivery may also be performed directly by administering a composition comprising an iRNA, e.g., a dsRNA, to a subject. Alternatively, in vivo delivery may be performed indirectly by administering one or more vectors that encode and direct the expression of the iRNA. These alternatives are discussed further below.

In general, any method of delivering a nucleic acid molecule (in vitro or in vivo) can be adapted for use with an iRNA of the invention (see e.g., Akhtar S. and Julian R L. (1992) *Trends Cell. Biol.* 2(5):139-144 and WO94/02595, which are incorporated herein by reference in their entireties). For in vivo delivery, factors to consider in order to deliver an iRNA molecule include, for example, biological stability of the delivered molecule, prevention of non-specific effects, and accumulation of the delivered molecule in the target tissue. The non-specific effects of an iRNA can be minimized by local administration, for example, by direct injection or implantation into a tissue or topically administering the preparation. Local administration to a treatment site maximizes local concentration of the agent, limits the exposure of the agent to systemic tissues that can otherwise be harmed by the agent or that can degrade the agent, and permits a lower total dose of the iRNA molecule to be administered. Several studies have shown successful knockdown of gene products when an iRNA is administered locally. For example, intraocular delivery of a VEGF dsRNA by intravitreal injection in cynomolgus monkeys (Tolentino, M J., et al (2004) *Retina* 24:132-138) and subretinal injections in mice (Reich, S J., et al (2003) *Mol. Vis.* 9:210-216) were both shown to prevent neovascularization in an experimental model of age-related macular degeneration. In addition, direct intratumoral injection of a dsRNA in mice reduces tumor volume (Pille, J., et al (2005) *Mol. Ther.* 11:267-274) and can prolong survival of tumor-bearing mice (Kim, W J., et al (2006) *Mol. Ther.* 14:343-350; Li, S., et al (2007) *Mol. Ther.* 15:515-523). RNA interference has also shown success with local delivery to the CNS by direct injection (Dorn, G., et al. (2004) *Nucleic Acids* 32:e49; Tan, P H., et al (2005) *Gene Ther.* 12:59-66; Makimura, H., et al (2002) *BMC Neurosci.* 3:18; Shishkina, G T., et al (2004) *Neuroscience* 129:521-528; Thakker, E R., et al (2004) *Proc. Natl. Acad. Sci. U.S.A.* 101:17270-17275; Akaneya, Y., et al (2005) *J. Neurophysiol.* 93:594-602) and to the lungs by intranasal administration (Howard, K A., et al (2006) *Mol. Ther.* 14:476-484; Zhang, X., et al (2004) *J. Biol. Chem.* 279:10677-10684; Bitko, V., et al (2005) *Nat. Med.* 11:50-55). For administering an iRNA systemically for the treatment of a disease, the RNA can be modified or alternatively delivered using a drug delivery system; both methods act to prevent the rapid degradation of the dsRNA by endo- and exo-nucleases in vivo. Modification of the RNA or the pharmaceutical carrier can also permit targeting of the iRNA composition to the target tissue and avoid undesirable off-target effects. iRNA molecules can be modified by chemical conjugation to lipophilic groups such as cholesterol to enhance cellular uptake and prevent degradation. For example, an iRNA directed against ApoB conjugated to a lipophilic cholesterol moiety was injected systemically into mice and resulted in knockdown of apoB mRNA in both the liver and jejunum (Soutschek, J., et al (2004) *Nature* 432:173-178). Conjugation of an iRNA to an aptamer has been shown to inhibit tumor growth and mediate tumor regression in a mouse model of prostate cancer (McNamara, J O., et al (2006) *Nat. Biotechnol.* 24:1005-1015). In an alternative embodiment, the iRNA can be delivered using drug delivery systems such as a nanoparticle, a dendrimer, a polymer, liposomes, or a cationic delivery system. Positively charged cationic delivery systems facilitate binding of an iRNA molecule (negatively charged) and also enhance interactions at the negatively charged cell membrane to permit efficient uptake of an iRNA by the cell. Cationic lipids, dendrimers, or polymers can either be bound to an iRNA, or induced to form a vesicle or micelle (see e.g., Kim SH., et al (2008) *Journal of Controlled Release* 129(2):107-116) that encases an iRNA.

The formation of vesicles or micelles further prevents degradation of the iRNA when administered systemically. Methods for making and administering cationic-iRNA complexes are well within the abilities of one skilled in the art (see e.g., Sorensen, D R., et al (2003) *J. Mol. Biol* 327:761-766; Verma, U N., et al (2003) *Clin. Cancer Res.* 9:1291-1300; Arnold, A S et al (2007) *J. Hypertens.* 25:197-205, which are incorporated herein by reference in their entirety). Some non-limiting examples of drug delivery systems useful for systemic delivery of iRNAs include DOTAP (Sorensen, D R., et al (2003), supra; Verma, U N., et al (2003), supra), Oligofectamine, "solid nucleic acid lipid particles" (Zimmermann, T S., et al (2006) *Nature* 441:111-114), cardiolipin (Chien, P Y., et al (2005) *Cancer Gene Ther.* 12:321-328; Pal, A., et al (2005) *Int J. Oncol.* 26:1087-1091), polyethyleneimine (Bonnet M E., et al (2008) *Pharm. Res. August* 16 Epub ahead of print; Aigner, A. (2006) *J. Biomed. Biotechnol.* 71659), Arg-Gly-Asp (RGD) peptides (Liu, S. (2006) *Mol. Pharm.* 3:472-487), and polyamidoamines (Tomalia, D A., et al (2007) *Biochem. Soc. Trans.* 35:61-67; Yoo, H., et al (1999) *Pharm. Res.* 16:1799-1804). In some embodiments, an iRNA forms a complex with cyclodextrin for systemic administration. Methods for administration and pharmaceutical compositions of iRNAs and cyclodextrins can be found in U.S. Pat. No. 7,427,605, which is herein incorporated by reference in its entirety.

A. Vector Encoded iRNAs of the Invention iRNA targeting the AGT gene can be expressed from transcription units inserted into DNA or RNA vectors (see, e.g., Couture, A, et al., *TIG.* (1996), 12:5-10; Skillern, A., et al., International PCT Publication No. WO 00/22113, Conrad, International PCT Publication No. WO 00/22114, and Conrad, U.S. Pat. No. 6,054,299). Expression can be transient (on the order of hours to weeks) or sustained (weeks to months or longer), depending upon the specific construct used and the target tissue or cell type. These transgenes can be introduced as a linear construct, a circular plasmid, or a viral vector, which can be an integrating or non-integrating vector. The transgene can also be constructed to permit it to be inherited as an extrachromosomal plasmid (Gassmann, et al., *Proc. Natl. Acad. Sci. USA* (1995) 92:1292).

The individual strand or strands of an iRNA can be transcribed from a promoter on an expression vector. Where two separate strands are to be expressed to generate, for example, a dsRNA, two separate expression vectors can be co-introduced (e.g., by transfection or infection) into a target cell. Alternatively each individual strand of a dsRNA can be transcribed by promoters both of which are located on the same expression plasmid. In one embodiment, a dsRNA is expressed as inverted repeat polynucleotides joined by a linker polynucleotide sequence such that the dsRNA has a stem and loop structure.

iRNA expression vectors are generally DNA plasmids or viral vectors. Expression vectors compatible with eukaryotic cells, preferably those compatible with vertebrate cells, can be used to produce recombinant constructs for the expression of an iRNA as described herein. Eukaryotic cell expression vectors are well known in the art and are available from a number of commercial sources. Typically, such vectors are provided containing convenient restriction sites for insertion of the desired nucleic acid segment. Delivery of iRNA expressing vectors can be systemic, such as by intravenous or intramuscular administration, by administration to target cells ex-planted from the patient followed by reintroduction into the patient, or by any other means that allows for introduction into a desired target cell.

iRNA expression plasmids can be transfected into target cells as a complex with cationic lipid carriers (e.g., Oligofectamine) or non-cationic lipid-based carriers (e.g., Transit-TKO™). Multiple lipid transfections for iRNA-mediated knockdowns targeting different regions of a target RNA over a period of a week or more are also contemplated by the invention. Successful introduction of vectors into host cells can be monitored using various known methods. For example, transient transfection can be signaled with a reporter, such as a fluorescent marker, such as Green Fluorescent Protein (GFP). Stable transfection of cells ex vivo can be ensured using markers that provide the transfected cell with resistance to specific environmental factors (e.g., antibiotics and drugs), such as hygromycin B resistance.

Viral vector systems which can be utilized with the methods and compositions described herein include, but are not limited to, (a) adenovirus vectors; (b) retrovirus vectors, including but not limited to lentiviral vectors, moloney murine leukemia virus, etc.; (c) adeno-associated virus vectors; (d) herpes simplex virus vectors; (e) SV 40 vectors; (f) polyoma virus vectors; (g) papilloma virus vectors; (h) picornavirus vectors; (i) pox virus vectors such as an orthopox, e.g., vaccinia virus vectors or avipox, e.g. canary pox or fowl pox; and (j) a helper-dependent or gutless adenovirus. Replication-defective viruses can also be advantageous. Different vectors will or will not become incorporated into the cells' genome. The constructs can include viral sequences for transfection, if desired. Alternatively, the construct can be incorporated into vectors capable of episomal replication, e.g. EPV and EBV vectors. Constructs for the recombinant expression of an iRNA will generally require regulatory elements, e.g., promoters, enhancers, etc., to ensure the expression of the iRNA in target cells. Other aspects to consider for vectors and constructs are further described below.

Vectors useful for the delivery of an iRNA will include regulatory elements (promoter, enhancer, etc.) sufficient for expression of the iRNA in the desired target cell or tissue. The regulatory elements can be chosen to provide either constitutive or regulated/inducible expression.

Expression of the iRNA can be precisely regulated, for example, by using an inducible regulatory sequence that is sensitive to certain physiological regulators, e.g., circulating glucose levels, or hormones (Docherty et al., 1994, *FASEB J.* 8:20-24). Such inducible expression systems, suitable for the control of dsRNA expression in cells or in mammals include, for example, regulation by ecdysone, by estrogen, progesterone, tetracycline, chemical inducers of dimerization, and isopropyl-beta-D1-thiogalactopyranoside (IPTG). A person skilled in the art would be able to choose the appropriate regulatory/promoter sequence based on the intended use of the iRNA transgene.

Viral vectors that contain nucleic acid sequences encoding an iRNA can be used. For example, a retroviral vector can be used (see Miller et al., *Meth. Enzymol.* 217:581-599 (1993)). These retroviral vectors contain the components necessary for the correct packaging of the viral genome and integration into the host cell DNA. The nucleic acid sequences encoding an iRNA are cloned into one or more vectors, which facilitate delivery of the nucleic acid into a patient. More detail about retroviral vectors can be found, for example, in Boesen et al., *Biotherapy* 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., *J. Clin. Invest.* 93:644-651 (1994); Kiem et al., Blood 83:1467-1473 (1994); Salmons and Gunzberg, *Human Gene Therapy* 4:129-141 (1993); and Grossman and Wilson, *Curr. Opin. in Genetics and Devel.* 3:110-114 (1993). Lentiviral vectors contemplated for use include, for example, the HIV based vectors described in U.S. Pat. Nos. 6,143,520; 5,665,557; and 5,981,276, which are herein incorporated by reference.

Adenoviruses are also contemplated for use in delivery of iRNAs of the invention. Adenoviruses are especially attractive vehicles, e.g., for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, *Current Opinion in Genetics and Development* 3:499-503 (1993) present a review of adenovirus-based gene therapy. Bout et al., *Human Gene Therapy* 5:3-10 (1994) demonstrated the use of adenovirus vectors to transfer genes to the respiratory epithelia of rhesus monkeys. Other instances of the use of adenoviruses in gene therapy can be found in Rosenfeld et al., *Science* 252:431-434 (1991); Rosenfeld et al., *Cell* 68:143-155 (1992); Mastrangeli et al., *J. Clin. Invest.* 91:225-234 (1993); PCT Publication WO94/12649; and Wang, et al., *Gene Therapy* 2:775-783 (1995). A suitable AV vector for expressing an iRNA featured in the invention, a method for constructing the recombinant AV vector, and a method for delivering the vector into target cells, are described in Xia H et al. (2002), *Nat. Biotech.* 20: 1006-1010.

Adeno-associated virus (AAV) vectors may also be used to delivery an iRNA of the invention (Walsh et al., Proc. Soc. Exp. Biol. Med. 204:289-300 (1993); U.S. Pat. No. 5,436, 146). In one embodiment, the iRNA can be expressed as two separate, complementary single-stranded RNA molecules from a recombinant AAV vector having, for example, either the U6 or H1 RNA promoters, or the cytomegalovirus (CMV) promoter. Suitable AAV vectors for expressing the dsRNA featured in the invention, methods for constructing the recombinant AV vector, and methods for delivering the vectors into target cells are described in Samulski R et al. (1987), *J. Virol.* 61: 3096-3101; Fisher K J et al. (1996), *J. Virol,* 70: 520-532; Samulski R et al. (1989), *J. Virol.* 63: 3822-3826; U.S. Pat. No. 5,252,479; U.S. Pat. No. 5,139, 941; International Patent Application No. WO 94/13788; and International Patent Application No. WO 93/24641, the entire disclosures of which are herein incorporated by reference.

Another viral vector suitable for delivery of an iRNA of the invention is a pox virus such as a vaccinia virus, for example an attenuated vaccinia such as Modified Virus Ankara (MVA) or NYVAC, an avipox such as fowl pox or canary pox.

The tropism of viral vectors can be modified by pseudotyping the vectors with envelope proteins or other surface antigens from other viruses, or by substituting different viral capsid proteins, as appropriate. For example, lentiviral vectors can be pseudotyped with surface proteins from vesicular stomatitis virus (VSV), rabies, Ebola, Mokola, and the like.

AAV vectors can be made to target different cells by engineering the vectors to express different capsid protein serotypes; see, e.g., Rabinowitz J E et al. (2002), *J Virol* 76:791-801, the entire disclosure of which is herein incorporated by reference.

The pharmaceutical preparation of a vector can include the vector in an acceptable diluent, or can include a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

VI. Pharmaceutical Compositions of the Invention

The present invention also includes pharmaceutical compositions and formulations which include the iRNAs of the invention. In one embodiment, provided herein are pharmaceutical compositions containing an iRNA, as described herein, and a pharmaceutically acceptable carrier. The pharmaceutical compositions containing the iRNA are useful for treating a disease or disorder associated with the expression or activity of an AGT gene. Such pharmaceutical compositions are formulated based on the mode of delivery. One example is compositions that are formulated for systemic administration via parenteral delivery, e.g., by subcutaneous (SC) or intravenous (IV) delivery. Another example is compositions that are formulated for direct delivery into the brain parenchyma, e.g., by infusion into the brain, such as by continuous pump infusion. The pharmaceutical compositions of the invention may be administered in dosages sufficient to inhibit expression of an AGT gene. In general, a suitable dose of an iRNA of the invention will be in the range of about 0.001 to about 200.0 milligrams per kilogram body weight of the recipient per day, generally in the range of about 1 to 50 mg per kilogram body weight per day. For example, the dsRNA can be administered at about 0.01 mg/kg, about 0.05 mg/kg, about 0.5 mg/kg, about 1 mg/kg, about 1.5 mg/kg, about 2 mg/kg, about 3 mg/kg, about 10 mg/kg, about 20 mg/kg, about 30 mg/kg, about 40 mg/kg, or about 50 mg/kg per single dose.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.1 to about 50 mg/kg, about 0.25 to about 50 mg/kg, about 0.5 to about 50 mg/kg, about 0.75 to about 50 mg/kg, about 1 to about 50 mg/kg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/kg, about 1.5 to about 45 mg/kg, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/kg, about 1.5 to about 40 mg/kg, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/kg, about 1.5 to about 30 mg/kg, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/kg, about 1.5 to about 20 mg/kg, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. Values and ranges intermediate to the recited values are also intended to be part of this invention.

For example, the dsRNA may be administered at a dose of about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In another embodiment, the dsRNA is administered at a dose of about 0.5 to about 50 mg/kg, about 0.75 to about 50 mg/kg, about 1 to about 50 mg/kg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.5 to about 45 mg/kg, about 0.75 to about 45 mg/kg, about 1 to about 45 mg/kg, about 1.5 to about 45 mg/kg, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.5 to about 40 mg/kg, about 0.75 to about 40 mg/kg, about 1 to about 40 mg/kg, about 1.5 to about 40 mg/kg, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.5 to about 30 mg/kg, about 0.75 to about 30 mg/kg, about 1 to about 30 mg/kg, about 1.5 to about 30 mg/kg, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.5 to about 20 mg/kg, about 0.75 to about 20 mg/kg, about 1 to about 20 mg/kg, about 1.5 to about 20 mg/kg, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, the dsRNA is administered at a dose of about 10 mg/kg to about 30 mg/kg. Values and ranges intermediate to the recited values are also intended to be part of this invention.

For example, subjects can be administered, e.g., subcutaneously or intravenously, a single therapeutic amount of iRNA, such as about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 35, 36, 37, 38, 39, 40, 41, 42, 43, 44, 45, 46, 47, 48, 49, or about 50 mg/kg. Values and ranges intermediate to the recited values are also intended to be part of this invention.

In some embodiments, subjects are administered, e.g., subcutaneously or intravenously, multiple doses of a therapeutic amount of iRNA, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. A multi-dose regimen may include administration of a therapeutic amount of iRNA daily, such as for two days, three days, four days, five days, six days, seven days, or longer.

In other embodiments, subjects are administered, e.g., subcutaneously or intravenously, a repeat dose of a therapeutic amount of iRNA, such as a dose about 0.1, 0.125, 0.15, 0.175, 0.2, 0.225, 0.25, 0.275, 0.3, 0.325, 0.35, 0.375, 0.4, 0.425, 0.45, 0.475, 0.5, 0.525, 0.55, 0.575, 0.6, 0.625, 0.65, 0.675, 0.7, 0.725, 0.75, 0.775, 0.8, 0.825, 0.85, 0.875, 0.9, 0.925, 0.95, 0.975, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. A repeat-dose regimine may include administration of a therapeutic amount of iRNA on a regular basis, such as every other day, every third day, every fourth day, twice a week, once a week, every other week, or once a month. In certain embodiments, the iRNA is administered about once per month to about once per quarter (i.e., about once every three months).

After an initial treatment regimen, the treatments can be administered on a less frequent basis.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In certain embodiments of the invention, for example, when a double-stranded RNAi agent includes a modification (e.g., one or more motifs of three identical modifications on three consecutive nucleotides), including one such motif at or near the cleavage site of the agent, six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/kg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

The pharmaceutical composition can be administered by intravenous infusion over a period of time, such as over a 5, 6, 7, 8, 9, 10, 11, 12, 13, 14, 15, 16, 17, 18, 19, 20, and 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

The pharmaceutical composition can be administered by subcutaneous administration.

The pharmaceutical composition can be administered once daily, or the iRNA can be administered as two, three, or more sub-doses at appropriate intervals throughout the day or even using continuous infusion or delivery through a controlled release formulation. In that case, the iRNA contained in each sub-dose must be correspondingly smaller in order to achieve the total daily dosage. The dosage unit can also be compounded for delivery over several days, e.g., using a conventional sustained release formulation which provides sustained release of the iRNA over a several day period. Sustained release formulations are well known in the art and are particularly useful for delivery of agents at a particular site, such as could be used with the agents of the present invention. In this embodiment, the dosage unit contains a corresponding multiple of the daily dose. A higher dose may be administered initially (i.e., a loading dose), followed by a lower dosage for a sustained period of time.

In other embodiments, a single dose of the pharmaceutical compositions can be long lasting, such that subsequent doses are administered at not more than 3, 4, or 5 day intervals, or at not more than 1, 2, 3, or 4 week intervals. In some embodiments of the invention, a single dose of the pharmaceutical compositions of the invention is administered once per week. In other embodiments of the invention, a single dose of the pharmaceutical compositions of the invention is administered bi-monthly. In certain embodiments, the iRNA is administered about once per month to about once per quarter (i.e., about once every three months).

The pharmaceutical composition can be administered for an indefinite period of time, e.g., in a subject experiencing elevated blood pressure due to obesity, or during the time at which the cause of an elevated level of AGT is present, e.g., during pregnancy induced high blood pressure.

The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or a series of treatments. Estimates of effective dosages and in vivo half-lives for the individual iRNAs encompassed by the invention can be made using conventional methodologies or on the basis of in vivo testing using an appropriate animal model, as described elsewhere herein.

The pharmaceutical compositions of the present invention can be administered in a number of ways depending upon whether local or systemic treatment is desired and upon the area to be treated. Administration can be topical (e.g., by a transdermal patch), pulmonary, e.g., by inhalation or insufflation of powders or aerosols, including by nebulizer; intratracheal, intranasal, epidermal and transdermal, oral or parenteral. Parenteral administration includes intravenous, intraarterial, subcutaneous, intraperitoneal or intramuscular injection or infusion; subdermal, e.g., via an implanted device; or intracranial, e.g., by intraparenchymal, intrathecal or intraventricular, administration.

The iRNA can be delivered in a manner to target a particular tissue, such as the liver (e.g., the hepatocytes of the liver).

Pharmaceutical compositions and formulations for topical administration can include transdermal patches, ointments, lotions, creams, gels, drops, suppositories, sprays, liquids and powders. Conventional pharmaceutical carriers, aqueous, powder or oily bases, thickeners and the like can be necessary or desirable. Coated condoms, gloves and the like can also be useful. Suitable topical formulations include those in which the iRNAs featured in the invention are in admixture with a topical delivery agent such as lipids, liposomes, fatty acids, fatty acid esters, steroids, chelating agents and surfactants. Suitable lipids and liposomes include neutral (e.g., dioleoylphosphatidyl DOPE ethanolamine, dimyristoylphosphatidyl choline DMPC, distearolyphosphatidyl choline) negative (e.g., dimyristoylphosphatidyl glycerol DMPG) and cationic (e.g., dioleoyltetramethylaminopropyl DOTAP and dioleoylphosphatidyl ethanolamine DOTMA). iRNAs featured in the invention can be encapsulated within liposomes or can form complexes thereto, in particular to cationic liposomes. Alternatively, iRNAs can be complexed to lipids, in particular to cationic lipids. Suitable fatty acids and esters include but are not limited to arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-20}$ alkyl ester (e.g., isopropylmyristate IPM), monoglyceride, diglyceride or pharmaceutically acceptable salt thereof). Topical formulations are described in detail in U.S. Pat. No. 6,747,014, which is incorporated herein by reference.

A. iRNA Formulations Comprising Membranous Molecular Assemblies

An iRNA for use in the compositions and methods of the invention can be formulated for delivery in a membranous molecular assembly, e.g., a liposome or a micelle. As used herein, the term "liposome" refers to a vesicle composed of amphiphilic lipids arranged in at least one bilayer, e.g., one bilayer or a plurality of bilayers. Liposomes include unilamellar and multilamellar vesicles that have a membrane formed from a lipophilic material and an aqueous interior. The aqueous portion contains the iRNA composition. The lipophilic material isolates the aqueous interior from an aqueous exterior, which typically does not include the iRNA composition, although in some examples, it may. Liposomes are useful for the transfer and delivery of active ingredients to the site of action. Because the liposomal membrane is structurally similar to biological membranes, when liposomes are applied to a tissue, the liposomal bilayer fuses with bilayer of the cellular membranes. As the merging of the liposome and cell progresses, the internal aqueous contents that include the iRNA are delivered into the cell where the iRNA can specifically bind to a target RNA and can mediate iRNA. In some cases the liposomes are also specifically targeted, e.g., to direct the iRNA to particular cell types.

A liposome containing an iRNA agent can be prepared by a variety of methods. In one example, the lipid component of a liposome is dissolved in a detergent so that micelles are formed with the lipid component. For example, the lipid component can be an amphipathic cationic lipid or lipid conjugate. The detergent can have a high critical micelle concentration and may be nonionic. Exemplary detergents include cholate, CHAPS, octylglucoside, deoxycholate, and lauroyl sarcosine. The iRNA agent preparation is then added to the micelles that include the lipid component. The cationic groups on the lipid interact with the iRNA agent and condense around the iRNA agent to form a liposome. After condensation, the detergent is removed, e.g., by dialysis, to yield a liposomal preparation of iRNA agent.

If necessary a carrier compound that assists in condensation can be added during the condensation reaction, e.g., by controlled addition. For example, the carrier compound can be a polymer other than a nucleic acid (e.g., spermine or spermidine). pH can also adjusted to favor condensation.

Methods for producing stable polynucleotide delivery vehicles, which incorporate a polynucleotide/cationic lipid complex as structural components of the delivery vehicle, are further described in, e.g., WO 96/37194, the entire contents of which are incorporated herein by reference. Liposome formation can also include one or more aspects of exemplary methods described in Felgner, P. L. et al., *Proc. Natl. Acad. Sci., USA* 8:7413-7417, 1987; U.S. Pat. No. 4,897,355; U.S. Pat. No. 5,171,678; Bangham, et al. *M. Mol. Biol.* 23:238, 1965; Olson, et al. *Biochim. Biophys. Acta* 557:9, 1979; Szoka, et al. *Proc. Natl. Acad. Sci.* 75: 4194, 1978; Mayhew, et al. *Biochim. Biophys. Acta* 775:169, 1984; Kim, et al. *Biochim. Biophys. Acta* 728:339, 1983; and Fukunaga, et al. *Endocrinol.* 115:757, 1984. Commonly used techniques for preparing lipid aggregates of appropriate size for use as delivery vehicles include sonication and freeze-thaw plus extrusion (see, e.g., Mayer, et al. *Biochim. Biophys. Acta* 858:161, 1986). Microfluidization can be used when consistently small (50 to 200 nm) and relatively uniform aggregates are desired (Mayhew, et al. *Biochim. Biophys. Acta* 775:169, 1984). These methods are readily adapted to packaging iRNA agent preparations into liposomes.

Liposomes fall into two broad classes. Cationic liposomes are positively charged liposomes which interact with the negatively charged nucleic acid molecules to form a stable complex. The positively charged nucleic acid/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980-985).

Liposomes which are pH-sensitive or negatively-charged, entrap nucleic acids rather than complex with it. Since both the nucleic acid and the lipid are similarly charged, repulsion rather than complex formation occurs. Nevertheless, some nucleic acid is entrapped within the aqueous interior of these liposomes. pH-sensitive liposomes have been used to deliver nucleic acids encoding the thymidine kinase gene to cell monolayers in culture. Expression of the exogenous gene was detected in the target cells (Zhou et al., *Journal of Controlled Release*, 1992, 19, 269-274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Examples of other methods to introduce liposomes into cells in vitro and in vivo include U.S. Pat. No. 5,283,185; U.S. Pat. No. 5,171,678; WO 94/00569; WO 93/24640; WO 91/16024; Felgner, *J. Biol. Chem.* 269:2550, 1994; Nabel, *Proc. Natl. Acad. Sci.* 90:11307, 1993; Nabel, *Human Gene Ther.* 3:649, 1992; Gershon, *Biochem.* 32:7143, 1993; and Strauss *EMBO J.* 11:417, 1992.

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporine A into different layers of the skin (Hu et al. *S.T.P. Pharma. Sci.*, 1994, 4(6) 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al).

In one embodiment, cationic liposomes are used. Cationic liposomes possess the advantage of being able to fuse to the cell membrane. Non-cationic liposomes, although not able to fuse as efficiently with the plasma membrane, are taken up by macrophages in vivo and can be used to deliver iRNA agents to macrophages.

Further advantages of liposomes include: liposomes obtained from natural phospholipids are biocompatible and biodegradable; liposomes can incorporate a wide range of water and lipid soluble drugs; liposomes can protect encapsulated iRNA agents in their internal compartments from metabolism and degradation (Rosoff, in "Pharmaceutical Dosage Forms," Lieberman, Rieger and Banker (Eds.), 1988, volume 1, p. 245). Important considerations in the preparation of liposome formulations are the lipid surface charge, vesicle size and the aqueous volume of the liposomes.

A positively charged synthetic cationic lipid, N-[1-(2,3-dioleyloxy)propyl]-N,N,N-trimethylammonium chloride (DOTMA) can be used to form small liposomes that interact spontaneously with nucleic acid to form lipid-nucleic acid complexes which are capable of fusing with the negatively charged lipids of the cell membranes of tissue culture cells, resulting in delivery of iRNA agent (see, e.g., Felgner, P. L.

et al., Proc. Natl. Acad. Sci., USA 8:7413-7417, 1987 and U.S. Pat. No. 4,897,355 for a description of DOTMA and its use with DNA).

A DOTMA analogue, 1,2-bis(oleoyloxy)-3-(trimethylammonia)propane (DOTAP) can be used in combination with a phospholipid to form DNA-complexing vesicles. Lipofectin™ Bethesda Research Laboratories, Gaithersburg, Md.) is an effective agent for the delivery of highly anionic nucleic acids into living tissue culture cells that comprise positively charged DOTMA liposomes which interact spontaneously with negatively charged polynucleotides to form complexes. When enough positively charged liposomes are used, the net charge on the resulting complexes is also positive. Positively charged complexes prepared in this way spontaneously attach to negatively charged cell surfaces, fuse with the plasma membrane, and efficiently deliver functional nucleic acids into, for example, tissue culture cells. Another commercially available cationic lipid, 1,2-bis(oleoyloxy)-3,3-(trimethylammonia)propane ("DOTAP") (Boehringer Mannheim, Indianapolis, Ind.) differs from DOTMA in that the oleoyl moieties are linked by ester, rather than ether linkages.

Other reported cationic lipid compounds include those that have been conjugated to a variety of moieties including, for example, carboxyspermine which has been conjugated to one of two types of lipids and includes compounds such as 5-carboxyspermylglycine dioctaoleoylamide ("DOGS") (Transfectam™, Promega, Madison, Wis.) and dipalmitoyl-phosphatidylethanolamine 5-carboxyspermyl-amide ("DPPES") (see, e.g., U.S. Pat. No. 5,171,678).

Another cationic lipid conjugate includes derivatization of the lipid with cholesterol ("DC-Chol") which has been formulated into liposomes in combination with DOPE (See, Gao, X. and Huang, L., *Biochim. Biophys. Res. Commun.* 179:280, 1991). Lipopolylysine, made by conjugating polylysine to DOPE, has been reported to be effective for transfection in the presence of serum (Zhou, X. et al., *Biochim. Biophys. Acta* 1065:8, 1991). For certain cell lines, these liposomes containing conjugated cationic lipids, are said to exhibit lower toxicity and provide more efficient transfection than the DOTMA-containing compositions.

Other commercially available cationic lipid products include DMRIE and DMRIE-HP (Vical, La Jolla, Calif.) and Lipofectamine (DOSPA) (Life Technology, Inc., Gaithersburg, Md.). Other cationic lipids suitable for the delivery of oligonucleotides are described in WO 98/39359 and WO 96/37194.

Liposomal formulations are particularly suited for topical administration, liposomes present several advantages over other formulations. Such advantages include reduced side effects related to high systemic absorption of the administered drug, increased accumulation of the administered drug at the desired target, and the ability to administer iRNA agent into the skin. In some implementations, liposomes are used for delivering iRNA agent to epidermal cells and also to enhance the penetration of iRNA agent into dermal tissues, e.g., into skin. For example, the liposomes can be applied topically. Topical delivery of drugs formulated as liposomes to the skin has been documented (see, e.g., Weiner et al., *Journal of Drug Targeting*, 1992, vol. 2,405-410 and du Plessis et al., *Antiviral Research*, 18, 1992, 259-265; Mannino, R. J. and Fould-Fogerite, S., Biotechniques 6:682-690, 1988; Itani, T. et al. *Gene* 56:267-276.1987; Nicolau, C. et al. *Meth. Enz.* 149:157-176, 1987; Straubinger, R. M. and Papahadjopoulos, D. *Meth. Enz.* 101:512-527, 1983; Wang, C. Y. and Huang, L., *Proc. Natl. Acad. Sci. USA* 84:7851-7855, 1987).

Non-ionic liposomal systems have also been examined to determine their utility in the delivery of drugs to the skin, in particular systems comprising non-ionic surfactant and cholesterol. Non-ionic liposomal formulations comprising Novasome I (glyceryl dilaurate/cholesterol/polyoxyethylene-10-stearyl ether) and Novasome II (glyceryl distearate/cholesterol/polyoxyethylene-10-stearyl ether) were used to deliver a drug into the dermis of mouse skin. Such formulations with iRNA agent are useful for treating a dermatological disorder.

Liposomes that include iRNA can be made highly deformable. Such deformability can enable the liposomes to penetrate through pore that are smaller than the average radius of the liposome. For example, transfersomes are a type of deformable liposomes. Transferosomes can be made by adding surface edge activators, usually surfactants, to a standard liposomal composition. Transfersomes that include iRNA agent can be delivered, for example, subcutaneously by infection in order to deliver iRNA agent to keratinocytes in the skin. In order to cross intact mammalian skin, lipid vesicles must pass through a series of fine pores, each with a diameter less than 50 nm, under the influence of a suitable transdermal gradient. In addition, due to the lipid properties, these transferosomes can be self-optimizing (adaptive to the shape of pores, e.g., in the skin), self-repairing, and can frequently reach their targets without fragmenting, and often self-loading.

Other formulations amenable to the present invention are described in U.S. provisional application Ser. No. 61/018,616, filed Jan. 2, 2008; 61/018,611, filed Jan. 2, 2008; 61/039,748, filed Mar. 26, 2008; 61/047,087, filed Apr. 22, 2008 and 61/051,528, filed May 8, 2008. PCT application no PCT/US2007/080331, filed Oct. 3, 2007 also describes formulations that are amenable to the present invention.

Transfersomes are yet another type of liposomes, and are highly deformable lipid aggregates which are attractive candidates for drug delivery vehicles. Transfersomes can be described as lipid droplets which are so highly deformable that they are easily able to penetrate through pores which are smaller than the droplet. Transfersomes are adaptable to the environment in which they are used, e.g., they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in "Pharmaceutical Dosage Forms", Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in "Pharmaceutical Dosage Forms", Marcel Dekker, Inc., New York, N.Y., 1988, p. 285).

The iRNA for use in the methods of the invention can also be provided as micellar formulations. "Micelles" are defined herein as a particular type of molecular assembly in which amphipathic molecules are arranged in a spherical structure such that all the hydrophobic portions of the molecules are directed inward, leaving the hydrophilic portions in contact with the surrounding aqueous phase. The converse arrangement exists if the environment is hydrophobic.

A mixed micellar formulation suitable for delivery through transdermal membranes may be prepared by mixing an aqueous solution of the siRNA composition, an alkali metal $C_8$ to $C_{22}$ alkyl sulphate, and a micelle forming compounds. Exemplary micelle forming compounds include lecithin, hyaluronic acid, pharmaceutically acceptable salts of hyaluronic acid, glycolic acid, lactic acid, chamomile extract, cucumber extract, oleic acid, linoleic acid, linolenic acid, monoolein, monooleates, monolaurates, borage oil, evening of primrose oil, menthol, trihydroxy oxo cholanyl glycine and pharmaceutically acceptable salts thereof, glycerin, polyglycerin, lysine, polylysine, triolein, polyoxyethylene ethers and analogues thereof, polidocanol alkyl ethers and analogues thereof, chenodeoxycholate, deoxycholate, and mixtures thereof. The micelle forming compounds may be added at the same time or after addition of the alkali metal alkyl sulphate. Mixed micelles will form with substantially any kind of mixing of the ingredients but vigorous mixing in order to provide smaller size micelles.

In one method a first micellar composition is prepared which contains the siRNA composition and at least the alkali metal alkyl sulphate. The first micellar composition is then mixed with at least three micelle forming compounds to form a mixed micellar composition. In another method, the micellar composition is prepared by mixing the siRNA composition, the alkali metal alkyl sulphate and at least one of the micelle forming compounds, followed by addition of the remaining micelle forming compounds, with vigorous mixing.

Phenol and/or m-cresol may be added to the mixed micellar composition to stabilize the formulation and protect against bacterial growth. Alternatively, phenol and/or m-cresol may be added with the micelle forming ingredients. An isotonic agent such as glycerin may also be added after formation of the mixed micellar composition.

For delivery of the micellar formulation as a spray, the formulation can be put into an aerosol dispenser and the dispenser is charged with a propellant. The propellant, which is under pressure, is in liquid form in the dispenser. The ratios of the ingredients are adjusted so that the aqueous and propellant phases become one, i.e., there is one phase. If there are two phases, it is necessary to shake the dispenser prior to dispensing a portion of the contents, e.g., through a metered valve. The dispensed dose of pharmaceutical agent is propelled from the metered valve in a fine spray.

Propellants may include hydrogen-containing chlorofluorocarbons, hydrogen-containing fluorocarbons, dimethyl ether and diethyl ether. In certain embodiments, HFA 134a (1,1,1,2 tetrafluoroethane) may be used.

The specific concentrations of the essential ingredients can be determined by relatively straightforward experimentation. For absorption through the oral cavities, it is often desirable to increase, e.g., at least double or triple, the dosage for through injection or administration through the gastrointestinal tract.

B. Lipid Particles iRNAs, e.g., dsRNAs of in the invention may be fully encapsulated in a lipid formulation, e.g., a LNP, or other nucleic acid-lipid particle.

As used herein, the term "LNP" refers to a stable nucleic acid-lipid particle. LNPs typically contain a cationic lipid, a non-cationic lipid, and a lipid that prevents aggregation of the particle (e.g., a PEG-lipid conjugate). LNPs are extremely useful for systemic applications, as they exhibit extended circulation lifetimes following intravenous (i.v.) injection and accumulate at distal sites (e.g., sites physically separated from the administration site). LNPs include "pSPLP," which include an encapsulated condensing agent-nucleic acid complex as set forth in PCT Publication No. WO 00/03683. The particles of the present invention typically have a mean diameter of about 50 nm to about 150 nm, more typically about 60 nm to about 130 nm, more typically about 70 nm to about 110 nm, most typically about 70 nm to about 90 nm, and are substantially nontoxic. In addition, the nucleic acids when present in the nucleic acid-lipid particles of the present invention are resistant in aqueous solution to degradation with a nuclease. Nucleic acid-lipid particles and their method of preparation are disclosed in, e.g., U.S. Pat. Nos. 5,976,567; 5,981,501; 6,534,484; 6,586,410; 6,815,432; U.S. Publication No. 2010/0324120 and PCT Publication No. WO 96/40964.

In one embodiment, the lipid to drug ratio (mass/mass ratio) (e.g., lipid to dsRNA ratio) will be in the range of from about 1:1 to about 50:1, from about 1:1 to about 25:1, from about 3:1 to about 15:1, from about 4:1 to about 10:1, from about 5:1 to about 9:1, or about 6:1 to about 9:1. Ranges intermediate to the above recited ranges are also contemplated to be part of the invention.

The cationic lipid can be, for example, N,N-dioleyl-N,N-dimethylammonium chloride (DODAC), N,N-distearyl-N,N-dimethylammonium bromide (DDAB), N—(I-(2,3-dioleyloxy)propyl)-N,N,N-trimethylammonium chloride (DOTAP), N—(I-(2,3-dioleyloxy)propyl)-N,N,N-trimethylammonium chloride (DOTMA), N,N-dimethyl-2,3-dioleyloxy)propylamine (DODMA), 1,2-DiLinoleyloxy-N,N-dimethylaminopropane (DLinDMA), 1,2-Dilinolenyloxy-N,N- dimethylaminopropane (DLenDMA), 1,2-Dilinoleylcarbamoyloxy-3-dimethylaminopropane (DLin-C-DAP), 1,2-Dilinoleyoxy-3-(dimethylamino) acetoxypropane (DLin-DAC), 1,2-Dilinoleyoxy-3-morpholinopropane (DLin-MA), 1,2-Dilinoleoyl-3-dimethylaminopropane (DLinDAP), 1,2-Dilinoleylthio-3-dimethylaminopropane (DLin-S-DMA), 1-Linoleoyl-2-linoleyloxy-3-dimethylaminopropane (DLin-2-DMAP), 1,2-Dilinoleyloxy-3-trimethylaminopropane chloride salt (DLin-TMA.C1), 1,2-Dilinoleoyl-3-trimethylaminopropane chloride salt (DLin-TAP.C1), 1,2-Dilinoleyloxy-3-(N-methylpiperazino)propane (DLin-MPZ), or 3-(N,N-Dilinoleylamino)-1,2-propanediol (DLinAP), 3-(N,N-Dioleylamino)-1,2-propanedio (DOAP), 1,2-Dilinoleyloxo-3-(2-N,N-dimethylamino)ethoxypropane (DLin-EG-DMA), 1,2-Dilinolenyloxy-N,N-dimethylaminopropane (DLinDMA), 2,2-Dilinoleyl-4-dimethylaminomethyl-[1,3]-dioxolane (DLin-K-DMA) or analogs thereof, (3aR,5s,6aS)—N,N-dimethyl-2,2-di((9Z,12Z)-octadeca-9,12-dienyl)tetrahydro-3aH-cyclopenta[d][1,3]dioxol-5-amine (ALN100), (6Z,9Z, 28Z,31Z)-heptatriaconta-6,9,28,31-tetraen-19-yl 4-(dimethylamino)butanoate (MC3), 1,1'-(2-(4-(2-((2-(bis(2-hydroxydodecyl)amino)ethyl)(2-hydroxydodecyl)amino) ethyl)piperazin-1-yl)ethylazanediyl)didodecan-2-ol (Tech G1), or a mixture thereof. The cationic lipid can comprise from about 20 mol % to about 50 mol % or about 40 mol % of the total lipid present in the particle.

In another embodiment, the compound 2,2-Dilinoleyl-4-dimethylaminoethyl-[1,3]-dioxolane can be used to prepare lipid-siRNA nanoparticles. Synthesis of 2,2-Dilinoleyl-4-dimethylaminoethyl-[1,3]-dioxolane is described in U.S. provisional patent application No. 61/107,998 filed on Oct. 23, 2008, which is herein incorporated by reference.

In one embodiment, the lipid-siRNA particle includes 40% 2, 2-Dilinoleyl-4-dimethylaminoethyl-[1,3]-dioxolane: 10% DSPC: 40% Cholesterol: 10% PEG-C-DOMG (mole percent) with a particle size of 63.0±20 nm and a 0.027 siRNA/Lipid Ratio.

The ionizable/non-cationic lipid can be an anionic lipid or a neutral lipid including, but not limited to, distearoylphosphatidylcholine (DSPC), dioleoylphosphatidylcholine (DOPC), dipalmitoylphosphatidylcholine (DPPC), dioleoylphosphatidylglycerol (DOPG), dipalmitoylphosphatidylglycerol (DPPG), dioleoyl-phosphatidylethanolamine (DOPE), palmitoyloleoylphosphatidylcholine (POPC), palmitoyloleoylphosphatidylethanolamine (POPE), dioleoyl-phosphatidylethanolamine 4-(N-maleimidomethyl)-cyclohexane-1-carboxylate (DOPE-mal), dipalmitoyl phosphatidyl ethanolamine (DPPE), dimyristoylphosphoethanolamine (DMPE), distearoyl-phosphatidyl-ethanolamine (DSPE), 16-O-monomethyl PE, 16-O-dimethyl PE, 18-1-trans PE, 1-stearoyl-2-oleoyl-phosphatidyethanolamine (SOPE), cholesterol, or a mixture thereof. The non-cationic lipid can be from about 5 mol % to about 90 mol %, about 10 mol %, or about 58 mol % if cholesterol is included, of the total lipid present in the particle.

The conjugated lipid that inhibits aggregation of particles can be, for example, a polyethyleneglycol (PEG)-lipid including, without limitation, a PEG-diacylglycerol (DAG), a PEG-dialkyloxypropyl (DAA), a PEG-phospholipid, a PEG-ceramide (Cer), or a mixture thereof. The PEG-DAA conjugate can be, for example, a PEG-dilauryloxypropyl ($C_{12}$), a PEG-dimyristyloxypropyl ($C_{14}$), a PEG-dipalmityloxypropyl ($C_{16}$), or a PEG-distearyloxypropyl ($C_{18}$). The conjugated lipid that prevents aggregation of particles can be from 0 mol % to about 20 mol % or about 2 mol % of the total lipid present in the particle.

In some embodiments, the nucleic acid-lipid particle further includes cholesterol at, e.g., about 10 mol % to about 60 mol % or about 48 mol % of the total lipid present in the particle.

In one embodiment, the lipidoid ND98.4HC1 (MW 1487) (see U.S. patent application Ser. No. 12/056,230, filed Mar. 26, 2008, which is incorporated herein by reference), Cholesterol (Sigma-Aldrich), and PEG-Ceramide C16 (Avanti Polar Lipids) can be used to prepare lipid-dsRNA nanoparticles (i.e., LNP01 particles). Stock solutions of each in ethanol can be prepared as follows: ND98, 133 mg/ml; Cholesterol, 25 mg/ml, PEG-Ceramide C16, 100 mg/ml. The ND98, Cholesterol, and PEG-Ceramide C16 stock solutions can then be combined in a, e.g., 42:48:10 molar ratio. The combined lipid solution can be mixed with aqueous dsRNA (e.g., in sodium acetate pH 5) such that the final ethanol concentration is about 35-45% and the final sodium acetate concentration is about 100-300 mM. Lipid-dsRNA nanoparticles typically form spontaneously upon mixing. Depending on the desired particle size distribution, the resultant nanoparticle mixture can be extruded through a polycarbonate membrane (e.g., 100 nm cut-off) using, for example, a thermobarrel extruder, such as Lipex Extruder (Northern Lipids, Inc). In some cases, the extrusion step can be omitted. Ethanol removal and simultaneous buffer exchange can be accomplished by, for example, dialysis or tangential flow filtration. Buffer can be exchanged with, for example, phosphate buffered saline (PBS) at about pH 7, e.g., about pH 6.9, about pH 7.0, about pH 7.1, about pH 7.2, about pH 7.3, or about pH 7.4.

Formula 1

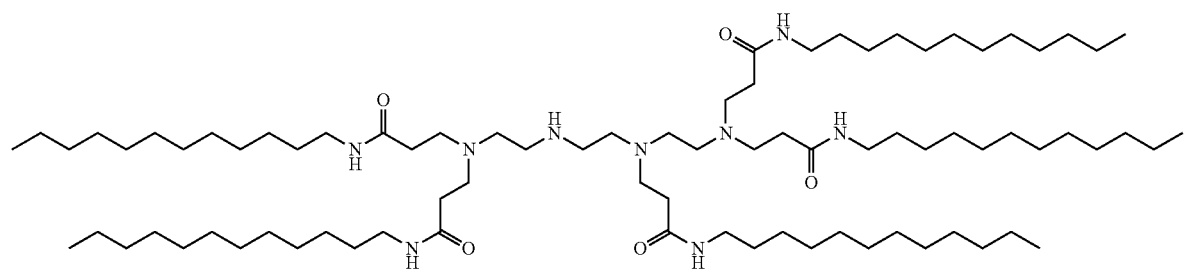

ND98 Isomer I

LNP01 formulations are described, e.g., in International Application Publication No. WO 2008/042973, which is hereby incorporated by reference.

Additional exemplary lipid-dsRNA formulations are described in Table 1.

TABLE 1

| | Ionizable/Cationic Lipid | cationic lipid/non-cationic lipid/cholesterol/PEG-lipid conjugate Lipid:siRNA ratio |
|---|---|---|
| SNALP-1 | 1,2-Dilinolenyloxy-N,N-dimethylaminopropane (DLinDMA) | DLinDMA/DPPC/Cholesterol/PEG-cDMA (57.1/7.1/34.4/1.4) lipid:siRNA~7:1 |
| 2-XTC | 2,2-Dilinoleyl-4-dimethylaminoethyl-[1,3]-dioxolane (XTC) | XTC/DPPC/Cholesterol/PEG-cDMA 57.1/7.1/34.4/1.4 lipid:siRNA~7:1 |
| LNP05 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~6:1 |
| LNP06 | 2,2-Dilinoleyl-4-dimethylaminoethyl-[1,3]-dioxolane (XTC) | XTC/DSPC/Cholesterol/PEG-DMG 57.5/7.5/31.5/3.5 lipid:siRNA~11:1 |
| LNP07 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~6:1 |
| LNP08 | 2,2-Dilinoleyl-4-dimethylaminoethyl-[1,3]-dioxolane (XTC) | XTC/DSPC/Cholesterol/PEG-DMG 60/7.5/31/1.5, lipid:siRNA~11:1 |
| LNP09 | 2,2-Dilinoleyl-4-dimethylaminoethyl-[1,3]-dioxolane (XTC) | XTC/DSPC/Cholesterol/PEG-DMG 50/10/38.5/1.5 Lipid:siRNA 10:1 |
| LNP10 | (3aR,5s,6aS)-N,N-dimethyl-2,2-di((9Z,12Z)-octadeca-9,12-dienyl)tetrahydro-3aH-cyclopenta[d][1,3]dioxol-5-amine (ALN100) | ALN100/DSPC/Cholesterol/PEG-DMG 50/10/38.5/1.5 Lipid:siRNA 10:1 |
| LNP11 | (6Z,9Z,28Z,31Z)-heptatriaconta-6,9,28,31-tetraen-19-yl 4-(dimethylamino)butanoate (MC3) | MC-3/DSPC/Cholesterol/PEG-DMG 50/10/38.5/1.5 Lipid:siRNA 10:1 |
| LNP12 | 1,1'-(2-(4-(2-((2-(bis(2-hydroxydodecyl)amino)ethyl)(2-hydroxydodecyl)amino)ethyl)piperazin-1-yl)ethylazanediyl)didodecan-2-ol (Tech G1) | Tech G1/DSPC/Cholesterol/PEG-DMG 50/10/38.5/1.5 Lipid:siRNA 10:1 |
| LNP13 | XTC | XTC/DSPC/Chol/PEG-DMG 50/10/38.5/1.5 Lipid:siRNA: 33:1 |
| LNP14 | MC3 | MC3/DSPC/Chol/PEG-DMG 40/15/40/5 Lipid:siRNA: 11:1 |
| LNP15 | MC3 | MC3/DSPC/Chol/PEG-DSG/GalNAc-PEG-DSG 50/10/35/4.5/0.5 Lipid:siRNA: 11:1 |
| LNP16 | MC3 | MC3/DSPC/Chol/PEG-DMG 50/10/38.5/1.5 Lipid:siRNA: 7:1 |
| LNP17 | MC3 | MC3/DSPC/Chol/PEG-DSG 50/10/38.5/1.5 Lipid:siRNA: 10:1 |
| LNP18 | MC3 | MC3/DSPC/Chol/PEG-DMG 50/10/38.5/1.5 Lipid:siRNA: 12:1 |
| LNP19 | MC3 | MC3/DSPC/Chol/PEG-DMG 50/10/35/5 Lipid:siRNA: 8:1 |
| LNP20 | MC3 | MC3/DSPC/Chol/PEG-DPG 50/10/38.5/1.5 Lipid:siRNA: 10:1 |
| LNP21 | C12-200 | C12-200/DSPC/Chol/PEG-DSG 50/10/38.5/1.5 Lipid:siRNA: 7:1 |

TABLE 1-continued

| Ionizable/Cationic Lipid | | cationic lipid/non-cationic lipid/cholesterol/PEG-lipid conjugate Lipid:siRNA ratio |
|---|---|---|
| LNP22 | XTC | XTC/DSPC/Chol/PEG-DSG 50/10/38.5/1.5 Lipid:siRNA: 10:1 |

DSPC: distearoylphosphatidylcholine
DPPC: dipalmitoylphosphatidylcholine
PEG-DMG: PEG-didimyristoyl glycerol (C14-PEG, or PEG-C14) (PEG with avg mol wt of 2000)
PEG-DSG: PEG-distyryl glycerol (C18-PEG, or PEG-C18) (PEG with avg mol wt of 2000)
PEG-cDMA: PEG-carbamoyl-1,2-dimyristyloxypropylamine (PEG with avg mol wt of 2000)
SNALP (1,2-Dilinolenyloxy-N,N-dimethylaminopropane (DLinDMA)) comprising formulations are described in International Publication No. WO2009/127060, filed Apr. 15, 2009, which is hereby incorporated by reference.

XTC comprising formulations are described, e.g., in U.S. Provisional Ser. No. 61/148,366, filed Jan. 29, 2009; U.S. Provisional Ser. No. 61/156,851, filed Mar. 2, 2009; U.S. Provisional Serial No. filed Jun. 10, 2009; U.S. Provisional Ser. No. 61/228,373, filed Jul. 24, 2009; U.S. Provisional Ser. No. 61/239,686, filed Sep. 3, 2009, and International Application No. PCT/US2010/022614, filed Jan. 29, 2010, which are hereby incorporated by reference.

MC3 comprising formulations are described, e.g., in U.S. Publication No. 2010/0324120, filed Jun. 10, 2010, the entire contents of which are hereby incorporated by reference.

ALNY-100 comprising formulations are described, e.g., International patent application number PCT/US09/63933, filed on Nov. 10, 2009, which is hereby incorporated by reference.

C12-200 comprising formulations are described in U.S. Provisional Ser. No. 61/175,770, filed May 5, 2009 and International Application No. PCT/US10/33777, filed May 5, 2010, which are hereby incorporated by reference.

Synthesis of Ionizable/Cationic Lipids

Any of the compounds, e.g., cationic lipids and the like, used in the nucleic acid-lipid particles of the invention can be prepared by known organic synthesis techniques, including the methods described in more detail in the Examples. All substituents are as defined below unless indicated otherwise.

"Alkyl" means a straight chain or branched, noncyclic or cyclic, saturated aliphatic hydrocarbon containing from 1 to 24 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, and the like; while unsaturated cyclic alkyls include cyclopentenyl and cyclohexenyl, and the like.

"Alkenyl" means an alkyl, as defined above, containing at least one double bond between adjacent carbon atoms. Alkenyls include both cis and trans isomers. Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like.

"Alkynyl" means any alkyl or alkenyl, as defined above, which additionally contains at least one triple bond between adjacent carbons. Representative straight chain and branched alkynyls include acetylenyl, propynyl, 1-butynyl, 2-butynyl, 1-pentynyl, 2-pentynyl, 3-methyl-1 butynyl, and the like.

"Acyl" means any alkyl, alkenyl, or alkynyl wherein the carbon at the point of attachment is substituted with an oxo group, as defined below. For example, —C(=O)alkyl, —C(=O)alkenyl, and —C(=O)alkynyl are acyl groups.

"Heterocycle" means a 5- to 7-membered monocyclic, or 7- to 10-membered bicyclic, heterocyclic ring which is either saturated, unsaturated, or aromatic, and which contains from 1 or 2 heteroatoms independently selected from nitrogen, oxygen and sulfur, and wherein the nitrogen and sulfur heteroatoms can be optionally oxidized, and the nitrogen heteroatom can be optionally quaternized, including bicyclic rings in which any of the above heterocycles are fused to a benzene ring. The heterocycle can be attached via any heteroatom or carbon atom. Heterocycles include heteroaryls as defined below. Heterocycles include morpholinyl, pyrrolidinonyl, pyrrolidinyl, piperidinyl, piperizynyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

The terms "optionally substituted alkyl", "optionally substituted alkenyl", "optionally substituted alkynyl", "optionally substituted acyl", and "optionally substituted heterocycle" means that, when substituted, at least one hydrogen atom is replaced with a substituent. In the case of an oxo substituent (=O) two hydrogen atoms are replaced. In this regard, substituents include oxo, halogen, heterocycle, —CN, —ORx, —NRxRy, —NRxC(=O)Ry, —NRxSO2Ry, —C(=O)Rx, —C(=O)ORx, —C(=O)NRxRy, —SOnRx and —SOnNRxRy, wherein n is 0, 1 or 2, Rx and Ry are the same or different and independently hydrogen, alkyl or heterocycle, and each of said alkyl and heterocycle substituents can be further substituted with one or more of oxo, halogen, —OH, —CN, alkyl, —ORx, heterocycle, —NRxRy, —NRxC(=O)Ry, —NRxSO2Ry, —C(=O)Rx, —C(=O)ORx, —C(=O)NRxRy, —SOnRx and —SOnNRxRy.

"Halogen" means fluoro, chloro, bromo and iodo.

In some embodiments, the methods of the invention can require the use of protecting groups. Protecting group methodology is well known to those skilled in the art (see, for example, Protective Groups in Organic Synthesis, Green, T. W. et al., Wiley-Interscience, New York City, 1999). Briefly, protecting groups within the context of this invention are any group that reduces or eliminates unwanted reactivity of a functional group. A protecting group can be added to a functional group to mask its reactivity during certain reactions and then removed to reveal the original functional group. In some embodiments an "alcohol protecting group" is used. An "alcohol protecting group" is any group which decreases or eliminates unwanted reactivity of an alcohol functional group. Protecting groups can be added and removed using techniques well known in the art.

Synthesis of Formula A

In some embodiments, nucleic acid-lipid particles of the invention are formulated using a cationic lipid of formula A:

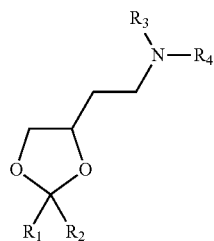

where R1 and R2 are independently alkyl, alkenyl or alkynyl, each can be optionally substituted, and R3 and R4 are independently lower alkyl or R3 and R4 can be taken together to form an optionally substituted heterocyclic ring. In some embodiments, the cationic lipid is XTC (2,2-Dilinoleyl-4-dimethylaminoethyl-[1,3]-dioxolane). In general, the lipid of formula A above can be made by the following Reaction Schemes 1 or 2, wherein all substituents are as defined above unless indicated otherwise.

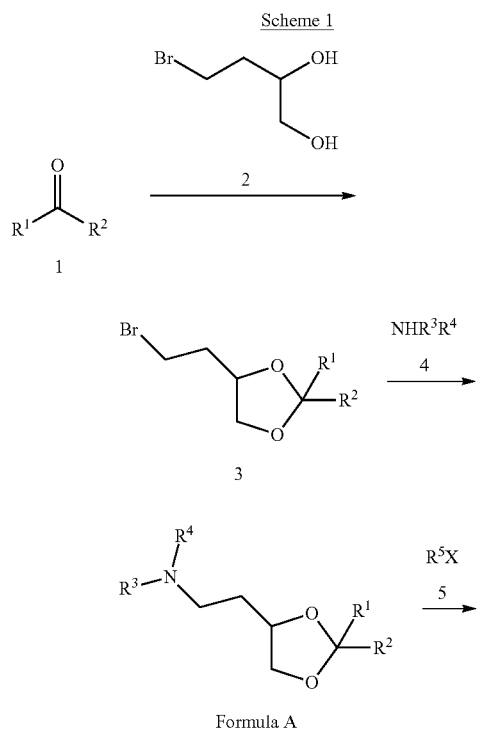

Formula A

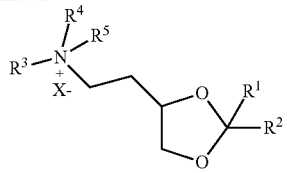

Lipid A, where R1 and R2 are independently alkyl, alkenyl or alkynyl, each can be optionally substituted, and R3 and R4 are independently lower alkyl or R3 and R4 can be taken together to form an optionally substituted heterocyclic ring, can be prepared according to Scheme 1. Ketone 1 and bromide 2 can be purchased or prepared according to methods known to those of ordinary skill in the art. Reaction of 1 and 2 yields ketal 3. Treatment of ketal 3 with amine 4 yields lipids of formula A. The lipids of formula A can be converted to the corresponding ammonium salt with an organic salt of formula 5, where X is anion counter ion selected from halogen, hydroxide, phosphate, sulfate, or the like.

Scheme 2

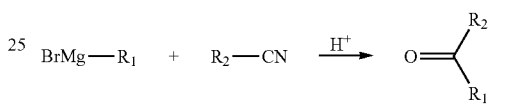

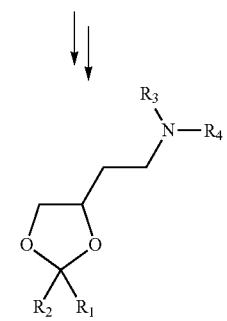

Alternatively, the ketone 1 starting material can be prepared according to Scheme 2. Grignard reagent 6 and cyanide 7 can be purchased or prepared according to methods known to those of ordinary skill in the art. Reaction of 6 and 7 yields ketone 1. Conversion of ketone 1 to the corresponding lipids of formula A is as described in Scheme 1.

Synthesis of MC3

Preparation of DLin-M-C3-DMA (i.e., (6Z,9Z,28Z,31Z)-heptatriaconta-6,9,28,31-tetraen-19-yl 4-(dimethylamino)butanoate) was as follows. A solution of (6Z,9Z,28Z,31Z)-heptatriaconta-6,9,28,31-tetraen-19-ol (0.53 g), 4-N,N-dimethylaminobutyric acid hydrochloride (0.51 g), 4-N,N-dimethylaminopyridine (0.61 g) and 1-ethyl-3-(3-dimethylaminopropyl)carbodiimide hydrochloride (0.53 g) in dichloromethane (5 mL) was stirred at room temperature overnight. The solution was washed with dilute hydrochloric acid followed by dilute aqueous sodium bicarbonate. The organic fractions were dried over anhydrous magnesium sulphate, filtered and the solvent removed on a rotovap. The residue was passed down a silica gel column (20 g) using a 1-5% methanol/dichloromethane elution gradient. Fractions containing the purified product were combined and the solvent removed, yielding a colorless oil (0.54 g).

Synthesis of ALNY-100

Synthesis of ketal 519 [ALNY-100] was performed using the following scheme 3:

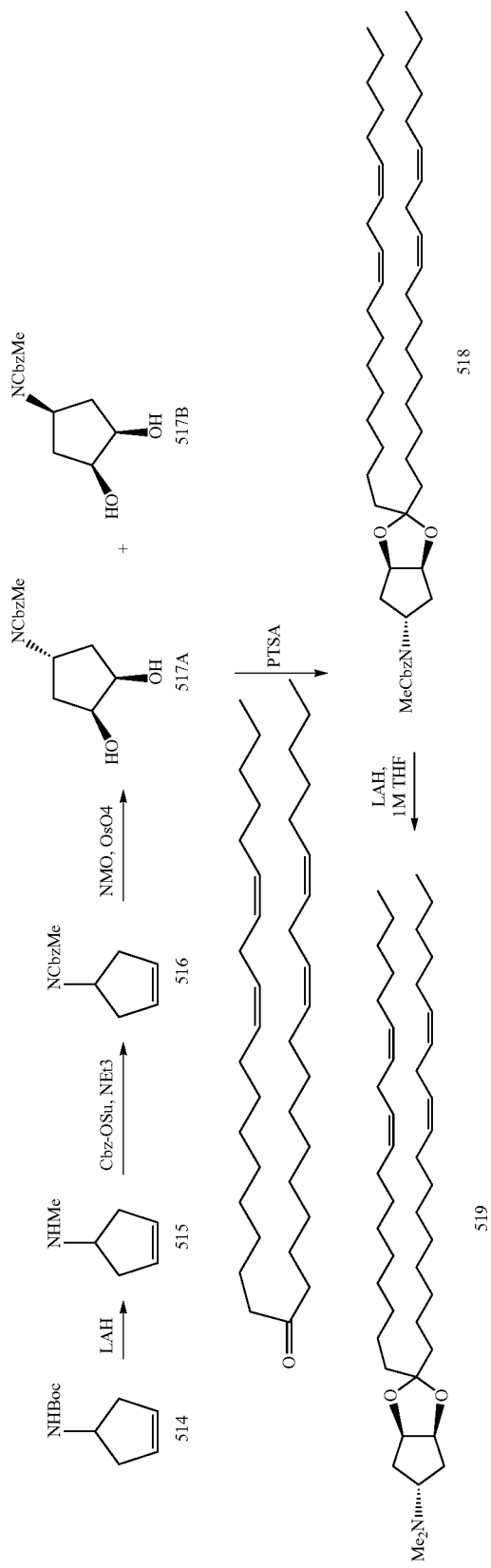

Synthesis of 515

To a stirred suspension of LiAlH4 (3.74 g, 0.09852 mol) in 200 ml anhydrous THF in a two neck RBF (IL), was added a solution of 514 (10 g, 0.04926 mol) in 70 mL of THF slowly at 0° C. under nitrogen atmosphere. After complete addition, reaction mixture was warmed to room temperature and then heated to reflux for 4 h. Progress of the reaction was monitored by TLC. After completion of reaction (by TLC) the mixture was cooled to 0° C. and quenched with careful addition of saturated Na2SO4 solution. Reaction mixture was stirred for 4 h at room temperature and filtered off. Residue was washed well with THF. The filtrate and washings were mixed and diluted with 400 mL dioxane and 26 mL conc. HCl and stirred for 20 minutes at room temperature. The volatilities were stripped off under vacuum to furnish the hydrochloride salt of 515 as a white solid. Yield: 7.12 g 1H-NMR (DMSO, 400 MHz): $\delta$=9.34 (broad, 2H), 5.68 (s, 2H), 3.74 (m, 1H), 2.66-2.60 (m, 2H), 2.50-2.45 (m, 5H).

Synthesis of 516

To a stirred solution of compound 515 in 100 mL dry DCM in a 250 mL two neck RBF, was added NEt3 (37.2 mL, 0.2669 mol) and cooled to 0° C. under nitrogen atmosphere. After a slow addition of N-(benzyloxy-carbonyloxy)-succinimide (20 g, 0.08007 mol) in 50 mL dry DCM, reaction mixture was allowed to warm to room temperature. After completion of the reaction (2-3 h by TLC) mixture was washed successively with iN HCl solution (1×100 mL) and saturated NaHCO3 solution (1×50 mL). The organic layer was then dried over anhyd. Na2SO4 and the solvent was evaporated to give crude material which was purified by silica gel column chromatography to get 516 as sticky mass. Yield: 11 g (89%). 1H-NMR (CDCl3, 400 MHz): $\delta$=7.36-7.27 (m, 5H), 5.69 (s, 2H), 5.12 (s, 2H), 4.96 (br., 1H) 2.74 (s, 3H), 2.60 (m, 2H), 2.30-2.25 (m, 2H). LC-MS [M+H]-232.3 (96.94%).

Synthesis of 517A and 517B

The cyclopentene 516 (5 g, 0.02164 mol) was dissolved in a solution of 220 mL acetone and water (10:1) in a single neck 500 mL RBF and to it was added N-methyl morpholine-N-oxide (7.6 g, 0.06492 mol) followed by 4.2 mL of 7.6% solution of OsO4 (0.275 g, 0.00108 mol) in tert-butanol at room temperature. After completion of the reaction (~3 h), the mixture was quenched with addition of solid Na2SO3 and resulting mixture was stirred for 1.5 h at room temperature. Reaction mixture was diluted with DCM (300 mL) and washed with water (2×100 mL) followed by saturated NaHCO3 (1×50 mL) solution, water (1×30 mL) and finally with brine (lx 50 mL). Organic phase was dried over an.Na2SO4 and solvent was removed in vacuum. Silica gel column chromatographic purification of the crude material was afforded a mixture of diastereomers, which were separated by prep HPLC. Yield: ~6 g crude 517A—Peak-1 (white solid), 5.13 g (96%). 1H-NMR (DMSO, 400 MHz): $\delta$=7.39-7.31 (m, 5H), 5.04 (s, 2H), 4.78-4.73 (m, 1H), 4.48-4.47 (d, 2H), 3.94-3.93 (m, 2H), 2.71 (s, 3H), 1.72-1.67 (m, 4H). LC-MS-[M+H]-266.3, [M+NH4+]-283.5 present, HPLC-97.86%. Stereochemistry confirmed by X-ray.

Synthesis of 518

Using a procedure analogous to that described for the synthesis of compound 505, compound 518 (1.2 g, 41%) was obtained as a colorless oil. 1H-NMR (CDCl3, 400 MHz): $\delta$=7.35-7.33 (m, 4H), 7.30-7.27 (m, 1H), 5.37-5.27 (m, 8H), 5.12 (s, 2H), 4.75 (m, 1H), 4.58-4.57 (m, 2H), 2.78-2.74 (m, 7H), 2.06-2.00 (m, 8H), 1.96-1.91 (m, 2H), 1.62 (m, 4H), 1.48 (m, 2H), 1.37-1.25 (br m, 36H), 0.87 (m, 6H). HPLC-98.65%.

General Procedure for the Synthesis of Compound 519

A solution of compound 518 (1 eq) in hexane (15 mL) was added in a drop-wise fashion to an ice-cold solution of LAH in THF (1 M, 2 eq). After complete addition, the mixture was heated at 400° C. over 0.5 h then cooled again on an ice bath. The mixture was carefully hydrolyzed with saturated aqueous Na2SO4 then filtered through celite and reduced to an oil. Column chromatography provided the pure 519 (1.3 g, 68%) which was obtained as a colorless oil. 13C NMR $\delta$=130.2, 130.1 (x2), 127.9 (x3), 112.3, 79.3, 64.4, 44.7, 38.3, 35.4, 31.5, 29.9 (x2), 29.7, 29.6 (x2), 29.5 (x3), 29.3 (x2), 27.2 (x3), 25.6, 24.5, 23.3, 226, 14.1; Electrospray MS (+ve): Molecular weight for C44H80NO2 (M+H)+ Calc. 654.6, Found 654.6.

Formulations prepared by either the standard or extrusion-free method can be characterized in similar manners. For example, formulations are typically characterized by visual inspection. They should be whitish translucent solutions free from aggregates or sediment. Particle size and particle size distribution of lipid-nanoparticles can be measured by light scattering using, for example, a Malvern Zetasizer Nano ZS (Malvern, USA). Particles should be about 20-300 nm, such as 40-100 nm in size. The particle size distribution should be unimodal. The total dsRNA concentration in the formulation, as well as the entrapped fraction, is estimated using a dye exclusion assay. A sample of the formulated dsRNA can be incubated with an RNA-binding dye, such as Ribogreen (Molecular Probes) in the presence or absence of a formulation disrupting surfactant, e.g., 0.5% Triton-X100. The total dsRNA in the formulation can be determined by the signal from the sample containing the surfactant, relative to a standard curve. The entrapped fraction is determined by subtracting the "free" dsRNA content (as measured by the signal in the absence of surfactant) from the total dsRNA content. Percent entrapped dsRNA is typically >85%. For SNALP formulation, the particle size is at least 30 nm, at least 40 nm, at least 50 nm, at least 60 nm, at least 70 nm, at least 80 nm, at least 90 nm, at least 100 nm, at least 110 nm, and at least 120 nm. The suitable range is typically about at least 50 nm to about at least 110 nm, about at least 60 nm to about at least 100 nm, or about at least 80 nm to about at least 90 nm.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders can be desirable. In some embodiments, oral formulations are those in which dsRNAs featured in the invention are administered in conjunction with one or more penetration enhancer surfactants and chelators. Suitable surfactants include fatty acids and/or esters or salts thereof, bile acids and/or salts thereof. Suitable bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Suitable fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g., sodium). In some embodiments, combinations of penetration enhancers are used, for example, fatty acids/salts in combination with bile acids/salts. One exemplary combination is the sodium salt of lauric acid, capric acid and UDCA. Further penetration enhancers include polyoxyethylene-9-lauryl ether, polyoxyethylene-20-cetyl ether. DsRNAs featured in the invention can be delivered orally, in granular form including sprayed dried particles, or complexed to form micro or nanoparticles. DsRNA complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Suitable complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g., p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for dsRNAs and their preparation are described in detail in U.S. Pat. No. 6,887,906, US Publn. No. 20030027780, and U.S. Pat. No. 6,747,014, each of which is incorporated herein by reference.

Compositions and formulations for parenteral, intraparenchymal (into the brain), intrathecal, intraventricular or intrahepatic administration can include sterile aqueous solutions which can also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions can be generated from a variety of components that include, but are not limited to, preformed liquids, self-emulsifying solids and self-emulsifying semisolids. Particularly preferred are formulations that target the liver when treating hepatic disorders such as hepatic carcinoma.

The pharmaceutical formulations of the present invention, which can conveniently be presented in unit dosage form, can be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention can be formulated into any of many possible dosage forms such as, but not limited to, tablets, capsules, gel capsules, liquid syrups, soft gels, suppositories, and enemas. The compositions of the present invention can also be formulated as suspensions in aqueous, non-aqueous or mixed media. Aqueous suspensions can further contain substances which increase the viscosity of the suspension including, for example, sodium carboxymethylcellulose, sorbitol and/or dextran. The suspension can also contain stabilizers.

C. Additional Formulations i. Emulsions

The compositions of the present invention can be prepared and formulated as emulsions. Emulsions are typically heterogeneous systems of one liquid dispersed in another in the form of droplets usually exceeding 0.1 μm in diameter (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199; Rosoff, in Pharmaceutical Dosage Forms, Lieberman, Rieger and Banker (Eds.), 1988, Marcel Dekker, Inc., New York, N.Y., Volume 1, p. 245; Block in Pharmaceutical Dosage Forms, Lieberman, Rieger and Banker (Eds.), 1988, Marcel Dekker, Inc., New York, N.Y., volume 2, p. 335; Higuchi et al., in Remington's Pharmaceutical Sciences, Mack Publishing Co., Easton, Pa., 1985, p. 301). Emulsions are often biphasic systems comprising two immiscible liquid phases intimately mixed and dispersed with each other. In general, emulsions can be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions can contain additional components in addition to the dispersed phases, and the active drug which can be present as a solution in either the aqueous phase, oily phase or itself as a separate phase. Pharmaceutical excipients such as emulsifiers, stabilizers, dyes, and antioxidants can also be present in emulsions as needed. Pharmaceutical emulsions can also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion can be a semisolid or a solid, as is the case of emulsion-style ointment bases and creams. Other means of stabilizing emulsions entail the use of emulsifiers that can be incorporated into either phase of the emulsion. Emulsifiers can broadly be classified into four categories: synthetic surfactants, naturally occurring emulsifiers, absorption bases, and finely dispersed solids (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rieger, in Pharmaceutical Dosage Forms, Lieberman, Rieger and Banker (Eds.), 1988, Marcel Dekker, Inc., New York, N.Y., volume 1, p. 285; Idson, in Pharmaceutical Dosage Forms, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants can be classified into different classes based on the nature of the hydrophilic group: nonionic, anionic, cationic and amphoteric (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y. Rieger, in Pharmaceutical Dosage Forms, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in Pharmaceutical Dosage Forms, Lieberman, Rieger and Banker (Eds.), 1988, Marcel Dekker, Inc., New York, N.Y., volume 1, p. 335; Idson, in Pharmaceutical Dosage Forms, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that can readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used can be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (see e.g., Ansel's Pharmaceutical Dosage Forms and Drug Delivery Systems, Allen, L V., Popovich NG., and Ansel H C., 2004, Lippincott Williams & Wilkins (8th ed.), New York, N.Y.; Idson, in Pharmaceutical Dosage Forms, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Idson, in Pharmaceutical Dosage Forms, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

ii. Microemulsions

In one embodiment of the present invention, the compositions of iRNAs and nucleic acids are formulated as microemulsions. A microemulsion can be defined as a system of water, oil and amphiphile which is a single optically isotropic and thermodynamically stable liquid solution (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: Controlled Release of Drugs: Polymers and Aggregate Systems, Rosoff, M., Ed., 1989, VCH Publishers, New York, pages 185-215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in Remington's Pharmaceutical Sciences, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (see e.g., Ansel's Pharmaceutical Dosage Forms and Drug Delivery Systems, Allen, L V., Popovich N G., and Ansel H C., 2004, Lippincott Williams & Wilkins (8th ed.), New York, N.Y.; Rosoff, in Pharmaceutical Dosage Forms, Lieberman, Rieger and Banker (Eds.), 1988, Marcel Dekker, Inc., New York, N.Y., volume 1, p. 245; Block, in Pharmaceutical Dosage Forms, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions can, however, be prepared without the use of cosurfactants and alcohol-free self-emulsifying microemulsion systems are known in the art. The aqueous phase can typically be, but is not limited to, water, an aqueous solution of the drug, glycerol, PEG300, PEG400, polyglycerols, propylene glycols, and derivatives of ethylene glycol. The oil phase can include, but is not limited to, materials such as Captex 300, Captex 355, Capmul MCM, fatty acid esters, medium chain (C8-C12) mono, di, and tri-glycerides, polyoxyethylated glyceryl fatty acid esters, fatty alcohols, polyglycolized glycerides, saturated polyglycolized C8-C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (see e.g., U.S. Pat. Nos. 6,191,105; 7,063,860; 7,070,802; 7,157,099; Constantinides et al., Pharmaceutical Research, 1994, 11, 1385-1390; Ritschel, Meth. Find. Exp. Clin. Pharmacol., 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (see e.g., U.S. Pat. Nos. 6,191,105; 7,063,860; 7,070,802; 7,157,099; Constantinides et al., Pharmaceutical Research, 1994, 11, 1385; Ho et al., J. Pharm. Sci., 1996, 85, 138-143). Often microemulsions can form spontaneously when their components are brought together at ambient temperature. This can be particularly advantageous when formulating thermolabile drugs, peptides or iRNAs. Microemulsions have also been effective in the transdermal delivery of active components in both cosmetic and pharmaceutical applications. It is expected that the microemulsion compositions and formulations of the present invention will facilitate the increased systemic absorption of iRNAs and nucleic acids from the gastrointestinal tract, as well as improve the local cellular uptake of iRNAs and nucleic acids.

Microemulsions of the present invention can also contain additional components and additives such as sorbitan monostearate (Grill 3), Labrasol, and penetration enhancers to improve the properties of the formulation and to enhance the absorption of the iRNAs and nucleic acids of the present invention. Penetration enhancers used in the microemulsions of the present invention can be classified as belonging to one of five broad categories—surfactants, fatty acids, bile salts, chelating agents, and non-chelating non-surfactants (Lee et al., Critical Reviews in Therapeutic Drug Carrier Systems, 1991, p. 92). Each of these classes has been discussed above.

iii. Microparticles

An iRNA agent of the invention may be incorporated into a particle, e.g., a microparticle. Microparticles can be produced by spray-drying, but may also be produced by other methods including lyophilization, evaporation, fluid bed drying, vacuum drying, or a combination of these techniques.

iv. Penetration Enhancers

In one embodiment, the present invention employs various penetration enhancers to effect the efficient delivery of nucleic acids, particularly iRNAs, to the skin of animals. Most drugs are present in solution in both ionized and nonionized forms. However, usually only lipid soluble or lipophilic drugs readily cross cell membranes. It has been discovered that even non-lipophilic drugs can cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers can be classified as belonging to one of five broad categories, i.e., surfactants, fatty acids, bile salts, chelating agents, and non-chelating non-surfactants (see e.g., Malmsten, M. Surfactants and polymers in drug delivery, Informa Health Care, New York, N.Y., 2002; Lee et al., Critical Reviews in Therapeutic Drug Carrier Systems, 1991, p.92). Each of the above mentioned classes of penetration enhancers are described below in greater detail.

Surfactants (or "surface-active agents") are chemical entities which, when dissolved in an aqueous solution, reduce the surface tension of the solution or the interfacial tension between the aqueous solution and another liquid, with the result that absorption of iRNAs through the mucosa is enhanced. In addition to bile salts and fatty acids, these penetration enhancers include, for example, sodium lauryl sulfate, polyoxyethylene-9-lauryl ether and polyoxyethylene-20-cetyl ether) (see e.g., Malmsten, M. Surfactants and polymers in drug delivery, Informa Health Care, New York, N.Y., 2002; Lee et al., Critical Reviews in Therapeutic Drug Carrier Systems, 1991, p.92); and perfluorochemical emulsions, such as FC-43. Takahashi et al., J. Pharm. Pharmacol., 1988, 40, 252).

Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, C1-20 alkyl esters thereof (e.g., methyl, isopropyl and t-butyl), and mono- and di-glycerides thereof (i.e., oleate, laurate, caprate, myristate, palmitate, stearate, linoleate, etc.) (see e.g., Touitou, E., et al. Enhancement in Drug Delivery, CRC Press, Danvers, Mass., 2006; Lee et al., Critical Reviews in Therapeutic Drug Carrier Systems, 1991, p.92; Muranishi, Critical Reviews in Therapeutic Drug Carrier Systems, 1990, 7, 1-33; El Hariri et al., J. Pharm. Pharmacol., 1992, 44, 651-654).

The physiological role of bile includes the facilitation of dispersion and absorption of lipids and fat-soluble vitamins (see e.g., Malmsten, M. Surfactants and polymers in drug delivery, Informa Health Care, New York, N.Y., 2002; Brunton, Chapter 38 in: Goodman & Gilman's The Pharmacological Basis of Therapeutics, 9th Ed., Hardman et al. Eds., McGraw-Hill, New York, 1996, pp. 934-935). Various natural bile salts, and their synthetic derivatives, act as penetration enhancers. Thus the term "bile salts" includes any of the naturally occurring components of bile as well as any of their synthetic derivatives. Suitable bile salts include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (see e.g., Malmsten, M. Surfactants and polymers in drug delivery, Informa Health Care, New York, N.Y., 2002; Lee et al., Critical Reviews in Therapeutic Drug Carrier Systems, 1991, page 92; Swinyard, Chapter 39 In: Remington's Pharmaceutical Sciences, 18th Ed., Gennaro, ed., Mack Publishing Co., Easton, Pa., 1990, pages 782-783; Muranishi, Critical Reviews in Therapeutic Drug Carrier Systems, 1990, 7, 1-33; Yamamoto et al., J. Pharm. Exp. Ther., 1992, 263, 25; Yamashita et al., J. Pharm. Sci., 1990, 79, 579-583).

Chelating agents, as used in connection with the present invention, can be defined as compounds that remove metallic ions from solution by forming complexes therewith, with the result that absorption of iRNAs through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315-339). Suitable chelating agents include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(see e.g., Katdare, A. et al., Excipient development for pharmaceutical, biotechnology, and drug delivery, CRC Press, Danvers, Mass., 2006; Lee et al., Critical Reviews in Therapeutic Drug Carrier Systems, 1991, page 92; Muranishi, Critical Reviews in Therapeutic Drug Carrier Systems, 1990, 7, 1-33; Buur et al., J. Control Rel., 1990, 14, 43-51).

As used herein, non-chelating non-surfactant penetration enhancing compounds can be defined as compounds that demonstrate insignificant activity as chelating agents or as surfactants but that nonetheless enhance absorption of iRNAs through the alimentary mucosa (see e.g., Muranishi, Critical Reviews in Therapeutic Drug Carrier Systems, 1990, 7, 1-33). This class of penetration enhancers includes, for example, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621-626).

Agents that enhance uptake of iRNAs at the cellular level can also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of dsRNAs. Examples of commercially available transfection reagents include, for example Lipofectamine™ (Invitrogen™; Carlsbad, Calif.), Lipofectamine 2000™ (Invitrogen™; Carlsbad, Calif.), 293Fectin™ (Invitrogen™; Carlsbad, Calif.), Cellfectin™ (Invitrogen™; Carlsbad, Calif.), DMRIE-C™ (Invitrogen™; Carlsbad, Calif.), FreeStyle™ MAX (Invitrogen™; Carlsbad, Calif.), Lipofectamine™ 2000 CD (Invitrogen™; Carlsbad, Calif.), Lipofectamine™ (Invitrogen™; Carlsbad, Calif.), iRNAMAX (Invitrogen™; Carlsbad, Calif.), Oligofectamine™ (Invitrogen™; Carlsbad, Calif.), Optifect™ (Invitrogen™; Carlsbad, Calif.), X-tremeGENE Q2 Transfection Reagent (Roche; Grenzacherstrasse, Switzerland), DOTAP Liposomal Transfection Reagent (Grenzacherstrasse, Switzerland), DOSPER Liposomal Transfection Reagent (Grenzacherstrasse, Switzerland), or Fugene (Grenzacherstrasse, Switzerland), Transfectam® Reagent (Promega®; Madison, Wis.), TransFast™ Transfection Reagent (Promega®; Madison, Wis.), Tfx™-20 Reagent (Promega®; Madison, Wis.), Tfx™-50 Reagent (Promega®; Madison, Wis.), DreamFect™ (OZ Biosciences; Marseille, France), EcoTransfect (OZ Biosciences; Marseille, France), TransPass$^a$ D1 Transfection Reagent (New England Biolabs™; Ipswich, Mass., USA), LyoVec™/LipoGen™ (Invitrogen™; San Diego, Calif., USA), PerFectin Transfection Reagent (Genlantis™; San Diego, Calif., USA), NeuroPORTER® Transfection Reagent (Genlantis™; San Diego, Calif., USA), GenePORTER® Transfection reagent (Genlantis™; San Diego, Calif., USA), GenePORTER® 2 Transfection reagent (Genlantis™; San Diego, Calif., USA), Cytofectin Transfection Reagent (Genlantis™; San Diego, Calif., USA), BaculoPORTER® Transfection Reagent (Genlantis™; San Diego, Calif., USA), TroganPORTER™ transfection Reagent (Genlantis™; San Diego, Calif., USA), RiboFect (Bioline™; Taunton, Mass., USA), PlasFect (Bioline™; Taunton, Mass., USA), UniFECTOR (B-Bridge International™; Mountain View, Calif., USA), SureFECTOR (B-Bridge International™; Mountain View, Calif., USA), or HiFect™ (B-Bridge International™, Mountain View, Calif., USA), among others.

Other agents can be utilized to enhance the penetration of the administered nucleic acids, including glycols such as ethylene glycol and propylene glycol, pyrrols such as 2-pyrrol, azones, and terpenes such as limonene and menthone.

v. Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate dsRNA in hepatic tissue can be reduced when it is coadministered with polyinosinic acid, dextran sulfate, polycytidic acid or 4-acetamido-4'isothiocyano-stilbene-2,2'-disulfonic acid (Miyao et al., DsRNA Res. Dev., 1995, 5, 115-121; Takakura et al., DsRNA & Nucl. Acid Drug Dev., 1996, 6, 177-183.

vi. Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient can be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc).

Pharmaceutically acceptable organic or inorganic excipients suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids can include sterile and non-sterile aqueous solutions, non-aqueous solutions in common solvents such as alcohols, or solutions of the nucleic acids in liquid or solid oil bases. The solutions can also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

vii. Other Components

The compositions of the present invention can additionally contain other adjunct components conventionally found in pharmaceutical compositions, at their art-established usage levels. Thus, for example, the compositions can contain additional, compatible, pharmaceutically-active materials such as, for example, antipruritics, astringents, local anesthetics or anti-inflammatory agents, or can contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions can contain substances which increase the viscosity of the suspension including, for example, sodium carboxymethylcellulose, sorbitol and/or dextran. The suspension can also contain stabilizers.

In some embodiments, pharmaceutical compositions featured in the invention include (a) one or more iRNA compounds and (b) one or more agents which function by a non-iRNA mechanism and which are useful in treating a hemolytic disorder. Examples of such agents include, but are not limited to an anti-inflammatory agent, anti-steatosis agent, antiviral, and/or anti-fibrosis agent. In addition, other substances commonly used to protect the liver, such as silymarin, can also be used in conjunction with the iRNAs described herein. Other agents useful for treating liver diseases include telbivudine, entecavir, and protease inhibitors such as telaprevir and other disclosed, for example, in Tung et al., U.S. Application Publication Nos. 2005/0148548, 2004/0167116, and 2003/0144217; and in Hale et al., U.S. Application Publication No. 2004/0127488.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit high therapeutic indices are preferred.

The data obtained from cell culture assays and animal studies can be used in formulating a range of dosage for use in humans. The dosage of compositions featured herein in the invention lies generally within a range of circulating concentrations that include the ED50 with little or no toxicity. The dosage can vary within this range depending upon the dosage form employed and the route of administration utilized. For any compound used in the methods featured in the invention, the therapeutically effective dose can be estimated initially from cell culture assays. A dose can be formulated in animal models to achieve a circulating plasma concentration range of the compound or, when appropriate, of the polypeptide product of a target sequence (e.g., achieving a decreased concentration of the polypeptide) that includes the IC50 (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography.

In addition to their administration, as discussed above, the iRNAs featured in the invention can be administered in combination with other known agents effective in treatment of pathological processes mediated by AGT expression. In any event, the administering physician can adjust the amount and timing of iRNA administration on the basis of results observed using standard measures of efficacy known in the art or described herein.

VII. Methods of the Invention

The present invention provides therapeutic and prophylactic methods which include administering to a subject having, or prone to developing, an AGT-associated disease, disorder, and/or condition (e.g., hypertension), pharmaceutical compositions comprising an iRNA agent, or vector comprising an iRNA of the invention.

In one aspect, the present invention provides methods of treating a subject having a disorder that would benefit from reduction in AGT expression, e.g., a AGT-associated disease, e.g. hypertension, e.g., borderline hypertension (also known as prehypertension), primary hypertension (also known as essential hypertension or idiopathic hypertension), secondary hypertension (also known as inessential hypertension), hypertensive emergency (also known as malignant hypertension), hypertensive urgency, isolated systolic or diastolic hypertension, pregnancy-associated hypertension (e.g., preeclampsia, eclampsia, and post-partum preeclampsia), diabetic hypertension, resistant hypertension, refractory hypertension, paroxysmal hypertension, renovascular hypertension (also known as renal hypertension), Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy (including peripheral vascular disease), diabetic nephropathy, diabetic retinopathy, chronic heart failure, cardiomyopathy, diabetic cardiac myopathy, glomerulosclerosis, coarctation of the aorta, aortic aneurism, ventricular fibrosis, Cushing's syndrome, and other glucocorticoid excess states including chronic steroid therapy, pheochromocytoma, reninoma, secondary aldosteronism and other mineralocorticoid excess states, sleep apnea, thyroid/parathyroid disease, heart failure (e.g., left ventricular systolic dysfunction), myocardial infarction, angina, stroke, diabetes mellitus (e.g., diabetic nephropathy), renal disease e.g., chronic kidney disease or diabetic nephropathy optionally in the context of pregnancy, renal failure, e.g., chronic renal failure, cognitive dysfunction (such as Alzheimer's), and systemic sclerosis (e.g., scleroderma renal crisis). In certain embodiments, AGT-associated disease includes intrauterine growth restriction (IUGR) or fetal growth restriction. The treatment methods (and uses) of the invention include administering to the subject, e.g., a human, a therapeutically effective amount of an iRNA agent targeting an AGT gene or a pharmaceutical composition comprising an iRNA agent targeting an AGT gene, thereby treating the subject having a disorder that would benefit from reduction in AGT expression.

In one aspect, the invention provides methods of preventing at least one symptom in a subject having a disorder that would benefit from reduction in AGT expression, e.g., a AGT-associated disease, e.g., hypertension, e.g., borderline hypertension (also known as prehypertension), primary hypertension (also known as essential hypertension or idiopathic hypertension), secondary hypertension (also known as inessential hypertension), hypertensive emergency (also known as malignant hypertension), hypertensive urgency, isolated systolic or diastolic hypertension, pregnancy-associated hypertension (e.g., preeclampsia, eclampsia, and post-partum preeclampsia), diabetic hypertension, resistant hypertension, refractory hypertension, paroxysmal hypertension, renovascular hypertension (also known as renal hypertension), Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy (including peripheral vascular disease), diabetic nephropathy, diabetic retinopathy, chronic heart failure, cardiomyopathy, diabetic cardiac myopathy, glomerulosclerosis, coarctation of the aorta, aortic aneurism, ventricular fibrosis, Cushing's syndrome, and other glucocorticoid excess states including chronic steroid therapy, pheochromocytoma, reninoma, secondary aldosteronism and other mineralocorticoid excess states, sleep apnea, thyroid/parathyroid disease, heart failure (e.g., left ventricular systolic dysfunction), myocardial infarction, angina, stroke, diabetes mellitus (e.g., diabetic nephropathy), renal disease e.g., chronic kidney disease or diabetic nephropathy optionally in the context of pregnancy, renal failure, e.g., chronic renal failure, cognitive dysfunction (such as Alzheimer's), and systemic sclerosis (e.g., scleroderma renal crisis). In certain embodiments, AGT-associated disease includes intrauterine growth restriction (IUGR) or fetal growth restriction The methods include administering to the subject a therapeutically effective amount of the iRNA agent, e.g., dsRNA, or vector of the invention, thereby preventing at least one symptom in the subject having a disorder that would benefit from reduction in AGT expression.

In another aspect, the present invention provides uses of a therapeutically effective amount of an iRNA agent of the invention for treating a subject, e.g., a subject that would benefit from a reduction and/or inhibition of AGT expression.

In a further aspect, the present invention provides uses of an iRNA agent, e.g., a dsRNA, of the invention targeting an AGT gene or pharmaceutical composition comprising an iRNA agent targeting an AGT gene in the manufacture of a medicament for treating a subject, e.g., a subject that would benefit from a reduction and/or inhibition of AGT expression, such as a subject having a disorder that would benefit from reduction in AGT expression, e.g., a AGT-associated disease, e.g., hypertension, e.g., borderline hypertension (also known as prehypertension), primary hypertension (also known as essential hypertension or idiopathic hypertension), secondary hypertension (also known as inessential hypertension), hypertensive emergency (also known as malignant hypertension), hypertensive urgency, isolated systolic or diastolic hypertension, pregnancy-associated hypertension (e.g., preeclampsia, eclampsia, and post-partum preeclampsia), diabetic hypertension, resistant hypertension, refractory hypertension, paroxysmal hypertension, renovascular hypertension (also known as renal hypertension), Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy (including peripheral vascular disease), diabetic nephropathy, diabetic retinopathy, chronic heart failure, cardiomyopathy, diabetic cardiac myopathy, glomerulosclerosis, coarctation of the aorta, aortic aneurism, ventricular fibrosis, Cushing's syndrome, and other glucocorticoid excess states including chronic steroid therapy, pheochromocytoma, reninoma, secondary aldosteronism and other mineralocorticoid excess states, sleep apnea, thyroid/parathyroid disease, heart failure (e.g., left ventricular systolic dysfunction), myocardial infarction, angina, stroke, diabetes mellitus (e.g., diabetic nephropathy), renal disease e.g., chronic kidney disease or diabetic nephropathy optionally in the context of pregnancy, renal failure, e.g., chronic renal failure, cognitive dysfunction (such as Alzheimer's), and systemic sclerosis (e.g., scleroderma renal crisis). In certain embodiments, AGT-associated disease includes intrauterine growth restriction (IUGR) or fetal growth restriction.

In another aspect, the invention provides uses of an iRNA, e.g., a dsRNA, of the invention for preventing at least one symptom in a subject suffering from a disorder that would benefit from a reduction and/or inhibition of AGT expression, such as a AGT-associated disease, e.g., hypertension, e.g., borderline hypertension (also known as prehypertension), primary hypertension (also known as essential hypertension or idiopathic hypertension), secondary hypertension (also known as inessential hypertension), hypertensive emergency (also known as malignant hypertension), hypertensive urgency, isolated systolic or diastolic hypertension, pregnancy-associated hypertension (e.g., preeclampsia, eclampsia, and post-partum preeclampsia), diabetic hypertension, resistant hypertension, refractory hypertension, paroxysmal hypertension, renovascular hypertension (also known as renal hypertension), Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy (including peripheral vascular disease), diabetic nephropathy, diabetic retinopathy, chronic heart failure, cardiomyopathy, diabetic cardiac myopathy, glomerulosclerosis, coarctation of the aorta, aortic aneurism, ventricular fibrosis, Cushing's syndrome, and other glucocorticoid excess states including chronic steroid therapy, pheochromocytoma, reninoma, secondary aldosteronism and other mineralocorticoid excess states, sleep apnea, thyroid/parathyroid disease, heart failure (e.g., left ventricular systolic dysfunction), myocardial infarction, angina, stroke, diabetes mellitus (e.g., diabetic nephropathy), renal disease e.g., chronic kidney disease or diabetic nephropathy optionally in the context of pregnancy, renal failure, e.g., chronic renal failure, cognitive dysfunction (such as Alzheimer's), and systemic sclerosis (e.g., scleroderma renal crisis). In certain embodiments, AGT-associated disease includes intrauterine growth restriction (IUGR) or fetal growth restriction.

In a further aspect, the present invention provides uses of an iRNA agent of the invention in the manufacture of a medicament for preventing at least one symptom in a subject suffering from a disorder that would benefit from a reduction and/or inhibition of AGT expression, such as a AGT-associated disease, e.g., hypertension, e.g., borderline hypertension (also known as prehypertension), primary hypertension (also known as essential hypertension or idiopathic hypertension), secondary hypertension (also known as inessential hypertension), hypertensive emergency (also known as malignant hypertension), hypertensive urgency, isolated systolic or diastolic hypertension, pregnancy-associated hypertension (e.g., preeclampsia, eclampsia, and post-partum preelampsia), diabetic hypertension, resistant hypertension, refractory hypertension, paroxysmal hypertension, renovascular hypertension (also known as renal hypertension), Goldblatt hypertension, ocular hypertension, glaucoma, pulmonary hypertension, portal hypertension, systemic venous hypertension, systolic hypertension, labile hypertension; hypertensive heart disease, hypertensive nephropathy, atherosclerosis, arteriosclerosis, vasculopathy (including peripheral vascular disease), diabetic nephropathy, diabetic retinopathy, chronic heart failure, cardiomyopathy, diabetic cardiac myopathy, glomerulosclerosis, coarctation of the aorta, aortic aneurism, ventricular fibrosis, Cushing's syndrome, and other glucocorticoid excess states including chronic steroid therapy, pheochromocytoma, reninoma, secondary aldosteronism and other mineralocorticoid excess states, sleep apnea, thyroid/parathyroid disease, heart failure (e.g., left ventricular systolic dysfunction), myocardial infarction, angina, stroke, diabetes mellitus (e.g., diabetic nephropathy), renal disease e.g., chronic kidney disease or diabetic nephropathy optionally in the context of pregnancy, renal failure, e.g., chronic renal failure, cognitive dysfunction (such as Alzheimer's), and systemic sclerosis (e.g., scleroderma renal crisis). In certain embodiments, AGT-associated disease includes intrauterine growth restriction (IUGR) or fetal growth restriction.

In one embodiment, an iRNA agent targeting AGT is administered to a subject having a AGT-associated disease such that AGT levels, e.g., in a cell, tissue, blood or other tissue or fluid of the subject are reduced by at least about 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 62%, 64%, 65%, 66%, 67%, 68%, 69%, 70%, 71%, 72%, 72%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more when the dsRNA agent is administered to the subject. In preferred embodiments, the AGT level is reduced by at least 20%.

The methods and uses of the invention include administering a composition described herein such that expression of the target AGT gene is decreased, such as for about 1, 2, 3, 4 5, 6, 7, 8, 12, 16, 18, 24, 28, 32, 36, 40, 44, 48, 52, 56, 60, 64, 68, 72, 76, or about 80 hours. In one embodiment, expression of the target AGT gene is decreased for an extended duration, e.g., at least about two, three, four, five, six, seven days or more, e.g., about one week, two weeks, three weeks, or about four weeks or longer.

Administration of the dsRNA according to the methods and uses of the invention may result in a reduction of the severity, signs, symptoms, and/or markers of such diseases or disorders in a patient with an AGT-associated disease. By "reduction" in this context is meant a statistically significant decrease in such level. The reduction can be, for example, at least about 5%, 10%, 15%, 20%, 25%, 30%, 35%, 40%, 45%, 50%, 55%, 60%, 65%, 70%, 75%, 80%, 85%, 90%, 95%, or about 100%. In preferred embodiments, the AGT level is reduced by at least 20%.

Efficacy of treatment or prevention of disease can be assessed, for example by measuring disease progression, disease remission, symptom severity, reduction in pain, quality of life, dose of a medication required to sustain a treatment effect, level of a disease marker or any other measurable parameter appropriate for a given disease being treated or targeted for prevention. It is well within the ability of one skilled in the art to monitor efficacy of treatment or prevention by measuring any one of such parameters, or any combination of parameters. For example, efficacy of treatment of dyslipidemiahypertension may be assessed, for example, by periodic monitoring of blood pressure. Comparison of the later readings with the initial readings provide a physician an indication of whether the treatment is effective. It is well within the ability of one skilled in the art to monitor efficacy of treatment or prevention by measuring any one of such parameters, or any combination of parameters. In connection with the administration of an iRNA targeting AGT or pharmaceutical composition thereof, "effective against" an AGT-associated disease indicates that administration in a clinically appropriate manner results in a beneficial effect for at least a statistically significant fraction of patients, such as improvement of symptoms, a cure, a reduction in disease, extension of life, improvement in quality of life, or other effect generally recognized as positive by medical doctors familiar with treating a AGT-associated disease and the related causes.

A treatment or preventive effect is evident when there is a statistically significant improvement in one or more parameters of disease status, or by a failure to worsen or to develop symptoms where they would otherwise be anticipated. As an example, a favorable change of at least 10% in a measurable parameter of disease, and preferably at least 20%, 30%, 40%, 50% or more can be indicative of effective treatment. Efficacy for a given iRNA drug or formulation of that drug can also be judged using an experimental animal model for the given disease as known in the art. When using an experimental animal model, efficacy of treatment is evidenced when a statistically significant reduction in a marker or symptom is observed. Suitable animal models of an angiotensinogen-associated disease, e.g., hypertension, include, for example, genetic models of hypertension, e.g., BPH/2 mice, sponateously hypertensive rats (SHRs), Dahl salt-sensitive rates (DS), TGR(mREN2)27 transgenic rats in which endogenous renal renin has been suppressed, and borderline hypertensive rats (BHR), experimentally induced models of hypertension, e.g., experimentally induced models of renal hypertension the Goldblatt model of renal-induced experimental hypertension, subtotal nephrectomy models, and angiotensin II induced hypertension (see, e.g., Dornal and Silva (2011) *J Biosci* 36:731). Suitable animal models of pregnancy-associated hypertension include, for example, genetic models, e.g., borderline hypertensive mice (e.g., BPH/5 mice), rats and/or mice carrying a transgene encoding human renin and a transgene encoding human angiotensinogen, and experimentally induced models, e.g., sFlt-1 infusion models, $AT_1$-AA-induced models, reduced uteroplacental perfusion pressure (RUPP) models (see, e.g., McCarthy, et al. (2011) *Placenta* 32:413-419).

Subjects can be administered a therapeutic amount of iRNA, such as about 0.01 mg/kg, 0.02 mg/kg, 0.03 mg/kg, 0.04 mg/kg, 0.05 mg/kg, 0.1 mg/kg, 0.15 mg/kg, 0.2 mg/kg, 0.25 mg/kg, 0.3 mg/kg, 0.35 mg/kg, 0.4 mg/kg, 0.45 mg/kg, 0.5 mg/kg, 0.55 mg/kg, 0.6 mg/kg, 0.65 mg/kg, 0.7 mg/kg, 0.75 mg/kg, 0.8 mg/kg, 0.85 mg/kg, 0.9 mg/kg, 0.95 mg/kg, 1.0 mg/kg, 1.1 mg/kg, 1.2 mg/kg, 1.3 mg/kg, 1.4 mg/kg, 1.5 mg/kg, 1.6 mg/kg, 1.7 mg/kg, 1.8 mg/kg, 1.9 mg/kg, 2.0 mg/kg, 2.1 mg/kg, 2.2 mg/kg, 2.3 mg/kg, 2.4 mg/kg, 2.5 mg/kg dsRNA, 2.6 mg/kg dsRNA, 2.7 mg/kg dsRNA, 2.8 mg/kg dsRNA, 2.9 mg/kg dsRNA, 3.0 mg/kg dsRNA, 3.1 mg/kg dsRNA, 3.2 mg/kg dsRNA, 3.3 mg/kg dsRNA, 3.4 mg/kg dsRNA, 3.5 mg/kg dsRNA, 3.6 mg/kg dsRNA, 3.7 mg/kg dsRNA, 3.8 mg/kg dsRNA, 3.9 mg/kg dsRNA, 4.0 mg/kg dsRNA, 4.1 mg/kg dsRNA, 4.2 mg/kg dsRNA, 4.3 mg/kg dsRNA, 4.4 mg/kg dsRNA, 4.5 mg/kg dsRNA, 4.6 mg/kg dsRNA, 4.7 mg/kg dsRNA, 4.8 mg/kg dsRNA, 4.9 mg/kg dsRNA, 5.0 mg/kg dsRNA, 5.1 mg/kg dsRNA, 5.2 mg/kg dsRNA, 5.3 mg/kg dsRNA, 5.4 mg/kg dsRNA, 5.5 mg/kg dsRNA, 5.6 mg/kg dsRNA, 5.7 mg/kg dsRNA, 5.8 mg/kg dsRNA, 5.9 mg/kg dsRNA, 6.0 mg/kg dsRNA, 6.1 mg/kg dsRNA, 6.2 mg/kg dsRNA, 6.3 mg/kg dsRNA, 6.4 mg/kg dsRNA, 6.5 mg/kg dsRNA, 6.6 mg/kg dsRNA, 6.7 mg/kg dsRNA, 6.8 mg/kg dsRNA, 6.9 mg/kg dsRNA, 7.0 mg/kg dsRNA, 7.1 mg/kg dsRNA, 7.2 mg/kg dsRNA, 7.3 mg/kg dsRNA, 7.4 mg/kg dsRNA, 7.5 mg/kg dsRNA, 7.6 mg/kg dsRNA, 7.7 mg/kg dsRNA, 7.8 mg/kg dsRNA, 7.9 mg/kg dsRNA, 8.0 mg/kg dsRNA, 8.1 mg/kg dsRNA, 8.2 mg/kg dsRNA, 8.3 mg/kg dsRNA, 8.4 mg/kg dsRNA, 8.5 mg/kg dsRNA, 8.6 mg/kg dsRNA, 8.7 mg/kg dsRNA, 8.8 mg/kg dsRNA, 8.9 mg/kg dsRNA, 9.0 mg/kg dsRNA, 9.1 mg/kg dsRNA, 9.2 mg/kg dsRNA, 9.3 mg/kg dsRNA, 9.4 mg/kg dsRNA, 9.5 mg/kg dsRNA, 9.6 mg/kg dsRNA, 9.7 mg/kg dsRNA, 9.8 mg/kg dsRNA, 9.9 mg/kg dsRNA, 9.0 mg/kg dsRNA, 10 mg/kg dsRNA, 15 mg/kg dsRNA, 20 mg/kg dsRNA, 25 mg/kg dsRNA, 30 mg/kg dsRNA, 35 mg/kg dsRNA, 40 mg/kg dsRNA, 45 mg/kg dsRNA, or about 50 mg/kg dsRNA. Values and ranges intermediate to the recited values are also intended to be part of this invention.

In certain embodiments, for example, when a composition of the invention comprises a dsRNA as described herein and a lipid, subjects can be administered a therapeutic amount of iRNA, such as about 0.01 mg/kg to about 5 mg/kg, about 0.01 mg/kg to about 10 mg/kg, about 0.05 mg/kg to about 5 mg/kg, about 0.05 mg/kg to about 10 mg/kg, about 0.1 mg/kg to about 5 mg/kg, about 0.1 mg/kg to about 10 mg/kg, about 0.2 mg/kg to about 5 mg/kg, about 0.2 mg/kg to about 10 mg/kg, about 0.3 mg/kg to about 5 mg/kg, about 0.3 mg/kg to about 10 mg/kg, about 0.4 mg/kg to about 5 mg/kg, about 0.4 mg/kg to about 10 mg/kg, about 0.5 mg/kg to about 5 mg/kg, about 0.5 mg/kg to about 10 mg/kg, about 1 mg/kg to about 5 mg/kg, about 1 mg/kg to about 10 mg/kg, about 1.5 mg/kg to about 5 mg/kg, about 1.5 mg/kg to about 10 mg/kg, about 2 mg/kg to about 2.5 mg/kg, about 2 mg/kg to about 10 mg/kg, about 3 mg/kg to about 5 mg/kg, about 3 mg/kg to about 10 mg/kg, about 3.5 mg/kg to about 5 mg/kg, about 4 mg/kg to about 5 mg/kg, about 4.5 mg/kg to about 5 mg/kg, about 4 mg/kg to about 10 mg/kg, about 4.5 mg/kg to about 10 mg/kg, about 5 mg/kg to about 10 mg/kg, about 5.5 mg/kg to about 10 mg/kg, about 6 mg/kg to about 10 mg/kg, about 6.5 mg/kg to about 10 mg/kg, about 7 mg/kg to about 10 mg/kg, about 7.5 mg/kg to about 10 mg/kg, about 8 mg/kg to about 10 mg/kg, about 8.5 mg/kg to about 10 mg/kg, about 9 mg/kg to about 10 mg/kg, or about 9.5 mg/kg to about 10 mg/kg. Values and ranges intermediate to the recited values are also intended to be part of this invention.

For example, the dsRNA may be administered at a dose of about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, or about 10 mg/kg. Values and ranges intermediate to the recited values are also intended to be part of this invention.

In other embodiments, for example, when a composition of the invention comprises a dsRNA as described herein and an N-acetylgalactosamine, subjects can be administered a therapeutic amount of iRNA, such as a dose of about 0.1 to about 50 mg/kg, about 0.25 to about 50 mg/kg, about 0.5 to about 50 mg/kg, about 0.75 to about 50 mg/kg, about 1 to about 50 mg/kg, about 1.5 to about 50 mg/kg, about 2 to about 50 mg/kg, about 2.5 to about 50 mg/kg, about 3 to about 50 mg/kg, about 3.5 to about 50 mg/kg, about 4 to about 50 mg/kg, about 4.5 to about 50 mg/kg, about 5 to about 50 mg/kg, about 7.5 to about 50 mg/kg, about 10 to about 50 mg/kg, about 15 to about 50 mg/kg, about 20 to about 50 mg/kg, about 20 to about 50 mg/kg, about 25 to about 50 mg/kg, about 25 to about 50 mg/kg, about 30 to about 50 mg/kg, about 35 to about 50 mg/kg, about 40 to about 50 mg/kg, about 45 to about 50 mg/kg, about 0.1 to about 45 mg/kg, about 0.25 to about 45 mg/kg, about 0.5 to about 45 mg/kg, about 0.75 to about 45 mg/kg, about 1 to about 45 mg/kg, about 1.5 to about 45 mg/kg, about 2 to about 45 mg/kg, about 2.5 to about 45 mg/kg, about 3 to about 45 mg/kg, about 3.5 to about 45 mg/kg, about 4 to about 45 mg/kg, about 4.5 to about 45 mg/kg, about 5 to about 45 mg/kg, about 7.5 to about 45 mg/kg, about 10 to about 45 mg/kg, about 15 to about 45 mg/kg, about 20 to about 45 mg/kg, about 20 to about 45 mg/kg, about 25 to about 45 mg/kg, about 25 to about 45 mg/kg, about 30 to about 45 mg/kg, about 35 to about 45 mg/kg, about 40 to about 45 mg/kg, about 0.1 to about 40 mg/kg, about 0.25 to about 40 mg/kg, about 0.5 to about 40 mg/kg, about 0.75 to about 40 mg/kg, about 1 to about 40 mg/kg, about 1.5 to about 40 mg/kg, about 2 to about 40 mg/kg, about 2.5 to about 40 mg/kg, about 3 to about 40 mg/kg, about 3.5 to about 40 mg/kg, about 4 to about 40 mg/kg, about 4.5 to about 40 mg/kg, about 5 to about 40 mg/kg, about 7.5 to about 40 mg/kg, about 10 to about 40 mg/kg, about 15 to about 40 mg/kg, about 20 to about 40 mg/kg, about 20 to about 40 mg/kg, about 25 to about 40 mg/kg, about 25 to about 40 mg/kg, about 30 to about 40 mg/kg, about 35 to about 40 mg/kg, about 0.1 to about 30 mg/kg, about 0.25 to about 30 mg/kg, about 0.5 to about 30 mg/kg, about 0.75 to about 30 mg/kg, about 1 to about 30 mg/kg, about 1.5 to about 30 mg/kg, about 2 to about 30 mg/kg, about 2.5 to about 30 mg/kg, about 3 to about 30 mg/kg, about 3.5 to about 30 mg/kg, about 4 to about 30 mg/kg, about 4.5 to about 30 mg/kg, about 5 to about 30 mg/kg, about 7.5 to about 30 mg/kg, about 10 to about 30 mg/kg, about 15 to about 30 mg/kg, about 20 to about 30 mg/kg, about 20 to about 30 mg/kg, about 25 to about 30 mg/kg, about 0.1 to about 20 mg/kg, about 0.25 to about 20 mg/kg, about 0.5 to about 20 mg/kg, about 0.75 to about 20 mg/kg, about 1 to about 20 mg/kg, about 1.5 to about 20 mg/kg, about 2 to about 20 mg/kg, about 2.5 to about 20 mg/kg, about 3 to about 20 mg/kg, about 3.5 to about 20 mg/kg, about 4 to about 20 mg/kg, about 4.5 to about 20 mg/kg, about 5 to about 20 mg/kg, about 7.5 to about 20 mg/kg, about 10 to about 20 mg/kg, or about 15 to about 20 mg/kg. In one embodiment, when a composition of the invention comprises a dsRNA as described herein and an N-acetylgalactosamine, subjects can be administered a therapeutic amount of about 10 to about 30 mg/kg of dsRNA. Values and ranges intermediate to the recited values are also intended to be part of this invention.

For example, subjects can be administered a therapeutic amount of iRNA, such as about 0.1, 0.2, 0.3, 0.4, 0.5, 0.6, 0.7, 0.8, 0.9, 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, 6, 6.1, 6.2, 6.3, 6.4, 6.5, 6.6, 6.7, 6.8, 6.9, 7, 7.1, 7.2, 7.3, 7.4, 7.5, 7.6, 7.7, 7.8, 7.9, 8, 8.1, 8.2, 8.3, 8.4, 8.5, 8.6, 8.7, 8.8, 8.9, 9, 9.1, 9.2, 9.3, 9.4, 9.5, 9.6, 9.7, 9.8, 9.9, 10, 10.5, 11, 11.5, 12, 12.5, 13, 13.5, 14, 14.5, 15, 15.5, 16, 16.5, 17, 17.5, 18, 18.5, 19, 19.5, 20, 20.5, 21, 21.5, 22, 22.5, 23, 23.5, 24, 24.5, 25, 25.5, 26, 26.5, 27, 27.5, 28, 28.5, 29, 29.5, 30, 31, 32, 33, 34, 34, 35, 36, 37, 38, 39, 40, 41, 42, 43, 44, 45, 46, 47, 48, 49, or about 50 mg/kg. Values and ranges intermediate to the recited values are also intended to be part of this invention.

In certain embodiments of the invention, for example, when a double-stranded RNAi agent includes a modification (e.g., one or more motifs of three identical modifications on three consecutive nucleotides), including one such motif at or near the cleavage site of the agent, six phosphorothioate linkages, and a ligand, such an agent is administered at a dose of about 0.01 to about 0.5 mg/kg, about 0.01 to about 0.4 mg/kg, about 0.01 to about 0.3 mg/kg, about 0.01 to about 0.2 mg/kg, about 0.01 to about 0.1 mg/kg, about 0.01 mg/kg to about 0.09 mg/kg, about 0.01 mg/kg to about 0.08 mg/kg, about 0.01 mg/kg to about 0.07 mg/kg, about 0.01 mg/kg to about 0.06 mg/kg, about 0.01 mg/kg to about 0.05 mg/kg, about 0.02 to about 0.5 mg/kg, about 0.02 to about 0.4 mg/kg, about 0.02 to about 0.3 mg/kg, about 0.02 to about 0.2 mg/kg, about 0.02 to about 0.1 mg/kg, about 0.02 mg/kg to about 0.09 mg/kg, about 0.02 mg/kg to about 0.08 mg/kg, about 0.02 mg/kg to about 0.07 mg/kg, about 0.02 mg/kg to about 0.06 mg/kg, about 0.02 mg/kg to about 0.05 mg/kg, about 0.03 to about 0.5 mg/kg, about 0.03 to about 0.4 mg/kg, about 0.03 to about 0.3 mg/kg, about 0.03 to about 0.2 mg/kg, about 0.03 to about 0.1 mg/kg, about 0.03 mg/kg to about 0.09 mg/kg, about 0.03 mg/kg to about 0.08 mg/kg, about 0.03 mg/kg to about 0.07 mg/kg, about 0.03 mg/kg to about 0.06 mg/kg, about 0.03 mg/kg to about 0.05 mg/kg, about 0.04 to about 0.5 mg/kg, about 0.04 to about 0.4 mg/kg, about 0.04 to about 0.3 mg/kg, about 0.04 to about 0.2 mg/kg, about 0.04 to about 0.1 mg/kg, about 0.04 mg/kg to about 0.09 mg/kg, about 0.04 mg/kg to about 0.08 mg/kg, about 0.04 mg/kg to about 0.07 mg/kg, about 0.04 mg/kg to about 0.06 mg/kg, about 0.05 to about 0.5 mg/kg, about 0.05 to about 0.4 mg/kg, about 0.05 to about 0.3 mg/kg, about 0.05 to about 0.2 mg/kg, about 0.05 to about 0.1 mg/kg, about 0.05 mg/kg to about 0.09 mg/kg, about 0.05 mg/kg to about 0.08 mg/kg, or about 0.05 mg/kg to about 0.07 mg/kg. Values and ranges intermediate to the foregoing recited values are also intended to be part of this invention, e.g., the RNAi agent may be administered to the subject at a dose of about 0.015 mg/kg to about 0.45 mg/kg.

For example, the RNAi agent, e.g., RNAi agent in a pharmaceutical composition, may be administered at a dose of about 0.01 mg/kg, 0.0125 mg/kg, 0.015 mg/kg, 0.0175 mg/kg, 0.02 mg/kg, 0.0225 mg/kg, 0.025 mg/kg, 0.0275 mg/kg, 0.03 mg/kg, 0.0325 mg/kg, 0.035 mg/kg, 0.0375 mg/kg, 0.04 mg/kg, 0.0425 mg/kg, 0.045 mg/kg, 0.0475 mg/kg, 0.05 mg/kg, 0.0525 mg/kg, 0.055 mg/kg, 0.0575 mg/kg, 0.06 mg/kg, 0.0625 mg/kg, 0.065 mg/kg, 0.0675 mg/kg, 0.07 mg/kg, 0.0725 mg/kg, 0.075 mg/kg, 0.0775 mg/kg, 0.08 mg/kg, 0.0825 mg/kg, 0.085 mg/kg, 0.0875 mg/kg, 0.09 mg/kg, 0.0925 mg/kg, 0.095 mg/kg, 0.0975 mg/kg, 0.1 mg/kg, 0.125 mg/kg, 0.15 mg/kg, 0.175 mg/kg, 0.2 mg/kg, 0.225 mg/kg, 0.25 mg/kg, 0.275 mg/kg, 0.3 mg/kg, 0.325 mg/kg, 0.35 mg/kg, 0.375 mg/kg, 0.4 mg/kg, 0.425 mg/kg, 0.45 mg/kg, 0.475 mg/kg, or about 0.5 mg/kg. Values intermediate to the foregoing recited values are also intended to be part of this invention.

The iRNA can be administered by intravenous infusion over a period of time, such as over a 5, 6, 7, 8, 9, 10, 11, 12, 13, 14, 15, 16, 17, 18, 19, 20, 21, 22, 23, 24, or about a 25 minute period. The administration may be repeated, for example, on a regular basis, such as weekly, biweekly (i.e., every two weeks) for one month, two months, three months, four months or longer. After an initial treatment regimen, the treatments can be administered on a less frequent basis. For example, after administration weekly or biweekly for three months, administration can be repeated once per month, for six months or a year or longer.

Administration of the iRNA can reduce AGT levels, e.g., in a cell, tissue, blood, urine or other compartment of the patient by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or at least about 99% or more.

Before administration of a full dose of the iRNA, patients can be administered a smaller dose, such as a 5% infusion, and monitored for adverse effects, such as an allergic reaction. In another example, the patient can be monitored for unwanted immunostimulatory effects, such as increased cytokine (e.g., TNF-alpha or INF-alpha) levels.

Owing to the inhibitory effects on AGT expression, a composition according to the invention or a pharmaceutical composition prepared therefrom can enhance the quality of life.

An iRNA of the invention may be administered in "naked" form, where the modified or unmodified iRNA agent is directly suspended in aqueous or suitable buffer solvent, as a "free iRNA." A free iRNA is administered in the absence of a pharmaceutical composition. The free iRNA may be in a suitable buffer solution. The buffer solution may comprise acetate, citrate, prolamine, carbonate, or phosphate, or any combination thereof. In one embodiment, the buffer solution is phosphate buffered saline (PBS). The pH and osmolarity of the buffer solution containing the iRNA can be adjusted such that it is suitable for administering to a subject.

Alternatively, an iRNA of the invention may be administered as a pharmaceutical composition, such as a dsRNA liposomal formulation.

Subjects that would benefit from a reduction and/or inhibition of AGT gene expression are those having a AGT-associated disease or disorder as described herein.

Treatment of a subject that would benefit from a reduction and/or inhibition of AGT gene expression includes therapeutic and prophylactic treatment.

The invention further provides methods and uses of an iRNA agent or a pharmaceutical composition thereof for treating a subject that would benefit from reduction and/or inhibition of AGT expression, e.g., a subject having a AGT-associated disease, in combination with other pharmaceuticals and/or other therapeutic methods, e.g., with known pharmaceuticals and/or known therapeutic methods, such as, for example, those which are currently employed for treating these disorders. For example, in certain embodiments, an iRNA targeting AGT is administered in combination with, e.g., an agent useful in treating an AGT-associated disease as described elsewhere herein. For example, additional therapeutics and therapeutic methods suitable for treating a subject that would benefit from reduction in AGT expression, e.g., a subject having a AGT-associated disease, include angioplasty, aortorenal bypass, renal denervation, percutaneous transluminal renal angioplasty (PTRA) and stenting, surgical revascularization, catheter-based renal sympathetic denervation, and surgical removal of pheochromocytoma or reninoma, adrenalectomy, treatment with a diuretic, e.g., a thiazide-type diuretic, e.g., chlorothiazide, hydrochlorothiazide, chlorthalidone, metolazone, and indapamide, a potassium-sparring diuretic, such as triamterene and amiloride, a loop diuretic, e.g., furosemide, torsemide, ethacrynic acid, and bumetanide; an angiotensin converting enzyme (ACE) inhibitor, e.g., fosinopril, captopril, ramipril, enalapril, lisinopril, and quinapril; an angiotensin II receptor antagonist (also known as an angiotensin receptor blocker), e.g., losartan, valsartan, olmesartan, eprosartan, and azilsartan; a beta-blocker, such as a beta-1 selective beta-blocker, e.g., atenolol, metoprolol, propranolol, bisoprolol, and timolol, an alpha-1 receptor beta-blocker, e.g., labetalol, esmolol, and carvedilol, an intrinsic sympathomimetic beta-blocker, e.g., acebutolol and pindolol; a vasodialator, e.g., hydralazine, minoxidil, sodium nitroprusside, and nitroglycerin; a calcium channel blocker, e.g., nifedipine, clevidipine, amlodipine, felodipine, diltiazem, nicardipine, and verapamil; an aldosterone antagonist, such as a selective aldosterone antagonist, e.g., eplerenone and spironolactone; an $alpha_2$-agonist, such as a central-acting $alpha_2$-agonist, e.g., methyldopa, clonidine, and guanfacine, a renin inhibitor, e.g., aliskiren; an alpha-blocker, e.g., prazosin, terazosin, and doxazosin; a peripheral acting adrenergic agent, e.g., reserpine; a selective D1 receptor partial agonist, e.g., fenoldopam mesylate; a nonselective alpha-adrenergic antagonist, e.g., phentolamine; a synthetic, steroidal anti-mineralocorticoid agent, e.g., spironolactone, or a combination of any of the foregoing; and a therapeutic agent formulated as a combination of agents, e.g., a combination of amlodipine/benazepril (Lotrel), amlodipine/olmesartan (Azor), amlodipine/telmisartan (Twynsta), amlodipine/valsartan (Exforge), amlodipine/valsartan/hydrochlorothiazide (Exforge HCT), amlodipine/aliskiren (Tekamlo), amlodipine/aliskiren/hydrochlorothiazide (Amturnide), olmesartan/amlodipine/hydrochlorothiazide (Tribenzor), trandolapril/verapamil (Tarka), benazepril/hydrochlorothiazide (Lotensin HCT), captopril/hydrochlorothiazide (Capozide), enalapril/hydrochlorothiazide (Vaseretic), fosinopril/hydrochlorothiazide, lisinopril/hydrochlorothiazide (Prinzide, Zestoretic), moexipril/hydrochlorothiazide (Uniretic), quinapril/hydrochlorothiazide (Accuretic), candesartan/hydrochlorothiazide (Atacand HCT), eprosartan/hydrochlorothiazide (Teveten HCT), irbesartan/hydrochlorothiazide (Avalide), losartan/hydrochlorothiazide (Hyzaar), olmesartan/hydrochlorothiazide (Benicar HCT), telmisartan/hydrochlorothiazide (Micardis HCT), valsartan/hydrochlorothiazide (Diovan HCT), atenolol/chlorthalidone (Tenoretic), bisoprolol/hydrochlorothiazide (Ziac), metoprolol/hydrochlorothiazide (Lopressor HCT), nadolol/bendroflumethiazide (Corzide), propranolol/hydrochlorothiazide, aliskiren/hydrochlorothiazide (Tekturna HCT), clonidine/chlorthalidone (Clorpres), spironolactone/hydrochlorothiazide (Aldactazide), triamterene/hydrochlorothiazide (Dyazide, Maxzide), methyldopa/hydrochlorothiazide, and amiloride/hydrochlorothiazide, or other therapeutic agents for treating a AGT-associated disease.

The iRNA agent and an additional therapeutic agent and/or treatment may be administered at the same time and/or in the same combination, e.g., parenterally, or the additional therapeutic agent can be administered as part of a separate composition or at separate times and/or by another method known in the art or described herein.

The present invention also provides methods of using an iRNA agent of the invention and/or a composition containing an iRNA agent of the invention to reduce and/or inhibit AGT expression in a cell. In other aspects, the present invention provides an iRNA of the invention and/or a composition comprising an iRNA of the invention for use in reducing and/or inhibiting AGT expression in a cell. In yet other aspects, use of an iRNA of the invention and/or a composition comprising an iRNA of the invention for the manufacture of a medicament for reducing and/or inhibiting AGT expression in a cell are provided.

The methods and uses include contacting the cell with an iRNA, e.g., a dsRNA, of the invention and maintaining the cell for a time sufficient to obtain degradation of the mRNA transcript of an AGT gene, thereby inhibiting expression of the AGT gene in the cell.

Reduction in gene expression can be assessed by any methods known in the art. For example, a reduction in the expression of AGT may be determined by determining the mRNA expression level of AGT using methods routine to one of ordinary skill in the art, e.g., northern blotting, qRT-PCR, by determining the protein level of AGT using methods routine to one of ordinary skill in the art, such as western blotting, immunological techniques, flow cytometry methods, ELISA, and/or by determining a biological activity of AGT.

In the methods and uses of the invention the cell may be contacted in vitro or in vivo, i.e., the cell may be within a subject.

A cell suitable for treatment using the methods of the invention may be any cell that expresses an AGT gene. A cell suitable for use in the methods and uses of the invention may be a mammalian cell, e.g., a primate cell (such as a human cell or a non-human primate cell, e.g., a monkey cell or a chimpanzee cell), a non-primate cell (such as a cow cell, a pig cell, a camel cell, a llama cell, a horse cell, a goat cell, a rabbit cell, a sheep cell, a hamster, a guinea pig cell, a cat cell, a dog cell, a rat cell, a mouse cell, a lion cell, a tiger cell, a bear cell, or a buffalo cell), a bird cell (e.g., a duck cell or a goose cell), or a whale cell. In one embodiment, the cell is a human cell, e.g., a human liver cell.

AGT expression may be inhibited in the cell by at least about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or about 100%. In preferred embodiments, the AGT level is reduced by at least 20%.

The in vivo methods and uses of the invention may include administering to a subject a composition containing an iRNA, where the iRNA includes a nucleotide sequence that is complementary to at least a part of an RNA transcript of the AGT gene of the mammal to be treated. When the organism to be treated is a human, the composition can be administered by any means known in the art including, but not limited to subcutaneous, intravenous, oral, intraperitoneal, or parenteral routes, including intracranial (e.g., intraventricular, intraparenchymal and intrathecal), intramuscular, transdermal, airway (aerosol), nasal, rectal, and topical (including buccal and sublingual) administration. In certain embodiments, the compositions are administered by subcutaneous or intravenous infusion or injection.

In some embodiments, the administration is via a depot injection. A depot injection may release the iRNA in a consistent way over a prolonged time period. Thus, a depot injection may reduce the frequency of dosing needed to obtain a desired effect, e.g., a desired inhibition of AGT, or a therapeutic or prophylactic effect. A depot injection may also provide more consistent serum concentrations. Depot injections may include subcutaneous injections or intramuscular injections. In preferred embodiments, the depot injection is a subcutaneous injection.

In some embodiments, the administration is via a pump. The pump may be an external pump or a surgically implanted pump. In certain embodiments, the pump is a subcutaneously implanted osmotic pump. In other embodiments, the pump is an infusion pump. An infusion pump may be used for intravenous, subcutaneous, arterial, or epidural infusions. In preferred embodiments, the infusion pump is a subcutaneous infusion pump. In other embodiments, the pump is a surgically implanted pump that delivers the iRNA to the liver.

A higher dose may be administered initially (i.e., a loading dose), followed by a lower dosage for a sustained period of time.

The mode of administration may be chosen based upon whether local or systemic treatment is desired and based upon the area to be treated. The route and site of administration may be chosen to enhance targeting.

In one aspect, the present invention also provides methods for inhibiting the expression of an AGT gene in a mammal, e.g., a human. The present invention also provides a composition comprising an iRNA, e.g., a dsRNA, that targets an AGT gene in a cell of a mammal for use in inhibiting expression of the AGT gene in the mammal. In another aspect, the present invention provides use of an iRNA, e.g., a dsRNA, that targets an AGT gene in a cell of a mammal in the manufacture of a medicament for inhibiting expression of the AGT gene in the mammal.

The methods and uses include administering to the mammal, e.g., a human, a composition comprising an iRNA, e.g., a dsRNA, that targets an AGT gene in a cell of the mammal and maintaining the mammal for a time sufficient to obtain degradation of the mRNA transcript of the AGT gene, thereby inhibiting expression of the AGT gene in the mammal.

Reduction in gene expression can be assessed in peripheral blood sample of the iRNA-administered subject by any methods known it the art, e.g. qRT-PCR, described herein. Reduction in protein production can be assessed by any methods known it the art and by methods, e.g., ELISA or western blotting, described herein. In one embodiment, a puncture liver biopsy sample serves as the tissue material for monitoring the reduction in AGT gene and/or protein expression. In another embodiment, a blood sample serves as the tissue material for monitoring the reduction in AGT gene and/or protein expression.

In one embodiment, verification of RISC medicated cleavage of target in vivo following administration of iRNA agent is done by performing 5'-RACE or modifications of the protocol as known in the art (Lasham A et al., (2010) *Nucleic Acid Res.,* 38 (3) p-e19) (Zimmermann et al. (2006) *Nature* 441: 111-4).

This invention is further illustrated by the following examples which should not be construed as limiting. The entire contents of all references, patents and published patent applications cited throughout this application, as well as the Figures and the Sequence Listing, are hereby incorporated herein by reference.

EXAMPLES

Example 1. iRNA Synthesis

Source of Reagents

Where the source of a reagent is not specifically given herein, such reagent can be obtained from any supplier of reagents for molecular biology at a quality/purity standard for application in molecular biology.

Transcripts siRNA design was carried out to identify siRNAs targeting human (*Homo sapiens*), cynomolgus monkey (Macaca-fascicularis; henceforth "cyno"), mouse (*Mus musculus*), and rat (*Rattus norvegicus*) AGT transcripts annotated in the NCBI Gene database (www.ncbi.nlm.nih.gov/gene/). Design used the following transcripts from NCBI: Human—NM_000029.3; Monkey—AB170313.1; Mouse—NM_007428.3. The cynomolgus monkey transcript was extended using sequence obtained from a liver-derived cDNA library. Due to high primate/rodent sequence divergence, siRNA duplexes were designed in separate batches, including but not limited to batches containing duplexes matching human and monkey transcripts only and mouse transcript only. All siRNA duplexes were designed that shared 100% identity to the listed human transcript and other species transcripts considered in each design batch.

siRNA Design, Specificity, and Efficacy Prediction

The predicted specificity of all possible 19mers was predicted from each sequence. Candidate 19mers were then selected that lacked repeats longer than seven nucleotides. These 706 candidate human/monkey and 1815 mouse siRNAs were used in comprehensive searches against the appropriate transcriptomes (defined as the set of NM_and XM_records within the human, monkey, or mouse NCBI Refseq sets) using an exhaustive "brute-force" algorithm implemented in the python script 'BruteForce.py'. The script next parsed the transcript-oligo alignments to generate a score based on the position and number of mismatches between the siRNA and any potential "off-target" transcript. The off-target score was weighted to emphasize differences in the "seed region" of siRNAs, in positions 2-9 from the 5' end of the molecule. Each oligo-transcript pair from the brute-force search was given a mismatch score by summing the individual mismatch scores; mismatches in the position 2-9 were counted as 2.8, mismatches in the cleavage site positions 10-11 were counted as 1.2, and mismatches in region 12-19 counted as 1.0. An additional off-target prediction was carried out by comparing the frequency of heptamers and octamers derived from 3 distinct, seed-derived hexamers of each oligo. The hexamers from positions 2-7 relative to the 5' start is used to create 2 heptamers and one octamer. "Heptamer1" was created by adding a 3' A to the hexamer; "heptamer2" was created by adding a 5' A to the hexamer; the octamer was created by adding an A to both 5' and 3' ends of the hexamer. The frequency of octomers and heptamers in the human, monkey, or mouse 3'UTRome (defined as the subsequence of the transcriptome from NCBI's Refseq database where the end of the coding region, the 'CDS', is clearly defined) was pre-calculated. The octamer frequency was normalized to the heptamer frequency using the median value from the range of octamer frequencies. A "mirSeedScore" was then calculated by calculating the sum of ((3×normalized octomer count)+(2× heptamer2 count)+(1×heptamer1 count)).

Both siRNA strands were assigned to a category of specificity according to the calculated scores: a score above 3 qualifies as highly specific, equal to 3 as specific and between 2.2 and 2.8 as moderately specific. The duplexes were sorted by the specificity of the antisense strand. Duplexes from the human/monkey and mouse sets whose antisense oligos lacked GC at the first position, lacked G at both positions 13 and 14, and had 3 or more Us or As in the seed region (characteristics of duplexes with high predicted efficacy) were selected.

Candidate GalNAc-conjugated duplexes, 21 and 23 nucleotides long on the sense and antisense strands, respectively, were designed by extending antisense 19mers four additional nucleotides in the 3' direction (preserving perfect complementarity with the target transcript). The sense strand was specified as the reverse complement of the first 21 nucleotides of the antisense 23mer. Duplexes were selected that maintained perfect matches to all selected species transcripts across all 23 nucleotides.

siRNA Sequence Selection

A total of 117 sense and 117 antisense derived human/ monkey and 42 sense and 42 antisense derived mouse siRNA 19mer oligos were synthesized and formed into GalNAc-conjugated duplexes. A total of 38 sense and 38 antisense derived human/monkey 21/23mer oligos and a total of 26 mouse 21/23mer oligos were synthesized and formed into GalNAc-conjugated duplexes.

A detailed list of the unmodified 19mer AGT sense and antisense strand sequences is shown in Table 3.

A detailed list of the modified 19mer AGT sense and antisense strand sequences is shown in Table 4.

A detailed list of the unmodified 21/23mer AGT sense and antisense strand sequences is shown in Table 7.

A detailed list of the modified 21/23mer AGT sense and antisense strand sequences is shown in Table 8.

A detailed list of unmodified 19mer AGT sense and antisense strand sequences is shown in Table 11.

A detailed list of the unmodified 21/23mer AGT sense and antisense strand sequences is shown in Table 13.

A detailed list of the modified 21/23mer AGT sense and antisense strand sequences is shown in Table 15.

siRNA Synthesis

General Small and Medium Scale RNA Synthesis Procedure

RNA oligonucleotides are synthesized at scales between 0.2-500 μmol using commercially available 5'-O-(4,4'-dimethoxytrityl)-2'-O-t-butyldimethylsilyl-3'-O-(2-cyanoethyl-N,N-diisopropyl)phosphoramidite monomers of uridine, 4-N-acetylcytidine, 6-N-benzoyladenosine and 2-N-isobutyrylguanosine and the corresponding 2'-O-methyl and 2'-fluoro phosphoramidites according to standard solid phase oligonucleotide synthesis protocols. The amidite solutions are prepared at 0.1-0.15 M concentration and 5-ethyl-thio-1H-tetrazole (0.25-0.6 M in acetonitrile) is used as the activator. Phosphorothioate backbone modifications are introduced during synthesis using 0.2 M phenylacetyl disulfide (PADS) in lutidine:acetonitrile (1:1) (v;v) or 0.1 M 3-(dimethylaminomethylene) amino-3H-1,2,4-dithiazole-5-thione (DDTT) in pyridine for the oxidation step. After completion of synthesis, the sequences are cleaved from the solid support and deprotected using methylamine followed by triethylamine.3HF to remove any 2'-O-t-butyldimethylsilyl protecting groups present.

For synthesis scales between 5-500 μmol and fully 2' modified sequences (2'-fluoro and/or 2'-O-methyl or combinations thereof) the oligonucleotides are deprotected using 3:1 (v/v) ethanol and concentrated (28-32%) aqueous ammonia either at 35° C. 16 h or 55° C. for 5.5 h. Prior to ammonia deprotection the oligonucleotides are treated with 0.5 M piperidine in acetonitrile for 20 min on the solid support. The crude oligonucleotides are analyzed by LC-MS and anion-exchange HPLC (IEX-HPLC). Purification of the oligonucleotides is carried out by IEX HPLC using: 20 mM phosphate, 10%-15% ACN, pH=8.5 (buffer A) and 20 mM phosphate, 10%-15% ACN, 1 M NaBr, pH=8.5 (buffer B). Fractions are analyzed for purity by analytical HPLC. The product-containing fractions with suitable purity are pooled and concentrated on a rotary evaporator prior to desalting. The samples are desalted by size exclusion chromatography and lyophilized to dryness. Equal molar amounts of sense and antisense strands are annealed in 1×PBS buffer to prepare the corresponding siRNA duplexes.

For small scales (0.2-1 μmol), synthesis is performed on a MerMade 192 synthesizer in a 96 well format. In case of fully 2'-modified sequences (2'-fluoro and/or 2'-O-methyl or combinations thereof) the oligonucleotides are deprotected using methylamine at room temperature for 30-60 min followed by incubation at 60° C. for 30 min or using 3:1 (v/v) ethanol and concentrated (28-32%) aqueous ammonia at room temperature for 30-60 min followed by incubation at 40° C. for 1.5 hours. The crude oligonucleotides are then precipitated in a solution of acetonitrile:acetone (9:1) and isolated by centrifugation and decanting the supernatant. The crude oligonucleotide pellet is re-suspended in 20 mM NaOAc buffer and analyzed by LC-MS and anion exchange HPLC. The crude oligonucleotide sequences are desalted in 96 deep well plates on a 5 mL HiTrap Sephadex G25 column (GE Healthcare). In each well about 1.5 mL samples corresponding to an individual sequence is collected. These purified desalted oligonucleotides are analyzed by LC-MS and anion exchange chromatography. Duplexes are prepared by annealing equimolar amounts of sense and antisense sequences on a Tecan robot. Concentration of duplexes is adjusted to 10 M in Ix PBS buffer.

Synthesis of GalNAc-Conjugated Oligonucleotides for In Vivo Analysis

Oligonucleotides conjugated with GalNAc ligand at their 3'-terminus are synthesized at scales between 0.2-500 μmol using a solid support pre-loaded with a Y-shaped linker bearing a 4,4'-dimethoxytrityl (DMT)-protected primary hydroxy group for oligonucleotide synthesis and a GalNAc ligand attached through a tether.

For synthesis of GalNAc conjugates in the scales between 5-500 μmol, the above synthesis protocol for RNA is followed with the following adaptions: For polystyrene-based synthesis supports 5% dichloroacetic acid in toluene is used for DMT-cleavage during synthesis. Cleavage from the support and deprotection is performed as described above. Phosphorothioate-rich sequences (usually >5 phorphorothioates) are synthesized without removing the final 5'-DMT group ("DMT-on") and, after cleavage and deprotection as described above, purified by reverse phase HPLC using 50 mM ammonium acetate in water (buffer A) and 50 mM ammoniumacetate in 80% acetonitirile (buffer B). Fractions are analyzed for purity by analytical HPLC and/or LC-MS. The product-containing fractions with suitable purity are pooled and concentrated on a rotary evaporator. The DMT-group is removed using 20%-25% acetic acid in water until completion. The samples are desalted by size exclusion chromatography and lyophilized to dryness. Equal molar amounts of sense and antisense strands are annealed in 1×PBS buffer to prepare the corresponding siRNA duplexes.

For small scale synthesis of GalNAc conjugates (0.2-1 μmol), including sequences with multiple phosphorothioate linkages, the protocols described above for synthesis of RNA or fully 2'-F/2'-OMe-containing sequences on Mer-Made platform are applied. Synthesis is performed on pre-packed columns containing GalNAc-functionalized controlled pore glass support.

Example 2. In Vitro Screening of siRNA Duplexes

Cell Culture and 96-Well Transfections

Hep3B cells (ATCC, Manassas, Va.) were grown to near confluence at 37° C. in an atmosphere of 5% $CO_2$ in Eagle's Minimum Essential Medium (ATCC) supplemented with 10% FBS, streptomycin, and glutamine (ATCC) before being released from the plate by trypsinization. Cells were washed and re-suspended at 0.125×10⁶ cells/ml. During transfections, cells were plated onto a 96-well plate with about 20,000 cells per well.

Transfection was carried out by adding 14.8 μl of Opti-MEM plus 0.2 μl of Lipofectamine RNAiMax per well (Invitrogen™, Carlsbad Calif. catalog number 13778-150) to 5 μl of each siRNA duplex to an individual well in a 96-well plate. The mixture was then incubated at room temperature for 20 minutes. Eighty μl of complete growth media without antibiotic containing the appropriate cell number was then added to the siRNA mixture. Cells were incubated for 24 hours prior to RNA purification.

Single dose experiments were performed at O1 nM and 0.01 nM final duplex concentration. Dose response experiments were done at 10, 1.67, 0.28, 0.046, 0.0077, 0.0013, 0.00021, 0.000036 nM final duplex concentration.

Cell Culture and 384-Well Transfections

Hep3B cells (ATCC, Manassas, Va.) were grown to near confluence at 37° C. in an atmosphere of 5% $CO_2$ in Eagle's Minimum Essential Medium (ATCC®) supplemented with 10% FBS, streptomycin, and glutamine (ATCC®) before being released from the plate by trypsinization. Cells were washed and re-suspended at 0.125×10⁶ cells/ml. During transfections, cells were plated onto a 384-well plate with about 5,000 cells per well.

Transfection was carried out by adding 4.9 μl of Opti-MEM plus 0.1 μl of Lipofectamine RNAiMax per well (Invitrogen™, Carlsbad Calif. catalog number 13778-150) to 5 μl of each siRNA duplex to an individual well in a 96-well plate. The mixture was then incubated at room temperature for 20 minutes. Forty μl of complete growth media without antibiotic containing the appropriate cell number was then added to the siRNA mixture. Cells were incubated for 24 hours prior to RNA purification.

Single dose experiments were performed at O1 nM and 0.01 nM final duplex concentration. Dose response experiments were done at 10, 1.67, 0.28, 0.046, 0.0077, 0.0013, 0.00021, 0.000036 nM final duplex concentration Total RNA Isolation Using DYNABEADS mRNA Isolation Kit (Invitrogen™, Part #: 610-12)—96-Well Isolation Cells were harvested and lysed in 150 μl of Lysis/Binding Buffer then mixed for five minutes at 850 rpm using an Eppendorf Thermomixer (the mixing speed was the same throughout the process). Ten microliters of magnetic beads and 80 μl Lysis/Binding Buffer mixture were added to a round bottom plate and mixed for 1 minute. Magnetic beads were captured using magnetic stand and the supernatant was removed without disturbing the beads. After removing supernatant, the lysed cells were added to the remaining beads and mixed for 5 minutes. After removing supernatant, magnetic beads were washed 2 times with 150 μl Wash Buffer A and mixed for 1 minute. Beads were captured again and supernatant removed. Beads were then washed with 150 μl Wash Buffer B, captured and supernatant was removed. Beads were next washed with 150 μl Elution Buffer, captured and supernatant removed. Beads were allowed to dry for 2 minutes. After drying, 50 μl of Elution Buffer was added and mixed for 5 minutes at 70° C. Beads were captured on magnet for 5 minutes. Forty μl of supernatant was removed and added to another 96 well plate.

cDNA Synthesis Using ABI High Capacity cDNA Reverse Transcription Kit (Applied Biosystems, Foster City, Calif., Cat #4368813)

A master mix of 2 μl 10× Buffer, 0.8 μl 25×dNTPs, 2 μl Random primers, 1 μl Reverse Transcriptase, 1 μl RNase inhibitor and 3.2 μl of $H_2O$ per reaction were added into 10 μl total RNA. cDNA was generated using a Bio-Rad C-1000 or S-1000 thermal cycler (Hercules, Calif.) through the following steps: 25° C. 10 min, 37° C. 120 min, 85° C. 5 sec, 4° C. hold.

Total RNA Isolation Using DYNABEADS mRNA Isolation Kit (Invitrogen™, Part #: 610-12)-384-Well Extraction Cells were lysed in 50 μl of Lysis/Binding Buffer. Magenetic Dynabeads were washed in Lysis/Binding Buffer and resuspended in the same. 25 μl Lysis/Binding Buffer containing 2 μl of Dynabeads were then added per well. After shaking plates for 10 minutes at "7" on a Vibratranslator (UnionScientific), an automated plate washing system was utilized (Biotek EL406 with Biostacker, and magnetic capture plate). Plates were then washed in a manner similar to that described for the 96-well process: twice with buffer A (90 μl), once with buffer B (90 μl), and twice with buffer C (100 μl). The last wash was removed from the plate, and cDNA synthesis begun immediately.

cDNA Synthesis Using ABI High Capacity cDNA Reverse Transcription Kit (Applied Biosystems, Foster City, Calif., Cat #4368813)—384-Well Synthesis A master mix of 2 μl 10× Buffer, 0.8 μl 25×dNTPs, 2 μl Random primers, 1 μl Reverse Transcriptase, 1 μl RNase inhibitor and 13.2 μl of H$_2$O per reaction were added to the wells of a 384-well plate containing only extracted RNA and magnetic beads (20 μl total volume). cDNA was generated by incubation at 25° C. for 10 min, 37° C. for 120 min, and 85° C. for 8 minutes.

Real Time PCR:

Two μl of cDNA were added to a master mix containing 0.5 μl human GAPDH TaqMan Probe (Applied Biosystems Cat #4326317E) and 0.5 μl human AGT TaqMan probe (Applied Biosystems cat # Hs00174854 ml), 2 μL of nuclease-free water and 5 μl Lightcycler 480 probe master mix (Roche Cat #04887301001) per well in a 384 well plates (Roche cat #04887301001). qPCR was performed in a LightCycler 480 real-time PCR machine (Roche). To calculate relative fold change, data were analyzed using the ΔΔCt method and normalized to assays performed with cells transfected with 10 nM AD-1955, or mock transfected cells. IC$_{50}$s were calculated using a 4 parameter fit model using XLFit and normalized to cells transfected with AD-1955 or mock-transfected.

The sense and antisense sequences of AD-1955 are:

```
SENSE:
                                (SEQ ID NO: 13)
cuuAcGcuGAGuAcuucGAdTsdT ANTISENSE:
                                (SEQ ID NO: 14)
UCGAAGuACUcAGCGuAAGdTsdT.
```

Table 5 shows the results of a single dose screen in Hep3B cells transfected using the 96-well method with the indicated 19mer AGT iRNAs. Data are expressed as percent of mRNA remaining relative to untreated cells.

Table 6 shows the dose response of Hep3B cells transfected using the 96-well method with the indicated 19mer AGT iRNAs. The indicated IC$_{50}$ values represent the IC$_{50}$ values relative to untreated cells.

Table 9 shows the results of a single dose screen in Hep3B cells transfected using the 384-well method with the indicated 21/23mer conjugate AGT iRNAs. Data are expressed as percent of mRNA remaining relative to untreated cells.

Table 10 shows the dose response of Hep3B cells transfected using the 384-well method with the indicated 21/23mer conjugate AGT iRNAs. The indicated IC$_{50}$ values represent the IC$_{50}$ values relative to untreated cells.

Table 12 shows the results of a single dose screen in Hep3B cells transfected using the 96-well method with the indicated 19mer AGT iRNAs. Data are expressed as percent of mRNA remaining relative to untreated cells.

Table 14 shows the results of a single dose, dose-response screen of hAGT knockdown with the indicated 21/23mer conjugate AGT iRNAs in mice infected with an AAV vector expressing hAGT.

Table 16 shows the results of a single dose, dose-response screen of hAGT knockdown with the indicated 21/23mer conjugate AGT iRNAs in mice infected with an AAV vector expressing hAGT.

TABLE 2

Abbreviations of nucleotide monomers used in nucleic acid sequence representation. It will be understood that these monomers, when present in an oligonucleotide, are mutually linked by 5'-3'-phosphodiester bonds.

| Abbreviation | Nucleotide(s) |
|---|---|
| A | Adenosine-3'-phosphate |
| Af | 2'-fluoroadenosine-3'-phosphate |
| Afs | 2'-fluoroadenosine-3'-phosphorothioate |
| As | adenosine-3'-phosphorothioate |
| C | cytidine-3'-phosphate |
| Cf | 2'-fluorocytidine-3'-phosphate |
| Cfs | 2'-fluorocytidine-3'-phosphorothioate |
| Cs | cytidine-3'-phosphorothioate |
| G | guanosine-3'-phosphate |
| Gf | 2'-fluoroguanosine-3'-phosphate |
| Gfs | 2'-fluoroguanosine-3'-phosphorothioate |
| Gs | guanosine-3'-phosphorothioate |
| T | 5'-methyluridine-3'-phosphate |
| Tf | 2'-fluoro-5-methyluridine-3'-phosphate |
| Tfs | 2'-fluoro-5-methyluridine-3'-phosphorothioate |
| Ts | 5-methyluridine-3'-phosphorothioate |
| U | Uridine-3'-phosphate |
| Uf | 2'-fluorouridine-3'-phosphate |
| Ufs | 2'-fluorouridine-3'-phosphorothioate |
| Us | uridine-3'-phosphorothioate |
| N | any nucleotide (G, A, C, T or U) |
| a | 2'-O-methyladenosine-3'-phosphate |
| as | 2'-O-methyladenosine-3'-phosphorothioate |
| c | 2'-O-methylcytidine-3'-phosphate |
| cs | 2'-O-methylcytidine-3'-phosphorothioate |
| g | 2'-O-methylguanosine-3'-phosphate |
| gs | 2'-O-methylguanosine-3'-phosphorothioate |
| t | 2'-O-methyl-5-methyluridine-3'-phosphate |
| ts | 2'-O-methyl-5-methyluridine-3'-phosphorothioate |
| u | 2'-O-methyluridine-3'-phosphate |
| us | 2'-O-methyluridine-3'-phosphorothioate |
| s | phosphorothioate linkage |
| L96 | N-[tris(GalNAc-alkyl)-amidodecanoyl)]-4-hydroxyprolinol Hyp-(GalNAc-alkyl)3 |
| (dt) or dT | deoxy-thymine |
| dC | 2'-deoxycytidine-3'-phosphate |
| Y44 | inverted abasic DNA (2-hydroxymethyl-tetrahydrofurane-5-phosphate) |
| (Tgn) | Thymidine-glycol nucleic acid (GNA) S-Isomer |
| P | Phosphate |
| VP | Vinyl-phosphate |
| (Aam) | 2'-O-(N-methylacetamide)adenosine-3'-phosphate |
| (Aams) | 2'-O-(N-methylacetamide)adenosine-3'-phosphorothioate |
| (Tgn) | Thymidine-glycol nucleic acid (GNA) S-Isomer |
| (Cgn) | Cytidine-glycol nucleic acid (GNA) |

TABLE 3

Unmodified Sense and Antisense Strand Sequences of AGT dsRNAs (19 mers)

| Duplex Name | Position relative to NM_000029.3 | Sense Name | Sense Sequence | SEQ ID NO |
|---|---|---|---|---|
| UM AD-56041.1 | 485-503 | A-115161.1 | UUCUGGGUACUACAGCAGA | 15 |
| UM AD-52431.1 | 491-509 | A-107992.1 | GUACUACAGCAGAAGGGUA | 16 |

TABLE 3-continued

Unmodified Sense and Antisense Strand Sequences of AGT dsRNAs (19 mers)

| | | | | |
|---|---|---|---|---|
| UM AD-56057.1 | 606-624 | A-115229.1 | GUGACCGGGUGUACAUACA | 17 |
| UM AD-56047.1 | 635-653 | A-115163.1 | CUCGUCAUCCACAAUGAGA | 18 |
| UM AD-52437.1 | 643-661 | A-107994.1 | CCACAAUGAGAGUACCUGU | 19 |
| UM AD-56064.1 | 644-662 | A-115247.1 | CACAAUGAGAGUACCUGUG | 20 |
| UM AD-56021.1 | 658-676 | A-115123.1 | CUGUGAGCAGCUGGCAAAG | 21 |
| UM AD-56067.1 | 741-759 | A-115201.1 | CUGUGGAUGAAAAGGCCCU | 22 |
| UM AD-56030.1 | 822-840 | A-115173.1 | UGGUCGGGAUGCUGGCCAA | 23 |
| UM AD-56034.1 | 825-843 | A-115237.1 | UCGGGAUGCUGGCCAACUU | 24 |
| UM AD-52443.1 | 828-846 | A-107996.1 | GGAUGCUGGCCAACUUCUU | 25 |
| UM AD-56017.1 | 834-852 | A-115153.1 | UGGCCAACUUCUUGGGCUU | 26 |
| UM AD-52449.1 | 841-859 | A-107998.1 | CUUCUUGGGCUUCCGUAUA | 27 |
| UM AD-52455.1 | 844-862 | A-108000.1 | CUUGGGCUUCCGUAUAUAU | 28 |
| UM AD-52461.1 | 849-867 | A-108002.1 | GCUUCCGUAUAUAUGGCAU | 29 |
| UM AD-56025.1 | 855-873 | A-115187.1 | GUAUAUAUGGCAUGCACAG | 30 |
| UM AD-52467.1 | 863-881 | A-108004.1 | GGCAUGCACAGUGAGCUAU | 31 |
| UM AD-56061.1 | 878-896 | A-115199.1 | CUAUGGGGCGUGGUCCAUG | 32 |
| UM AD-52473.1 | 910-928 | A-108006.1 | CUCCCCAACGGCUGUCUUU | 33 |
| UM AD-56063.1 | 911-929 | A-115231.1 | UCCCCAACGGCUGUCUUUG | 34 |
| UM AD-56046.1 | 1002-1020 | A-115241.1 | CUUGGAAGGACAAGAACUG | 35 |
| UM AD-52432.1 | 1214-1232 | A-108008.1 | CCACGCUCUCUGGACUUCA | 36 |
| UM AD-52438.1 | 1247-1265 | A-108010.1 | GCUGCUGAGAAGAUUGACA | 37 |
| UM AD-56059.1 | 1248-1266 | A-115167.1 | CUGCUGAGAAGAUUGACAG | 38 |
| UM AD-56016.1 | 1249-1267 | A-115137.1 | UGCUGAGAAGAUUGACAGG | 39 |
| UM AD-56068.1 | 1250-1268 | A-115217.1 | GCUGAGAAGAUUGACAGGU | 40 |
| UM AD-55989.1 | 1251-1269 | A-115081.1 | CUGAGAAGAUUGACAGGUU | 41 |
| UM AD-56040.1 | 1260-1278 | A-115239.1 | UUGACAGGUUCAUGCAGGC | 42 |
| UM AD-56069.1 | 1277-1295 | A-115233.1 | GCUGUGACAGGAUGGAAGA | 43 |
| UM AD-52444.1 | 1403-1421 | A-108012.1 | GAGUUCUGGGUGGACAACA | 44 |
| UM AD-56033.1 | 1408-1426 | A-115221.1 | CUGGGUGGACAACAGCACC | 45 |
| UM AD-56058.1 | 1413-1431 | A-115245.1 | UGGACAACAGCACCUCAGU | 46 |
| UM AD-52450.1 | 1417-1435 | A-108014.1 | CAACAGCACCUCAGUGUCU | 47 |
| UM AD-55981.1 | 1566-1584 | A-115141.1 | UGGACAAGGUGGAGGGUCU | 48 |
| UM AD-56032.1 | 1570-1588 | A-115205.1 | CAAGGUGGAGGGUCUCACU | 49 |
| UM AD-56066.1 | 1572-1590 | A-115185.1 | AGGUGGAGGGUCUCACUUU | 50 |
| UM AD-52456.1 | 1587-1605 | A-108016.1 | CUUUCCAGCAAAACUCCCU | 51 |
| UM AD-56054.1 | 1591-1609 | A-115181.1 | CCAGCAAAACUCCCUCAAC | 52 |
| UM AD-56035.1 | 1592-1610 | A-115159.1 | CAGCAAAACUCCCUCAACU | 53 |
| UM AD-52462.1 | 1595-1613 | A-108018.1 | CAAAACUCCCUCAACUGGA | 54 |
| UM AD-56026.1 | 1601-1619 | A-115203.1 | UCCCUCAACUGGAUGAAGA | 55 |

TABLE 3-continued

Unmodified Sense and Antisense Strand Sequences of AGT dsRNAs (19 mers)

| | | | | |
|---|---|---|---|---|
| UM AD-56022.1 | 1602-1620 | A-115139.1 | CCCUCAACUGGAUGAAGAA | 56 |
| UM AD-55983.1 | 1605-1623 | A-115079.1 | UCAACUGGAUGAAGAAACU | 57 |
| UM AD-56028.1 | 1728-1746 | A-115235.1 | CCGAGCUGAACCUGCAAAA | 58 |
| UM AD-55980.1 | 1729-1747 | A-115125.1 | CGAGCUGAACCUGCAAAAA | 59 |
| UM AD-56036.1 | 1735-1753 | A-115175.1 | GAACCUGCAAAAAUUGAGC | 60 |
| UM AD-56014.1 | 1737-1755 | A-115105.1 | ACCUGCAAAAAUUGAGCAA | 61 |
| UM AD-56007.1 | 1738-1756 | A-115087.1 | CCUGCAAAAAUUGAGCAAU | 62 |
| UM AD-56012.1 | 1739-1757 | A-115073.1 | CUGCAAAAAUUGAGCAAUG | 63 |
| UM AD-56055.1 | 1740-1758 | A-115197.1 | UGCAAAAAUUGAGCAAUGA | 64 |
| UM AD-56029.1 | 1741-1759 | A-115157.1 | GCAAAAAUUGAGCAAUGAC | 65 |
| UM AD-52469.1 | 1767-1785 | A-108036.1 | GGGUGGGGGAGGUGCUGAA | 66 |
| UM AD-56053.1 | 1810-1828 | A-115165.1 | GGAUGAGAGAGAGCCCACA | 67 |
| UM AD-52468.1 | 1879-1897 | A-108020.1 | CCGCCCAUUCCUGUUUGCU | 68 |
| UM AD-56045.1 | 1885-1903 | A-115225.1 | AUUCCUGUUUGCUGUGUAU | 69 |
| UM AD-56056.1 | 1887-1905 | A-115213.1 | UCCUGUUUGCUGUGUAUGA | 70 |
| UM AD-56010.1 | 1891-1909 | A-115135.1 | GUUUGCUGUGUAUGAUCAA | 71 |
| UM AD-56015.1 | 1892-1910 | A-115121.1 | UUUGCUGUGUAUGAUCAAA | 72 |
| UM AD-56039.1 | 2070-2088 | A-115223.1 | CCCCCAGUCUCCCACCUUU | 73 |
| UM AD-55991.1 | 2080-2098 | A-115113.1 | CCCACCUUUUCUUCUAAUG | 74 |
| UM AD-52474.1 | 2081-2099 | A-108022.1 | CCACCUUUUCUUCUAAUGA | 75 |
| UM AD-56024.1 | 2082-2100 | A-115171.1 | CACCUUUUCUUCUAAUGAG | 76 |
| UM AD-52433.1 | 2125-2143 | A-108024.1 | GUUUCUCCUUGGUCUAAGU | 77 |
| UM AD-56037.1 | 2199-2217 | A-115191.1 | UUGCUGGGUUUAUUUUAGA | 78 |
| UM AD-56049.1 | 2200-2218 | A-115195.1 | UGCUGGGUUUAUUUUAGAG | 79 |
| UM AD-52439.1 | 2201-2219 | A-108026.1 | GCUGGGUUUAUUUUAGAGA | 80 |
| UM AD-55978.1 | 2202-2220 | A-115093.1 | CUGGGUUUAUUUUAGAGAA | 81 |
| UM AD-55999.1 | 2203-2221 | A-115147.1 | UGGGUUUAUUUUAGAGAAU | 82 |
| UM AD-56050.1 | 2206-2224 | A-115211.1 | GUUUAUUUUAGAGAAUGGG | 83 |
| UM AD-56031.1 | 2209-2227 | A-115189.1 | UAUUUUAGAGAAUGGGGGU | 84 |
| UM AD-56027.1 | 2227-2245 | A-115219.1 | UGGGGAGGCAAGAACCAGU | 85 |
| UM AD-55987.1 | 2230-2248 | A-115143.1 | GGAGGCAAGAACCAGUGUU | 86 |
| UM AD-56043.1 | 2266-2284 | A-115193.1 | UCCAAAAGAAUUCCAACC | 87 |
| UM AD-56001.1 | 2268-2286 | A-115085.1 | CAAAAGAAUUCCAACCGA | 88 |
| UM AD-52445.1 | 2279-2297 | A-108028.1 | CCAACCGACCAGCUUGUUU | 89 |
| UM AD-52451.1 | 2283-2301 | A-108030.1 | CCGACCAGCUUGUUUGUGA | 90 |
| UM AD-52457.1 | 2284-2302 | A-108032.1 | CGACCAGCUUGUUUGUGAA | 91 |
| UM AD-52463.1 | 2285-2303 | A-108034.1 | GACCAGCUUGUUUGUGAAA | 92 |
| UM AD-55982.1 | 2290-2308 | A-115063.1 | GCUUGUUUGUGAAACAAAA | 93 |

TABLE 3-continued

Unmodified Sense and Antisense Strand Sequences of AGT dsRNAs (19 mers)

| | | | | |
|---|---|---|---|---|
| UM AD-56019.1 | 2291-2309 | A-115091.1 | CUUGUUUGUGAAACAAAAA | 94 |
| UM AD-55988.1 | 2292-2310 | A-115065.1 | UUGUUUGUGAAACAAAAAA | 95 |
| UM AD-55994.1 | 2294-2312 | A-115067.1 | GUUUGUGAAACAAAAAGU | 96 |
| UM AD-56013.1 | 2296-2314 | A-115089.1 | UUGUGAAACAAAAAGUGU | 97 |
| UM AD-56065.1 | 2299-2317 | A-115169.1 | UGAAACAAAAAGUGUUCC | 98 |
| UM AD-56008.1 | 2304-2322 | A-115103.1 | CAAAAAGUGUUCCCUUUU | 99 |
| UM AD-56048.1 | 2306-2324 | A-115179.1 | AAAAGUGUUCCCUUUUCA | 100 |
| UM AD-56003.1 | 2307-2325 | A-115117.1 | AAAGUGUUCCCUUUUCAA | 101 |
| UM AD-56051.1 | 2314-2332 | A-115227.1 | UUCCCUUUUCAAGUUGAGA | 102 |
| UM AD-56044.1 | 2317-2335 | A-115209.1 | CCUUUUCAAGUUGAGAACA | 103 |
| UM AD-55996.1 | 2320-2338 | A-115099.1 | UUUCAAGUUGAGAACAAAA | 104 |
| UM AD-56002.1 | 2321-2339 | A-115101.1 | UUCAAGUUGAGAACAAAAA | 105 |
| UM AD-55976.1 | 2323-2341 | A-115061.1 | CAAGUUGAGAACAAAAAUU | 106 |
| UM AD-56062.1 | 2325-2343 | A-115215.1 | AGUUGAGAACAAAAAUUGG | 107 |
| UM AD-56011.1 | 2326-2344 | A-115151.1 | GUUGAGAACAAAAAUUGGG | 108 |
| UM AD-56009.1 | 2328-2346 | A-115119.1 | UGAGAACAAAAAUUGGGUU | 109 |
| UM AD-56020.1 | 2329-2347 | A-115107.1 | GAGAACAAAAAUUGGGUUU | 110 |
| UM AD-55979.1 | 2331-2349 | A-115109.1 | GAACAAAAAUUGGGUUUUA | 111 |
| UM AD-55997.1 | 2332-2350 | A-115115.1 | AACAAAAAUUGGGUUUUAA | 112 |
| UM AD-56000.1 | 2333-2351 | A-115069.1 | ACAAAAAUUGGGUUUUAAA | 113 |
| UM AD-56006.1 | 2334-2352 | A-115071.1 | CAAAAAUUGGGUUUUAAAA | 114 |
| UM AD-55990.1 | 2339-2357 | A-115097.1 | AUUGGGUUUUAAAAUUAAA | 115 |
| UM AD-55984.1 | 2340-2358 | A-115095.1 | UUGGGUUUUAAAAUUAAAG | 116 |
| UM AD-55995.1 | 2341-2359 | A-115083.1 | UGGGUUUUAAAAUUAAAGU | 117 |
| UM AD-56004.1 | 2346-2364 | A-115133.1 | UUUAAAAUUAAAGUAUACA | 118 |
| UM AD-56042.1 | 2347-2365 | A-115177.1 | UUAAAAUUAAAGUAUACAU | 119 |
| UM AD-55992.1 | 2384-2402 | A-115129.1 | UUGUAUUUAGUGUCUUGAA | 120 |
| UM AD-55977.1 | 2385-2403 | A-115077.1 | UGUAUUUAGUGUCUUGAAU | 121 |
| UM AD-56005.1 | 2391-2409 | A-115149.1 | UAGUGUCUUGAAUGUAAGA | 122 |
| UM AD-56052.1 | 2397-2415 | A-115243.1 | CUUGAAUGUAAGAACAUGA | 123 |
| UM AD-55985.1 | 2398-2416 | A-115111.1 | UUGAAUGUAAGAACAUGAC | 124 |
| UM AD-56038.1 | 2439-2457 | A-115207.1 | CUUAGUUUUUCCACAGAU | 125 |
| UM AD-56023.1 | 2450-2468 | A-115155.1 | CCACAGAUGCUUGUGAUUU | 126 |
| UM AD-56018.1 | 2452-2470 | A-115075.1 | ACAGAUGCUUGUGAUUUUU | 127 |
| UM AD-56060.1 | 2497-2515 | A-115183.1 | CUGAAUUUCUGUUUGAAUG | 128 |
| UM AD-55993.1 | 2519-2537 | A-115145.1 | AACCAUAGCUGGUUAUUUC | 129 |
| UM AD-55986.1 | 2521-2539 | A-115127.1 | CCAUAGCUGGUUAUUUCUC | 130 |

TABLE 3-continued

Unmodified Sense and Antisense Strand Sequences of AGT dsRNAs (19 mers)

| Antisense Name | Position relative to NM_000029.3 | Antisense Sequence | SEQ ID NO |
|---|---|---|---|
| A-115162.1 | 485-503 | UCUGCUGUAGUACCCAGAA | 131 |
| A-107993.1 | 491-509 | UACCCUUCUGCUGUAGUAC | 132 |
| A-115230.1 | 606-624 | UGUAUGUACACCCGGUCAC | 133 |
| A-115164.1 | 635-653 | UCUCAUUGUGGAUGACGAG | 134 |
| A-107995.1 | 643-661 | ACAGGUACUCUCAUUGUGG | 135 |
| A-115248.1 | 644-662 | CACAGGUACUCUCAUUGUG | 136 |
| A-115124.1 | 658-676 | CUUUGCCAGCUGCUCACAG | 137 |
| A-115202.1 | 741-759 | AGGGCCUUUUCAUCCACAG | 138 |
| A-115174.1 | 822-840 | UUGGCCAGCAUCCCGACCA | 139 |
| A-115238.1 | 825-843 | AAGUUGGCCAGCAUCCCGA | 140 |
| A-107997.1 | 828-846 | AAGAAGUUGGCCAGCAUCC | 141 |
| A-115154.1 | 834-852 | AAGCCCAAGAAGUUGGCCA | 142 |
| A-107999.1 | 841-859 | UAUACGGAAGCCCAAGAAG | 143 |
| A-108001.1 | 844-862 | AUAUAUACGGAAGCCCAAG | 144 |
| A-108003.1 | 849-867 | AUGCCAUAUAUACGGAAGC | 145 |
| A-115188.1 | 855-873 | CUGUGCAUGCCAUAUAUAC | 146 |
| A-108005.1 | 863-881 | AUAGCUCACUGUGCAUGCC | 147 |
| A-115200.1 | 878-896 | CAUGGACCACGCCCCAUAG | 148 |
| A-108007.1 | 910-928 | AAAGACAGCCGUUGGGAG | 149 |
| A-115232.1 | 911-929 | CAAAGACAGCCGUUGGGGA | 150 |
| A-115242.1 | 1002-1020 | CAGUUCUUGUCCUUCCAAG | 151 |
| A-108009.1 | 1214-1232 | UGAAGUCCAGAGAGCGUGG | 152 |
| A-108011.1 | 1247-1265 | UGUCAAUCUUCUCAGCAGC | 153 |
| A-115168.1 | 1248-1266 | CUGUCAAUCUUCUCAGCAG | 154 |
| A-115138.1 | 1249-1267 | CCUGUCAAUCUUCUCAGCA | 155 |
| A-115218.1 | 1250-1268 | ACCUGUCAAUCUUCUCAGC | 156 |
| A-115082.1 | 1251-1269 | AACCUGUCAAUCUUCUCAG | 157 |
| A-115240.1 | 1260-1278 | GCCUGCAUGAACCUGUCAA | 158 |
| A-115234.1 | 1277-1295 | UCUUCCAUCCUGUCACAGC | 159 |
| A-108013.1 | 1403-1421 | UGUUGUCCACCCAGAACUC | 160 |
| A-115222.1 | 1408-1426 | GGUGCUGUUGUCCACCCAG | 161 |
| A-115246.1 | 1413-1431 | ACUGAGGUGCUGUUGUCCA | 162 |
| A-108015.1 | 1417-1435 | AGACACUGAGGUGCUGUUG | 163 |
| A-115142.1 | 1566-1584 | AGACCCUCCACCUUGUCCA | 164 |
| A-115206.1 | 1570-1588 | AGUGAGACCCUCCACCUUG | 165 |
| A-115186.1 | 1572-1590 | AAAGUGAGACCCUCCACCU | 166 |
| A-108017.1 | 1587-1605 | AGGGAGUUUUGCUGGAAAG | 167 |

TABLE 3-continued

Unmodified Sense and Antisense Strand Sequences of AGT dsRNAs (19 mers)

| | | | |
|---|---|---|---|
| A-115182.1 | 1591-1609 | GUUGAGGGAGUUUUGCUGG | 168 |
| A-115160.1 | 1592-1610 | AGUUGAGGGAGUUUUGCUG | 169 |
| A-108019.1 | 1595-1613 | UCCAGUUGAGGGAGUUUUG | 170 |
| A-115204.1 | 1601-1619 | UCUUCAUCCAGUUGAGGGA | 171 |
| A-115140.1 | 1602-1620 | UUCUUCAUCCAGUUGAGGG | 172 |
| A-115080.1 | 1605-1623 | AGUUUCUUCAUCCAGUUGA | 173 |
| A-115236.1 | 1728-1746 | UUUUGCAGGUUCAGCUCGG | 174 |
| A-115126.1 | 1729-1747 | UUUUUGCAGGUUCAGCUCG | 175 |
| A-115176.1 | 1735-1753 | GCUCAAUUUUUGCAGGUUC | 176 |
| A-115106.1 | 1737-1755 | UUGCUCAAUUUUUGCAGGU | 177 |
| A-115088.1 | 1738-1756 | AUUGCUCAAUUUUUGCAGG | 178 |
| A-115074.1 | 1739-1757 | CAUUGCUCAAUUUUUGCAG | 179 |
| A-115198.1 | 1740-1758 | UCAUUGCUCAAUUUUUGCA | 180 |
| A-115158.1 | 1741-1759 | GUCAUUGCUCAAUUUUUGC | 181 |
| A-108037.1 | 1767-1785 | UUCAGCACCUCCCCCACCC | 182 |
| A-115166.1 | 1810-1828 | UGUGGGCUCUCUCUCAUCC | 183 |
| A-108021.1 | 1879-1897 | AGCAAACAGGAAUGGGCGG | 184 |
| A-115226.1 | 1885-1903 | AUACACAGCAAACAGGAAU | 185 |
| A-115214.1 | 1887-1905 | UCAUACACAGCAAACAGGA | 186 |
| A-115136.1 | 1891-1909 | UUGAUCAUACACAGCAAAC | 187 |
| A-115122.1 | 1892-1910 | UUUGAUCAUACACAGCAAA | 188 |
| A-115224.1 | 2070-2088 | AAAGGUGGGAGACUGGGGG | 189 |
| A-115114.1 | 2080-2098 | CAUUAGAAGAAAAGGUGGG | 190 |
| A-108023.1 | 2081-2099 | UCAUUAGAAGAAAAGGUGG | 191 |
| A-115172.1 | 2082-2100 | CUCAUUAGAAGAAAAGGUG | 192 |
| A-108025.1 | 2125-2143 | ACUUAGACCAAGGAGAAAC | 193 |
| A-115192.1 | 2199-2217 | UCUAAAAUAAACCCAGCAA | 194 |
| A-115196.1 | 2200-2218 | CUCUAAAAUAAACCCAGCA | 195 |
| A-108027.1 | 2201-2219 | UCUCUAAAAUAAACCCAGC | 196 |
| A-115094.1 | 2202-2220 | UUCUCUAAAAUAAACCCAG | 197 |
| A-115148.1 | 2203-2221 | AUUCUCUAAAAUAAACCCA | 198 |
| A-115212.1 | 2206-2224 | CCCAUUCUCUAAAAUAAAC | 199 |
| A-115190.1 | 2209-2227 | ACCCCCAUUCUCUAAAAUA | 200 |
| A-115220.1 | 2227-2245 | ACUGGUUCUUGCCUCCCCA | 201 |
| A-115144.1 | 2230-2248 | AACACUGGUUCUUGCCUCC | 202 |
| A-115194.1 | 2266-2284 | GGUUGGAAUUCUUUUUGGA | 203 |
| A-115086.1 | 2268-2286 | UCGGUUGGAAUUCUUUUUG | 204 |
| A-108029.1 | 2279-2297 | AAACAAGCUGGUCGGUUGG | 205 |
| A-108031.1 | 2283-2301 | UCACAAACAAGCUGGUCGG | 206 |

TABLE 3-continued

Unmodified Sense and Antisense Strand Sequences of AGT dsRNAs (19 mers)

| | | | |
|---|---|---|---|
| A-108033.1 | 2284-2302 | UUCACAAACAAGCUGGUCG | 207 |
| A-108035.1 | 2285-2303 | UUUCACAAACAAGCUGGUC | 208 |
| A-115064.1 | 2290-2308 | UUUUGUUUCACAAACAAGC | 209 |
| A-115092.1 | 2291-2309 | UUUUUGUUUCACAAACAAG | 210 |
| A-115066.1 | 2292-2310 | UUUUUUGUUUCACAAACAA | 211 |
| A-115068.1 | 2294-2312 | ACUUUUUUGUUUCACAAAC | 212 |
| A-115090.1 | 2296-2314 | ACACUUUUUUGUUUCACAA | 213 |
| A-115170.1 | 2299-2317 | GGAACACUUUUUUGUUUCA | 214 |
| A-115104.1 | 2304-2322 | AAAAGGGAACACUUUUUUG | 215 |
| A-115180.1 | 2306-2324 | UGAAAAGGGAACACUUUUU | 216 |
| A-115118.1 | 2307-2325 | UUGAAAAGGGAACACUUUU | 217 |
| A-115228.1 | 2314-2332 | UCUCAACUUGAAAGGGAA | 218 |
| A-115210.1 | 2317-2335 | UGUUCUCAACUUGAAAAGG | 219 |
| A-115100.1 | 2320-2338 | UUUUGUUCUCAACUUGAAA | 220 |
| A-115102.1 | 2321-2339 | UUUUUGUUCUCAACUUGAA | 221 |
| A-115062.1 | 2323-2341 | AAUUUUUGUUCUCAACUUG | 222 |
| A-115216.1 | 2325-2343 | CCAAUUUUUGUUCUCAACU | 223 |
| A-115152.1 | 2326-2344 | CCCAAUUUUUGUUCUCAAC | 224 |
| A-115120.1 | 2328-2346 | AACCCAAUUUUUGUUCUCA | 225 |
| A-115108.1 | 2329-2347 | AAACCCAAUUUUUGUUCUC | 226 |
| A-115110.1 | 2331-2349 | UAAAACCCAAUUUUUGUUC | 227 |
| A-115116.1 | 2332-2350 | UUAAAACCCAAUUUUUGUU | 228 |
| A-115070.1 | 2333-2351 | UUUAAAACCCAAUUUUUGU | 229 |
| A-115072.1 | 2334-2352 | UUUUAAAACCCAAUUUUUG | 230 |
| A-115098.1 | 2339-2357 | UUUAAUUUUAAAACCCAAU | 231 |
| A-115096.1 | 2340-2358 | CUUUAAUUUUAAAACCCAA | 232 |
| A-115084.1 | 2341-2359 | ACUUUAAUUUUAAAACCCA | 233 |
| A-115134.1 | 2346-2364 | UGUAUACUUUAAUUUUAAA | 234 |
| A-115178.1 | 2347-2365 | AUGUAUACUUUAAUUUUAA | 235 |
| A-115130.1 | 2384-2402 | UUCAAGACACUAAAUACAA | 236 |
| A-115078.1 | 2385-2403 | AUUCAAGACACUAAAUACA | 237 |
| A-115150.1 | 2391-2409 | UCUUACAUUCAAGACACUA | 238 |
| A-115244.1 | 2397-2415 | UCAUGUUCUUACAUUCAAG | 239 |
| A-115112.1 | 2398-2416 | GUCAUGUUCUUACAUUCAA | 240 |
| A-115208.1 | 2439-2457 | AUCUGUGGAAAAAACUAAG | 241 |
| A-115156.1 | 2450-2468 | AAAUCACAAGCAUCUGUGG | 242 |
| A-115076.1 | 2452-2470 | AAAAAUCACAAGCAUCUGU | 243 |
| A-115184.1 | 2497-2515 | CAUUCAAACAGAAAUUCAG | 244 |

TABLE 3-continued

Unmodified Sense and Antisense Strand Sequences of AGT dsRNAs (19 mers)

| | | | |
|---|---|---|---|
| A-115146.1 | 2519-2537 | GAAAUAACCAGCUAUGGUU | 245 |
| A-115128.1 | 2521-2539 | GAGAAAUAACCAGCUAUGG | 246 |

TABLE 4

Modified Sense and Antisense Strand Sequences of AGT dsRNAs (19 mers)

| Duplex Name | Sense Name | Sense Sequence | SEQ ID NO. | Antisense Name | Antisense Sequence | SEQ ID NO. |
|---|---|---|---|---|---|---|
| AD-56041.1 | A-115161.1 | uucuGGGuAcuAcAGcAGAdTsdT | 247 | A-115162.1 | UCUGCUGuAGuACCcAGAAdTsdT | 363 |
| AD-52431.1 | A-107992.1 | GuAcuAcAGcAGAAGGGuAdTsdT | 248 | A-107993.1 | uACCCUUCUGCUGuAGuACdTsdT | 364 |
| AD-56057.1 | A-115229.1 | GuGAccGGGuGuAcAuAcAdTsdT | 249 | A-115230.1 | UGuAUGuAcACCCGGUcACdTsdT | 365 |
| AD-56047.1 | A-115163.1 | cucGucAuccAcAAuGAGAdTsdT | 250 | A-115164.1 | UCUcAUUGUGGAUGACGAGdTsdT | 366 |
| AD-52437.1 | A-107994.1 | ccAcAAuGAGAGuAccuGudTsdT | 251 | A-107995.1 | AcAGGuACUCUcAUUGUGGdTsdT | 367 |
| AD-56064.1 | A-115247.1 | cAcAAuGAGAGuAccuGuGdTsdT | 252 | A-115248.1 | cAcAGGuACUCUcAUUGUGdTsdT | 368 |
| AD-56021.1 | A-115123.1 | cuGuGAGcAGcuGGcAAAGdTsdT | 253 | A-115124.1 | CUUUGCcAGCUGCUcAcAGdTsdT | 369 |
| AD-56067.1 | A-115201.1 | cuGuGGAuGAAAAGGcccudTsdT | 254 | A-115202.1 | AGGGCCUUUUcAUCcAcAGdTsdT | 370 |
| AD-56030.1 | A-115173.1 | uGGucGGGAuGcuGGccAAdTsdT | 255 | A-115174.1 | UUGGCcAGcAUCCCGACcAdTsdT | 371 |
| AD-56034.1 | A-115237.1 | ucGGGAuGcuGGccAAcuudTsdT | 256 | A-115238.1 | AAGUUGGCcAGcAUCCCGAdTsdT | 372 |
| AD-52443.1 | A-107996.1 | GGAuGcuGGccAAcuucuudTsdT | 257 | A-107997.1 | AAGAAGUUGGCcAGcAUCCdTsdT | 373 |
| AD-56017.1 | A-115153.1 | uGGccAAcuucuuGGGcuudTsdT | 258 | A-115154.1 | AAGCCcAAGAAGUUGGCcAdTsdT | 374 |
| AD-52449.1 | A-107998.1 | cuucuuGGGcuuccGuAuAdTsdT | 259 | A-107999.1 | uAuACGGAAGCCcAAGAAGdTsdT | 375 |
| AD-52455.1 | A-108000.1 | cuuGGGcuuccGuAuAuAudTsdT | 260 | A-108001.1 | AuAuAuACGGAAGCCcAAGdTsdT | 376 |
| AD-52461.1 | A-108002.1 | GcuuccGuAuAuAuGGcAudTsdT | 261 | A-108003.1 | AUGCcAuAuAuACGGAAGCdTsdT | 377 |
| AD-56025.1 | A-115187.1 | GuAuAuAuGGcAuGcAcAGdTsdT | 262 | A-115188.1 | CUGUGcAUGCcAuAuAuACdTsdT | 378 |
| AD-52467.1 | A-108004.1 | GGcAuGcAcAGuGAGcuAudTsdT | 263 | A-108005.1 | AuAGCUcACUGUGcAUGCCdTsdT | 379 |
| AD-56061.1 | A-115199.1 | cuAuGGGGcGuGGuccAuGdTsdT | 264 | A-115200.1 | cAUGGACcACGCCCcAuAGdTsdT | 380 |
| AD-52473.1 | A-108006.1 | cucccccAAcGGcuGucuuudTsdT | 265 | A-108007.1 | AAAGAcAGCCGUUGGGGAGdTsdT | 381 |
| AD-56063.1 | A-115231.1 | ucccccAAcGGcuGucuuGdTsdT | 266 | A-115232.1 | cAAAGAcAGCCGUUGGGGAdTsdT | 382 |
| AD-56046.1 | A-115241.1 | cuuGGAAGGAcAAGAAcuGdTsdT | 267 | A-115242.1 | cAGUUCUUGUCCUUCcAAGdTsdT | 383 |
| AD-52432.1 | A-108008.1 | ccAcGcucucuGGAcuucAdTsdT | 268 | A-108009.1 | UGAAGUCcAGAGAGCGUGGdTsdT | 384 |
| AD-52438.1 | A-108010.1 | GcuGcuGAGAAGAuuGAcAdTsdT | 269 | A-108011.1 | UGUcAAUCUUCUcAGcAGCdTsdT | 385 |
| AD-56059.1 | A-115167.1 | cuGcuGAGAAGAuuGAcAGdTsdT | 270 | A-115168.1 | CUGUcAAUCUUCUcAGcAGdTsdT | 386 |
| AD-56016.1 | A-115137.1 | uGcuGAGAAGAuuGAcAGGdTsdT | 271 | A-115138.1 | CCUGUcAAUCUUCUcAGcAdTsdT | 387 |
| AD-56068.1 | A-115217.1 | GcuGAGAAGAuuGAcAGGudTsdT | 272 | A-115218.1 | ACCUGUcAAUCUUCUcAGCdTsdT | 388 |
| AD-55989.1 | A-115081.1 | cuGAGAAGAuuGAcAGGuudTsdT | 273 | A-115082.1 | AACCUGUcAAUCUUCUcAGdTsdT | 389 |
| AD-56040.1 | A-115239.1 | uuGAcAGGuucAuGcAGGcdTsdT | 274 | A-115240.1 | GCCUGcAUGAACCUGUcAAdTsdT | 390 |
| AD-56069.1 | A-115233.1 | GcuGuGAcAGGAuGGAAGAdTsdT | 275 | A-115234.1 | UCUUCcAUCCUGUcAcAGCdTsdT | 391 |
| AD-52444.1 | A-108012.1 | GAGuucuGGGuGGAcAAcAdTsdT | 276 | A-108013.1 | UGUUGUCcACCcAGAACUCdTsdT | 392 |
| AD-56033.1 | A-115221.1 | cuGGGuGGAcAAcAGcAccdTsdT | 277 | A-115222.1 | GGUGCUGUUGUCcACCcAGdTsdT | 393 |
| AD-56058.1 | A-115245.1 | uGGAcAAcAGcAccucAGudTsdT | 278 | A-115246.1 | ACUGAGGUGCUGUUGUCcAdTsdT | 394 |

TABLE 4-continued

Modified Sense and Antisense Strand Sequences of AGT dsRNAs (19 mers)

| Duplex Name | Sense Name | Sense Sequence | SEQ ID NO. | Antisense Name | Antisense Sequence | SEQ ID NO. |
|---|---|---|---|---|---|---|
| AD-52450.1 | A-108014.1 | cAAcAGcAccucAGuGucudTsdT | 279 | A-108015.1 | AGAcACUGAGGUGCUGUUGdTsdT | 395 |
| AD-55981.1 | A-115141.1 | uGGAcAAGGuGGAGGGucudTsdT | 280 | A-115142.1 | AGACCCUCcACCUUGUCcAdTsdT | 396 |
| AD-56032.1 | A-115205.1 | cAAGGuGGAGGGucucAcudTsdT | 281 | A-115206.1 | AGUGAGACCCUCcACCUUGdTsdT | 397 |
| AD-56066.1 | A-115185.1 | AGGuGGAGGGucucAcuuudTsdT | 282 | A-115186.1 | AAAGUGAGACCCUCcACCUdTsdT | 398 |
| AD-52456.1 | A-108016.1 | cuuuccAGcAAAAcucccudTsdT | 283 | A-108017.1 | AGGGAGUUUUGCUGGAAAGdTsdT | 399 |
| AD-56054.1 | A-115181.1 | ccAGcAAAAcucccucAAcdTsdT | 284 | A-115182.1 | GUUGAGGGAGUUUUGCUGGdTsdT | 400 |
| AD-56035.1 | A-115159.1 | cAGcAAAAcucccucAAcudTsdT | 285 | A-115160.1 | AGUUGAGGGAGUUUUGCUGdTsdT | 401 |
| AD-52462.1 | A-108018.1 | cAAAAcucccucAAcuGGAdTsdT | 286 | A-108019.1 | UCcAGUUGAGGGAGUUUUGdTsdT | 402 |
| AD-56026.1 | A-115203.1 | ucccucAAcuGGAuGAAGAdTsdT | 287 | A-115204.1 | UCUUcAUCcAGUUGAGGGAdTsdT | 403 |
| AD-56022.1 | A-115139.1 | cccucAAcuGGAuGAAGAAdTsdT | 288 | A-115140.1 | UUCUUcAUCcAGUUGAGGGdTsdT | 404 |
| AD-55983.1 | A-115079.1 | ucAAcuGGAuGAAGAAAcudTsdT | 289 | A-115080.1 | AGUUUCUUcAUCcAGUUGAdTsdT | 405 |
| AD-56028.1 | A-115235.1 | ccGAGcuGAAccuGcAAAAdTsdT | 290 | A-115236.1 | UUUUGcAGGUUcAGCUCGGdTsdT | 406 |
| AD-55980.1 | A-115125.1 | cGAGcuGAAccuGcAAAAAdTsdT | 291 | A-115126.1 | UUUUUGcAGGUUcAGCUCGdTsdT | 407 |
| AD-56036.1 | A-115175.1 | GAAccuGcAAAAAuuGAGcdTsdT | 292 | A-115176.1 | GCUcAAUUUUUGcAGGUUCdTsdT | 408 |
| AD-56014.1 | A-115105.1 | AccuGcAAAAAuuGAGcAAdTsdT | 293 | A-115106.1 | UUGCUcAAUUUUUGcAGGUdTsdT | 409 |
| AD-56007.1 | A-115087.1 | ccuGcAAAAAuuGAGcAAudTsdT | 294 | A-115088.1 | AUUGCUcAAUUUUUGcAGGdTsdT | 410 |
| AD-56012.1 | A-115073.1 | cuGcAAAAAuuGAGcAAuGdTsdT | 295 | A-115074.1 | cAUUGCUcAAUUUUUGcAGdTsdT | 411 |
| AD-56055.1 | A-115197.1 | uGcAAAAAuuGAGcAAuGAdTsdT | 296 | A-115198.1 | UcAUUGCUcAAUUUUUGcAdTsdT | 412 |
| AD-56029.1 | A-115157.1 | GcAAAAAuuGAGcAAuGAcdTsdT | 297 | A-115158.1 | GUcAUUGCUcAAUUUUUGcdTsdT | 413 |
| AD-52469.1 | A-108036.1 | GGGuGGGGGAGGuGcuGAAdTsdT | 298 | A-108037.1 | UUcAGcACCUCCCCcACCCdTsdT | 414 |
| AD-56053.1 | A-115165.1 | GGAuGAGAGAGAGcccAcAdTsdT | 299 | A-115166.1 | UGUGGGCUCUCUCUcAUCCdTsdT | 415 |
| AD-52468.1 | A-108020.1 | ccGcccAuuccuGuuuGcudTsdT | 300 | A-108021.1 | AGcAAAcAGGAAUGGGCGGdTsdT | 416 |
| AD-56045.1 | A-115225.1 | AuuccuGuuuGcuGuGuAudTsdT | 301 | A-115226.1 | AuAcAcAGcAAAcAGGAAUdTsdT | 417 |
| AD-56056.1 | A-115213.1 | uccuGuuuGcuGuGuAuGAdTsdT | 302 | A-115214.1 | UcAuAcAcAGcAAAcAGGAdTsdT | 418 |
| AD-56010.1 | A-115135.1 | GuuuGcuGuGuAuGAucAAdTsdT | 303 | A-115136.1 | UUGAUcAuAcAcAGcAAACdTsdT | 419 |
| AD-56015.1 | A-115121.1 | uuuGcuGuGuAuGAucAAAdTsdT | 304 | A-115122.1 | UUUGAUcAuAcAcAGcAAAdTsdT | 420 |
| AD-56039.1 | A-115223.1 | cccccAGucucccAccuuudTsdT | 305 | A-115224.1 | AAAGGUGGGAGACUGGGGGdTsdT | 421 |
| AD-55991.1 | A-115113.1 | cccAccuuuucuucuAAuGdTsdT | 306 | A-115114.1 | cAUuAGAAGAAAAGGUGGGdTsdT | 422 |
| AD-52474.1 | A-108022.1 | ccAccuuuucuucuAAuGAdTsdT | 307 | A-108023.1 | UcAUuAGAAGAAAAGGUGGdTsdT | 423 |
| AD-56024.1 | A-115171.1 | cAccuuuucuucuAAuGAGdTsdT | 308 | A-115172.1 | CUcAUuAGAAGAAAAGGUGdTsdT | 424 |
| AD-52433.1 | A-108024.1 | GuuucccuuGGucuAAGudTsdT | 309 | A-108025.1 | ACUuAGACcAAGGAGAAACdTsdT | 425 |
| AD-56037.1 | A-115191.1 | uuGcuGGGuuuAuuuuAGAdTsdT | 310 | A-115192.1 | UCuAAAAuAAACCcAGcAAdTsdT | 426 |
| AD-56049.1 | A-115195.1 | uGcuGGGuuuAuuuuAGAGdTsdT | 311 | A-115196.1 | CUCuAAAAuAAACCcAGcAdTsdT | 427 |
| AD-52439.1 | A-108026.1 | GcuGGGuuuAuuuuAGAGAdTsdT | 312 | A-108027.1 | UCUCuAAAAuAAACCcAGCdTsdT | 428 |
| AD-55978.1 | A-115093.1 | cuGGGuuuAuuuuAGAGAAdTsdT | 313 | A-115094.1 | UUCUCuAAAAuAAACCcAGdTsdT | 429 |
| AD-55999.1 | A-115147.1 | uGGGuuuAuuuuAGAGAAudTsdT | 314 | A-115148.1 | AUUCUCuAAAAuAAACCcAdTsdT | 430 |
| AD-56050.1 | A-115211.1 | GuuuAuuuuAGAGAAuGGGdTsdT | 315 | A-115212.1 | CCcAUUCUCuAAAAuAAACdTsdT | 431 |

TABLE 4-continued

Modified Sense and Antisense Strand Sequences of AGT dsRNAs (19 mers)

| Duplex Name | Sense Name | Sense Sequence | SEQ ID NO. | Antisense Name | Antisense Sequence | SEQ ID NO. |
|---|---|---|---|---|---|---|
| AD-56031.1 | A-115189.1 | uAuuuuAGAGAAuGGGGGudTsdT | 316 | A-115190.1 | ACCCCcAUUCUCuAAAAuAdTsdT | 432 |
| AD-56027.1 | A-115219.1 | uGGGGAGGcAAGAAccAGudTsdT | 317 | A-115220.1 | ACUGGUUCUUGCCUCCCcAdTsdT | 433 |
| AD-55987.1 | A-115143.1 | GGAGGcAAGAAccAGuGuudTsdT | 318 | A-115144.1 | AAcACUGGUUCUUGCCUCCdTsdT | 434 |
| AD-56043.1 | A-115193.1 | uccAAAAAGAAuuccAAccdTsdT | 319 | A-115194.1 | GGUUGGAAUUCUUUUUGGAdTsdT | 435 |
| AD-56001.1 | A-115085.1 | cAAAAAGAAuuccAAccGAdTsdT | 320 | A-115086.1 | UCGGUUGGAAUUCUUUUUGdTsdT | 436 |
| AD-52445.1 | A-108028.1 | ccAAccGAccAGcuuGuuudTsdT | 321 | A-108029.1 | AAAcAAGCUGGUCGGUUGGdTsdT | 437 |
| AD-52451.1 | A-108030.1 | ccGAccAGcuuGuuuGuGAdTsdT | 322 | A-108031.1 | UcAcAAAcAAGCUGGUCGGdTsdT | 438 |
| AD-52457.1 | A-108032.1 | cGAccAGcuuGuuuGuGAAdTsdT | 323 | A-108033.1 | UUcAcAAAcAAGCUGGUCGdTsdT | 439 |
| AD-52463.1 | A-108034.1 | GAccAGcuuGuuuGuGAAAdTsdT | 324 | A-108035.1 | UUUcAcAAAcAAGCUGGUCdTsdT | 440 |
| AD-55982.1 | A-115063.1 | GcuuGuuuGuGAAAcAAAAdTsdT | 325 | A-115064.1 | UUUUGUUUcAcAAAcAAGCdTsdT | 441 |
| AD-56019.1 | A-115091.1 | cuuGuuuGuGAAAcAAAAAdTsdT | 326 | A-115092.1 | UUUUUGUUUcAcAAAcAAGdTsdT | 442 |
| AD-55988.1 | A-115065.1 | uuGuuuGuGAAAcAAAAAAdTsdT | 327 | A-115066.1 | UUUUUUGUUUcAcAAAcAAdTsdT | 443 |
| AD-55994.1 | A-115067.1 | GuuuGuGAAAcAAAAAAGudTsdT | 328 | A-115068.1 | ACUUUUUUGUUUcAcAAAcdTsdT | 444 |
| AD-56013.1 | A-115089.1 | uuGuGAAAcAAAAAAGuGudTsdT | 329 | A-115090.1 | AcACUUUUUUGUUUcAcAAdTsdT | 445 |
| AD-56065.1 | A-115169.1 | uGAAAcAAAAAAGuGuuccdTsdT | 330 | A-115170.1 | GGAAcACUUUUUUGUUUcAdTsdT | 446 |
| AD-56008.1 | A-115103.1 | cAAAAAAGuGuucccuuuudTsdT | 331 | A-115104.1 | AAAAGGGAAcACUUUUUUGdTsdT | 447 |
| AD-56048.1 | A-115179.1 | AAAAAGuGuucccuuuucAdTsdT | 332 | A-115180.1 | UGAAAGGGAAcACUUUUUUdTsdT | 448 |
| AD-56003.1 | A-115117.1 | AAAAGuGuucccuuuucAAdTsdT | 333 | A-115118.1 | UUGAAAGGGAAcACUUUUUdTsdT | 449 |
| AD-56051.1 | A-115227.1 | uucccuuuucAAGuuGAGAdTsdT | 334 | A-115228.1 | UCUcAACUUGAAAAGGGAAdTsdT | 450 |
| AD-56044.1 | A-115209.1 | ccuuuucAAGuuGAGAAcAdTsdT | 335 | A-115210.1 | UGUUCUcAACUUGAAAAGGdTsdT | 451 |
| AD-55996.1 | A-115099.1 | uuucAAGuuGAGAAcAAAAdTsdT | 336 | A-115100.1 | UUUUGUUCUcAACUUGAAAdTsdT | 452 |
| AD-56002.1 | A-115101.1 | uucAAGuuGAGAAcAAAAAdTsdT | 337 | A-115102.1 | UUUUUGUUCUcAACUUGAAdTsdT | 453 |
| AD-55976.1 | A-115061.1 | cAAGuuGAGAAcAAAAAuudTsdT | 338 | A-115062.1 | AAUUUUGUUCUcAACUUGdTsdT | 454 |
| AD-56062.1 | A-115215.1 | AGuuGAGAAcAAAAAuuGGdTsdT | 339 | A-115216.1 | CcAAUUUUUGUUCUcAACUdTsdT | 455 |
| AD-56011.1 | A-115151.1 | GuuGAGAAcAAAAAuuGGGdTsdT | 340 | A-115152.1 | CCcAAUUUUUGUUCUcAACdTsdT | 456 |
| AD-56009.1 | A-115119.1 | uGAGAAcAAAAAuuGGGuudTsdT | 341 | A-115120.1 | AACCcAAUUUUUGUUCUcAdTsdT | 457 |
| AD-56020.1 | A-115107.1 | GAGAAcAAAAAuuGGGuuudTsdT | 342 | A-115108.1 | AAACCcAAUUUUUGUUCUcdTsdT | 458 |
| AD-55979.1 | A-115109.1 | GAAcAAAAAuuGGGuuuuAdTsdT | 343 | A-115110.1 | uAAAACCcAAUUUUUGUUCdTsdT | 459 |
| AD-55997.1 | A-115115.1 | AAcAAAAAuuGGGuuuuAAdTsdT | 344 | A-115116.1 | UuAAAACCcAAUUUUUGUUdTsdT | 460 |
| AD-56000.1 | A-115069.1 | AcAAAAAuuGGGuuuuAAAdTsdT | 345 | A-115070.1 | UUuAAAACCcAAUUUUUGUdTsdT | 461 |
| AD-56006.1 | A-115071.1 | cAAAAAuuGGGuuuuAAAAdTsdT | 346 | A-115072.1 | UUUuAAAACCcAAUUUUUGdTsdT | 462 |
| AD-55990.1 | A-115097.1 | AuuGGGuuuuAAAAuuAAAdTsdT | 347 | A-115098.1 | UUuAAUUUuAAAACCcAAUdTsdT | 463 |
| AD-55984.1 | A-115095.1 | uuGGGuuuuAAAAuuAAAGdTsdT | 348 | A-115096.1 | CUUuAAUUUuAAAACCcAAdTsdT | 464 |
| AD-55995.1 | A-115083.1 | uGGGuuuuAAAAuuAAAGudTsdT | 349 | A-115084.1 | ACUUuAAUUUuAAAACCcAdTsdT | 465 |
| AD-56004.1 | A-115133.1 | uuuAAAAuuAAAGuAuAcAdTsdT | 350 | A-115134.1 | UGuAuACUUuAAUUUuAAAdTsdT | 466 |
| AD-56042.1 | A-115177.1 | uuAAAAuuAAAGuAuAcAudTsdT | 351 | A-115178.1 | AUGuAuACUUuAAUUUuAAdTsdT | 467 |
| AD-55992.1 | A-115129.1 | uuGuAuuuAGuGucuuGAAdTsdT | 352 | A-115130.1 | UUcAAGAcACuAAAuAcAAdTsdT | 468 |

TABLE 4-continued

Modified Sense and Antisense Strand Sequences of AGT dsRNAs (19 mers)

| Duplex Name | Sense Name | Sense Sequence | SEQ ID NO. | Antisense Name | Antisense Sequence | SEQ ID NO. |
|---|---|---|---|---|---|---|
| AD-55977.1 | A-115077.1 | uGuAuuuAGuGucuuGAAudTsdT | 353 | A-115078.1 | AUUcAAGAcACuAAAuAcAdTsdT | 469 |
| AD-56005.1 | A-115149.1 | uAGuGucuuGAAuGuAAGAdTsdT | 354 | A-115150.1 | UCUuAcAUUcAAGAcACuAdTsdT | 470 |
| AD-56052.1 | A-115243.1 | cuuGAAuGuAAGAAcAuGAdTsdT | 355 | A-115244.1 | UcAUGUUCUuAcAUUcAAGdTsdT | 471 |
| AD-55985.1 | A-115111.1 | uuGAAuGuAAGAAcAuGAcdTsdT | 356 | A-115112.1 | GUcAUGUUCUuAcAUUcAAdTsdT | 472 |
| AD-56038.1 | A-115207.1 | cuuAGuuuuuccAcAGAudTsdT | 357 | A-115208.1 | AUCUGUGGAAAAAACuAAGdTsdT | 473 |
| AD-56023.1 | A-115155.1 | ccAcAGAuGcuuGuGAuuudTsdT | 358 | A-115156.1 | AAAUcAcAAGcAUCUGUGGdTsdT | 474 |
| AD-56018.1 | A-115075.1 | AcAGAuGcuuGuGAuuuuudTsdT | 359 | A-115076.1 | AAAAAUcAcAAGcAUCUGUdTsdT | 475 |
| AD-56060.1 | A-115183.1 | cuGAAuuucuGuuuGAAuGdTsdT | 360 | A-115184.1 | cAUUcAAAcAGAAAUUcAGdTsdT | 476 |
| AD-55993.1 | A-115145.1 | AAccAuAGcuGGuuAuuucdTsdT | 361 | A-115146.1 | GAAAuAACcAGCuAUGGUUdTsdT | 477 |
| AD-55986.1 | A-115127.1 | ccAuAGcuGGuuAuuucucdTsdT | 362 | A-115128.1 | GAGAAAuAACcAGCuAUGGdTsdT | 478 |

TABLE 5

AGT single dose screen in Hep3B cells

| | 10 nM Avg | 10 nM SD | 0.1 nM Avg | 0.1 nM SD | 0.01 nM Avg | 0.01 nM SD | Start relative to NM_000029.3 |
|---|---|---|---|---|---|---|---|
| AD-52457.1 | 9.4 | 0.6 | 13.3 | 1.3 | 15.1 | 2.3 | 2284 |
| AD-52438.1 | 3.4 | 0.1 | 12.2 | 1.8 | 17.7 | 1.7 | 1247 |
| AD-52463.1 | 9.8 | 0.9 | 16.9 | 2.9 | 19.3 | 2.1 | 2285 |
| AD-52433.1 | 7.4 | 1.5 | 14.4 | 1.0 | 24.8 | 1.3 | 2125 |
| AD-52439.1 | 15.1 | 1.1 | 23.9 | 0.2 | 29.9 | 1.4 | 2201 |
| AD-52449.1 | 5.7 | 0.6 | 22.7 | 1.2 | 42.4 | 5.3 | 841 |
| AD-52451.1 | 10.4 | 0.5 | 29.0 | 1.1 | 47.4 | 1.1 | 2283 |
| AD-52474.1 | 5.0 | 0.3 | 30.6 | 2.2 | 49.1 | 1.9 | 2081 |
| AD-52462.1 | 6.1 | 0.1 | 23.7 | 2.7 | 50.8 | 1.6 | 1595 |
| AD-52445.1 | 11.0 | 0.3 | 24.2 | 1.4 | 55.1 | 0.4 | 2279 |
| AD-52456.1 | 11.9 | 0.3 | 38.7 | 0.5 | 71.7 | 1.4 | 1587 |
| AD-52469.1 | 15.9 | 0.6 | 40.6 | 3.1 | 84.1 | 0.8 | 1767 |
| AD-52461.1 | 62.8 | 1.1 | 78.5 | 0.3 | 85.0 | 0.6 | 849 |
| AD-52443.1 | 16.9 | 0.0 | 49.4 | 2.0 | 88.4 | 3.0 | 828 |
| AD-52468.1 | 27.6 | 1.5 | 85.1 | 3.7 | 91.6 | 1.4 | 1879 |
| AD-52431.1 | 24.6 | 3.7 | 75.2 | 1.8 | 92.3 | 3.1 | 491 |
| AD-52444.1 | 67.0 | 2.8 | 74.4 | 0.3 | 94.1 | 0.2 | 1403 |
| AD-52455.1 | 57.0 | 0.5 | 89.5 | 4.1 | 94.4 | 1.6 | 844 |
| AD-52432.1 | 70.6 | 2.3 | 93.6 | 8.2 | 95.7 | 3.7 | 1214 |
| AD-52473.1 | 46.4 | 0.2 | 75.6 | 0.2 | 95.8 | 0.1 | 910 |
| AD-52450.1 | 20.3 | 1.7 | 53.0 | 2.5 | 96.3 | 4.8 | 1417 |
| AD-52437.1 | 36.3 | 4.1 | 86.6 | 0.6 | 96.6 | 0.9 | 643 |
| AD-52467.1 | 59.5 | 0.8 | 94.5 | 1.7 | 102.9 | 5.1 | 863 |
| AD-55976.1 | | | 3.6 | 5.8 | | | 2323 |
| AD-55977.1 | | | 77.2 | 70.0 | | | 2385 |
| AD-55978.1 | | | 8.3 | 11.8 | | | 2202 |
| AD-55979.1 | | | 7.7 | 9.1 | | | 2331 |
| AD-55980.1 | | | 14.1 | 17.4 | | | 1729 |
| AD-55981.1 | | | 21.2 | 29.4 | | | 1566 |
| AD-56023.1 | | | 74.1 | 77.1 | | | 2450 |
| AD-56024.1 | | | 17.6 | 27.8 | | | 2082 |
| AD-56025.1 | | | 66.5 | 75.0 | | | 855 |
| AD-56026.1 | | | 13.7 | 20.2 | | | 1601 |
| AD-56027.1 | | | 16.9 | 22.2 | | | 2227 |
| AD-56028.1 | | | 63.8 | 74.0 | | | 1728 |
| AD-55982.1 | | | 22.9 | 26.1 | | | 2290 |
| AD-55983.1 | | | 6.2 | 8.7 | | | 1605 |
| AD-55984.1 | | | 52.0 | 59.9 | | | 2340 |
| AD-55985.1 | | | 70.1 | 65.1 | | | 2398 |
| AD-55986.1 | | | 80.5 | 79.3 | | | 2521 |
| AD-55987.1 | | | 12.5 | 15.5 | | | 2230 |
| AD-56029.1 | | | 51.3 | 62.2 | | | 1741 |
| AD-56030.1 | | | 53.3 | 58.0 | | | 822 |
| AD-56031.1 | | | 38.1 | 43.7 | | | 2204 |
| AD-56032.1 | | | 12.6 | 15.3 | | | 1570 |
| AD-56033.1 | | | 99.8 | 100.7 | | | 1408 |
| AD-56034.1 | | | 87.8 | 93.0 | | | 825 |
| AD-55988.1 | | | 46.4 | 49.5 | | | 2292 |
| AD-55989.1 | | | 5.8 | 9.7 | | | 1251 |
| AD-55990.1 | | | 6.5 | 5.0 | | | 2339 |
| AD-55991.1 | | | 50.4 | 38.2 | | | 2080 |
| AD-55992.1 | | | 76.4 | 60.5 | | | 2384 |
| AD-55993.1 | | | 66.5 | 62.9 | | | 2519 |
| AD-56035.1 | | | 17.9 | 17.6 | | | 1592 |
| AD-56036.1 | | | 47.7 | 59.9 | | | 1735 |
| AD-56037.1 | | | 80.8 | 83.5 | | | 2199 |
| AD-56038.1 | | | 84.8 | 90.4 | | | 2439 |
| AD-56039.1 | | | 47.9 | 66.7 | | | 2070 |
| AD-56040.1 | | | 95.0 | 98.3 | | | 1260 |
| AD-55994.1 | | | 3.6 | 5.5 | | | 2294 |
| AD-55995.1 | | | 31.4 | 47.8 | | | 2341 |
| AD-55996.1 | | | 5.1 | 5.0 | | | 2320 |
| AD-55997.1 | | | 83.3 | 76.6 | | | 2332 |
| AD-55999.1 | | | 74.6 | 75.0 | | | 2203 |
| AD-56041.1 | | | 21.9 | 21.4 | | | 485 |
| AD-56042.1 | | | 73.3 | 73.5 | | | 2347 |
| AD-56043.1 | | | 53.1 | 57.8 | | | 2266 |
| AD-56044.1 | | | 12.0 | 13.9 | | | 2317 |
| AD-56045.1 | | | 41.7 | 48.8 | | | 1885 |
| AD-56046.1 | | | 83.0 | 90.1 | | | 1002 |
| AD-56000.1 | | | 13.3 | 20.3 | | | 2333 |
| AD-56001.1 | | | 4.7 | 5.7 | | | 2268 |
| AD-56002.1 | | | 5.4 | 6.6 | | | 2321 |
| AD-56003.1 | | | 4.2 | 4.4 | | | 2307 |
| AD-56004.1 | | | 54.0 | 68.5 | | | 2346 |
| AD-56005.1 | | | 60.2 | 62.2 | | | 2391 |
| AD-56047.1 | | | 24.7 | 28.2 | | | 635 |
| AD-56048.1 | | | 7.1 | 7.4 | | | 2306 |
| AD-56049.1 | | | 73.0 | 62.6 | | | 2200 |
| AD-56050.1 | | | 96.4 | 102.1 | | | 2206 |
| AD-56051.1 | | | 17.4 | 23.0 | | | 2314 |
| AD-56052.1 | | | 85.1 | 102.5 | | | 2397 |
| AD-56006.1 | | | 8.1 | 10.7 | | | 2334 |
| AD-56007.1 | | | 17.8 | 19.1 | | | 1738 |
| AD-56008.1 | | | 5.4 | 4.8 | | | 2304 |
| AD-56009.1 | | | 12.2 | 14.4 | | | 2328 |

TABLE 5-continued

AGT single dose screen in Hep3B cells

| | 10 nM Avg | 10 nM SD | 0.1 nM Avg | 0.1 nM SD | 0.01 nM Avg | 0.01 nM SD | Start relative to NM_000029.3 |
|---|---|---|---|---|---|---|---|
| AD-56010.1 | | | 62.1 | 69.0 | | | 1891 |
| AD-56011.1 | | | 35.3 | 40.3 | | | 2326 |
| AD-56053.1 | | | 5.0 | 6.7 | | | 1810 |
| AD-56054.1 | | | 30.9 | 35.5 | | | 1591 |
| AD-56055.1 | | | 61.4 | 50.9 | | | 1740 |
| AD-56056.1 | | | 83.6 | 94.0 | | | 1887 |
| AD-56057.1 | | | 85.7 | 97.9 | | | 606 |
| AD-56058.1 | | | 68.6 | 87.4 | | | 1413 |
| AD-56012.1 | | | 35.0 | 47.1 | | | 1739 |
| AD-56013.1 | | | 49.2 | 57.6 | | | 2296 |
| AD-56014.1 | | | 54.4 | 60.3 | | | 1737 |
| AD-56015.1 | | | 42.2 | 46.7 | | | 1892 |
| AD-56016.1 | | | 11.2 | 15.6 | | | 1249 |
| AD-56017.1 | | | 10.6 | 12.9 | | | 834 |
| AD-56059.1 | | | 37.3 | 45.2 | | | 1248 |
| AD-56060.1 | | | 94.1 | 94.3 | | | 2497 |
| AD-56061.1 | | | 99.8 | 94.6 | | | 878 |
| AD-56062.1 | | | 19.2 | 32.2 | | | 2325 |
| AD-56063.1 | | | 102.2 | 102.8 | | | 911 |
| AD-56064.1 | | | 80.2 | 92.3 | | | 644 |
| AD-56018.1 | | | 72.0 | 74.5 | | | 2452 |
| AD-56019.1 | | | 25.2 | 27.7 | | | 2291 |
| AD-56020.1 | | | 10.2 | 15.3 | | | 2329 |
| AD-56021.1 | | | 36.0 | 40.9 | | | 658 |
| AD-56022.1 | | | 37.5 | 52.7 | | | 1602 |
| AD-56065.1 | | | 56.5 | 71.9 | | | 2299 |
| AD-56066.1 | | | 12.3 | 18.9 | | | 1572 |
| AD-56067.1 | | | 64.9 | 81.8 | | | 741 |
| AD-56068.1 | | | 68.6 | 82.1 | | | 1250 |
| AD-56069.1 | | | 48.9 | 72.7 | | | 1277 |

TABLE 6

AGT IC$_{50}$ data in Hep3B Cells

| Duplex Name | IC$_{50}$ (nM) |
|---|---|
| AD-52431 | 5.719 |
| AD-52432 | >10 nM |
| AD-52433 | 0.057 |
| AD-52437 | >10 nM |
| AD-52438 | 0.063 |
| AD-52439 | 0.192 |
| AD-52443 | 0.504 |
| AD-52444 | >10 nM |
| AD-52445 | 0.183 |
| AD-52449 | 0.211 |
| AD-52450 | 2.052 |
| AD-52451 | 0.318 |
| AD-52455 | >10 nM |
| AD-52456 | 1.569 |
| AD-52461 | >10 nM |
| AD-52462 | 0.242 |
| AD-52463 | 0.112 |
| AD-52467 | >10 nM |
| AD-52468 | >10 nM |
| AD-52469 | 0.540 |
| AD-52473 | >10 nM |
| AD-52474 | 0.323 |
| AD-55983 | 0.017 |
| AD-55983 | 0.020 |
| AD-55989 | 0.017 |
| AD-55989 | 0.019 |
| AD-56016 | 0.018 |
| AD-56016 | 0.019 |
| AD-56017 | 0.027 |
| AD-56017 | 0.031 |
| AD-56053 | 0.007 |
| AD-56053 | 0.009 |

TABLE 7

Unmodified Sense and Antisense Strand Sequences of AGT dsRNAs (21/23 mers)

| Duplex Name | Position relative to NM_000029.3 | Sense Name | Sense Sequence | SEQ ID NO. |
|---|---|---|---|---|
| UM AD-60803.1 | 830-850 | A-122599.1 | CGGGAUGCUGGCCAACUUCUU | 479 |
| UM AD-60775.1 | 843-863 | A-122541.1 | AACUUCUUGGGCUUCCGUAUA | 480 |
| UM AD-60779.1 | 855-875 | A-122605.1 | UUCCGUAUAUAUGGCAUGCAA | 481 |
| UM AD-60797.1 | 857-877 | A-122581.1 | CCGUAUAUAUGGCAUGCACAA | 482 |
| UM AD-60806.1 | 880-900 | A-122585.1 | AGCUAUGGGGCGUGGUCCAUA | 483 |
| UM AD-60787.1 | 912-932 | A-122577.1 | CUCUCCCCAACGGCUGUCUUU | 484 |
| UM AD-60807.1 | 913-933 | A-122601.1 | UCUCCCCAACGGCUGUCUUUA | 485 |
| UM AD-60794.1 | 1276-1296 | A-122611.1 | UGCAGGCUGUGACAGGAUGGA | 486 |
| UM AD-60796.1 | 1568-1588 | A-122565.1 | CCUGGACAAGGUGGAGGGUCU | 487 |
| UM AD-60778.1 | 1572-1592 | A-122589.1 | GACAAGGUGGAGGGUCUCACU | 488 |
| UM AD-60792.1 | 1574-1594 | A-122579.1 | CAAGGUGGAGGGUCUCACUUU | 489 |
| UM AD-60772.1 | 1594-1614 | A-122571.1 | UCCAGCAAAACUCCCUCAACU | 490 |
| UM AD-60773.1 | 1603-1623 | A-122587.1 | ACUCCCUCAACUGGAUGAAGA | 491 |
| UM AD-60782.1 | 1737-1757 | A-122575.1 | CUGAACCUGCAAAAAUUGAGA | 492 |
| UM AD-60800.1 | 1739-1759 | A-122551.1 | GAACCUGCAAAAAUUGAGCAA | 493 |
| UM AD-60785.1 | 1741-1761 | A-122545.1 | ACCUGCAAAAAUUGAGCAAUA | 494 |

TABLE 7-continued

Unmodified Sense and Antisense Strand Sequences of AGT dsRNAs (21/23 mers)

| | | | | |
|---|---|---|---|---|
| UM AD-60802.1 | 1742-1762 | A-122583.1 | CCUGCAAAAAUUGAGCAAUGA | 495 |
| UM AD-60799.1 | 1812-1832 | A-122613.1 | GCGGAUGAGAGAGAGCCCACA | 496 |
| UM AD-60781.1 | 1894-1914 | A-122559.1 | UGUUUGCUGUGUAUGAUCAAA | 497 |
| UM AD-60793.1 | 2072-2092 | A-122595.1 | CACCCCCAGUCUCCCACCUUU | 498 |
| UM AD-60784.1 | 2081-2101 | A-122607.1 | UCUCCCACCUUUUCUUCUAAU | 499 |
| UM AD-60777.1 | 2084-2104 | A-122573.1 | CCCACCUUUUCUUCUAAUGAA | 500 |
| UM AD-60795.1 | 2270-2290 | A-122549.1 | UCCAAAAAGAAUUCCAACCGA | 501 |
| UM AD-60783.1 | 2281-2301 | A-122591.1 | UUCCAACCGACCAGCUUGUUU | 502 |
| UM AD-60788.1 | 2286-2306 | A-122593.1 | ACCGACCAGCUUGUUUGUGAA | 503 |
| UM AD-60789.1 | 2291-2311 | A-122609.1 | CCAGCUUGUUUGUGAAACAAA | 504 |
| UM AD-60770.1 | 2292-2312 | A-122539.1 | CAGCUUGUUUGUGAAACAAAA | 505 |
| UM AD-60776.1 | 2309-2329 | A-122557.1 | AAAAAGUGUUCCCUUUUCAA | 506 |
| UM AD-60798.1 | 2316-2336 | A-122597.1 | UGUUCCCUUUUCAAGUUGAGA | 507 |
| UM AD-60801.1 | 2328-2348 | A-122567.1 | AAGUUGAGAACAAAAAUUGGA | 508 |
| UM AD-60791.1 | 2329-2349 | A-122563.1 | AGUUGAGAACAAAAAUUGGGU | 509 |
| UM AD-60771.1 | 2334-2354 | A-122555.1 | AGAACAAAAAUUGGGUUUUAA | 510 |
| UM AD-60780.1 | 2335-2355 | A-122543.1 | GAACAAAAAUUGGGUUUUAAA | 511 |
| UM AD-60786.1 | 2386-2406 | A-122561.1 | GUUUGUAUUUAGUGUCUUGAA | 512 |
| UM AD-60790.1 | 2387-2407 | A-122547.1 | UUUGUAUUUAGUGUCUUGAAU | 513 |
| UM AD-60774.1 | 2399-2419 | A-122603.1 | GUCUUGAAUGUAAGAACAUGA | 514 |
| UM AD-60804.1 | 2400-2420 | A-122553.1 | UCUUGAAUGUAAGAACAUGAA | 515 |
| UM AD-60805.1 | 2452-2472 | A-122569.1 | UUCCACAGAUGCUUGUGAUUU | 516 |

| Antisense Name | Position relative to NM_000029.3 | Antisense Sequence | SEQ ID NO. |
|---|---|---|---|
| A-122600.1 | 828-850 | AAGAAGUUGGCCAGCAUCCCGAC | 517 |
| A-122542.1 | 841-863 | UAUACGGAAGCCCAAGAAGUUGG | 518 |
| A-122606.1 | 853-875 | UUGCAUGCCAUAUAUACGGAAGC | 519 |
| A-122582.1 | 855-877 | UUGUGCAUGCCAUAUAUACGGAA | 520 |
| A-122586.1 | 878-900 | UAUGGACCACGCCCCAUAGCUCA | 521 |
| A-122578.1 | 910-932 | AAAGACAGCCGUUGGGGAGAGGA | 522 |
| A-122602.1 | 911-933 | UAAAGACAGCCGUUGGGGAGAGG | 523 |
| A-122612.1 | 1274-1296 | UCCAUCCUGUCACAGCCUGCAUG | 524 |
| A-122566.1 | 1566-1588 | AGACCCUCCACCUUGUCCAGGUC | 525 |
| A-122590.1 | 1570-1592 | AGUGAGACCCUCCACCUUGUCCA | 526 |
| A-122580.1 | 1572-1594 | AAAGUGAGACCCUCCACCUUGUC | 527 |
| A-122572.1 | 1592-1614 | AGUUGAGGGAGUUUUGCUGGAAA | 528 |
| A-122588.1 | 1601-1623 | UCUUCAUCCAGUUGAGGGAGUUU | 529 |
| A-122576.1 | 1735-1757 | UCUCAAUUUUUGCAGGUUCAGCU | 530 |
| A-122552.1 | 1737-1759 | UUGCUCAAUUUUUGCAGGUUCAG | 531 |

TABLE 7-continued

Unmodified Sense and Antisense Strand Sequences of AGT dsRNAs (21/23 mers)

| | | | |
|---|---|---|---|
| A-122546.1 | 1739-1761 | UAUUGCUCAAUUUUUGCAGGUUC | 532 |
| A-122584.1 | 1740-1762 | UCAUUGCUCAAUUUUUGCAGGUU | 533 |
| A-122614.1 | 1810-1832 | UGUGGGCUCUCUCUCAUCCGCUU | 534 |
| A-122560.1 | 1892-1914 | UUUGAUCAUACACAGCAAACAGG | 535 |
| A-122596.1 | 2070-2092 | AAAGGUGGGAGACUGGGGUGAC | 536 |
| A-122608.1 | 2079-2101 | AUUAGAAGAAAAGGUGGGAGACU | 537 |
| A-122574.1 | 2082-2104 | UUCAUUAGAAGAAAAGGUGGGAG | 538 |
| A-122550.1 | 2268-2290 | UCGGUUGGAAUUCUUUUUGGAAC | 539 |
| A-122592.1 | 2279-2301 | AAACAAGCUGGUCGGUUGGAAUU | 540 |
| A-122594.1 | 2284-2306 | UUCACAAACAAGCUGGUCGGUUG | 541 |
| A-122610.1 | 2289-2311 | UUUGUUUCACAAACAAGCUGGUC | 542 |
| A-122540.1 | 2290-2312 | UUUUGUUUCACAAACAAGCUGGU | 543 |
| A-122558.1 | 2307-2329 | UUGAAAAGGGAACACUUUUUUGU | 544 |
| A-122598.1 | 2314-2336 | UCUCAACUUGAAAAGGGAACACU | 545 |
| A-122568.1 | 2326-2348 | UCCAAUUUUUGUUCUCAACUUGA | 546 |
| A-122564.1 | 2327-2349 | ACCCAAUUUUUGUUCUCAACUUG | 547 |
| A-122556.1 | 2332-2354 | UUAAAACCCAAUUUUUGUUCUCA | 548 |
| A-122544.1 | 2333-2355 | UUUAAAACCCAAUUUUUGUUCUC | 549 |
| A-122562.1 | 2384-2406 | UUCAAGACACUAAAUACAAACCG | 550 |
| A-122548.1 | 2385-2407 | AUUCAAGACACUAAAUACAAACC | 551 |
| A-122604.1 | 2397-2419 | UCAUGUUCUUACAUUCAAGACAC | 552 |
| A-122554.1 | 2398-2420 | UUCAUGUUCUUACAUUCAAGACA | 553 |
| A-122570.1 | 2450-2472 | AAAUCACAAGCAUCUGUGGAAAA | 554 |

TABLE 8

Modified Sense and Antisense Strand Sequences of AGT dsRNAs (21/23mers)

| Duplex Name | Sense Name | Sense Sequence | SEQ ID NO. |
|---|---|---|---|
| AD-60770.1 | A-122539.1 | CfsasGfcUfuGfuUfUfGfuGfaAfaCfaAfaAfL96 | 555 |
| AD-60771.1 | A-122555.1 | AfsgsAfaCfaAfaAfAfUfuGfgGfuUfuUfaAfL96 | 556 |
| AD-60772.1 | A-122571.1 | UfscsCfaGfcAfaAfAfCfuCfcCfuCfaAfcUfL96 | 557 |
| AD-60773.1 | A-122587.1 | AfscsUfcCfcUfcAfAfCfuGfgAfuGfaAfgAfL96 | 558 |
| AD-60774.1 | A-122603.1 | GfsusCfuUfgAfaUfGfUfaAfgAfaCfaUfgAfL96 | 559 |
| AD-60775.1 | A-122541.1 | AfsasCfuUfcUfuGfGfGfcUfcCfgUfaAfuAfL96 | 560 |
| AD-60776.1 | A-122557.1 | AfsasAfaAfaGfuGfUfUfcCfcUfuUfuCfaAfL96 | 561 |
| AD-60777.1 | A-122573.1 | CfscsCfaCfcUfuUfUfCfuUfcUfaAfuGfaAfL96 | 562 |
| AD-60778.1 | A-122589.1 | GfsasCfaAfgGfuGfGfAfgGfgUfcUfcAfcUfL96 | 563 |
| AD-60779.1 | A-122605.1 | UfsusCfcGfuAfuAfFfAfuGfgCfaUfgCfaAfL96 | 564 |
| AD-60780.1 | A-122543.1 | GfsasAfcAfaAfaAfUfUfgGfgUfuUfaAfaAfL96 | 565 |

TABLE 8-continued

Modified Sense and Antisense Strand Sequences of AGT dsRNAs (21/23mers)

| | | | |
|---|---|---|---|
| AD-60781.1 | A-122559.1 | UfsgsUfuUfgCfuGfUfGfuAfuGfaUfcAfaAfL96 | 566 |
| AD-60782.1 | A-122575.1 | CfsusGfaAfcCfuGfCfAfaAfaAfuUfgAfgAfL96 | 567 |
| AD-60783.1 | A-122591.1 | UfsusCfcAfaCfcGfAfCfcAfgCfuUfgUfuUfL96 | 568 |
| AD-60784.1 | A-122607.1 | UfscsUfcCfcAfcCfUfUfuUfcUfuCfuAfaUfL96 | 569 |
| AD-60785.1 | A-122545.1 | AfscsCfuGfcAfaAfAfAfuUfgAfgCfaAfuAfL96 | 570 |
| AD-60786.1 | A-122561.1 | GfsusUfuGfuAfuUfUfAfgUfgUfcUfuGfaaAfL96 | 571 |
| AD-60787.1 | A-122577.1 | CfsusCfuCfcCfcAfaAfCfgGfcUfgUfcUfuUfL96 | 572 |
| AD-60788.1 | A-122593.1 | AfscsCfgAfcCfaGfCfUfuGfuUfuGfuGfaAfL96 | 573 |
| AD-60789.1 | A-122609.1 | CfscsAfgCfuUfgUfUfUfgUfgAfaAfcAfaAfL96 | 574 |
| AD-60790.1 | A-122547.1 | UfsusUfgUfaUfuUfAfGfuGfuCfuUfgAfaUfL96 | 575 |
| AD-60791.1 | A-122563.1 | AfsgsUfuGfaGfaAfCfAfaAfaAfuUfgGfuUfL96 | 576 |
| AD-60792.1 | A-122579.1 | CfsasAfgGfuGfgAfGfGfgUfcUfcAfcUfuUfL96 | 577 |
| AD-60793.1 | A-122595.1 | CfsasCfcCfcCfaGfUfCfuCfcCfaCfcUfuUfL96 | 578 |
| AD-60794.1 | A-122611.1 | UfsgsCfaGfgCfuGfUfGfaCfaGfgAfuGfgAfL96 | 579 |
| AD-60795.1 | A-122549.1 | UfscsCfaAfaAfaGfAfAfuUfcCfaAfcCfgAfL96 | 580 |
| AD-60796.1 | A-122565.1 | CfscsUfgGfaCfaAfGfGfuGfaAfgGfgUfcUfL96 | 581 |
| AD-60797.1 | A-122581.1 | CfscsGfuAfuAfuAfUfgGfgCfaUfgCfaCfaAfL96 | 582 |
| AD-60798.1 | A-122597.1 | UfsgsUfuCfcCfuUfUfUfcAfaGfuUfgAfgAfL96 | 583 |
| AD-60799.1 | A-122613.1 | GfscsGfaUfgAfaAfGfaGfaGfcCfcAfcAfL96 | 584 |
| AD-60800.1 | A-122551.1 | GfsasAfcCfuGfcAfAfAfaAfuUfgAfgCfaAfL96 | 585 |
| AD-60801.1 | A-122567.1 | AfsasGfuUfgAfgAfAfCfaAfaAfaUfuGfgAfL96 | 586 |
| AD-60802.1 | A-122583.1 | CfscsUfgCfaAfaAfUfuGfaGfcAfaUfgAfL96 | 587 |
| AD-60803.1 | A-122599.1 | CfsgsGfgAfuGfcUfGfGfcCfaAfcUfcUfuUfL96 | 588 |
| AD-60804.1 | A-122553.1 | UfscsUfgAfaUfgUfAfaGfaAfcAfuGfaAfL96 | 589 |
| AD-60805.1 | A-122569.1 | UfsusCfcAfcAfgAfUfGfcUfuGfuGfaUfuUfL96 | 590 |
| AD-60806.1 | A-122585.1 | AfsgsCfuAfuGfgGfGfCfgUfgGfuCfcAfuAfL96 | 591 |
| AD-60807.1 | A-122601.1 | UfscsUfcCfcCfaAfCfGfgCfuGfuCfuUfuAfL96 | 592 |

| Antisense Name | Antisense Sequence | SEQ ID NO. |
|---|---|---|
| A-122540.1 | usUfsuUfgUfuUfcAfcaaAfcAfaGfcUfgsgsu | 593 |
| A-122556.1 | usUfsaAfaAfcCfcAfauuUfuUfgUfuCfuscsa | 594 |
| A-122572.1 | asGfsuUfgAfgGfgAfguuUfuGfcUfgGfasasa | 595 |
| A-122588.1 | usCfsuUfcAfuCfcAfguuGfaGfgGfaGfususu | 596 |
| A-122604.1 | usCfsaUfgUfuCfuUfacaUfuCfaAfgAfcsasc | 597 |
| A-122542.1 | usAfsuAfcGfgAfaGfcccAfaGfaAfgUfusgsg | 598 |
| A-122558.1 | usUfsgAfaAfaGfgGfaacAfcUfuUfuUfusgsu | 599 |
| A-122574.1 | usUfscAfuUfaGfaAfgaaAfaGfgUfgGfgsasg | 600 |
| A-122590.1 | asGfsuGfaGfaCfcCfuccAfcCfuUfgUfcscsa | 601 |
| A-122606.1 | usUfsgCfaUfgCfcAfuauAfuAfcGfgAfasgsc | 602 |
| A-122544.1 | usUfsuAfaAfaCfcCfaauUfuUfuGfuUfcsusc | 603 |

TABLE 8-continued

Modified Sense and Antisense Strand Sequences of AGT dsRNAs (21/23mers)

| | | |
|---|---|---|
| A-122560.1 | usUfsuGfaUfcAfuAfcacAfgCfaAfaCfasgsg | 604 |
| A-122576.1 | usCfsuCfaAfuUfuUfugcAfgGfuUfcAfgscsu | 605 |
| A-122592.1 | asAfsaCfaAfgCfuGfgucGfgUfuGfgAfasusu | 606 |
| A-122608.1 | asUfsuAfgAfaGfaAfaagGfuGfgGfaGfascsu | 607 |
| A-122546.1 | usAfsuUfgCfuCfaAfuuuUfuGfcAfgGfususc | 608 |
| A-122562.1 | usUfscAfaGfaCfaCfuaaAfuAfcAfaAfcscsg | 609 |
| A-122578.1 | asAfsaGfaCfaGfcCfguuGfgGfaAfgAfgsgsa | 610 |
| A-122594.1 | usUfscAfcAfaAfcAfagcUfgGfuCfgGfususg | 611 |
| A-122610.1 | usUfsuGfuUfuCfaCfaaaCfaAfgCfuGfgsusc | 612 |
| A-122548.1 | asUfsuCfaAfgAfcAfcuaAfaUfaCfaAfascsc | 613 |
| A-122564.1 | asCfscCfaAfuUfuUfuguUfcUfcAfaCfususg | 614 |
| A-122580.1 | asAfsaGfuGfaGfaCfccuCfcAfcCfuUfgsusc | 615 |
| A-122596.1 | asAfsaGfgUfgGfgAfgacUfgGfgGfuGfgsasc | 616 |
| A-122612.1 | usCfscAfuCfcUfgUfcacAfgCfcUfgCfasusg | 617 |
| A-122550.1 | usCfsgGfuUfgGfaAfuucUfuUfuUfgGfasasc | 618 |
| A-122566.1 | asGfsaCfcCfuCfcAfccuUfgUfcCfaGfgsusc | 619 |
| A-122582.1 | usUfsgUfgCfaUfgCfcauAfuAfuAfcGfgsasa | 620 |
| A-122598.1 | usCfsuCfaAfcUfuGfaaaAfgGfgAfaCfascsu | 621 |
| A-122614.1 | usGfsuGfgCfuCfucUfcAfuCfcGfcsusu | 622 |
| A-122552.1 | usUfsgCfuCfaAfuUfuuuGfcAfgGfuUfcsasg | 623 |
| A-122568.1 | usCfscAfaUfuUfuUfguuCfuCfaAfcUfusgsa | 624 |
| A-122584.1 | usCfsaUfuGfcUfcAfauuUfuUfgCfaGfgsusu | 625 |
| A-122600.1 | asAfsgAfaGfuUfgGfccaGfcAfuCfcCfgsasc | 626 |
| A-122554.1 | usUfscAfuGfuUfcUfuacAfuUfcAfaGfascsa | 627 |
| A-122570.1 | asAfsaUfcAfcAfaGfcauCfuGfuGfgAfasasa | 628 |
| A-122586.1 | usAfsuGfgAfcCfaCfgccCfcAfuAfgCfuscsa | 629 |
| A-122602.1 | usAfsaAfgAfcAfgCfcguUfgGfgGfaGfasgsg | 630 |

TABLE 9

AGT single dose screen in Hep3B cells (21/23mers)

| Duplex Name | 10 nM Avg | 10 nM SD | 0.1 nM Avg | 0.1 nM SD | Start position relative to NM_000029.3 |
|---|---|---|---|---|---|
| AD-60770.1 | 4.7 | 0.7 | 27.4 | 7.4 | 2292 |
| AD-60771.1 | 4.6 | 1.2 | 10.9 | 5.9 | 2334 |
| AD-60772.1 | 14.8 | 7.9 | 63.7 | 13.2 | 1594 |
| AD-60773.1 | 43.9 | 8.7 | 88.8 | 5.4 | 1603 |
| AD-60774.1 | 64.0 | 3.8 | 79.1 | 4.2 | 2399 |
| AD-60775.1 | 8.4 | 2.8 | 62.2 | 8.8 | 843 |
| AD-60776.1 | 5.9 | 2.8 | 11.1 | 5.1 | 2309 |
| AD-60777.1 | 4.3 | 1.7 | 26.7 | 5.3 | 2084 |
| AD-60778.1 | 11.5 | 7.4 | 52.5 | 15.5 | 1572 |
| AD-60779.1 | 5.2 | 2.8 | 24.1 | 4.1 | 855 |
| AD-60780.1 | 5.7 | 2.3 | 12.0 | 5.2 | 2335 |
| AD-60781.1 | 6.9 | 2.1 | 18.5 | 3.1 | 1894 |
| AD-60782.1 | 9.2 | 5.0 | 47.0 | 8.6 | 1737 |
| AD-60783.1 | 15.9 | 9.0 | 35.7 | 7.6 | 2281 |
| AD-60784.1 | 5.6 | 1.0 | 12.3 | 2.5 | 2081 |
| AD-60785.1 | 6.1 | 0.9 | 29.7 | 13.7 | 1741 |
| AD-60786.1 | 56.9 | 5.4 | 74.0 | 5.1 | 2386 |
| AD-60787.1 | 94.4 | 0.7 | 104.4 | 6.0 | 912 |
| AD-60788.1 | 10.5 | 3.6 | 49.8 | 4.8 | 2286 |
| AD-60789.1 | 5.2 | 2.0 | 25.3 | 16.0 | 2291 |
| AD-60790.1 | 70.4 | 3.3 | 86.3 | 19.7 | 2387 |
| AD-60791.1 | 7.8 | 3.7 | 33.4 | 18.0 | 2329 |
| AD-60792.1 | 17.0 | 3.3 | 72.8 | 9.0 | 1574 |
| AD-60793.1 | 18.4 | 5.6 | 58.3 | 12.5 | 2072 |
| AD-60794.1 | 54.3 | 11.5 | 101.6 | 4.3 | 1276 |
| AD-60795.1 | 6.2 | 3.4 | 36.3 | 8.6 | 2270 |

TABLE 9-continued

AGT single dose screen in Hep3B cells (21/23mers)

| Duplex Name | 10 nM Avg | 10 nM SD | 0.1 nM Avg | 0.1 nM SD | Start position relative to NM_000029.3 |
|---|---|---|---|---|---|
| AD-60796.1 | 41.6 | 3.3 | 100.9 | 8.6 | 1568 |
| AD-60797.1 | 72.5 | 2.8 | 97.1 | 6.1 | 857 |
| AD-60798.1 | 13.2 | 4.8 | 29.1 | 16.4 | 2316 |
| AD-60799.1 | 29.7 | 7.5 | 86.2 | 4.2 | 1812 |
| AD-60800.1 | 31.0 | 7.5 | 81.8 | 11.2 | 1739 |
| AD-60801.1 | 10.9 | 2.2 | 35.4 | 11.3 | 2328 |
| AD-60802.1 | 14.8 | 5.5 | 52.8 | 9.7 | 1742 |
| AD-60803.1 | 29.2 | 10.9 | 71.4 | 9.6 | 830 |
| AD-60804.1 | 39.2 | 2.9 | 75.6 | 6.1 | 2400 |
| AD-60805.1 | 60.3 | 10.1 | 97.4 | 2.3 | 2452 |
| AD-60806.1 | 89.3 | 11.8 | 92.8 | 6.5 | 880 |
| AD-60807.1 | 64.1 | 3.7 | 91.5 | 10.1 | 913 |

TABLE 10

AGT $IC_{50}$ data in Hep3B Cells (21/23mers)

| Duplex Name | $IC_{50}$ (nM) |
|---|---|
| AD-60771.1 | 0.028 |
| AD-60776.1 | 0.033 |
| AD-60780.1 | 0.038 |
| AD-60784.1 | 0.045 |
| AD-60781.1 | 0.089 |

Example 2. In Vivo AGT Silencing—Amelioration of Preeclamptic Sequelae

Transgenic female Sprague-Dawley rats harboring the complete genomic human AGT gene (e.g., [TGR(hAGT) L1623] (see, e.g., Bohlender J, et al. (1996) *Hypertension* 27: 535-540 and Bohlender J, et al. (2000) *J Am Soc Nephrol* 11: 2056-2061)) were surgically implemented with a device for measuring blood pressure by telemetry. Subsequent to recovery from the procedure, these rats were mated with transgenic male Sprague-Dawley rats harboring the entire genomic human REN gene (e.g., [TGR(hREN)L10J] (see, e.g., Bohlender J, et al. (1997) Hypertension 29: 428-434 and Bohlender J, et al. (2000) *J Am Soc Nephrol* 11: 2056-2061)). The female progeny of this cross (referred to herein as "PE rats") are a model of preeclampsia and develop albuminuria and intrauterine growth restriction (IUGR), and have a blood pressure spike beginning around gestation day 13 (see, e.g., FIG. 2A).

Beginning on day 3 of gestation, a subset of pregnant PE rats was administered 10 mg/kg siRNA targeting hAGT (AD-60771). A second subset of pregnant PE rats were left untreated as a control. Dosing continued every third day to gestation day 15. Rats were sacrificed on about day 19 of gestation, and blood and tissue samples were collected from the mothers and the fetuses.

Figure 2B:
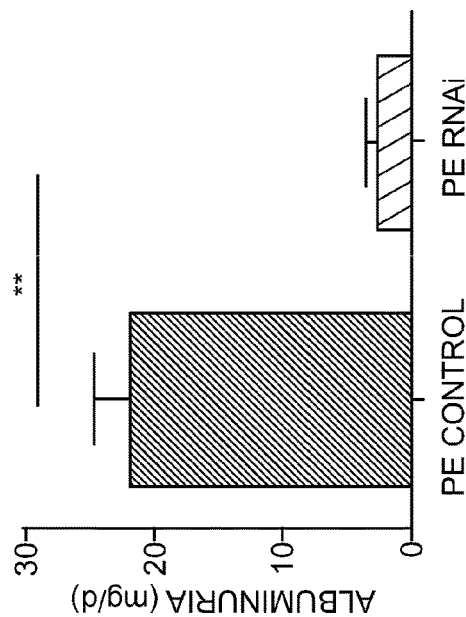
FIG. 2B is a graph depicting reduction of serum albumin in pregnant transgenic rats following administration of AD-60771.
Figure 2A:
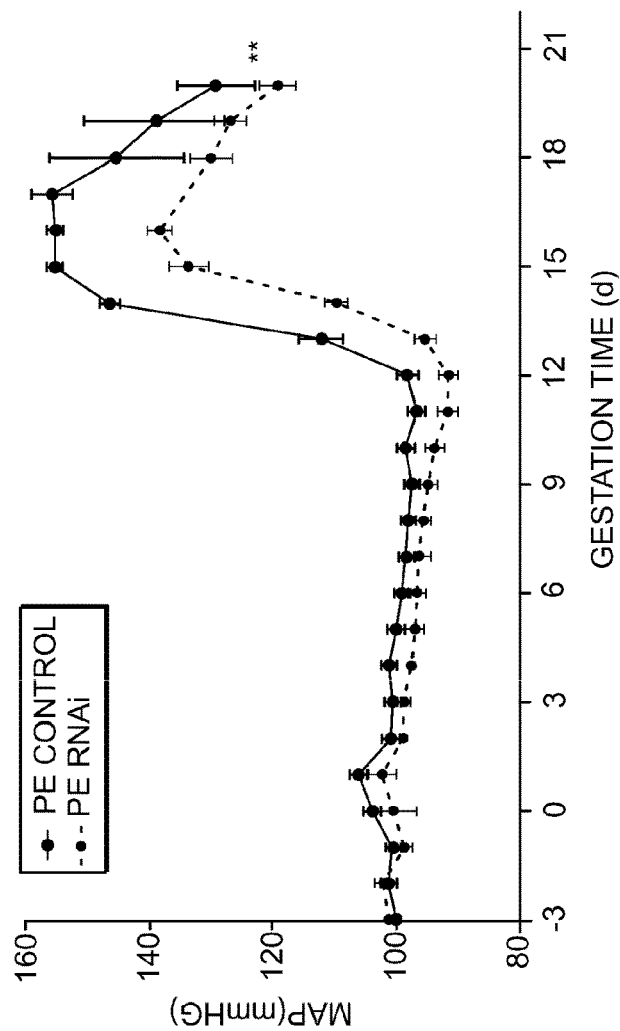
FIG. 2A is a graph depicting the reduction in mean arterial blood pressure in pregnant transgenic rats following administration of AD-60771.

Maternal blood pressure was monitored throughout the experiment via surgically implemented devices for measuring blood pressure by telemetry. FIG. 2A shows that following administration of AD-60771, maternal mean arterial blood pressure was significantly lowered. In addition, as determined by ELISA analysis of serum albumin, maternal albuminuria was significantly reduced following administration of AD-60771 (FIG. 2B). These two conditions are the hallmarks of preeclampsia. The reduced blood pressure reduces cardiovascular events associated with the disease, while reduced albuminuria is indicative of improved renal function.

Figure 3A:
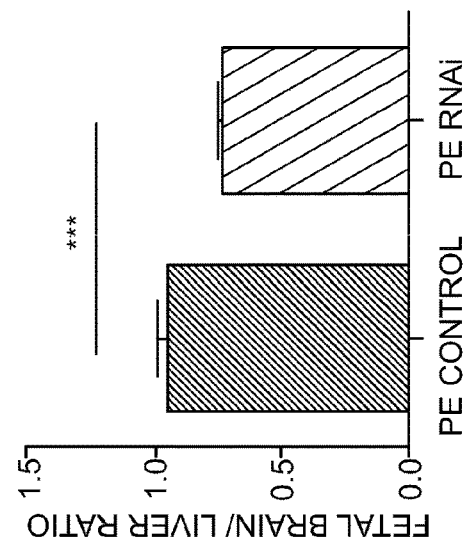
FIG. 3A is a graph depicting increased uteroplacental unit weight following maternal administration of AD-60771 demonstrating the improvement of fetal outcome following maternal administration of AD-60771.
Figure 3B:
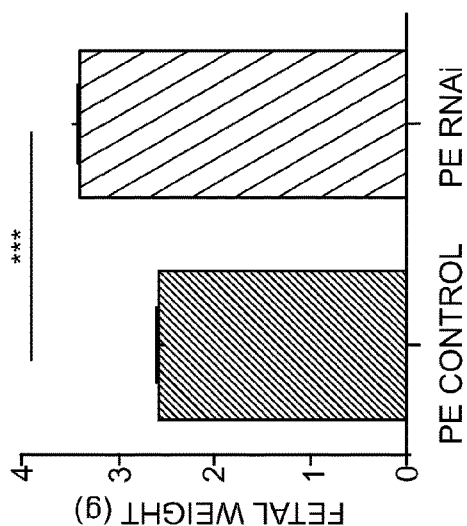
FIG. 3B is a graph depicting increased fetal weight following maternal administration of AD-60771 demonstrating the improvement of fetal outcome following maternal administration of AD-60771.
Figure 3C:
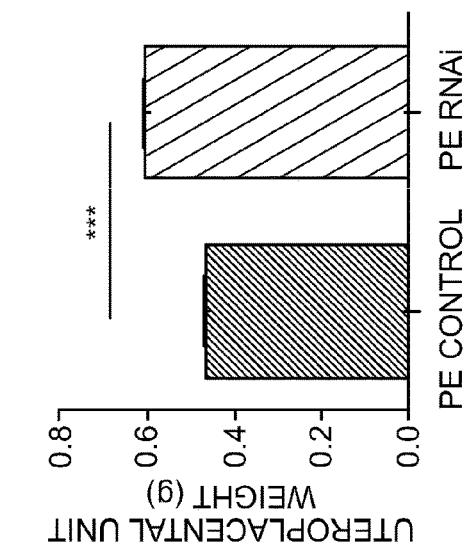
FIG. 3C is a graph depicting a normalized fetal brain:liver ratio following maternal administration of AD-60771 demonstrating the improvement of fetal outcome following maternal administration of AD-60771.

Preeclampsia is also associated with reduced placental size, possibly related to poor perfusion. As a result of the condition, fetal growth is impaired. Following maternal administration of AD-60771, however, uteroplacental unit weight (FIG. 3A) and fetal weight (FIG. 3B) were increased, and there was normalization of the fetal brain:liver ratio (FIG. 3C), all indicative of a more normal placental and fetal development.

Figure 4A:
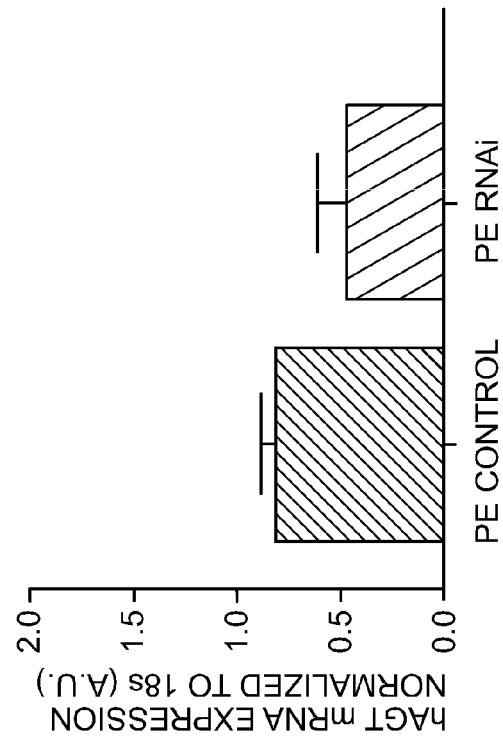
FIG. 4A is a graph depicting reduction of hAGT mRNA in the maternal liver following administration of AD-60771 demonstrating that the iRNA does not enter the placental barrier.
Figure 4B:
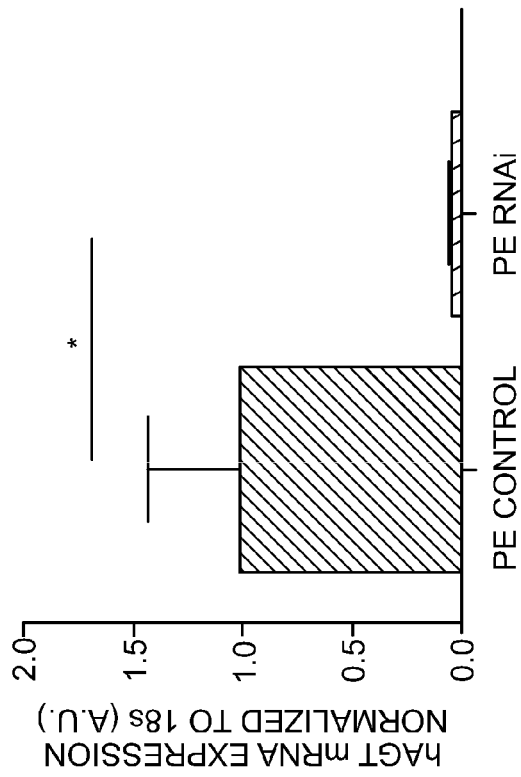
FIG. 4B is a graph depicting that there is no significant reduction of hAGT mRNA in the placenta demonstrating that the iRNA does not enter the placental barrier.

As determined by RT-qPCR analysis of mRNA expression of hAGT in maternal liver and placenta, it was shown that, while there is substantial silencing of hAGT in the maternal liver (FIG. 4A), there was no significant silencing in the placenta (FIG. 4B). This indicates a lack of penetration of the iRNA into the placenta.

Figure 5:
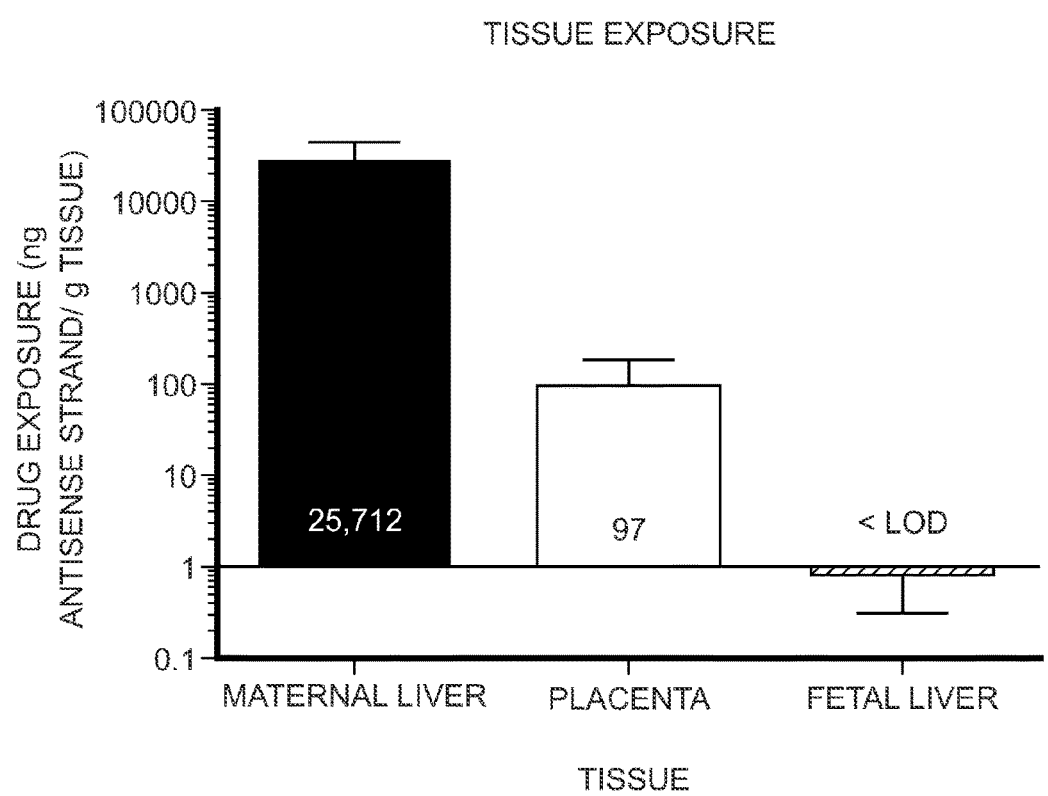
FIG. 5 is a graph depicting the tissue exposure of the maternal liver, placenta and fetal liver to AD-60771.

In addition, analysis of four maternal liver samples, four placenta samples, and eight fetal liver samples demonstrated that the exposure of the fetal liver to the iRNA was about 1.2 ng siRNA/g (below the limit of detection, 1.3 ng siRNA/g tissue) of tissue and that exposure of the maternal liver to the iRNA was about 265-fold greater than the exposure of the placenta to the iRNA (FIG. 5). Tissue exposure was determined by stem-loop qPCR, as previously described (see, e.g., Landesman, Y., et al. (2010) *Silence* 1:16).

Thus, maternal treatment with an iRNA targeting hAGT is superior to maternal treatment with small-molecule renin-angiotensin inhibitors, such as ACE inhibitors, and angiotensin receptor blockers, as these compounds cross the placenta and are fetotoxic.

Figure 6A:
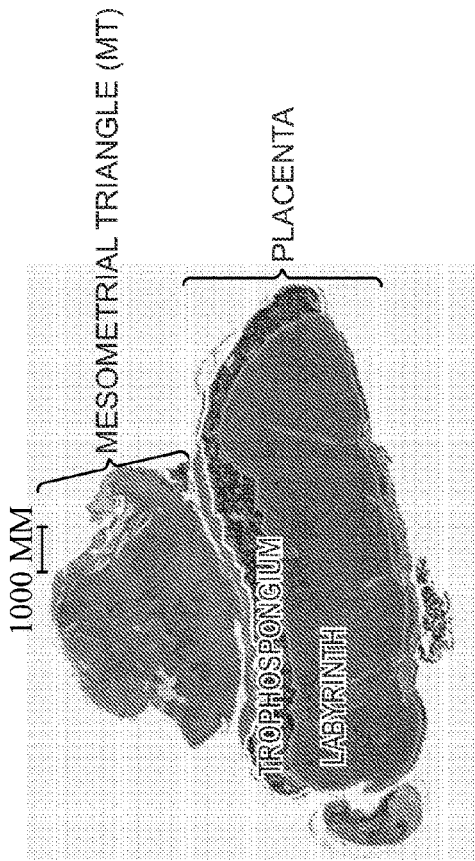
FIG. 6A is a placental section from a pregnant wild-type rat immunohistochemically stained for cytokeratin.
Figure 6C:
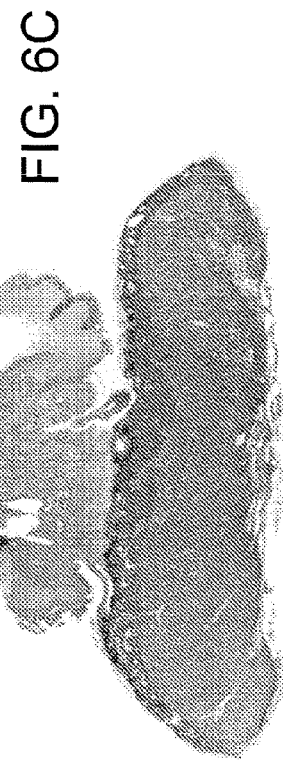
FIG. 6C is a placental section from a pregnant PE rat administered AD-60771 immunohistochemically stained for cytokeratin.
Figure 6B:
FIG. 6B is a placental section from an untreated pregnant PE rat immunohistochemically stained for cytokeratin.
Figure 6D:
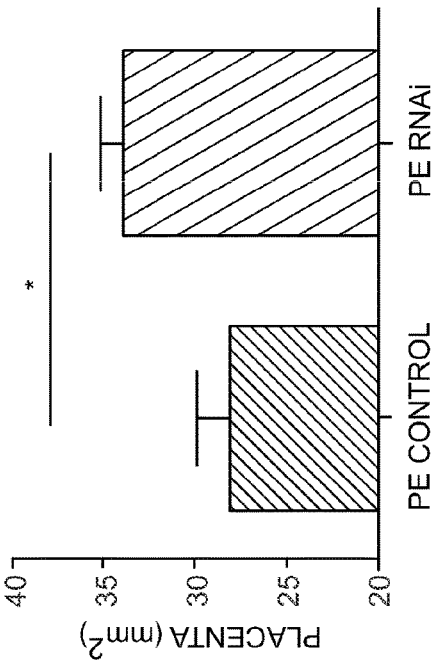
FIG. 6D is a graph depicting the size of the mesometrial triangle of a pregnant PE rat administered AD-60771 and an untreated pregnant PE rat.
Figure 6F:
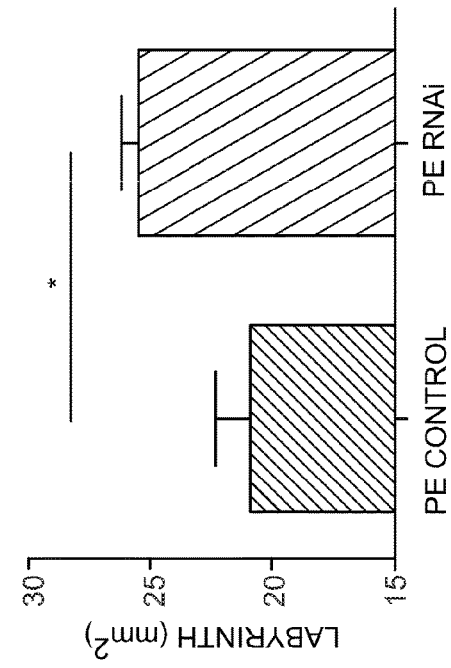
FIG. 6F is a graph depicting the size of the placenta of a pregnant PE rat administered AD-60771 and an untreated pregnant PE rat.
Figure 6E:
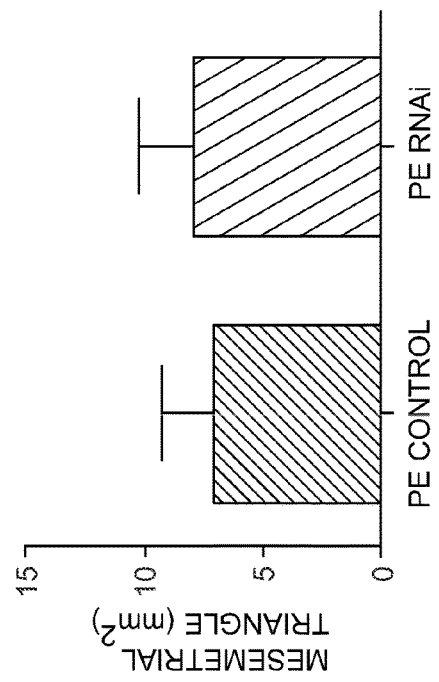
FIG. 6E is a graph depicting the size of the trophospongium of a pregnant PE rat administered AD-60771 and an untreated pregnant PE rat.
Figure 6G:
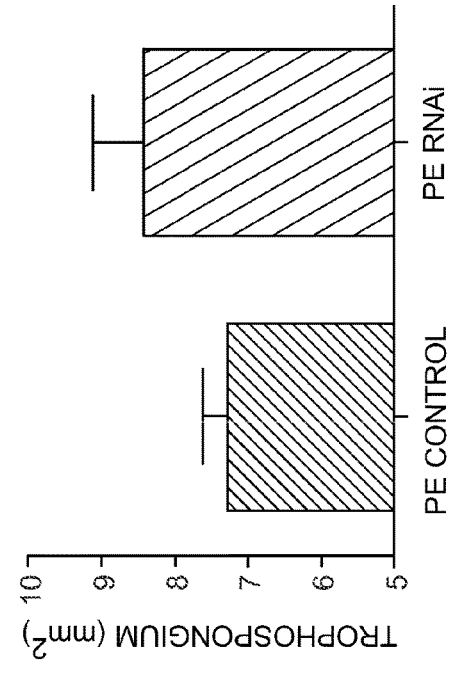
FIG. 6G is a graph depicting the size of the labyrinth of a pregnant PE rats administered AD-60771 and an untreated pregnant PE rat.

As the placenta acts as the conduit for nutrients to the fetus, and waste removal from the fetus, its composition is critical. Accordingly, placental pathology was evaluated (i.e., by measuring the area of tissue slices immunohistochemically stained for cytokeratin). FIG. 6 demonstrates that while the maternal portion of the placenta (the mesometrial triangle; FIG. 6D) and the trophospongium (a uniform layer of cells which are precursors of differentiated trophoblasts; FIG. 6E) were unchanged by administration of AD-60771, overall placental size was increased (FIGS. 6B, 6C, and 6F and FIG. 6A for reference). In particular, the size of the labyrinth, which is the site of nutritional exchange between fetal and maternal blood, was increased by maternal treatment with AD-60771 (FIG. 6G).

The anti-angiogenic soluble fms-like tyrosine kinase-1 (sFLT1) and the angiogenic placental growth factor (PLGF), which are regulated by angiotensins, play a key role in preeclampsia, being released from the placenta into the maternal blood stream and causing endothelial dysfunction. sFlt-1, is largely released from the placenta into the maternal blood stream and causes endothelial dysfunction. PLGF is placental derived, and promotes angiogenesis. The ratio of sFlt-1:PLGF is diagnostic, with a higher sFlt-1:PLGF associated with more severe disease.

Figure 7A:
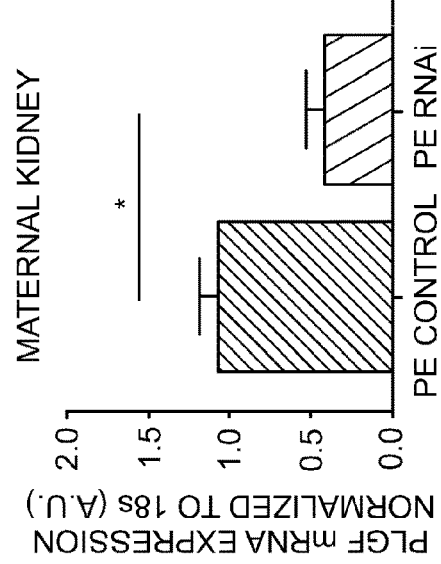
FIG. 7A is a graph depicting a reduction in the amount of mRNA of the anti-angiogenic factor sFLT1 in the maternal kidney following administration of AD-60771.
Figure 7B:
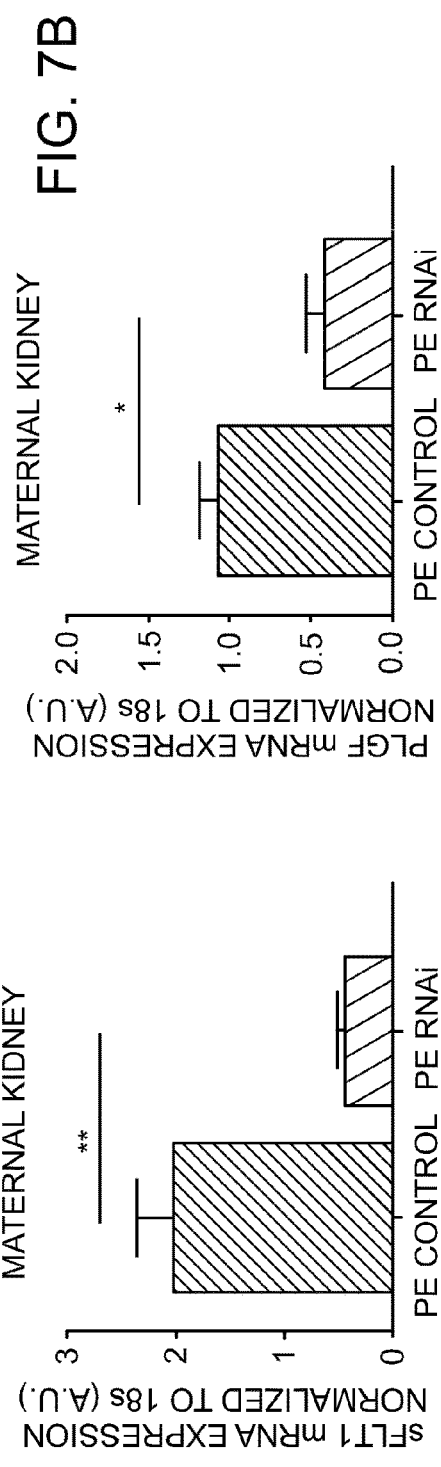
FIG. 7B is a graph depicting a reduction in the amount of mRNA of the angiogenic factor PLGF in the maternal kidney following administration of AD-60771.
Figure 7C:
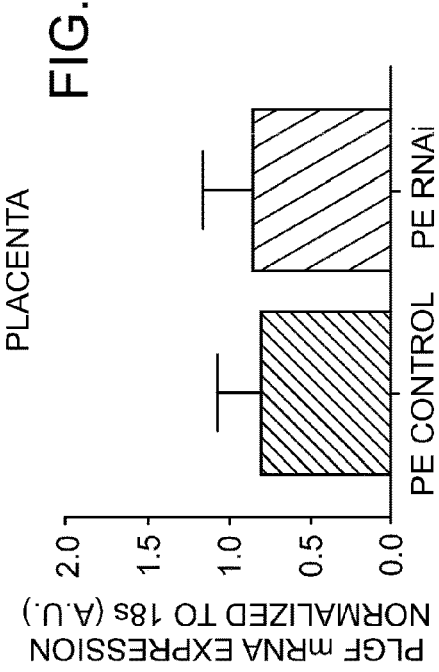
FIG. 7C is a graph depicting a reduction in the amount of mRNA of the anti-angiogenic factor sFLT1 in the placenta following maternal administration of AD-60771.
Figure 7D:
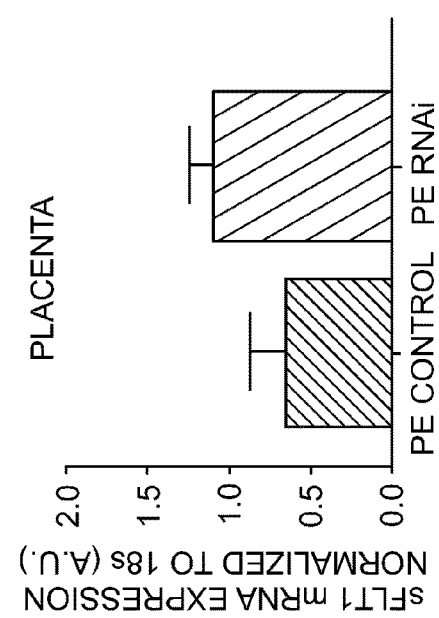
FIG. 7D is a graph depicting a reduction in the amount of mRNA of the angiogenic factor PLGF in the placenta following maternal administration of AD-60771.

Evaluation of the mRNA expression of sFLT1 and PLGF by RT-qPCR analysis demonstrated that the levels of both sFLT1 and PLGF were significantly reduced in the maternal kidney (FIGS. 7A and 7B, respectively), but remained unchanged in the placenta (FIGS. 7C and 7D, respectively) following maternal administration of AD-60771. However, as sFlt-1 was reduced to a greater extent than PLGF in the maternal kidney, the serum sFlt-1:PLGF ratio may be improved.

Figure 8:
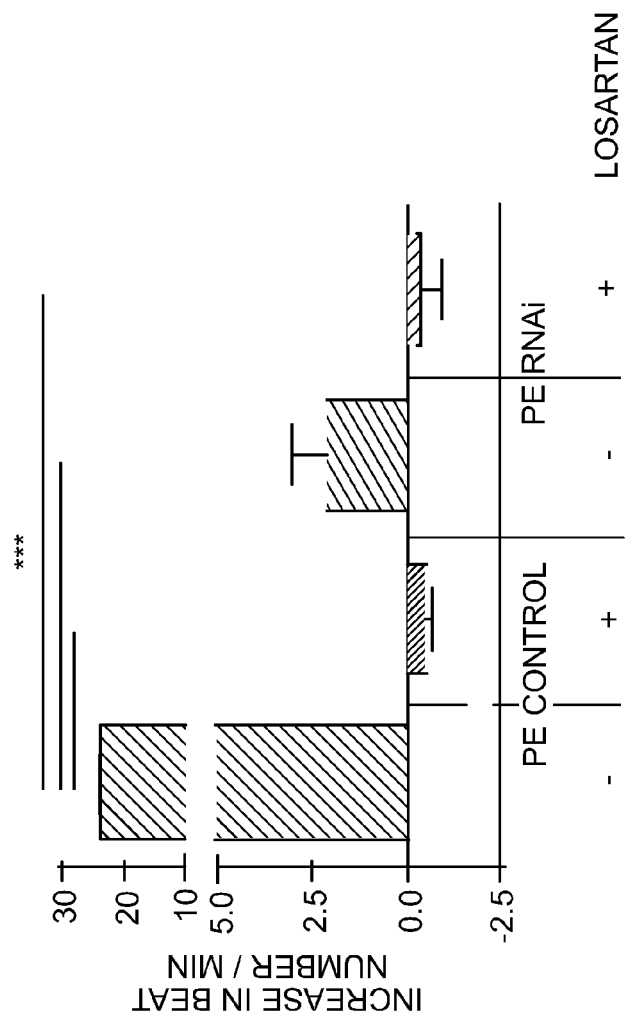
FIG. 8 is a graph depicting the reduction in AT1-AA levels in PE rats administered AD-60771 as assessed by the impact of AT1-AA isolated from control PE rats and pregnant PE rats on the spontaneous beating rate of neonatal rat cardiomyocytes.

Agonistic autoantibodies to the angiotensin II receptor type I (AT1) have been identified in preeclamptic women. When pregnant rodents are exposed to AT1 autoantibodies, a preeclampsia-like syndrome develops. As activation of AT1 is associated with vasopressor effects as well as aldosterone secretion and sFlt-1 production, reduction of AT1 autoantibodies would be expected to reduce the preeclamptic phenotype. Accordingly, the level of production of agonistic autoantibodies to the AT1 receptor (AT1-AA) may also be evaluated by biochromatography and subsequent bioassay of isolated antibodies. AT1-AA levels were measured as has been described (see, e.g., Dechend, et al. (2005) Hypertension 45:742-746) by assessing the impact of isolated, purified AT1-AA antibodies on the spontaneous beating rate of neonatal rat cardiomyocytes. FIG. 8 demonstrates that there was a significant reduction in the level of AT1-AA following administration of AD-60771 to pregnant PE rats.

Example 3. In Vivo AGT Silencing in a Transgenic Rat Model of Preeclampsia

Figure 9B:
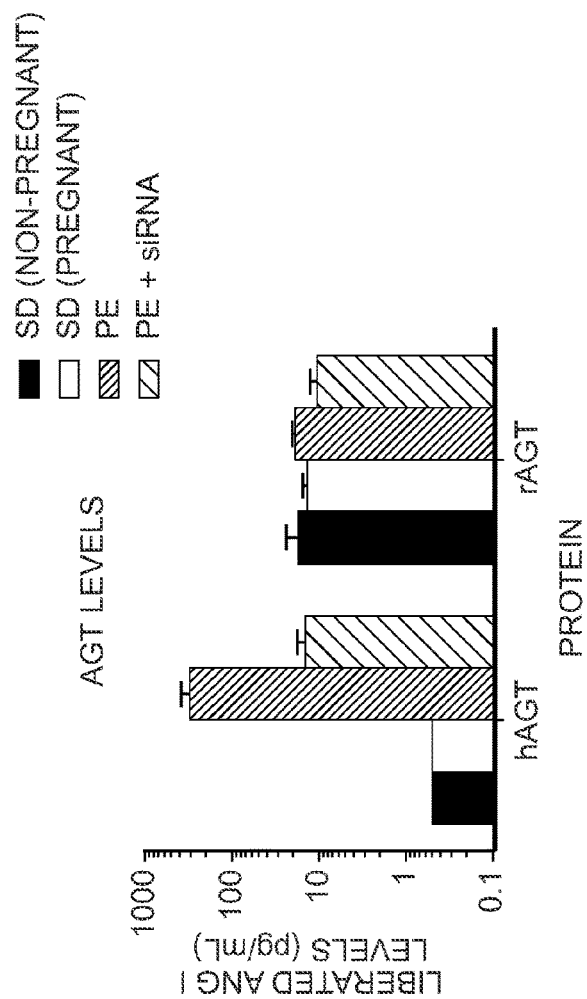
FIG. 9B is a graph depicting the reduction in serum human AGT (hAGT) and rat AGT (rAGT) levels in pregnant PE rats administered AD-60771 as compared to non-pregnant PE rats and as compared to pregnant control Sprague-Dawley rats.
Figure 9A:
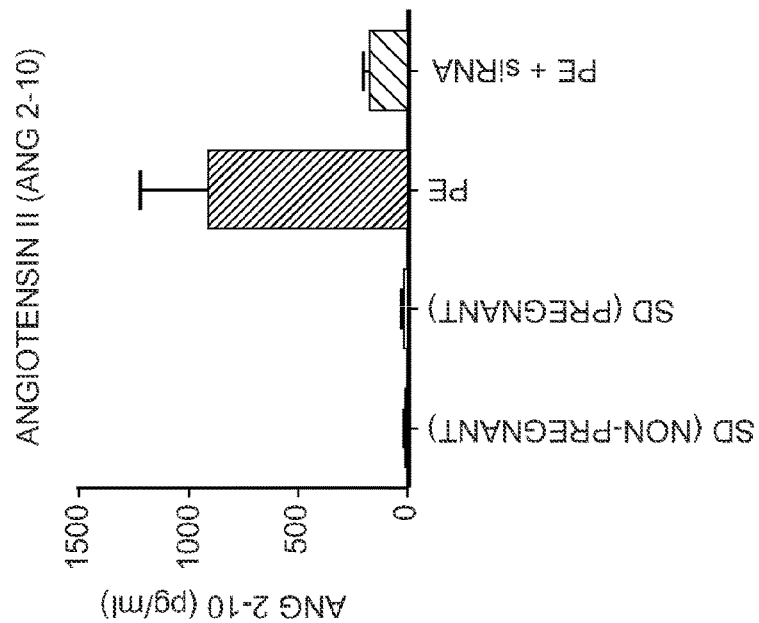
FIG. 9A is a graph depicting the reduction in serum Angiotensin II (Ang 2-10) levels in pregnant PE rats administered AD-60771 as compared to non-pregnant PE rats and as compared to pregnant control Sprague-Dawley rats.

The AD-60771 duplex was tested for the ability to silence hAGT expression in pregnant PE rats, described in the previous example. Beginning on day 3 of gestation, a subset of pregnant PE rats was administered 10 mg/kg siRNA targeting hAGT (AD-60771). Liver and blood were collected at gestation day 21 and the levels of hAGT and rAGT protein and mRNA were assayed and compared to the levels of hAGT and rAGT protein and mRNA present in untreated, pregnant transgenic rats, pregnant Sprague-Dawley rats, and non-pregnant Sprague-Dawley rats. The results of these assays are shown in FIGS. 9A and 9B and demonstrate that there was an 80% reduction of circulating AT2 and a 95% reduction of circulating hAT1 in the pregnant PE rats treated with AD-60771 as compared to control pregnant PE rats. A reduction of about 45% of rat AT2 was also observed in the pregnant PE rats treated with AD-60771 as compared to control pregnant PE rats. A 95% silencing of hepatic AGT mRNA was observed in the pregnant PE rats treated with AD-60771 as compared to control pregnant PE rats. FIGS. 9A and 9B also demonstrate that there was a significant reduction in the serum level of AT1 and AT2 following administration of AD-60771 to pregnant PE rats.

TABLE 11

Unmodified Sense and Antisense Strand Sequences of AGT dsRNAs (21/23mers)

| Duplex Name | Sense Oligo Name | Sequence | SEQ ID NO. | Antisense Oligo Name | Sequence | SEQ ID NO. | Location of NM_000029.3 |
|---|---|---|---|---|---|---|---|
| AD-67864.1 | A-135936.1 | CGGGCAGCAGGGUCAGAAA | 631 | A-135937.1 | UUUCUGACCCUGCUGCCCG | 828 | 10-28 |
| AD-67865.1 | A-135938.1 | UCAGAAGUGGCCCCCGUGU | 632 | A-135939.1 | ACACGGGGCCACUUCUGA | 829 | 22-40_as |
| AD-67866.1 | A-135940.1 | CCCGUGUUGCCUAAGCAAA | 633 | A-135941.1 | UUUGCUUAGGCAACACGGG | 830 | 34-52_G19A_as |
| AD-67867.1 | A-135948.1 | UGCACCUCCGGCCUGCAUA | 634 | A-135949.1 | UAUGCAGGCCGGAGGUGCA | 831 | 76-94_G19A_as |
| AD-67868.1 | A-135950.1 | UGCAUGUCCCUGUGGCCUA | 635 | A-135951.1 | UAGGCCACAGGGACAUGCA | 832 | 89-107 |
| AD-67869.1 | A-135952.1 | UGUGGCCUCUUGGGGGUAA | 636 | A-135953.1 | UUACCCCCAAGAGGCCACA | 833 | 99-117 |
| AD-67870.1 | A-135958.1 | GGUCAGAAGGCCUGGGUGA | 637 | A-135959.1 | UCACCCAGGCCUUCUGACC | 834 | 132-150_G19A_as |
| AD-67871.1 | A-135960.1 | UGGGUGGUUGGCCUCAGGA | 638 | A-135961.1 | UCCUGAGGCCAACCACCCA | 835 | 144-162 |
| AD-67872.1 | A-135962.1 | CCUCAGGCUGUCACACACA | 639 | A-135963.1 | UGUGUGUGACAGCCUGAGG | 836 | 155-173 |
| AD-67873.1 | A-135964.1 | CACACACCUAGGGAGAUGA | 640 | A-135965.1 | UCAUCUCCCUAGGUGUGUG | 837 | 166-184 |
| AD-67874.1 | A-135966.1 | AGGGAGAUGCUCCCGUUUA | 641 | A-135967.1 | UAAACGGGAGCAUCUCCCU | 838 | 175-193 |
| AD-67875.1 | A-135968.1 | CCGUUUCUGGGAACCUUGA | 642 | A-135969.1 | UCAAGGUUCCCAGAAACGG | 839 | 187-205_G19A_as |
| AD-67876.1 | A-135970.1 | AACCUUGGCCCCGACUCCU | 643 | A-135971.1 | AGGAGUCGGGGCCAAGGUU | 840 | 198-216_as |
| AD-67877.1 | A-135972.1 | CGACUCCUGCAAACUUCGA | 644 | A-135973.1 | UCGAAGUUUGCAGGAGUCG | 841 | 209-227_G19A_as |
| AD-67878.1 | A-135974.1 | AACUUCGGUAAAUGUGUAA | 645 | A-135975.1 | UUACACAUUUACCGAAGUU | 842 | 220-238_as |
| AD-67879.1 | A-135976.1 | UGUGUAACUCGACCCUGCA | 646 | A-135977.1 | UGCAGGGUCGAGUUACACA | 843 | 232-250_as |
| AD-67880.1 | A-135978.1 | ACCCUGCACCGGCUCACUA | 647 | A-135979.1 | UAGUGAGCCGGUGCAGGGU | 844 | 243-261 |
| AD-67881.1 | A-135980.1 | GCUCACUCUGUUCAGCAGU | 648 | A-135981.1 | ACUGCUGAACAGAGUGAGC | 845 | 254-272_as |
| AD-67882.1 | A-135982.1 | UUCAGCAGUGAAACUCUGA | 649 | A-135983.1 | UCAGAGUUUCACUGCUGAA | 846 | 264-282 |
| AD-67883.1 | A-135984.1 | AAACUCUGCAUCGAUCACU | 650 | A-135985.1 | AGUGAUCGAUGCAGAGUUU | 847 | 274-292_as |
| AD-67884.1 | A-135986.1 | CGAUCACUAAGACUUCCUA | 651 | A-135987.1 | UAGGAAGUCUUAGUGAUCG | 848 | 285-303_G19A_as |
| AD-67885.1 | A-135990.1 | GAGGUCCCAGCGUGAGUGU | 652 | A-135991.1 | ACACUCACGCUGGGACCUC | 849 | 307-325_as |
| AD-67886.1 | A-135994.1 | UUCUGGCAUCUGUCCUUCU | 653 | A-135995.1 | AGAAGGACAGAUGCCAGAA | 850 | 329-347_as |

TABLE 11-continued

Unmodified Sense and Antisense Strand Sequences of AGT dsRNAs (21/23mers)

| Duplex Name | Sense Oligo Name | Sequence | SEQ ID NO. | Antisense Oligo Name | Sequence | SEQ ID NO. | Location of NM_000029.3 |
|---|---|---|---|---|---|---|---|
| AD-67887.1 | A-135996.1 | CCUUCUGGCCAGCCUGUGA | 654 | A-135997.1 | UCACAGGCUGGCCAGAAGG | 851 | 342-360_G19A_as |
| AD-67888.1 | A-135998.1 | AGCCUGUGGUCUGGCCAAA | 655 | A-135999.1 | UUUGGCCAGACCACAGGCU | 852 | 352-370_G19A_as |
| AD-67889.1 | A-136000.1 | GGCCAAGUGAUGUAACCCU | 656 | A-136001.1 | AGGGUUACAUCACUUGGCC | 853 | 364-382_as |
| AD-67890.1 | A-136002.1 | UGUAACCCUCCUCUCCAGA | 657 | A-136003.1 | UCUGGAGAGGAGGGUUACA | 854 | 374-392 |
| AD-67891.1 | A-136004.1 | UCUCCAGCCUGUGCACAGA | 658 | A-136005.1 | UCUGUGCACAGGCUGGAGA | 855 | 385-403_G19A_as |
| AD-67892.1 | A-136006.1 | UGCACAGGCAGCCUGGGAA | 659 | A-136007.1 | UUCCCAGGCUGCCUGUGCA | 856 | 396-414_as |
| AD-67893.1 | A-136008.1 | CCUGGGAACAGCUCCAUCA | 660 | A-136009.1 | UGAUGGAGCUGUUCCCAGG | 857 | 407-425 |
| AD-67894.1 | A-136010.1 | UCCAUCCCCACCCCUCAGA | 661 | A-136011.1 | UCUGAGGGGUGGGGAUGGA | 858 | 419-437 |
| AD-67895.1 | A-136012.1 | CCCUCAGCUAUAAAUAGGA | 662 | A-136013.1 | UCCUAUUUAUAGCUGAGGG | 859 | 430-448_G19A_as |
| AD-67896.1 | A-136014.1 | UAAAUAGGGCAUCGUGACA | 663 | A-136015.1 | UGUCACGAUGCCCUAUUUA | 860 | 440-458 |
| AD-67897.1 | A-136016.1 | AUCGUGACCCGGCCGGGA | 664 | A-136017.1 | UCCCCGGCCGGGUCACGAU | 861 | 450-468_G19A_as |
| AD-67898.1 | A-136018.1 | CCGGGGGAAGAAGCUGCCA | 665 | A-136019.1 | UGGCAGCUUCUUCCCCCGG | 862 | 462-480_G19A_as |
| AD-67899.1 | A-136020.1 | AGCUGCCGUUGUUCUGGGU | 666 | A-136021.1 | ACCCAGAACAACGGCAGCU | 863 | 473-491_as |
| AD-67900.1 | A-136022.1 | UUCUGGGUACUACAGCAGA | 667 | A-136023.1 | UCUGCUGUAGUACCCAGAA | 864 | 484-502_as |
| AD-67901.1 | A-136024.1 | UACAGCAGAAGGGUAUGCA | 668 | A-136025.1 | UGCAUACCCUUCUGCUGUA | 865 | 494-512_G19A_as |
| AD-67902.1 | A-136026.1 | UAUGCGGAAGCGAGCACCA | 669 | A-136027.1 | UGGUGCUCGCUUCCGCAUA | 866 | 507-525 |
| AD-67903.1 | A-136028.1 | CGAGCACCCCAGUCUGAGA | 670 | A-136029.1 | UCUCAGACUGGGGUGCUCG | 867 | 517-535_as |
| AD-67904.1 | A-136032.1 | CUCCUGCCGGUGUGAGCCU | 671 | A-136033.1 | AGGCUCACACCGGCAGGAG | 868 | 539-557_as |
| AD-67905.1 | A-136034.1 | UGUGAGCCUGAGGGCCACA | 672 | A-136035.1 | UGUGGCCCUCAGGCUCACA | 869 | 549-567 |
| AD-67906.1 | A-136036.1 | GGGCCACCAUCCUCUGCCU | 673 | A-136037.1 | AGGCAGAGGAUGGUGGCCC | 870 | 560-578_as |
| AD-67907.1 | A-136038.1 | CUGCCUCCUGGCCUGGGCU | 674 | A-136039.1 | AGCCCAGGCCAGGAGGCAG | 871 | 573-591_as |
| AD-67908.1 | A-136042.1 | CCUGGCUGCAGGUGACCGA | 675 | A-136043.1 | UCGGUCACCUGCAGCCAGG | 872 | 594-612_G19A_as |
| AD-67909.1 | A-136044.1 | UGACCGGGUGUACAUACAA | 676 | A-136045.1 | UUGUAUGUACACCCGGUCA | 873 | 606-624 |
| AD-67910.1 | A-136046.1 | UACAUACACCCCUUCCACA | 677 | A-136047.1 | UGUGGAAGGGGUGUAUGUA | 874 | 616-634 |
| AD-67911.1 | A-136048.1 | UUCCACCUCGUCAUCCACA | 678 | A-136049.1 | UGUGGAUGACGAGGUGGAA | 875 | 628-646_as |
| AD-67912.1 | A-136050.1 | UCAUCCACAAUGAGAGUAA | 679 | A-136051.1 | UUACUCUCAUUGUGGAUGA | 876 | 638-656 |
| AD-67913.1 | A-136056.1 | AAAGGCCAAUGCCGGGAAA | 680 | A-136057.1 | UUUCCCGGCAUUGGCCUUU | 877 | 672-690_G19A_as |
| AD-67914.1 | A-136058.1 | CCGGGAAGCCCAAAGACCA | 681 | A-136059.1 | UGGUCUUUGGGCUUCCCGG | 878 | 683-701 |
| AD-67915.1 | A-136060.1 | AAAGACCCCACCUUCAUAA | 682 | A-136061.1 | UUAUGAAGGUGGGGUCUUU | 879 | 694-712 |
| AD-67916.1 | A-136062.1 | CCUUCAUACCUGCUCCAAU | 683 | A-136063.1 | AUUGGAGCAGGUAUGAAGG | 880 | 704-722_as |
| AD-67917.1 | A-136064.1 | CUCCAAUUCAGGCCAAGAA | 684 | A-136065.1 | UUCUUGGCCUGAAUUGGAG | 881 | 716-734 |
| AD-67918.1 | A-136066.1 | AGGCCAAGACAUCCCCUGU | 685 | A-136067.1 | ACAGGGGAUGUCUUGGCCU | 882 | 725-743_as |

TABLE 11-continued

Unmodified Sense and Antisense Strand Sequences of AGT dsRNAs (21/23mers)

| Duplex Name | Sense Oligo Name | Sequence | SEQ ID NO. | Antisense Oligo Name | Sequence | SEQ ID NO. | Location of NM_000029.3 |
|---|---|---|---|---|---|---|---|
| AD-67919.1 | A-136068.1 | UCCCCUGUGGAUGAAAAGA | 686 | A-136069.1 | UCUUUUCAUCCACAGGGGA | 883 | 736-754_G19A_as |
| AD-67920.1 | A-136070.1 | AAAAGGCCCUACAGGACCA | 687 | A-136071.1 | UGGUCCUGUAGGGCCUUUU | 884 | 749-767_as |
| AD-67921.1 | A-136072.1 | UACAGGACCAGCUGGUGCU | 688 | A-136073.1 | AGCACCAGCUGGUCCUGUA | 885 | 758-776_as |
| AD-67922.1 | A-136078.1 | UUGACACCGAAGACAAGUU | 689 | A-136079.1 | AACUUGUCUUCGGUGUCAA | 886 | 791-809_as |
| AD-67923.1 | A-136080.1 | ACAAGUUGAGGGCCGCAAU | 690 | A-136081.1 | AUUGCGGCCCUCAACUUGU | 887 | 803-821_as |
| AD-67924.1 | A-136082.1 | GCCGCAAUGGUCGGGAUGA | 691 | A-136083.1 | UCAUCCCGACCAUUGCGGC | 888 | 814-832 |
| AD-67925.1 | A-136084.1 | CGGGAUGCUGGCCAACUUA | 692 | A-136085.1 | UAAGUUGGCCAGCAUCCCG | 889 | 825-843 |
| AD-67926.1 | A-136086.1 | CAACUUCUUGGGCUUCCGU | 693 | A-136087.1 | ACGGAAGCCCAAGAAGUUG | 890 | 837-855_as |
| AD-67927.1 | A-136088.1 | GGCUUCCGUAUAUAUGGCA | 694 | A-136089.1 | UGCCAUAUAUACGGAAGCC | 891 | 847-865_as |
| AD-67928.1 | A-136090.1 | UAUGGCAUGCACAGUGAGA | 695 | A-136091.1 | UCUCACUGUGCAUGCCAUA | 892 | 859-877 |
| AD-67929.1 | A-136092.1 | ACAGUGAGCUAUGGGGCGU | 696 | A-136093.1 | ACGCCCCAUAGCUCACUGU | 893 | 869-887_as |
| AD-67930.1 | A-136098.1 | CGUCCUCUCCCCAACGGCU | 697 | A-136099.1 | AGCCGUUGGGGAGAGGACG | 894 | 903-921_as |
| AD-67931.1 | A-136102.1 | UUUGGCACCCUGGCCUCUA | 698 | A-136103.1 | UAGAGGCCAGGGUGCCAAA | 895 | 925-943 |
| AD-67932.1 | A-136104.1 | CUGGCCUCUCUCUAUCUGA | 699 | A-136105.1 | UCAGAUAGAGAGAGGCCAG | 896 | 934-952_G19A_as |
| AD-67933.1 | A-136106.1 | UAUCUGGGAGCCUUGGACA | 700 | A-136107.1 | UGUCCAAGGCUCCCAGAUA | 897 | 946-964 |
| AD-67934.1 | A-136108.1 | UUGGACCACACAGCUGACA | 701 | A-136109.1 | UGUCAGCUGUGUGGUCCAA | 898 | 958-976_as |
| AD-67935.1 | A-136110.1 | ACAGCUGACAGGCUACAGA | 702 | A-136111.1 | UCUGUAGCCUGUCAGCUGU | 899 | 967-985_G19A_as |
| AD-67936.1 | A-136112.1 | UACAGGCAAUCCUGGGUGU | 703 | A-136113.1 | ACACCCAGGAUUGCCUGUA | 900 | 980-998_as |
| AD-67937.1 | A-136114.1 | UCCUGGGUGUUCCUUGGAA | 704 | A-136115.1 | UUCCAAGGAACACCCAGGA | 901 | 989-1007_as |
| AD-67938.1 | A-136116.1 | UUGGAAGGACAAGAACUGA | 705 | A-136117.1 | UCAGUUCUUGUCCUUCCAA | 902 | 1002-1020 |
| AD-67939.1 | A-136118.1 | AGAACUGCACCUCCCGGCU | 706 | A-136119.1 | AGCCGGGAGGUGCAGUUCU | 903 | 1013-1031_as |
| AD-67940.1 | A-136122.1 | UGCGCACAAGGUCCUGUCU | 707 | A-136123.1 | AGACAGGACCUUGUGCGCA | 904 | 1035-1053_as |
| AD-67947.1 | A-136126.1 | CUGCAGGCUGUACAGGGCA | 708 | A-136127.1 | UGCCCUGUACAGCCUGCAG | 905 | 1057-1075 |
| AD-67948.1 | A-136128.1 | UACAGGGCCUGCUAGUGGA | 709 | A-136129.1 | UCCACUAGCAGGCCCUGUA | 906 | 1067-1085 |
| AD-67949.1 | A-136130.1 | UAGUGGCCCAGGGCAGGGA | 710 | A-136131.1 | UCCCUGCCCUGGGCCACUA | 907 | 1079-1097 |
| AD-67950.1 | A-136132.1 | AGGGCAGGGCUGAUAGCCA | 711 | A-136133.1 | UGGCUAUCAGCCCUGCCCU | 908 | 1088-1106_as |
| AD-67951.1 | A-136134.1 | UAGCCAGGCCCAGCUGCUA | 712 | A-136135.1 | UAGCAGCUGGGCCUGGCUA | 909 | 1101-1119_G19A_as |
| AD-67952.1 | A-136136.1 | AGCUGCUGCUGUCCACGGU | 713 | A-136137.1 | ACCGUGGACAGCAGCAGCU | 910 | 1112-1130_as |
| AD-67954.1 | A-136140.1 | UGGGCGUGUUCACAGCCCA | 714 | A-136141.1 | UGGGCUGUGAACACGCCCA | 911 | 1133-1151 |
| AD-67955.1 | A-136142.1 | CACAGCCCCAGGCCUGCAA | 715 | A-136143.1 | UUGCAGGCCUGGGGCUGUG | 912 | 1143-1161 |
| AD-67956.1 | A-136144.1 | CUGCACCUGAAGCAGCCGU | 716 | A-136145.1 | ACGGCUGCUUCAGGUGCAG | 913 | 1156-1174_as |
| AD-67957.1 | A-136146.1 | AGCAGCCGUUUGUGCAGGA | 717 | A-136147.1 | UCCUGCACAAACGGCUGCU | 914 | 1166-1184_G19A_as |
| AD-67958.1 | A-136148.1 | UGCAGGGCCUGGCUCUCUA | 718 | A-136149.1 | UAGAGAGCCAGGCCCUGCA | 915 | 1178-1196_as |
| AD-67959.1 | A-136150.1 | UGGCUCUCUAUACCCCUGU | 719 | A-136151.1 | ACAGGGGUAUAGAGAGCCA | 916 | 1187-1205_as |
| AD-67960.1 | A-136152.1 | ACCCCUGUGGUCCUCCCAA | 720 | A-136153.1 | UUGGGAGGACCACAGGGGU | 917 | 1198-1216 |

TABLE 11-continued

Unmodified Sense and Antisense Strand Sequences of AGT dsRNAs (21/23mers)

| Duplex Name | Sense Oligo Name | Sequence | SEQ ID NO. | Antisense Oligo Name | Sequence | SEQ ID NO. | Location of NM_000029.3 |
|---|---|---|---|---|---|---|---|
| AD-67962.1 | A-136156.1 | CUGGACUUCACAGAACUGA | 721 | A-136157.1 | UCAGUUCUGUGAAGUCCAG | 918 | 1222-1240_G19A_as |
| AD-67963.1 | A-136158.1 | AGAACUGGAUGUUGCUGCU | 722 | A-136159.1 | AGCAGCAACAUCCAGUUCU | 919 | 1233-1251_as |
| AD-67964.1 | A-136160.1 | UUGCUGCUGAGAAGAUUGA | 723 | A-136161.1 | UCAAUCUUCUCAGCAGCAA | 920 | 1244-1262_as |
| AD-67965.1 | A-136162.1 | AGAAGAUUGACAGGUUCAU | 724 | A-136163.1 | AUGAACCUGUCAAUCUUCU | 921 | 1253-1271_as |
| AD-67966.1 | A-136164.1 | AGGUUCAUGCAGGCUGUGA | 725 | A-136165.1 | UCACAGCCUGCAUGAACCU | 922 | 1264-1282_as |
| AD-67967.1 | A-136166.1 | GCUGUGACAGGAUGGAAGA | 726 | A-136167.1 | UCUUCCAUCCUGUCACAGC | 923 | 1276-1294_as |
| AD-67968.1 | A-136168.1 | UGGAAGACUGGCUGCUCCA | 727 | A-136169.1 | UGGAGCAGCCAGUCUUCCA | 924 | 1288-1306 |
| AD-67970.1 | A-136172.1 | AUGGGAGCCAGUGUGGACA | 728 | A-136173.1 | UGUCCACACUGGCUCCCAU | 925 | 1309-1327_as |
| AD-67971.1 | A-136174.1 | UGUGGACAGCACCCUGGCU | 729 | A-136175.1 | AGCCAGGGUGCUGUCCACA | 926 | 1320-1338_as |
| AD-67972.1 | A-136176.1 | CCUGGCUUUCAACACCUAA | 730 | A-136177.1 | UUAGGUGUUGAAAGCCAGG | 927 | 1332-1350 |
| AD-67973.1 | A-136178.1 | CAACACCUACGUCCACUUA | 731 | A-136179.1 | UAAGUGGACGUAGGUGUUG | 928 | 1341-1359 |
| AD-67974.1 | A-136180.1 | CACUUCCAAGGGAAGAUGA | 732 | A-136181.1 | UCAUCUUCCCUUGGAAGUG | 929 | 1354-1372_as |
| AD-67975.1 | A-136182.1 | GGGAAGAUGAAGGGCUUCU | 733 | A-136183.1 | AGAAGCCCUUCAUCUUCCC | 930 | 1363-1381_as |
| AD-67976.1 | A-136184.1 | GCUUCUCCCUGCUGGCCGA | 734 | A-136185.1 | UCGGCCAGCAGGGAGAAGC | 931 | 1376-1394_as |
| AD-67978.1 | A-136188.1 | CCAGGAGUUCUGGGUGGAA | 735 | A-136189.1 | UUCCACCCAGAACUCCUGG | 932 | 1398-1416 |
| AD-67979.1 | A-136190.1 | UGGGUGGACAACAGCACCU | 736 | A-136191.1 | AGGUGCUGUUGUCCACCCA | 933 | 1408-1426_as |
| AD-67980.1 | A-136192.1 | ACAGCACCUCAGUGUCUGU | 737 | A-136193.1 | ACAGACACUGAGGUGCUGU | 934 | 1418-1436_as |
| AD-67981.1 | A-136194.1 | UGUCUGUUCCCAUGCUCUA | 738 | A-136195.1 | UAGAGCAUGGGAACAGACA | 935 | 1430-1448 |
| AD-67982.1 | A-136196.1 | CAUGCUCUCUGGCAUGGGA | 739 | A-136197.1 | UCCCAUGCCAGAGAGCAUG | 936 | 1440-1458 |
| AD-67983.1 | A-136198.1 | AUGGGCACCUUCCAGCACU | 740 | A-136199.1 | AGUGCUGGAAGGUGCCCAU | 937 | 1453-1471_as |
| AD-67984.1 | A-136200.1 | UUCCAGCACUGGAGUGACA | 741 | A-136201.1 | UGUCACUCCAGUGCUGGAA | 938 | 1462-1480_as |
| AD-67986.1 | A-136204.1 | AGGACAACUUCUCGGUGAA | 742 | A-136205.1 | UUCACCGAGAAGUUGUCCU | 939 | 1484-1502 |
| AD-67987.1 | A-136206.1 | UCGGUGACUCAAGUGCCCU | 743 | A-136207.1 | AGGGCACUUGAGUCACCGA | 940 | 1495-1513_as |
| AD-67988.1 | A-136208.1 | UGCCCUUCACUGAGAGCGA | 744 | A-136209.1 | UCGCUCUCAGUGAAGGGCA | 941 | 1508-1526 |
| AD-67989.1 | A-136210.1 | UGAGAGCGCCUGCCUGCUA | 745 | A-136211.1 | UAGCAGGCAGGCGCUCUCA | 942 | 1518-1536_G19A_as |
| AD-67990.1 | A-136212.1 | CCUGCUGCUGAUCCAGCCU | 746 | A-136213.1 | AGGCUGGAUCAGCAGCAGG | 943 | 1530-1548_as |
| AD-67991.1 | A-136214.1 | AUCCAGCCUCACUAUGCCU | 747 | A-136215.1 | AGGCAUAGUGAGGCUGGAU | 944 | 1540-1558_as |
| AD-67992.1 | A-136216.1 | UAUGCCUCUGACCUGGACA | 748 | A-136217.1 | UGUCCAGGUCAGAGGCAUA | 945 | 1552-1570_as |
| AD-67993.1 | A-136218.1 | ACCUGGACAAGGUGGAGGA | 749 | A-136219.1 | UCCUCCACCUUGUCCAGGU | 946 | 1562-1580_G19A_as |
| AD-67994.1 | A-136220.1 | UGGAGGGUCUCACUUUCCA | 750 | A-136221.1 | UGGAAAGUGAGACCCUCCA | 947 | 1574-1592_as |
| AD-67995.1 | A-136222.1 | CACUUUCCAGCAAAACUCA | 751 | A-136223.1 | UGAGUUUUGCUGGAAAGUG | 948 | 1584-1602 |
| AD-67996.1 | A-136224.1 | AAAACUCCCUCAACUGGAU | 752 | A-136225.1 | AUCCAGUUGAGGGAGUUUU | 949 | 1595-1613_as |
| AD-67997.1 | A-136226.1 | AACUGGAUGAAGAAACUAU | 753 | A-136227.1 | AUAGUUUCUUCAUCCAGUU | 950 | 1606-1624_as |
| AD-67998.1 | A-136228.1 | AAACUAUCUCCCCGGACCA | 754 | A-136229.1 | UGGUCCGGGGAGAUAGUUU | 951 | 1618-1636_as |
| AD-67999.1 | A-136230.1 | CCGGACCAUCCACCUGACA | 755 | A-136231.1 | UGUCAGGUGGAUGGUCCGG | 952 | 1629-1647 |
| AD-68001.1 | A-136234.1 | UGCCCCAACUGGUGCUGCA | 756 | A-136235.1 | UGCAGCACCAGUUGGGGCA | 953 | 1649-1667_as |

TABLE 11-continued

Unmodified Sense and Antisense Strand Sequences of AGT dsRNAs (21/23mers)

| Duplex Name | Sense Oligo Name | Sequence | SEQ ID NO. | Antisense Oligo Name | Sequence | SEQ ID NO. | Location of NM_000029.3 |
|---|---|---|---|---|---|---|---|
| AD-68002.1 | A-136236.1 | UGCUGCAAGGAUCUUAUGA | 757 | A-136237.1 | UCAUAAGAUCCUUGCAGCA | 954 | 1661-1679_as |
| AD-68003.1 | A-136238.1 | UCUUAUGACCUGCAGGACA | 758 | A-136239.1 | UGUCCUGCAGGUCAUAAGA | 955 | 1672-1690 |
| AD-68004.1 | A-136240.1 | UGCAGGACCUGCUCGCCCA | 759 | A-136241.1 | UGGGCGAGCAGGUCCUGCA | 956 | 1682-1700_as |
| AD-68005.1 | A-136242.1 | UCGCCCAGGCUGAGCUGCA | 760 | A-136243.1 | UGCAGCUCAGCCUGGGCGA | 957 | 1694-1712 |
| AD-68006.1 | A-136244.1 | UGAGCUGCCCGCCAUUCUA | 761 | A-136245.1 | UAGAAUGGCGGGCAGCUCA | 958 | 1704-1722_G19A_as |
| AD-68009.1 | A-136250.1 | UGCAAAAUUGAGCAAUGA | 762 | A-136251.1 | UCAUUGCUCAAUUUUUGCA | 959 | 1739-1757_as |
| AD-68010.1 | A-136252.1 | AGCAAUGACCGCAUCAGGA | 763 | A-136253.1 | UCCUGAUGCGGUCAUUGCU | 960 | 1750-1768_G19A_as |
| AD-68011.1 | A-136254.1 | CAUCAGGGUGGGGAGGUA | 764 | A-136255.1 | UACCUCCCCACCCUGAUG | 961 | 1761-1779_G19A_as |
| AD-68012.1 | A-136256.1 | GGGGAGGUGCUGAACAGCA | 765 | A-136257.1 | UGCUGUUCAGCACCUCCCC | 962 | 1771-1789_as |
| AD-68013.1 | A-136258.1 | AACAGCAUUUUUUUGAGA | 766 | A-136259.1 | UCUCAAAAAAAUGCUGUU | 963 | 1783-1801 |
| AD-68014.1 | A-136260.1 | UUUUUGAGCUUGAAGCGGA | 767 | A-136261.1 | UCCGCUUCAAGCUCAAAAA | 964 | 1793-1811_as |
| AD-68017.1 | A-136266.1 | AGAGUCUACCCAACAGCUU | 768 | A-136267.1 | AAGCUGUUGGGUAGACUCU | 965 | 1827-1845_as |
| AD-68018.1 | A-136268.1 | CAACAGCUUAACAAGCCUA | 769 | A-136269.1 | UAGGCUUGUUAAGCUGUUG | 966 | 1837-1855_G19A_as |
| AD-68019.1 | A-136270.1 | CAAGCCUGAGGUCUUGGAA | 770 | A-136271.1 | UUCCAAGACCUCAGGCUUG | 967 | 1848-1866_G19A_as |
| AD-68020.1 | A-136272.1 | CUUGGAGGUGACCCUGAAA | 771 | A-136273.1 | UUUCAGGGUCACCUCCAAG | 968 | 1860-1878 |
| AD-68021.1 | A-136274.1 | ACCCUGAACCGCCCAUUCA | 772 | A-136275.1 | UGAAUGGGCGGUUCAGGGU | 969 | 1870-1888 |
| AD-68022.1 | A-136276.1 | GCCCAUUCCUGUUUGCUGU | 773 | A-136277.1 | ACAGCAAACAGGAAUGGGC | 970 | 1880-1898_as |
| AD-68025.1 | A-136284.1 | CACUUCCUGGGCCGCGUGA | 774 | A-136285.1 | UCACGCGGCCCAGGAAGUG | 971 | 1924-1942_G19A_as |
| AD-68026.1 | A-136286.1 | CGCGUGGCCAACCCGCUGA | 775 | A-136287.1 | UCAGCGGGUUGGCCACGCG | 972 | 1936-1954_as |
| AD-68027.1 | A-136288.1 | ACCCGCUGAGCACAGCAUA | 776 | A-136289.1 | UAUGCUGUGCUCAGCGGGU | 973 | 1946-1964_G19A_as |
| AD-68028.1 | A-136290.1 | ACAGCAUGAGGCCAGGGCA | 777 | A-136291.1 | UGCCCUGGCCUCAUGCUGU | 974 | 1957-1975 |
| AD-68029.1 | A-136292.1 | CAGGGCCCCAGAACACAGU | 778 | A-136293.1 | ACUGUGUUCUGGGGCCCUG | 975 | 1969-1987_as |
| AD-68032.1 | A-136298.1 | UCUGCCCCUGGCCUUUGAA | 779 | A-136299.1 | UUCAAAGGCCAGGGGCAGA | 976 | 2001-2019_G19A_as |
| AD-68033.1 | A-136300.1 | UUUGAGGCAAAGGCCAGCA | 780 | A-136301.1 | UGCUGGCCUUUGCCUCAAA | 977 | 2014-2032_as |
| AD-68034.1 | A-136302.1 | AGGCCAGCAGCAGAUAACA | 781 | A-136303.1 | UGUUAUCUGCUGCUGGCCU | 978 | 2024-2042_as |
| AD-68035.1 | A-136304.1 | AGAUAACAACCCCGGACAA | 782 | A-136305.1 | UUGUCCGGGGUUGUUAUCU | 979 | 2035-2053_as |
| AD-68036.1 | A-136306.1 | CCGGACAAUCAGCGAUGU | 783 | A-136307.1 | ACAUCGCUGAUUUGUCCGG | 980 | 2046-2064_as |
| AD-68037.1 | A-136308.1 | AGCGAUGUGUCACCCCCAA | 784 | A-136309.1 | UUGGGGGUGACACAUCGCU | 981 | 2057-2075_G19A_as |
| AD-68084.2 | A-136314.1 | UUCUAAUGAGUCGACUUUA | 785 | A-136315.1 | UAAAGUCGACUCAUUAGAA | 982 | 2090-2108_G19A_as |
| AD-68085.2 | A-136320.1 | GUUUCUCCUUGGUCUAAGU | 786 | A-136321.1 | ACUUAGACCAAGGAGAAAC | 983 | 2124-2142_as |
| AD-68086.2 | A-136328.1 | AGCCUGCAGCGGCACAAAU | 787 | A-136329.1 | AUUUGUGCCGCUGCAGGCU | 984 | 2167-2185_as |
| AD-68087.2 | A-136330.1 | CACAAAUGCACCUCCCAGU | 788 | A-136331.1 | ACUGGGAGGUGCAUUUGUG | 985 | 2179-2197_as |

TABLE 11-continued

Unmodified Sense and Antisense Strand Sequences of AGT dsRNAs (21/23mers)

| Duplex Name | Sense Oligo Name | Sequence | SEQ ID NO. | Antisense Oligo Name | Sequence | SEQ ID NO. | Location of NM_000029.3 |
|---|---|---|---|---|---|---|---|
| AD-68088.2 | A-136332.1 | ACCUCCCAGUUUGCUGGGU | 789 | A-136333.1 | ACCCAGCAAACUGGGAGGU | 986 | 2188-2206_as |
| AD-68089.2 | A-136334.1 | UGCUGGGUUUAUUUUAGAA | 790 | A-136335.1 | UUCUAAAAUAAACCCAGCA | 987 | 2199-2217_G19A_as |
| AD-68090.2 | A-136340.1 | CAAGAACCAGUGUUUAGCA | 791 | A-136341.1 | UGCUAAACACUGGUUCUUG | 988 | 2234-2252_G19A_as |
| AD-68091.2 | A-136354.1 | AGUGUUCCCUUUUCAAGUU | 792 | A-136355.1 | AACUUGAAAAGGGAACACU | 989 | 2309-2327_as |
| AD-68092.2 | A-136356.1 | UUCAAGUUGAGAACAAAAA | 793 | A-136357.1 | UUUUUGUUCUCAACUUGAA | 990 | 2320-2338_as |
| AD-68093.2 | A-136358.1 | CAAAAUUGGGUUUUAAAA | 794 | A-136359.1 | UUUUAAAACCCAAUUUUUG | 991 | 2333-2351_as |
| AD-68094.2 | A-136362.1 | AAAGUAUACAUUUUGCAU | 795 | A-136363.1 | AUGCAAAAUGUAUACUUU | 992 | 2354-2372_as |
| AD-68095.2 | A-136368.1 | UUUAGUGUCUUGAAUGUAA | 796 | A-136369.1 | UUACAUUCAAGACACUAAA | 993 | 2388-2406_as |
| AD-68096.2 | A-136370.1 | GAAUGUAAGAACAUGACCU | 797 | A-136371.1 | AGGUCAUGUUCUUACAUUC | 994 | 2399-2417_as |
| AD-68097.2 | A-136374.1 | UGUAGUGUCUGUAAUACCU | 798 | A-136375.1 | AGGUAUUACAGACACUACA | 995 | 2421-2439_as |
| AD-68098.2 | A-136376.1 | UGUAAUACCUUAGUUUUUU | 799 | A-136377.1 | AAAAAACUAAGGUAUUACA | 996 | 2430-2448_as |
| AD-68099.2 | A-136378.1 | UUUUUUCCACAGAUGCUUA | 800 | A-136379.1 | UAAGCAUCUGUGGAAAAAA | 997 | 2443-2461_G19A_as |
| AD-68100.2 | A-136382.1 | UUUUUGAACAAUACGUGAA | 801 | A-136383.1 | UUCACGUAUUGUUCAAAAA | 998 | 2465-2483_as |
| AD-68101.2 | A-136392.1 | ACCAUAGCUGGUUAUUUCU | 802 | A-136393.1 | AGAAAUAACCAGCUAUGGU | 999 | 2519-2537_as |
| AD-68102.2 | A-136394.1 | UUAUUUCUCCCUUGUGUUA | 803 | A-136395.1 | UAACACAAGGGAGAAAUAA | 1000 | 2530-2548_as |
| AD-68116.1 | A-136312.1 | UCCCACCUUUUCUUCUAAU | 804 | A-136313.1 | AUUAGAAGAAAAGGUGGGA | 1001 | 2078-2096_as |
| AD-68117.1 | A-136316.1 | UCGACUUUGAGCUGGAAAG | 805 | A-136317.1 | CUUUCCAGCUCAAAGUCGA | 1002 | 2100-2118_as |
| AD-68118.1 | A-136318.1 | CUGGAAAGCAGCCGUUUCU | 806 | A-136319.1 | AGAAACGGCUGCUUUCCAG | 1003 | 2111-2129_as |
| AD-68119.1 | A-136322.1 | UGGUCUAAGUGUGCUGCAU | 807 | A-136323.1 | AUGCAGCACACUUAGACCA | 1004 | 2133-2151_as |
| AD-68120.1 | A-136324.1 | GCUGCAUGGAGUGAGCAGU | 808 | A-136325.1 | ACUGCUCACUCCAUGCAGC | 1005 | 2145-2163_as |
| AD-68121.1 | A-136326.1 | UGAGCAGUAGAAGCCUGCA | 809 | A-136327.1 | UGCAGGCUUCUACUGCUCA | 1006 | 2156-2174_as |
| AD-68122.1 | A-136336.1 | UUAGAGAAUGGGGUGGGA | 810 | A-136337.1 | UCCCACCCCAUUCUCUAA | 1007 | 2212-2230_G19A_as |
| AD-68123.1 | A-136338.1 | GGGUGGGGAGGCAAGAACA | 811 | A-136339.1 | UGUUCUUGCCUCCCCACCC | 1008 | 2223-2241 |
| AD-68124.1 | A-136342.1 | UGUUUAGCGCGGGACUACU | 812 | A-136343.1 | AGUAGUCCCGCGCUAAACA | 1009 | 2244-2262_as |
| AD-68125.1 | A-136344.1 | GGACUACUGUUCCAAAAAG | 813 | A-136345.1 | CUUUUUGGAACAGUAGUCC | 1010 | 2255-2273_as |
| AD-68126.1 | A-136350.1 | AGCUUGUUUGUGAAACAAA | 814 | A-136351.1 | UUUGUUUCACAAACAAGCU | 1011 | 2288-2306_as |
| AD-68127.1 | A-136352.1 | AAACAAAAAGUGUUCCCU | 815 | A-136353.1 | AGGGAACACUUUUUGUUU | 1012 | 2300-2318_as |
| AD-68128.1 | A-136360.1 | UUUUAAAAUUAAAGUAUAA | 816 | A-136361.1 | UUAUACUUUAAUUUUAAAA | 1013 | 2344-2362 |
| AD-68129.1 | A-136364.1 | UUUUGCAUUGCCUUCGGUU | 817 | A-136365.1 | AACCGAAGGCAAUGCAAAA | 1014 | 2365-2383_as |
| AD-68130.1 | A-136366.1 | UUCGGUUUGUAUUUAGUGU | 818 | A-136367.1 | ACACUAAAUACAAACCGAA | 1015 | 2377-2395_as |
| AD-68131.1 | A-136372.1 | AACAUGACCUCCGUGUAGU | 819 | A-136373.1 | ACUACACGGAGGUCAUGUU | 1016 | 2408-2426_as |
| AD-68132.1 | A-136380.1 | CAGAUGCUUGUGAUUUUUA | 820 | A-136381.1 | UAAAAAUCACAAGCAUCUG | 1017 | 2452-2470_G19A_as |
| AD-68133.1 | A-136384.1 | UACGUGAAAGAUGCAAGCA | 821 | A-136385.1 | UGCUUGCAUCUUUCACGUA | 1018 | 2476-2494_as |
| AD-68134.1 | A-136386.1 | UGCAAGCACCUGAAUUUCU | 822 | A-136387.1 | AGAAAUUCAGGUGCUUGCA | 1019 | 2487-2505_as |

TABLE 11-continued

Unmodified Sense and Antisense Strand Sequences of AGT dsRNAs (21/23mers)

| Duplex Name | Sense Oligo Name | Sequence | SEQ ID NO. | Antisense Oligo Name | Sequence | SEQ ID NO. | Location of NM_000029.3 |
|---|---|---|---|---|---|---|---|
| AD-68135.1 | A-136388.1 | GAAUUUCUGUUUGAAUGCA | 823 | A-136389.1 | UGCAUUCAAACAGAAAUUC | 1020 | 2498-2516_G19A_as |
| AD-68136.1 | A-136390.1 | UUUGAAUGCGGAACCAUAA | 824 | A-136391.1 | UUAUGGUUCCGCAUUCAAA | 1021 | 2507-2525_G19A_as |
| AD-68137.1 | A-136396.1 | UUGUGUUAGUAAUAAACGU | 825 | A-136397.1 | ACGUUUAUUACUAACACAA | 1022 | 2541-2559_as |
| AD-68138.1 | A-136398.1 | AUAAACGUCUUGCCACAAU | 826 | A-136399.1 | AUUGUGGCAAGACGUUUAU | 1023 | 2552-2570_as |
| AD-68139.1 | A-136400.1 | UGCCACAAUAAGCCUCCAA | 827 | A-136401.1 | UUGGAGGCUUAUUGUGGCA | 1024 | 2562-2580_as |

TABLE 12

AGT single dose screen in Hep3B cells (21/23mers)

| Duplex Name | 10 nM Avg | 10 nM SD | 0.1 nM Avg | 0.1 nM SD |
|---|---|---|---|---|
| AD-67864.1 | 86.08 | 0.42 | 100.66 | 4.93 |
| AD-67865.1 | 90.98 | 0.44 | 97.56 | 4.30 |
| AD-67866.1 | 107.85 | 3.17 | 108.20 | 1.59 |
| AD-67867.1 | 96.24 | 5.18 | 96.22 | 4.24 |
| AD-67868.1 | 92.25 | 0.45 | 93.87 | 0.92 |
| AD-67869.1 | 107.24 | 8.40 | 96.54 | 3.78 |
| AD-67870.1 | 89.43 | 1.75 | 96.84 | 0.47 |
| AD-67871.1 | 100.66 | 4.93 | 96.91 | 5.22 |
| AD-67872.1 | 92.27 | 2.26 | 87.75 | 7.73 |
| AD-67873.1 | 118.49 | 6.38 | 105.63 | 3.10 |
| AD-67874.1 | 98.36 | 8.18 | 99.57 | 1.46 |
| AD-67875.1 | 98.55 | 2.89 | 100.76 | 14.27 |
| AD-67876.1 | 98.951 | 5.33 | 105.24 | 0.51 |
| AD-67877.1 | 104.94 | 5.14 | 100.97 | 2.47 |
| AD-67878.1 | 101.79 | 7.47 | 100.61 | 0.98 |
| AD-67879.1 | 99.66 | 6.34 | 101.66 | 0.49 |
| AD-67880.1 | 99.23 | 1.94 | 93.79 | 9.63 |
| AD-67881.1 | 95.84 | 0.93 | 104.16 | 2.04 |
| AD-67882.1 | 97.52 | 1.43 | 98.09 | 9.60 |
| AD-67883.1 | 94.53 | 1.85 | 95.88 | 3.75 |
| AD-67884.1 | 110.16 | 5.39 | 105.25 | 1.54 |
| AD-67885.1 | 101.70 | 4.48 | 97.94 | 5.75 |
| AD-67886.1 | 107.09 | 2.09 | 102.03 | 3.00 |
| AD-67887.1 | 95.51 | 0.46 | 94.24 | 4.15 |
| AD-67888.1 | 105.98 | 1.55 | 101.03 | 5.44 |
| AD-67889.1 | 89.42 | 0.87 | 102.44 | 5.52 |
| AD-67890.1 | 96.51 | 0.94 | 99.34 | 6.81 |
| AD-67891.1 | 89.73 | 0.43 | 102.01 | 0.99 |
| AD-67892.1 | 85.81 | 3.36 | 91.97 | 3.60 |
| AD-67893.1 | 104.89 | 2.05 | 93.25 | 3.65 |
| AD-67894.1 | 95.95 | 6.57 | 100.61 | 0.98 |
| AD-67895.1 | 87.61 | 3.43 | 92.99 | 5.92 |
| AD-67896.1 | 102.36 | 0.50 | 102.37 | 1.50 |
| AD-67897.1 | 89.23 | 6.55 | 101.66 | 1.49 |
| AD-67898.1 | 87.68 | 6.01 | 97.89 | 3.83 |
| AD-67899.1 | 10.98 | 1.28 | 28.08 | 7.87 |
| AD-67900.1 | 16.91 | 2.47 | 42.49 | 5.81 |
| AD-67901.1 | 51.36 | 1.00 | 73.53 | 10.77 |
| AD-67902.1 | 32.91 | 6.25 | 49.54 | 4.60 |
| AD-67903.1 | 8.23 | 3.73 | 25.89 | 8.71 |
| AD-67904.1 | 76.02 | 3.35 | 92.35 | 5.88 |
| AD-67905.1 | 99.22 | 0.97 | 103.21 | 7.58 |
| AD-67906.1 | 12.68 | 6.52 | 31.29 | 0.76 |
| AD-67907.1 | 25.24 | 0.86 | 68.71 | 0.67 |
| AD-67908.1 | 15.32 | 6.82 | 41.71 | 0.40 |
| AD-67909.1 | 57.21 | 2.52 | 81.72 | 1.60 |
| AD-67910.1 | 11.66 | 3.10 | 54.68 | 6.68 |
| AD-67911.1 | 40.57 | 0.39 | 60.72 | 4.16 |
| AD-67912.1 | 21.45 | 0.84 | 50.16 | 2.70 |
| AD-67913.1 | 44.86 | 5.26 | 69.55 | 5.78 |
| AD-67914.1 | 13.41 | 4.82 | 14.58 | 2.84 |
| AD-67915.1 | 38.73 | 3.41 | 62.81 | 7.67 |
| AD-67916.1 | 5.21 | 2.70 | 19.28 | 6.84 |
| AD-67917.1 | 16.92 | 1.57 | 50.03 | 3.91 |
| AD-67918.1 | 52.71 | 4.38 | 95.29 | 6.53 |
| AD-67919.1 | 86.98 | 0.85 | 96.94 | 6.17 |
| AD-67920.1 | 28.31 | 8.20 | 62.46 | 8.84 |
| AD-67921.1 | 40.44 | 1.38 | 65.06 | 20.38 |
| AD-67922.1 | 37.99 | 0.93 | 68.09 | 5.00 |
| AD-67923.1 | 9.52 | 0.97 | 31.95 | 1.09 |
| AD-67924.1 | 20.28 | 2.28 | 53.38 | 6.78 |
| AD-67925.1 | 15.78 | 1.46 | 35.24 | 4.82 |
| AD-67926.1 | 12.85 | 0.88 | 28.20 | 0.41 |
| AD-67927.1 | 39.78 | 2.72 | 70.72 | 17.16 |
| AD-67928.1 | 48.92 | 8.11 | 76.56 | 4.12 |
| AD-67929.1 | 95.53 | 3.27 | 103.52 | 6.08 |
| AD-67930.1 | 7.70 | 3.25 | 38.13 | 1.12 |
| AD-67931.1 | 62.59 | 2.14 | 83.32 | 7.74 |
| AD-67932.1 | 12.85 | 4.97 | 48.21 | 4.95 |
| AD-67933.1 | 75.51 | 4.06 | 99.92 | 1.95 |
| AD-67934.1 | 95.55 | 4.21 | 95.85 | 1.87 |
| AD-67935.1 | 6.92 | 0.06 | 26.43 | 22.43 |
| AD-67936.1 | 30.62 | 3.29 | 64.66 | 5.06 |
| AD-67937.1 | 11.89 | 1.33 | 46.23 | 25.91 |
| AD-67938.1 | 84.08 | 4.94 | 94.19 | 0.46 |
| AD-67939.1 | 49.09 | 0.24 | 76.31 | 13.39 |
| AD-67940.1 | 77.85 | 0.76 | 90.12 | 5.29 |
| AD-67947.1 | 81.74 | 5.60 | 89.68 | 3.07 |
| AD-67948.1 | 57.40 | 3.93 | 75.94 | 12.96 |
| AD-67949.1 | 89.04 | 1.30 | 98.84 | 4.35 |
| AD-67950.1 | 30.38 | 6.93 | 50.01 | 4.40 |
| AD-67951.1 | 57.60 | 12.32 | 84.26 | 2.89 |
| AD-67952.1 | 30.08 | 9.84 | 71.83 | 1.76 |
| AD-67954.1 | 63.41 | 2.17 | 83.16 | 5.29 |
| AD-67955.1 | 66.78 | 1.30 | 88.74 | 2.60 |
| AD-67956.1 | 48.82 | 4.54 | 84.38 | 7.02 |
| AD-67957.1 | 66.79 | 1.96 | 96.46 | 3.78 |
| AD-67958.1 | 11.88 | 6.31 | 28.49 | 7.58 |
| AD-67959.1 | 50.08 | 5.87 | 78.05 | 1.14 |
| AD-67960.1 | 53.33 | 9.104 | 72.41 | 9.90 |
| AD-67962.1 | 17.29 | 5.41 | 54.30 | 13.17 |
| AD-67963.1 | 19.63 | 2.11 | 49.27 | 15.43 |
| AD-67964.1 | 14.83 | 0.14 | 46.79 | 6.40 |
| AD-67965.1 | 15.94 | 9.26 | 36.16 | 16.09 |
| AD-67966.1 | 41.84 | 9.95 | 80.28 | 3.54 |
| AD-67967.1 | 20.10 | 2.94 | 45.85 | 6.71 |
| AD-67968.1 | 24.10 | 0.47 | 45.77 | 0.22 |
| AD-67970.1 | 41.61 | 6.09 | 59.36 | 1.16 |
| AD-67971.1 | 92.20 | 3.16 | 97.48 | 4.29 |
| AD-67972.1 | 24.48 | 3.46 | 60.84 | 2.68 |
| AD-67973.1 | 67.49 | 2.31 | 93.19 | 4.56 |
| AD-67974.1 | 22.421 | 0.76 | 62.87 | 17.33 |
| AD-67975.1 | 20.05 | 2.157 | 52.74 | 5.93 |
| AD-67976.1 | 19.21 | 5.30 | 54.84 | 6.96 |

TABLE 12-continued

AGT single dose screen in Hep3B cells (21/23mers)

| Duplex Name | 10 nM Avg | 10 nM SD | 0.1 nM Avg | 0.1 nM SD |
|---|---|---|---|---|
| AD-67978.1 | 17.36 | 1.10 | 60.49 | 14.96 |
| AD-67979.1 | 104.18 | 7.14 | 104.08 | 3.06 |
| AD-67980.1 | 17.85 | 4.84 | 43.65 | 9.34 |
| AD-67981.1 | 28.91 | 4.09 | 63.61 | 0.62 |
| AD-67982.1 | 91.54 | 0.44 | 103.34 | |
| AD-67983.1 | 76.45 | 1.87 | 97.09 | 0.95 |
| AD-67984.1 | 23.20 | 0.34 | 75.39 | 8.84 |
| AD-67986.1 | 10.16 | 2.32 | 43.00 | 0.21 |
| AD-67987.1 | 82.21 | 0.80 | 90.90 | 10.66 |
| AD-67988.1 | 22.56 | 7.80 | 59.12 | 9.52 |
| AD-67989.1 | 34.16 | 10.22 | 67.14 | 9.83 |
| AD-67990.1 | 24.33 | 3.68 | 36.35 | 3.20 |
| AD-67991.1 | 81.13 | 3.97 | 100.55 | 3.94 |
| AD-67992.1 | 56.20 | 3.30 | 97.78 | 1.91 |
| AD-67993.1 | 29.38 | 5.01 | 78.86 | 13.08 |
| AD-67994.1 | 20.30 | 4.44 | 30.93 | |
| AD-67995.1 | 13.97 | 2.72 | 37.27 | 5.82 |
| AD-67996.1 | 14.48 | 0.49 | 30.62 | 6.25 |
| AD-67997.1 | 35.60 | 7.78 | 70.86 | 12.09 |
| AD-67998.1 | 29.38 | 5.01 | 62.37 | 15.13 |
| AD-67999.1 | 58.52 | 6.58 | 86.27 | 9.70 |
| AD-68001.1 | 39.90 | 11.75 | 68.76 | 5.38 |
| AD-68002.1 | 70.36 | 2.41 | 87.50 | 1.61 |
| AD-68003.1 | 31.65 | 2.78 | 86.01 | 2.10 |
| AD-68004.1 | 23.47 | 1.60 | 42.71 | 1.04 |
| AD-68005.1 | 30.41 | 6.21 | 68.42 | 1.00 |
| AD-68006.1 | 20.44 | 8.64 | 41.45 | 5.87 |
| AD-68009.1 | 26.59 | 6.45 | 50.87 | 12.58 |
| AD-68010.1 | 18.01 | 2.98 | 41.65 | 11.68 |
| AD-68011.1 | 48.64 | 4.28 | 75.01 | 10.99 |
| AD-68012.1 | 21.28 | 0.41 | 66.82 | 13.98 |
| AD-68013.1 | 101.46 | 9.93 | 109.28 | 4.28 |
| AD-68014.1 | 43.62 | 7.44 | 71.82 | 0.35 |
| AD-68017.1 | 16.05 | 11.61 | 38.14 | 14.23 |
| AD-68018.1 | 14.74 | 0.57 | 62.02 | 9.38 |
| AD-68019.1 | 20.85 | 3.66 | 84.24 | 1.23 |
| AD-68020.1 | 31.12 | 4.86 | 70.58 | 16.45 |
| AD-68021.1 | 18.98 | 3.8 | 56.30 | 10.96 |
| AD-68022.1 | 16.41 | 9.93 | 27.87 | 15.96 |
| AD-68025.1 | 86.91 | 1.70 | 99.51 | 3.41 |
| AD-68026.1 | 26.43 | 9.50 | 73.34 | 1.79 |
| AD-68027.1 | 39.43 | 0.38 | 72.57 | 1.42 |
| AD-68028.1 | 56.98 | 3.34 | 80.52 | |
| AD-68029.1 | 49.97 | 3.42 | 85.43 | 2.93 |
| AD-68032.1 | 71.12 | 3.48 | 91.96 | 6.30 |
| AD-68033.1 | 102.29 | 2.50 | 99.13 | 0.97 |
| AD-68034.1 | 15.54 | 3.32 | 32.03 | 3.91 |
| AD-68035.1 | 19.40 | 6.88 | 49.77 | 6.32 |
| AD-68036.1 | 16.23 | 8.62 | 29.22 | 4.28 |
| AD-68037.1 | 20.40 | 5.24 | 49.31 | 9.13 |
| AD-68084.2 | 15.14 | 3.24 | 42.67 | 5.63 |
| AD-68085.2 | 17.11 | 5.52 | 30.76 | 11.20 |
| AD-68086.2 | 8.96 | 0 | 21.05 | 2.98 |
| AD-68087.2 | 22.54 | 14.44 | 26.79 | 37.89 |
| AD-68088.2 | 34.54 | 2.19 | 76.58 | 1.87 |
| AD-68089.2 | 27.02 | 5.91 | 59.45 | 13.85 |
| AD-68090.2 | 19.90 | 0.97 | 35.94 | 7.00 |
| AD-68091.2 | 15.18 | 0.74 | 32.19 | 3.77 |
| AD-68092.2 | 13.21 | 0.25 | 40.48 | 1.38 |
| AD-68093.2 | 13.94 | 3.11 | 52.91 | 25.17 |
| AD-68094.2 | 48.22 | 7.06 | 89.18 | 25.43 |
| AD-68095.2 | 83.02 | 5.69 | 81.51 | 1.19 |
| AD-68096.2 | 74.34 | 5.82 | 75.78 | 1.21 |
| AD-68097.2 | 88.32 | 4.32 | 86.30 | 7.18 |
| AD-68098.2 | 69.49 | 0.34 | 69.49 | 1.02 |
| AD-68099.2 | 95.96 | 3.76 | 51.05 | 72.19 |
| AD-68100.2 | 81.51 | 1.19 | 92.05 | 3.60 |
| AD-68101.2 | 76.34 | 2.99 | 74.83 | 5.13 |
| AD-68102.2 | 71.02 | 4.52 | 76.99 | 6.78 |
| AD-68116.1 | 9.94 | 0.38 | 31.41 | 3.53 |
| AD-68117.1 | 18.24 | 0.62 | 51.01 | 7.96 |
| AD-68118.1 | 16.61 | 0.32 | 31.54 | 7.50 |
| AD-68119.1 | 48.03 | 3.76 | 77.61 | 12.49 |
| AD-68120.1 | 20.17 | 11.80 | 72.58 | 10.63 |
| AD-68121.1 | 16.25 | 4.55 | 57.64 | 25.65 |
| AD-68122.1 | 57.36 | 5.33 | 97.32 | 4.76 |
| AD-68123.1 | 15.84 | 1.24 | 45.55 | 2.00 |
| AD-68124.1 | 24.62 | 8.40 | 51.57 | 19.72 |
| AD-68125.1 | 18.71 | 9.38 | 35.98 | 6.14 |
| AD-68126.1 | 13.13 | 6.42 | 47.97 | 1.41 |
| AD-68127.1 | 41.04 | 12.66 | 85.58 | 2.93 |
| AD-68128.1 | 62.20 | 16.27 | 107.38 | 9.46 |
| AD-68129.1 | 79.00 | | 81.25 | 3.18 |
| AD-68130.1 | 72.97 | 2.50 | 88.00 | 3.88 |
| AD-68131.1 | 134.88 | 9.24 | 92.09 | 5.41 |
| AD-68132.1 | 81.05 | 5.95 | 89.85 | 3.96 |
| AD-68133.1 | 85.28 | 2.50 | 104.25 | 2.04 |
| AD-68134.1 | 62.63 | 0.92 | 83.94 | 6.98 |
| AD-68135.1 | 72.95 | 0.35 | 79.05 | 3.87 |
| AD-68136.1 | 74.86 | 10.60 | 88.88 | |
| AD-68137.1 | 85.08 | 6.24 | 90.50 | 4.87 |
| AD-68138.1 | 76.05 | 1.11 | 76.34 | 2.99 |
| AD-68139.1 | 102.25 | 8.01 | 99.42 | 6.81 |

Example 4: In Vivo AGT Silencing in a Mouse Expressing hAGT

A series of experiments were performed to assess hAGT target knockdown in mice expressing human AGT (hAGT) from an AAV8 expression vector which has strong liver tropism. Briefly, mice were infected with $1 \times 10^{11}$ AAV8 particles containing an expression construct for hAGT under the control of a constitutive promoter. Two weeks after infection, mice were administered a single 3.0 mg/kg, 1.0 mg/kg, 0.3 mg/kg, or 0.1 mg/kg dose of an siRNA targeting hAGT (AD-67327.2 or AD-67335.2), or PBS as a control (n=4 per group). The nucleotide sequences of the agents assessed in these experiments are provided in Table 13.

TABLE 13

Modified Sense and Antisense Strand Sequences of AGT dsRNAs (21/23 mers)

| Duplex Name | Location on NM_000029.3 | Sense Strand/ Antisense Strand | Sense Sequence/Antisense Sequence | SEQ ID NO. | Parent Duplex |
|---|---|---|---|---|---|
| AD-67327 | 2081-2101 | A-134527 | uscsucccAfcCfUfUfuucuucuaauL96 | 1025 | AD-60784 |
|  | 2079-2101 | A-134528 | asUfsuagAfagaaaagGfuGfggagascsu | 1026 |  |
| AD-67335 | 1894-1914 | A-134536 | usgsuuugCfuGfUfGfuaugaucaaaL96 | 1027 | AD-60781 |
|  | 1892-1914 | A-134538 | usUfsugaUfcAfUfacacAfgCfaaacasgsg | 1028 |  |

At days 0, 3, 7, and 14, after administration of the agents, blood samples were collected and serum was prepared to determine the level of hAGT mRNA expression relative to the prebleed level of hAGT. The results of these experiments are shown in Table 14.

TABLE 14 hAGT single dose dose-response screen in hAGT expressing mice

| Duplex | Dose mpk | Day 0 Avg | SD | Day 3 Avg | SD | Day 7 Avg | SD | Day 14 Avg | SD |
|---|---|---|---|---|---|---|---|---|---|
|  | PBS | 1.00 | 0.00 | 1.29 | 0.28 | 0.91 | 0.17 | 0.65 | 0.05 |
| AD-67327 | 3 | 1.00 | 0.00 | 0.42 | 0.09 | 0.16 | 0.04 | 0.11 | 0.04 |
|  | 1 | 1.00 | 0.00 | 0.63 | 0.05 | 0.44 | 0.04 | 0.31 | 0.06 |
|  | 0.3 | 1.00 | 0.00 | 1.04 | 0.13 | 0.90 | 0.12 | 0.77 | 0.06 |
|  | 0.1 | 1.00 | 0.00 | 0.91 | 0.06 | 0.88 | 0.07 | 0.74 | 0.15 |

TABLE 14-continued hAGT single dose dose-response screen in hAGT expressing mice

| Duplex | Dose mpk | Day 0 Avg | SD | Day 3 Avg | SD | Day 7 Avg | SD | Day 14 Avg | SD |
|---|---|---|---|---|---|---|---|---|---|
| AD-67335 | 3 | 1.00 | 0.00 | 0.58 | 0.14 | 0.42 | 0.13 | 0.37 | 0.10 |
|  | 1 | 1.00 | 0.00 | 0.59 | 0.41 | 0.64 | 0.03 | 0.56 | 0.12 |
|  | 0.3 | 1.00 | 0.00 | 1.06 | 0.28 | 0.81 | 0.14 | 0.80 | 0.07 |
|  | 0.1 | 1.00 | 0.00 | 1.18 | 0.18 | 1.02 | 0.10 | 0.85 | 0.08 |

Example 5: In Vivo AGT Silencing in a Mouse Expressing hAGT

A series of experiments were performed to assess hAGT target knockdown in mice expressing hAGT from an AAV8 expression vector which has a strong liver tropism. Briefly, mice were infected with $1 \times 10^{11}$ AAV8 particles containing an expression construct for hAGT under the control of a constitutive promoter. Two weeks after infection with the AAV8 virus, mice were administered a single 1 mg/kg dose of an siRNA targeting hAGT, or PBS as a control (n=3 per group). The nucleotide sequences of the duplexes assessed in these experiments are provided in Table 15.

TABLE 15

Modified Sense and Antisense Strand Sequences of AGT dsRNAs (21/23 mers)

| Duplex Name | Location on NM_000029.3 | Sense Strand/ Antisense Strand | Sense Sequence/Antisense Sequence | SEQ ID NO. | Parent Duplex |
|---|---|---|---|---|---|
| AD-68577 | 855-875 | A-137778 | ususccguAfuAfUfAfuggcaugcaaL96 | 1029 | AD-60779 |
|  | 853-875 | A-137779 | usUfsgcaUfgCfCfauauAfuAfcggaasgsc | 1030 |  |
| AD-68581 | 1741-1761 | A-137784 | ascscugcAfaAfAfAfuugagcaauaL96 | 1031 | AD-56029 |
|  | 1739-1761 | A-137785 | usAfsuugCfuCfAfauuuUfuGfcaggususc | 1032 |  |
| AD-68582 | 1741-1761 | A-137784 | ascscugcAfaAfAfAfuugagcaauaL96 | 1033 | AD-56029 |
|  | 1739-1761 | A-137786 | usAfsuugCfucaauuuUfuGfcaggususc | 1034 |  |
| AD-67335 | 1894-1914 | A-134536 | usgsuuugCfuGfUfGfuaugaucaaaL96 | 1035 | AD-60781 |
|  | 1892-1914 | A-134538 | usUfsugaUfcAfUfacacAfgCfaaacasgsg | 1036 |  |
| AD-67327 | 2081-2101 | A-134527 | uscsucccAfcCfUfUfuucuucuaauL96 | 1037 | AD-52474 |
|  | 2079-2101 | A-134528 | asUfsuagAfagaaaagGfuGfggagascsu | 1038 |  |
| AD-68575 | 2084-2104 | A-137775 | cscscaccUfuUfUfCfuucuaaugaaL96 | 1039 | AD-60777 |
|  | 2082-2104 | A-137776 | usUfscauUfaGfAfagaaAfaGfgugggsasg | 1040 |  |
| AD-68576 | 2084-2104 | A-137775 | cscscaccUfuUfUfCfuucuaaugaaL96 | 1041 | AD-60777 |
|  | 2082-2104 | A-137777 | usUfscauUfagaagaaAfaGfgugggsasg | 1042 |  |
| AD-68583 | 2291-2311 | A-137787 | cscsagcuUfgUfUfUfgugaaacaaaL96 | 1043 | AD-56019 |
|  | 2289-2311 | A-137788 | usUfsuguUfuCfAfcaaaCfaAfcuggsusc | 1044 |  |
| AD-68584 | 2291-2311 | A-137787 | cscsagcuUfgUfUfUfgugaaacaaaL96 | 1045 | AD-56019 |
|  | 2289-2311 | A-137789 | usUfsuguUfucacaaaCfaAfgcuggsusc | 1046 |  |
| AD-67313 | 2309-2329 | A-134509 | asasaaaaGfuGfUfUfcccuuuucaaL96 | 1047 | AD-60776 |
|  | 2307-2329 | A-134510 | usUfsgaaAfagggaacAfcUfuuuuusgsu | 1048 |  |
| AD-67314 | 2309-2329 | A-134509 | asasaaaaGfuGfUfUfcccuuuucaaL96 | 1049 | AD-60776 |
|  | 2307-2329 | A-134511 | usUfsgaaAfaGfGfgaacAfcUfuuuuusgsu | 1050 |  |

Seven days after administration of the agents, blood samples were collected and serum was prepared to determine the level of hAGT mRNA expression relative to the prebleed level of hAGT. The results of these experiments are provided in Table 16.

TABLE 16 hAGT single dose dose-response screen in hAGT expressing mice

| Duplex | Average | SD |
|---|---|---|
| PBS | 98.6 | 8.7 |
| AD-68577 | 65.1 | 7.7 |
| AD-68581 | 53.1 | 3.3 |
| AD-68582 | 44.8 | 11.1 |
| AD-67335 | 60.5 | 3.1 |
| AD-67327 | 43.0 | 1.0 |
| AD-68575 | 48.0 | 9.4 |

TABLE 16-continued hAGT single dose dose-response screen in hAGT expressing mice

| Duplex | Average | SD |
|---|---|---|
| AD-68576 | 47.4 | 5.9 |
| AD-68583 | 51.3 | 7.7 |
| AD-68584 | 61.0 | 2.1 |
| AD-67313 | 70.8 | 7.6 |
| AD-67314 | 66.2 | 5.7 |

EQUIVALENTS

Those skilled in the art will recognize, or be able to ascertain using no more than routine experimentation, many equivalents to the specific embodiments and methods described herein. Such equivalents are intended to be encompassed by the scope of the following claims.

We claim:

1. A double-stranded ribonucleic acid (RNAi) agent for inhibiting expression of angiotensinogen (AGT) in a cell, wherein said double-stranded RNAi agent comprises a sense strand and an antisense strand forming a double-stranded region, wherein the sense strand comprises at least 15 contiguous nucleotides differing by no more than 3 nucleotides from nucleotides 2081-2104 of the nucleotide sequence of SEQ ID NO: 1, wherein the antisense strand is substantially complementary to the sense strand, wherein each of the sense strand and the antisense strand is independently 15 to 30 nucleotides in length, and wherein the RNAi agent comprises at least one modified nucleotide.

2. The double-stranded RNAi agent of claim 1, wherein substantially all of the nucleotides of said sense strand are modified nucleotides, substantially all of the nucleotides of said antisense strand are modified nucleotides, or substantially all of the nucleotides of said sense strand and substantially all of the nucleotides of said antisense strand are modified nucleotides.

3. The double-stranded RNAi agent of claim 1, wherein said sense strand is conjugated to a ligand attached at the 3'-terminus.

4. The double-stranded RNAi agent of claim 1, wherein all of the nucleotides of said sense strand and all of the nucleotides of said antisense strand are modified nucleotides.

5. The double-stranded RNAi agent of claim 1, wherein the antisense strand comprises the nucleotide sequence of 5'-AUUAGAAGAAAAGGUGGGAGACU-3' (SEQ ID NO:537).

6. The double-stranded RNAi agent of claim 1, wherein at least one of said modified nucleotides is selected from the group consisting of a 3'-terminal deoxy-thymine (dT) nucleotide, a 2'-O-methyl modified nucleotide, a 2'-fluoro modified nucleotide, a 2'-deoxy-modified nucleotide, a locked nucleotide, an unlocked nucleotide, a conformationally restricted nucleotide, a constrained ethyl nucleotide, an abasic nucleotide, a 2'-amino-modified nucleotide, a 2'-alkyl-modified nucleotide, a morpholino nucleotide, a phosphoramidate, a non-natural base comprising nucleotide, a nucleotide comprising a 5'-phosphorothioate group, and a terminal nucleotide linked to a cholesteryl derivative or a dodecanoic acid bisdecylamide group.

7. The double-stranded RNAi agent of claim 1, wherein at least one strand comprises a 3' overhang of at least 1 nucleotide; or at least one strand comprises a 3' overhang of at least 2 nucleotides.

8. The double-stranded RNAi agent of claim 1, wherein the double-stranded region is 15-30 nucleotide pairs in length; 17-23 nucleotide pairs in length; 17-25 nucleotide pairs in length; 23-27 nucleotide pairs in length; 19-21 nucleotide pairs in length; or 21-23 nucleotide pairs in length.

9. The double-stranded RNAi agent of claim 1, wherein each of the sense strand and the antisense strand is independently 19 to 30 nucleotides in length or 21 to 23 nucleotides in length.

10. The double-stranded RNAi agent of claim 3, wherein the ligand is one or more GalNAc derivatives attached through a bivalent or trivalent branched linker.

11. The double-stranded RNAi agent of claim 3, wherein the ligand is

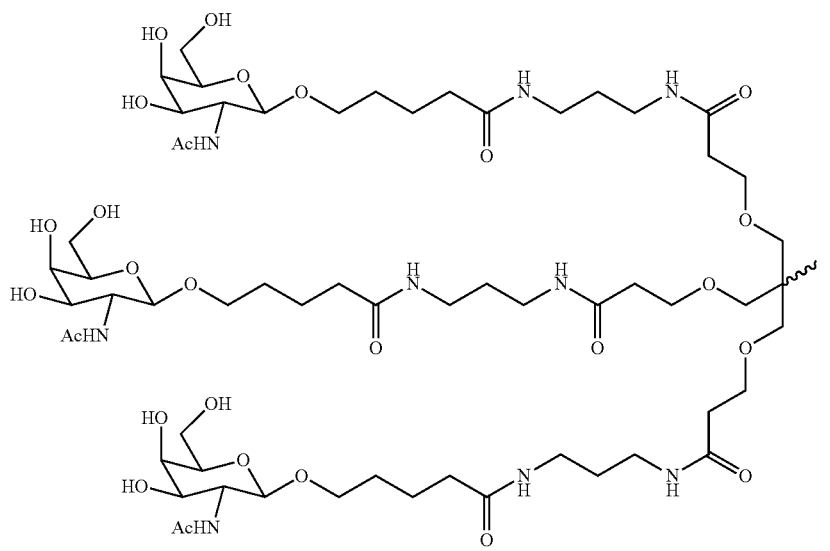

12. The double-stranded RNAi agent of claim 11, wherein the RNAi agent is conjugated to the ligand as shown in the following schematic

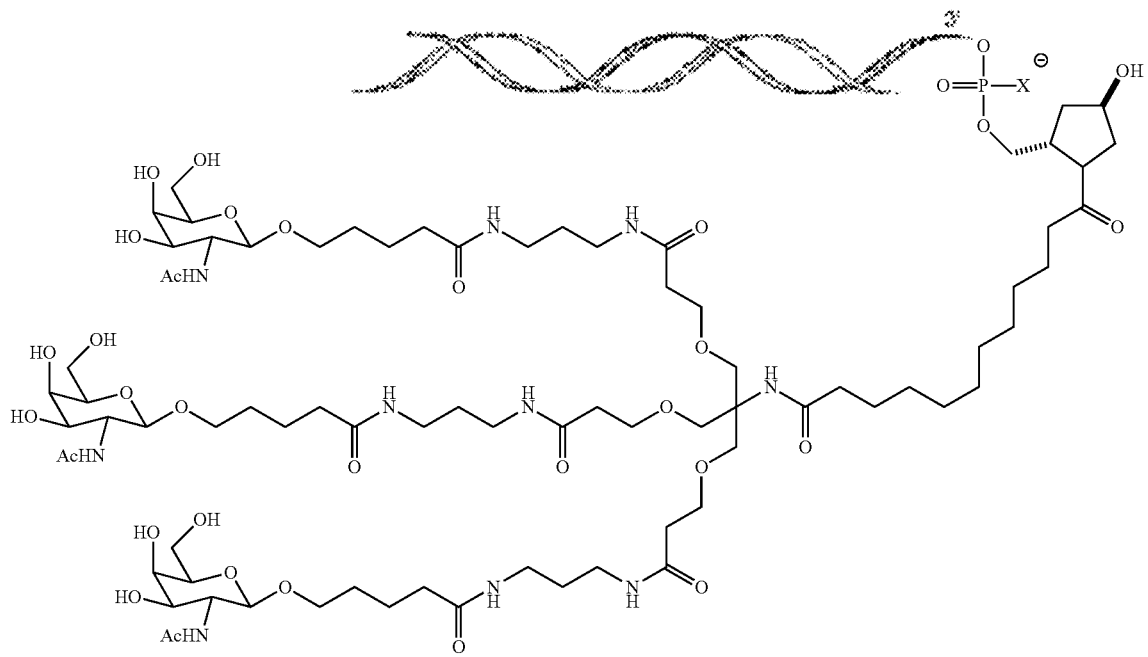

wherein X is O or S.

13. The double-stranded RNAi agent of claim 1, wherein said RNAi agent further comprises at least one phosphorothioate or methylphosphonate internucleotide linkage.

14. The double-stranded RNAi agent of claim 13, wherein the phosphorothioate or methylphosphonate internucleotide linkage is at the 3'-terminus of one strand; the 5'-terminus of one strand; or at both the 5'- and 3'-terminus of one strand.

15. The double-stranded RNAi agent of claim 14, wherein said strand is the antisense strand.

16. The double-stranded RNAi agent of claim 14, wherein said strand is the sense strand.

17. The double-stranded RNAi agent of claim 13, wherein said RNAi agent comprises 6-8 phosphorothioate internucleotide linkages.

18. The double-stranded RNAi of claim 17, wherein the antisense strand comprises two phosphorothioate internucleotide linkages at the 5'-terminus and two phosphorothioate internucleotide linkages at the 3'-terminus, and the sense strand comprises at least two phosphorothioate internucleotide linkages at either the 5'-terminus or the 3'-terminus.

19. The double-stranded RNAi agent of claim 1, wherein the base pair at the 1 position of the 5'-end of the antisense strand is an AU base pair.

20. The double-stranded RNAi agent of claim 5, wherein the sense strand of the RNAi agent comprises the nucleotide sequence of 5'-UCUCCCACCUUUUCUUCUAAU 3' (SEQ ID NO:499) and the antisense strand comprises the nucleotide sequence of 5'-AUUAGAAGAAAAGGUGGGA-GACU 3' (SEQ ID NO:537).

21. A double-stranded ribonucleic acid (RNAi) agent for inhibiting expression of angiotensinogen (AGT),
wherein said double-stranded RNAi agent comprises a sense strand and an antisense strand forming a double-stranded region, wherein said sense strand comprises at least 15 contiguous nucleotides differing by no more than 3 nucleotides from nucleotides 2081-2104 of SEQ ID NO:1, and said antisense strand comprises at least 15 contiguous nucleotides differing by no more than 3 nucleotides from the nucleotide sequence of SEQ ID NO: 2,
wherein each of the sense strand and the antisense strand is independently 15 to 30 nucleotides in length,
wherein substantially all of the nucleotides of said sense strand comprise a modification selected from the group consisting of a 2'-O-methyl modification and a 2'-fluoro modification,
wherein said sense strand comprises two phosphorothioate internucleotide linkages at the 5'-terminus,
wherein substantially all of the nucleotides of said antisense strand comprise a modification selected from the group consisting of a 2'-O-methyl modification and a 2'-fluoro modification,
wherein said antisense strand comprises two phosphorothioate internucleotide linkages at the 5'-terminus and two phosphorothioate internucleotide linkages at the 3'-terminus, and
wherein said sense strand is conjugated to one or more GalNAc derivatives attached through a branched bivalent or trivalent linker at the 3'-terminus.

22. The double-stranded RNAi agent of claim 21, wherein all of the nucleotides of said sense strand and all of the nucleotides of said antisense strand comprise a modification.

23. A double-stranded ribonucleic acid (RNAi) agent comprising a sense strand and an antisense strand, wherein said sense strand comprises the nucleotide sequence of 5'-UCUCCCACCUUUUCUUCUAAU-3' (SEQ ID NO:499), and said antisense strand comprises the nucleotide sequence of 5'-AUUAGAAGAAAAGGUGGGAGACU-3' (SEQ ID NO:537).

24. A composition comprising a modified antisense polynucleotide agent, wherein the agent comprises about 14 to about 30 contiguous nucleotides, wherein said agent is capable of inhibiting the expression of AGT in a cell, and comprises a nucleotide sequence substantially complementary to the nucleotide sequence of 5'-UCUCCCAC-CUUUUCUUCUAAU-3' (SEQ ID NO:499).

25. An isolated cell containing the double-stranded RNAi agent of claim 1.

26. A pharmaceutical composition comprising the double-stranded RNAi agent of claim 1.

27. The pharmaceutical composition of claim 26, wherein double-stranded RNAi agent is administered in an unbuffered solution; or a buffered solution.

28. A method of inhibiting angiotensinogen (AGT) expression in a cell, the method comprising:
(a) contacting the cell with the double-stranded RNAi agent of claim 1 or the pharmaceutical composition of claim 26; and
(b) maintaining the cell produced in step (a) for a time sufficient to obtain degradation of the mRNA transcript of an AGT gene, thereby inhibiting expression of the AGT gene in the cell.

29. The method of claim 28, wherein said cell is within a subject.

30. The method of claim 29, wherein the subject is a human.

31. The method of claim 30, wherein the subject suffers from a hypertension.

32. A method of treating a subject having a hypertension, comprising administering to the subject a therapeutically effective amount of the double-stranded RNAi agent of claim 1 or the pharmaceutical composition of claim 26, thereby treating said subject.

33. A method of treating a subject having a hypertension, comprising subcutaneously administering to the subject a therapeutically effective amount of a double-stranded ribonucleic acid (RNAi) agent,
wherein said double-stranded RNAi agent comprises a sense strand and an antisense strand forming a double-stranded region,
wherein said sense strand comprises at least 15 contiguous nucleotides differing by no more than 3 nucleotides from nucleotides 2081-2104 of SEQ ID NO:1, and said antisense strand comprises at least 15 nucleotides differing by no more than 3 nucleotides from the nucleotide sequence of SEQ ID NO: 2,
wherein each of the sense strand and the antisense strand is independently 15 to 30 nucleotides in length,
wherein substantially all of the nucleotides of said antisense strand comprise a modification selected from the group consisting of a 2'-O-methyl modification and a 2'-fluoromodification,
wherein said antisense strand comprises two phosphorothioate internucleotide linkages at the 5'-terminus and two phosphorothioate internucleotide linkages at the 3'-terminus,
wherein substantially all of the nucleotides of said sense strand comprise a modification selected from the group consisting of a 2'-O-methyl modification and a 2'-fluoro modification,
wherein said sense strand comprises two phosphorothioate internucleotide linkages at the 5'-terminus and, wherein said sense strand is conjugated to one or more GalNAc derivatives attached through a branched bivalent or trivalent linker at the 3'-terminus, thereby treating the subject.

34. The method of claim 33, wherein all of the nucleotides of said sense strand and all of the nucleotides of said antisense strand comprise a modification.

35. The method of claim 33, wherein the subject is a human.

36. The method of claim 33, wherein the hypertension is selected from the group consisting of borderline hypertension, primary hypertension, secondary hypertension, hypertensive emergency, hypertensive urgency, isolated systolic or diastolic hypertension, pregnancy-associated hypertension, diabetic hypertension, resistant hypertension, refractory hypertension, paroxysmal hypertension, renovascular hypertension, Goldblatt hypertension, ocular hypertension, glaucoma, pulmonary hypertension, portal hypertension, systemic venous hypertension, systolic hypertension, labile hypertension; hypertensive heart disease, and hypertensive nephropathy.

37. The method of claim 33, wherein the hypertension is pregnancy-associated hypertension.

38. The method of claim 33, wherein the double-stranded RNAi agent is administered to the subject at a dose of about 0.01 mg/kg to about 10 mg/kg or about 0.5 mg/kg to about 50 mg/kg; a dose of about 10 mg/kg to about 30 mg/kg; a dose of about 3 mg/kg; or a dose of about 10 mg/kg.

39. The method of claim 38, wherein the double-stranded RNAi agent is administered to the subject subcutaneously; or intravenously.

40. The method of claim 33, further comprising administering to the subject an additional therapeutic agent.

41. The method of claim 40, wherein the additional therapeutic agent is selected from the group consisting of a diuretic, an angiotensin converting enzyme (ACE) inhibitor, an angiotensin II receptor antagonist, a beta-blocker, a vasodilator, a calcium channel blocker, an aldosterone antagonist, an alpha$_2$-agonist, a renin inhibitor, an alpha-blocker, a peripheral acting adrenergic agent, a selective D1 receptor partial agonist, a nonselective alpha-adrenergic antagonist, a synthetic, steroidal antimineralocorticoid agent, or a combination of any of the foregoing, and a hypertension therapeutic agent formulated as a combination of agents.

42. The double-stranded RNAi agent of claim 20, wherein the sense strand comprises the nucleotide sequence of 5'-uscsucccAfcCfUfUfuucuucuaau-3' (SEQ ID NO:1025) and the antisense strand comprises the nucleotide sequence of 5'-asUfsuagAfagaaaagGfuGfggagascsu-3' (SEQ ID NO:1026).

43. The double-stranded RNAi agent of claim 1, wherein the antisense strand is fully complementary to the sense strand.

44. The composition of claim 24, wherein the modified antisense polynucleotide agent comprises a sequence fully complementary to the nucleotide sequence of 5'-UCUCCCACCUUUUCUUCUAAU-3' (SEQ ID NO:499).

* * * * *